US011051815B2

(12) United States Patent
Eaves et al.

(10) Patent No.: US 11,051,815 B2
(45) Date of Patent: Jul. 6, 2021

(54) FORCE MODULATING TISSUE BRIDGES, ASSOCIATED TOOLS, KITS, AND METHODS

(71) Applicant: EMRGE, LLC, Atlanta, GA (US)

(72) Inventors: Felmont F. Eaves, Atlanta, GA (US); David O. Kazmer, Georgetown, MA (US); Gary W. Knight, Lebanon, OH (US); Timothy G. Dietz, Reading, MA (US); William Eugene Clem, Bozeman, MT (US)

(73) Assignee: EMRGE, LLC, Atlanta, GA (US)

( * ) Notice: Subject to any disclaimer, the term of this patent is extended or adjusted under 35 U.S.C. 154(b) by 145 days.

(21) Appl. No.: 16/242,064

(22) Filed: Jan. 8, 2019

(65) Prior Publication Data

US 2019/0133582 A1 May 9, 2019

Related U.S. Application Data

(63) Continuation of application No. PCT/US2017/057569, filed on Oct. 20, 2017.
(Continued)

(51) Int. Cl.
*A61B 17/08* (2006.01)
*A61B 17/10* (2006.01)
(Continued)

(52) U.S. Cl.
CPC .......... *A61B 17/085* (2013.01); *A61B 17/083* (2013.01); *A61B 17/10* (2013.01); *A61B 17/105* (2013.01); *A61B 50/20* (2016.02); *A61B 50/22* (2016.02); *A61B 50/30* (2016.02); *A61B 50/33* (2016.02); *A61B 90/53* (2016.02);
(Continued)

(58) Field of Classification Search
CPC ....... A61B 17/10; A61B 17/085; A61B 17/08; A61B 2017/081; A61B 2017/00907
See application file for complete search history.

(56) References Cited

U.S. PATENT DOCUMENTS 815,264 A 3/1906 Chambers
1,248,450 A 3/1917 Burke
(Continued)

FOREIGN PATENT DOCUMENTS

AU 2012236205 B2 8/2016
AU 2016262734 12/2016
(Continued)

OTHER PUBLICATIONS

Partial Supplementary European Search Report in counterpart European Application No. 17861546.4 dated Apr. 22, 2020, pp. 1-12 [US Publication No. 201410128819 previously cited.].
(Continued)

*Primary Examiner* — Tuan V Nguyen
(74) *Attorney, Agent, or Firm* — Additon, Pendleton & Witherspoon, P.A.

(57) ABSTRACT

Force modulating tissue bridges, and associated applicators, kits and methods are provided. A force modulating tissue bridge can be a medical article for at least partially covering a wound and/or scar tissue. The medical article can include an elastic arch extending over an area, and a medial strut connected to the arch and extending into the area over which the central section extends.

22 Claims, 97 Drawing Sheets

Related U.S. Application Data

(60) Provisional application No. 62/411,023, filed on Oct. 21, 2016.

(51) Int. Cl.

| | | |
|---|---|---|
| *A61B 50/33* | (2016.01) | |
| *A61B 90/53* | (2016.01) | |
| *A61B 50/20* | (2016.01) | |
| *A61B 50/30* | (2016.01) | |
| *A61B 50/22* | (2016.01) | |
| A61B 17/00 | (2006.01) | |
| A61B 50/00 | (2016.01) | |

(52) U.S. Cl.
CPC ............... *A61B 2017/00862* (2013.01); *A61B 2017/00884* (2013.01); *A61B 2017/00893* (2013.01); *A61B 2017/00907* (2013.01); *A61B 2017/00951* (2013.01); *A61B 2017/081* (2013.01); *A61B 2050/0065* (2016.02)

(56) References Cited

U.S. PATENT DOCUMENTS

| | | | |
|---|---|---|---|
| 1,908,229 A | 5/1933 | Dyer | |
| 2,254,620 A | 9/1941 | Miller | |
| 2,341,121 A | 2/1944 | Schaaff | |
| 2,371,978 A * | 3/1945 | Perham | A61B 17/085 606/216 |
| 2,912,735 A | 11/1959 | Johnson et al. | |
| 3,068,870 A | 3/1960 | Levin | |
| 3,014,483 A | 12/1961 | McCarthy | |
| 3,082,773 A | 3/1963 | Renstrom et al. | |
| 3,120,687 A | 2/1964 | Greening et al. | |
| 3,487,836 A | 1/1970 | Niebel et al. | |
| 3,625,220 A | 12/1971 | Engelsher | |
| 3,695,271 A | 10/1972 | Chodorow | |
| 3,831,608 A | 8/1974 | Kletschka et al. | |
| 3,861,008 A | 1/1975 | Wannag | |
| 4,011,639 A | 3/1977 | Koleske | |
| 4,275,736 A | 6/1981 | Chodorow | |
| D260,681 S | 9/1981 | Chodorow et al. | |
| 4,506,669 A * | 3/1985 | Blake, III | A61B 17/30 294/99.2 |
| 4,539,990 A | 9/1985 | Stivala | |
| 4,702,251 A | 10/1987 | Sheehan | |
| D293,717 S | 1/1988 | Proulx et al. | |
| 4,815,468 A | 3/1989 | Armand | |
| 5,176,868 A | 1/1993 | Davis | |
| 5,230,701 A | 7/1993 | Meyer et al. | |
| 5,366,480 A | 11/1994 | Corriveau et al. | |
| D354,134 S | 1/1995 | Tanaka | |
| D359,144 S | 6/1995 | Healzer et al. | |
| 5,489,083 A | 2/1996 | Rollor | |
| 5,549,713 A | 8/1996 | Kim | |
| 5,775,345 A | 7/1998 | Chou | |
| D407,489 S | 3/1999 | Kalat | |
| 6,196,228 B1 | 3/2001 | Kreitzer et al. | |
| D530,420 S | 10/2006 | Chesnin | |
| 7,332,641 B2 | 2/2008 | Lebner et al. | |
| 7,683,234 B2 | 3/2010 | Gurtner et al. | |
| 8,157,839 B2 | 4/2012 | Riskin et al. | |
| 8,183,428 B2 | 5/2012 | Gurtner et al. | |
| 8,246,590 B2 | 8/2012 | Hu et al. | |
| D667,167 S | 9/2012 | Stewart | |
| D671,265 S | 11/2012 | Stewart | |
| 8,323,313 B1 | 12/2012 | Belson et al. | |
| D674,544 S | 1/2013 | Stewart | |
| 8,395,011 B2 | 3/2013 | Zepeda et al. | |
| 8,435,221 B2 | 5/2013 | Hu et al. | |
| D683,860 S | 6/2013 | Quimby | |
| D690,020 S | 9/2013 | Quimby | |
| 8,562,576 B2 | 10/2013 | Hu et al. | |
| 8,592,640 B2 | 11/2013 | Zepeda et al. | |
| 8,674,164 B2 | 3/2014 | Zepeda et al. | |
| 8,834,434 B2 | 9/2014 | Hu et al. | |
| 8,915,942 B2 | 12/2014 | Zhang | |
| 9,028,529 B2 | 5/2015 | Riskin et al. | |
| 9,050,086 B2 | 6/2015 | Belson et al. | |
| 9,089,328 B2 | 7/2015 | Belson et al. | |
| 9,119,620 B2 | 9/2015 | Peterson et al. | |
| 9,301,760 B2 | 4/2016 | Fox | |
| 9,421,133 B2 | 8/2016 | Hu et al. | |
| 9,517,163 B2 | 12/2016 | Goldman et al. | |
| D780,317 S | 2/2017 | Vandervoort | |
| 9,603,596 B2 | 3/2017 | Riskin et al. | |
| 9,649,226 B2 | 5/2017 | Zepeda et al. | |
| D790,072 S | 6/2017 | Hiebert | |
| D811,609 S | 2/2018 | Huff | |
| 9,974,532 B2 | 5/2018 | Baas et al. | |
| 10,064,616 B2 | 9/2018 | Lear et al. | |
| D831,220 S | 10/2018 | Chase et al. | |
| 10,213,350 B2 | 2/2019 | Jackson et al. | |
| 10,426,479 B2 | 10/2019 | Vold et al. | |
| 10,517,768 B2 | 12/2019 | Zepeda et al. | |
| D876,641 S | 2/2020 | Eaves, III et al. | |
| 2002/0111641 A1 | 8/2002 | Peterson et al. | |
| 2003/0221700 A1 | 12/2003 | La Fauci | |
| 2005/0080453 A1 | 4/2005 | Lebner | |
| 2005/0193527 A1 | 9/2005 | Gould | |
| 2006/0200198 A1 | 9/2006 | Riskin et al. | |
| 2009/0125052 A1 | 5/2009 | Pinna et al. | |
| 2009/0151128 A1 | 6/2009 | Gould | |
| 2009/0240186 A1 | 9/2009 | Frang | |
| 2009/0259203 A1 | 10/2009 | Hu et al. | |
| 2010/0051046 A1 | 3/2010 | Stevenson et al. | |
| 2010/0081983 A1 | 4/2010 | Zocher | |
| 2010/0228287 A1 | 9/2010 | Jeekel | |
| 2010/0236566 A1 | 9/2010 | Stachowski | |
| 2010/0262126 A1 | 10/2010 | Hu et al. | |
| 2011/0004173 A1 | 1/2011 | Hu et al. | |
| 2011/0023906 A1 | 2/2011 | Tu | |
| 2011/0040325 A1 | 2/2011 | Moehrle | |
| 2011/0054547 A1 | 3/2011 | Anderson | |
| 2011/0105963 A1 | 5/2011 | Hu et al. | |
| 2012/0172779 A1 | 7/2012 | Spinelli et al. | |
| 2012/0221044 A1 | 8/2012 | Archibald et al. | |
| 2013/0178897 A1 | 7/2013 | Wu et al. | |
| 2014/0107597 A1 | 4/2014 | Hu et al. | |
| 2014/0128819 A1 | 5/2014 | Eaves | |
| 2014/0227483 A1 | 8/2014 | Eaves | |
| 2014/0336701 A1 | 11/2014 | McLorg | |
| 2015/0005722 A1 | 1/2015 | Hu et al. | |
| 2015/0012037 A1 | 1/2015 | Goldman et al. | |
| 2015/0112311 A1 * | 4/2015 | Hammond | A61F 13/00068 604/543 |
| 2015/0305739 A1 | 10/2015 | Rolandi et al. | |
| 2016/0324693 A1 | 11/2016 | Hu et al. | |
| 2017/0049630 A1 | 2/2017 | Goldman et al. | |
| 2017/0071596 A1 | 3/2017 | Lear et al. | |
| 2017/0333039 A1 | 11/2017 | Leung | |
| 2018/0125492 A1 | 5/2018 | Eaves | |
| 2018/0303483 A1 | 10/2018 | Zhang | |
| 2018/0338757 A1 | 11/2018 | Lear et al. | |
| 2018/0353335 A1 | 12/2018 | Walker | |

FOREIGN PATENT DOCUMENTS

| | | |
|---|---|---|
| CA | 2830918 A1 | 10/2012 |
| CN | 1889903 A | 1/2007 |
| CN | 101606856 | 12/2009 |
| CN | 101828939 B | 9/2010 |
| CN | 201683935 U | 12/2010 |
| CN | 103892877 A | 7/2014 |
| CN | 105147344 A | 12/2015 |
| CN | 205144638 U | 4/2016 |
| CN | 103533900 A | 12/2016 |
| EP | 2691029 A2 | 2/2014 |
| FR | 119096 | 10/1910 |
| FR | 794710 | 2/1936 |
| JP | 2011-500170 A | 1/2011 |
| JP | 2014-516288 | 7/2014 |
| KR | 10-2009-0066415 A | 6/2009 |
| KR | 10-2014-0020993 | 2/2014 |

(56) References Cited

FOREIGN PATENT DOCUMENTS

| TW | M340039 U | 9/2008 |
|---|---|---|
| WO | 02/26181 A1 | 4/2002 |
| WO | 2006/124671 A2 | 11/2006 |
| WO | 2009049232 A1 | 4/2009 |
| WO | 2011/019859 A2 | 2/2011 |
| WO | 2013188884 A1 | 6/2012 |
| WO | 2012/135735 | 10/2012 |
| WO | 2013/059600 | 4/2013 |
| WO | 2016/107897 A1 | 7/2016 |
| WO | 2017/079782 A1 | 5/2017 |
| WO | 2018/075879 | 4/2018 |

OTHER PUBLICATIONS

Search Report in counterpart European Application No. 17861546.4 dated Jul. 31, 2020, pp. 1-10.
Examination Report No. 1 in related Australian Application No. 2016262734, dated Jan. 14, 2019, 3 pages [FR 419096; US 2010/0262126 & U.S. Pat. No. 4,702,251 previously cited].
International Preliminary Report on Patentability in commonly owned International Application No. PCT/US2017/057569, dated May 2, 2019, pp. 1-6.
Amazon, "Elastic Bandage Wrap Compression Tape", Review by Maria A. Dec. 18, 2017, <URL:https://www.amazon.com/Elastic-Bandage-Wrap-Compression-Tape/dp/B06XQ8BY8?th=1> (Year 2017) 12 pages.
Extended Search Report in related EP Application 12762897.2, dated May 27, 2015, 11 pages.
Japanese Office Action in related JP Application No. 2014-502866, dated Dec. 10, 2015, Translation provided, 11 pages.
Chinese First Office Action in related CN Application No. 201280017051.4, dated Jun. 1, 2015, Translation provided, 13 pages.
Chinese Second Office Action in related CN Application No. 201280017051.4, dated Dec. 31, 2015, Translation provided, 8 pages.
Australian Patent Examination Report No. 1 in related Australian Patent Application No. 201226205, dated Aug. 28, 2015, 5 pages.
International Search Report and Written Opinion issued in commonly owned PCT/US2012/031638 dated Nov. 29, 2012; 10 pages.
Supplementary Partial European Search Report in commonly owned EP Application No. 12762897, dated Dec. 23, 2014, 7 pages.
Japanese Notice of Reasons for Rejection in related JP Application No. 2014-502866, dated Oct. 3, 2016; 9 pages.
Southmedic Inc., SutureSafe Instructions for Use, 2 pages [Downloaded Jul. 25, 2017 from http://dynamictissuesystems.com/wp-content/uploads/2015/09/IFU0251_E_pdf].
SutureSafe Inc., Product Brochure SutureSafe Support closed wounds and provide stability; 2 pages [Downloaded Jul. 25, 2017 from http://dynamictissuesystems.com/wp-content/uploads/2015/09/SutureSafe-SS-lr2.pdf].
Search Report in counterpart PCT Application No. PCT/2018/057569, dated Feb. 2, 2018, pp. 1-6.
Written Opinion in counterpart PCT Application No. PCT/20181057569, dated Apr. 26, 2018, pp. 1-5.
Commonly owned U.S. Appl. No. 29/622,936, filed Oct. 20, 2017, pp. 1-56.
Commonly owned U.S. Appl. No. 29/622,941, filed Oct. 20, 2017, pp. 1-57.
Supplementary Partial European Search Report in related EP Application No. 12762897, dated Dec. 23, 2014, 7 pages.
Commonly owned U.S. Appl. No. 16/153,340, filed Oct. 5, 2018, pp. 1-111.
First Chinese Office Action in related CN Application No. 201611102500.1, dated Aug. 20, 2018, 21 pages (including English Translation).
Summons to attend oral proceedings in commonly owned European Application No. 12762897.2 dated Mar. 22, 2021, pp. 1-11.

\* cited by examiner

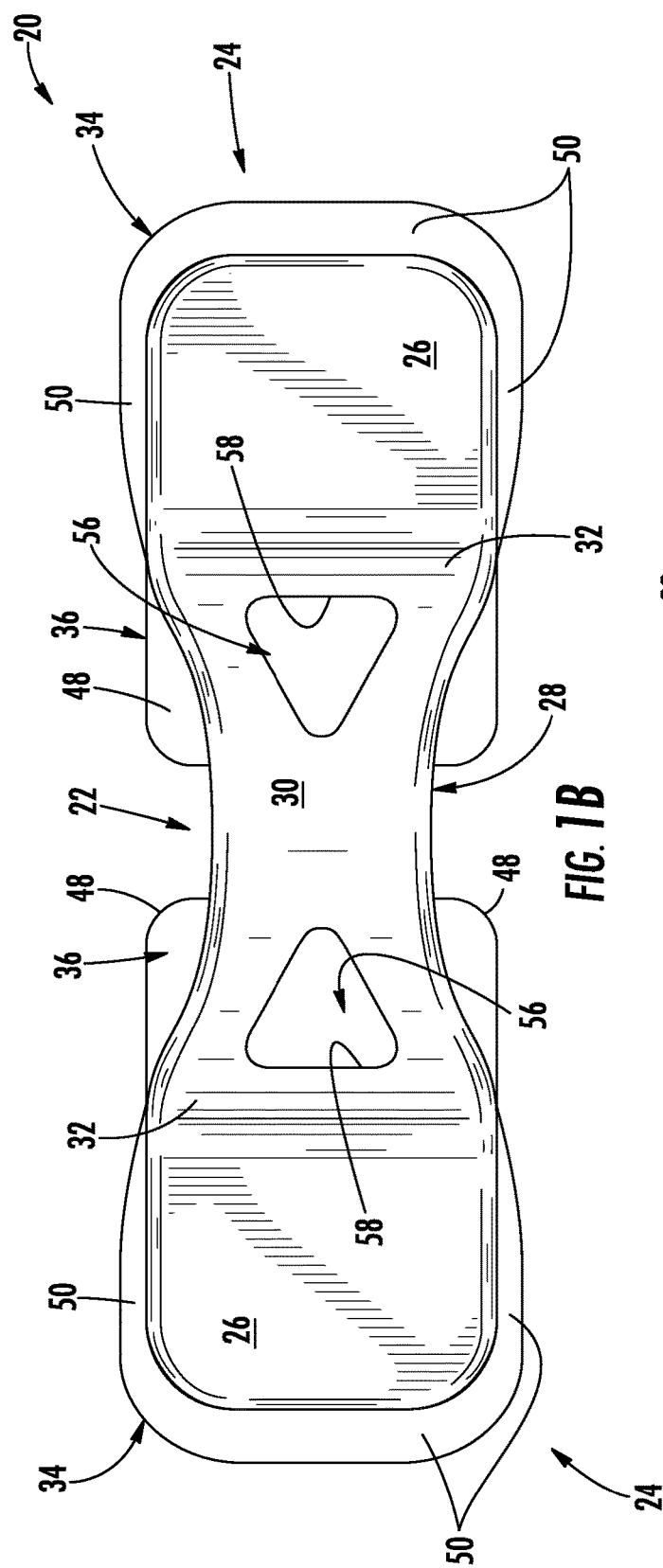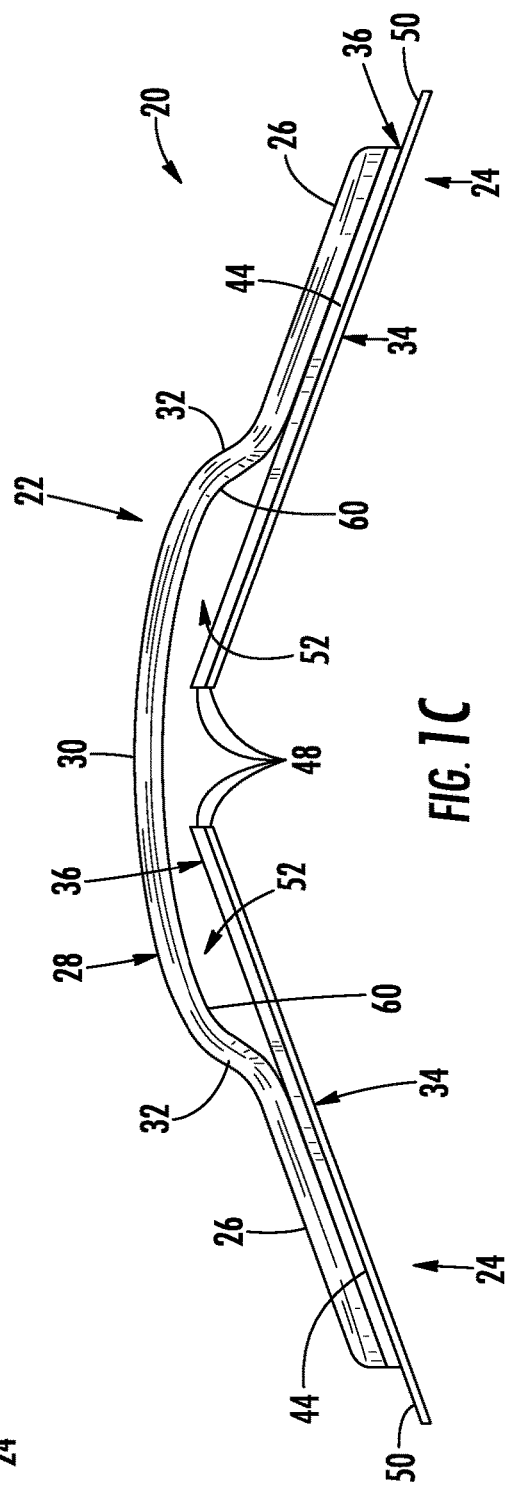
FIG. 1B
FIG. 1C

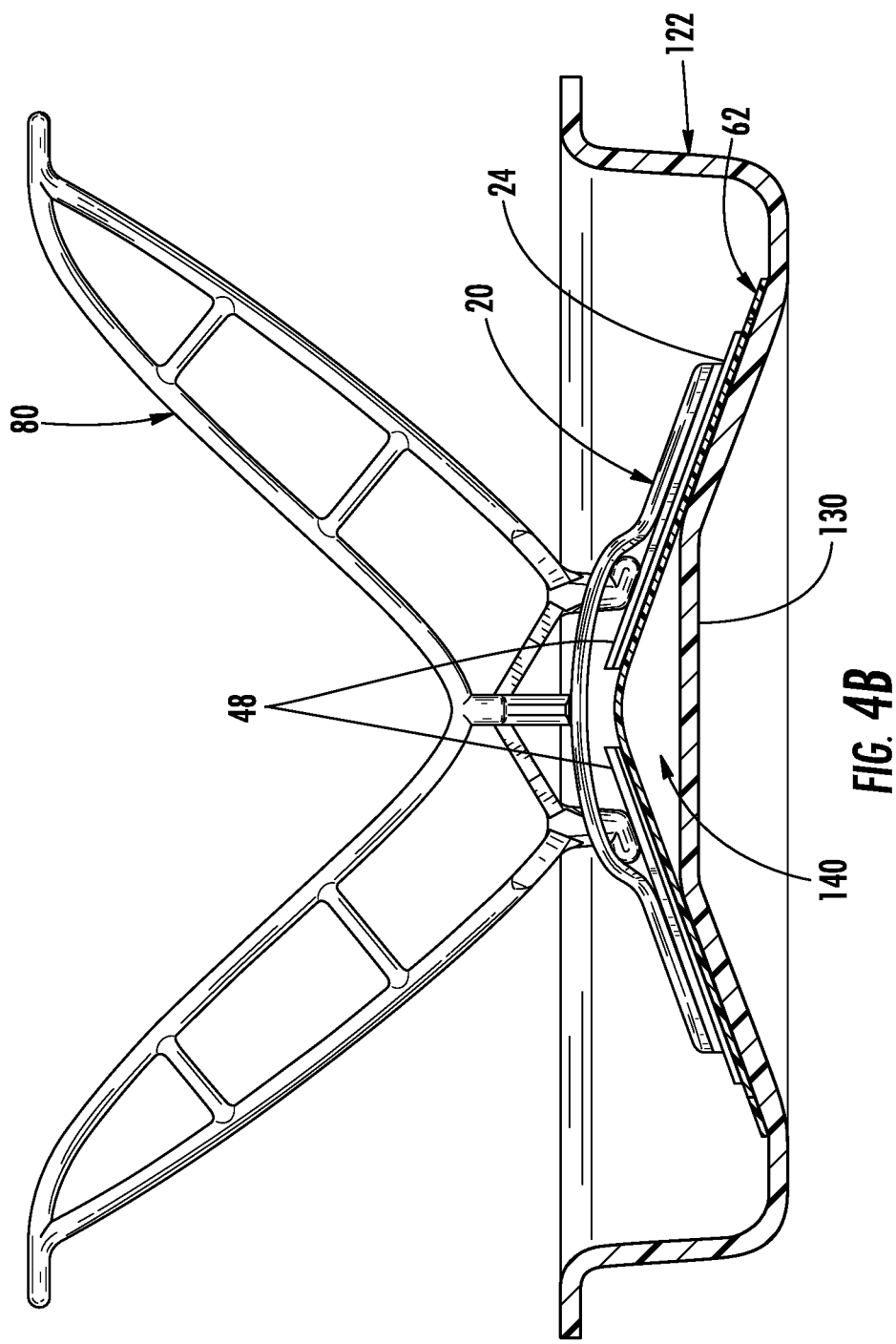

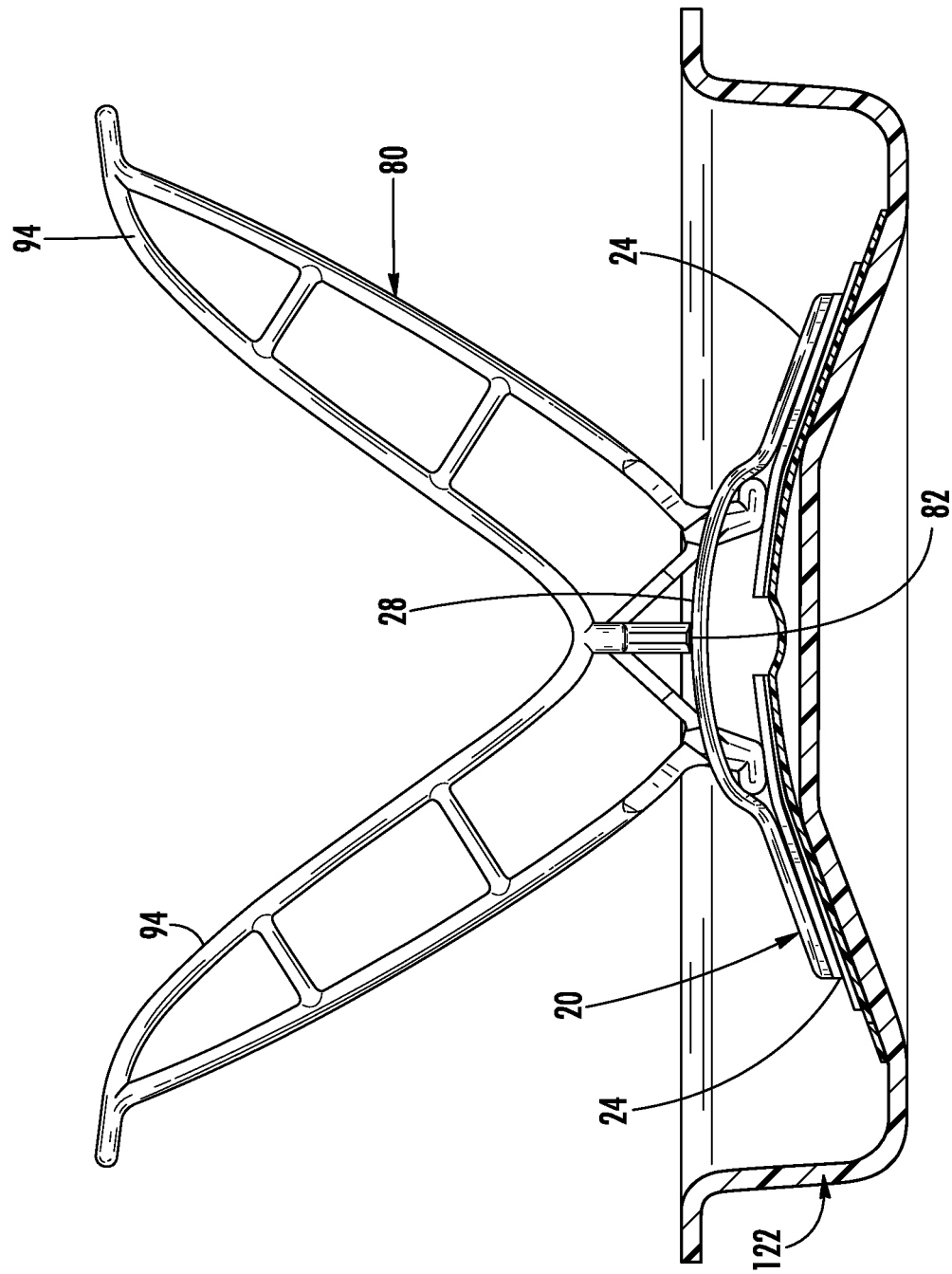

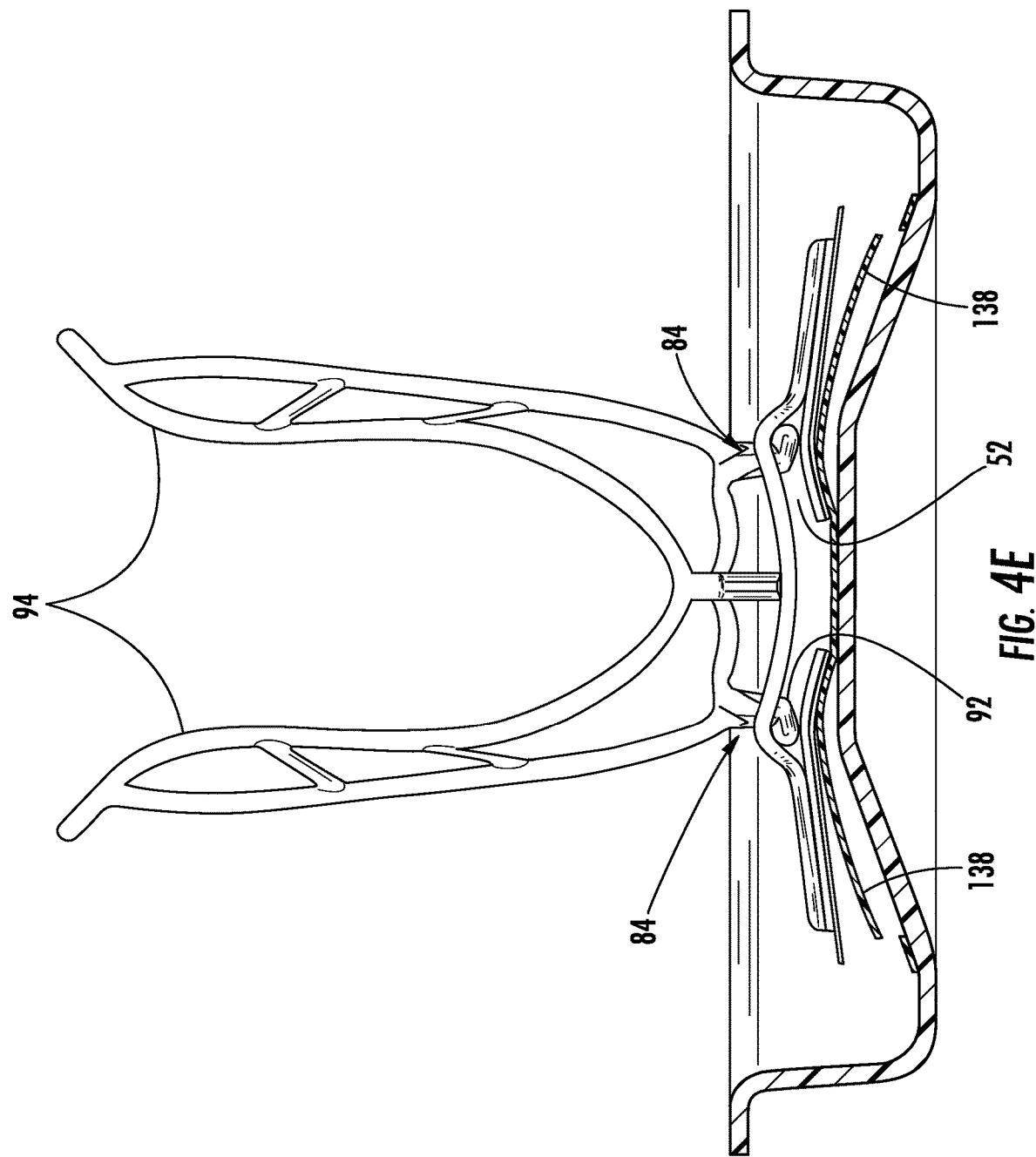

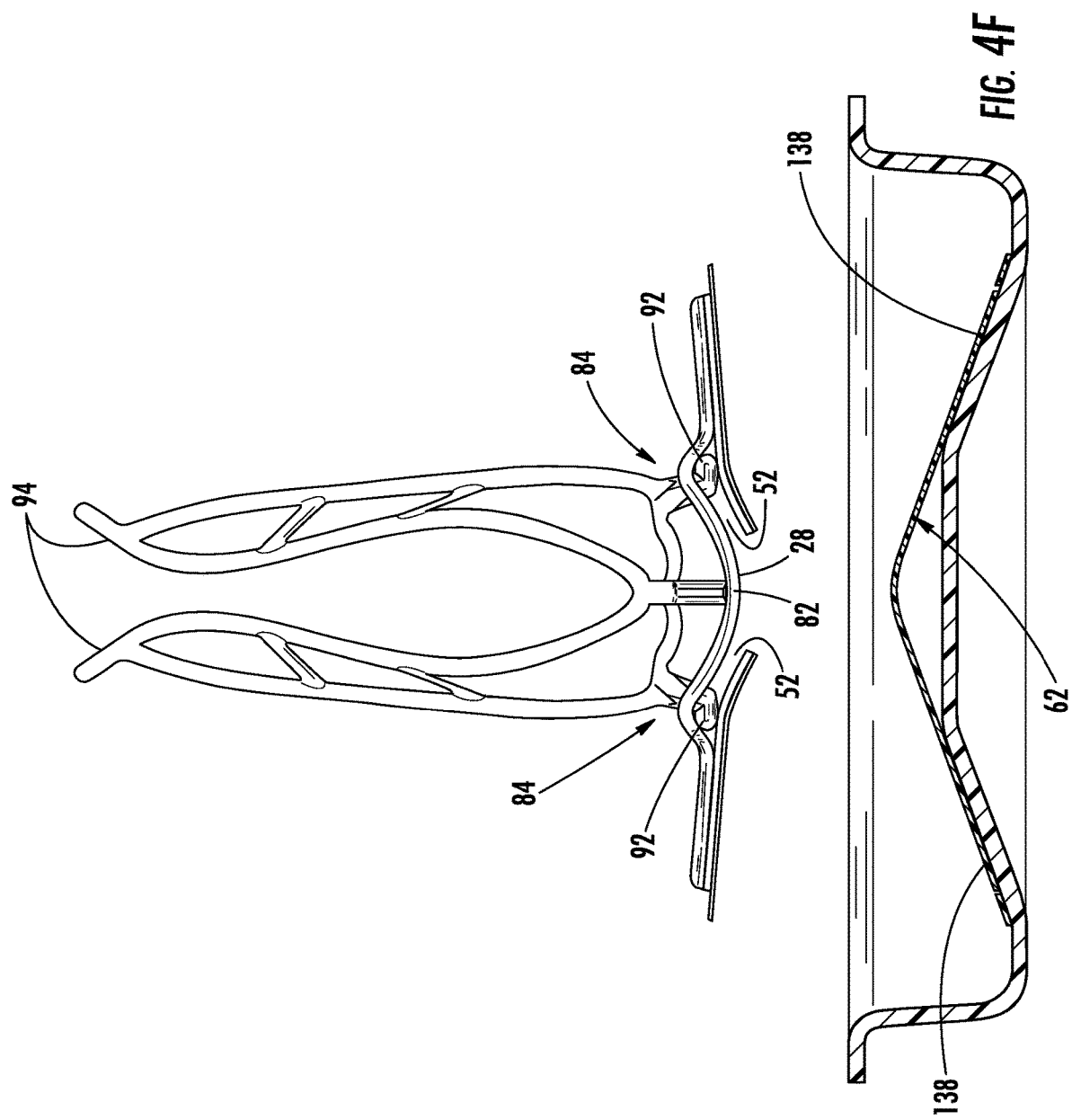

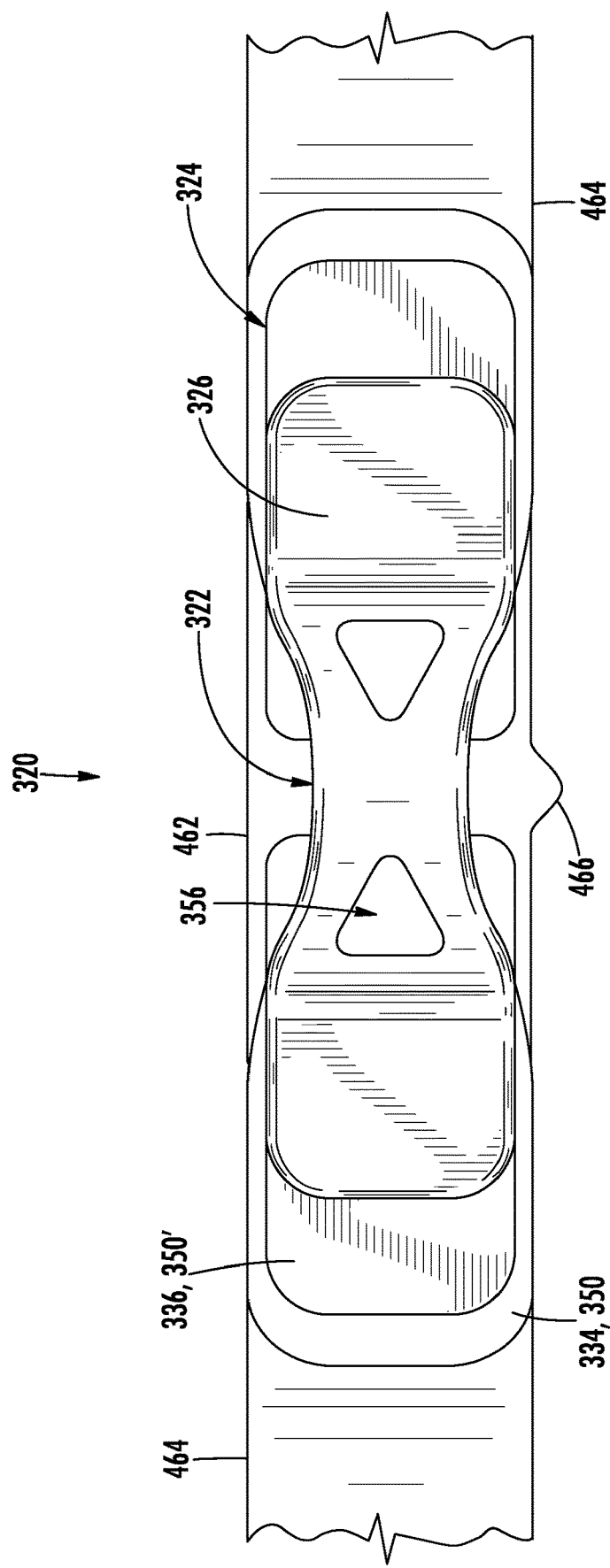

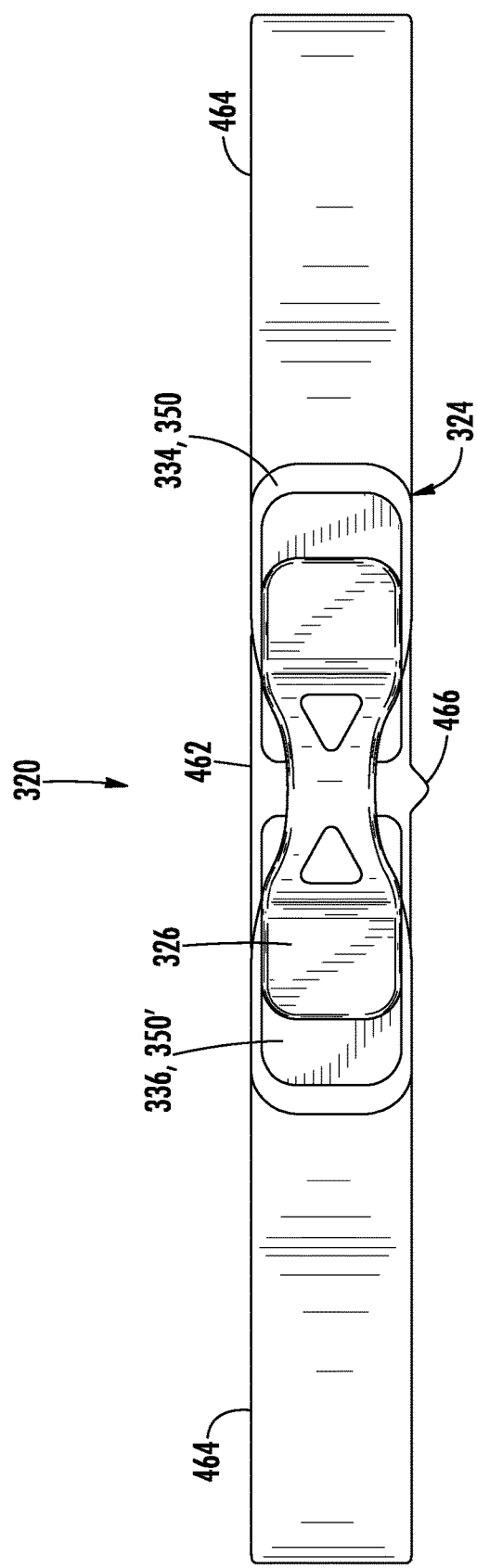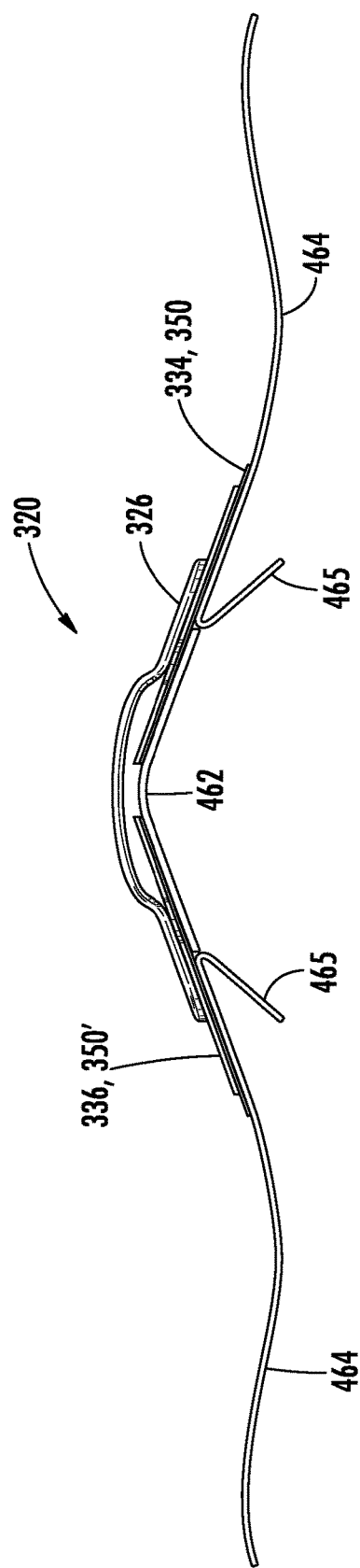

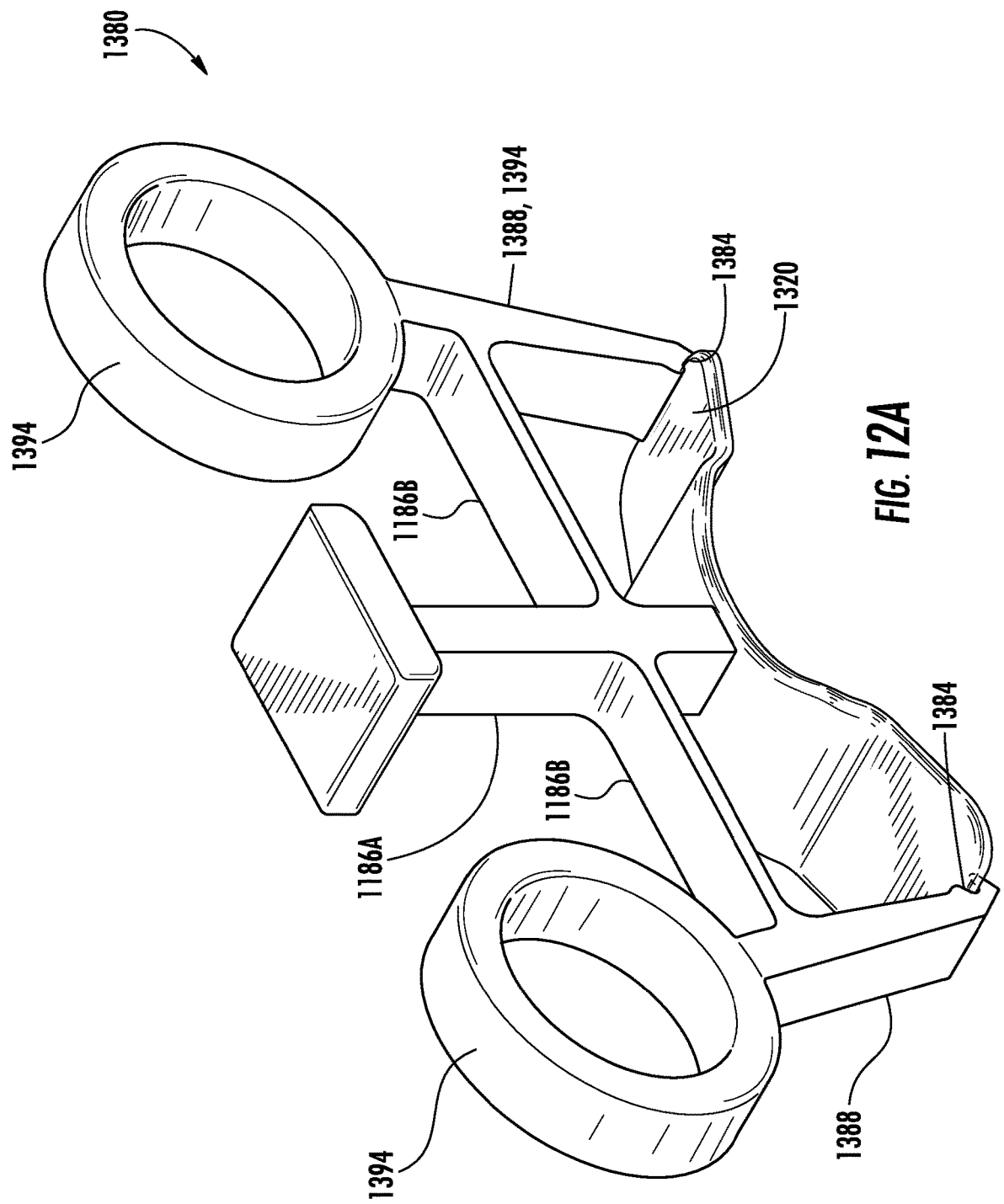

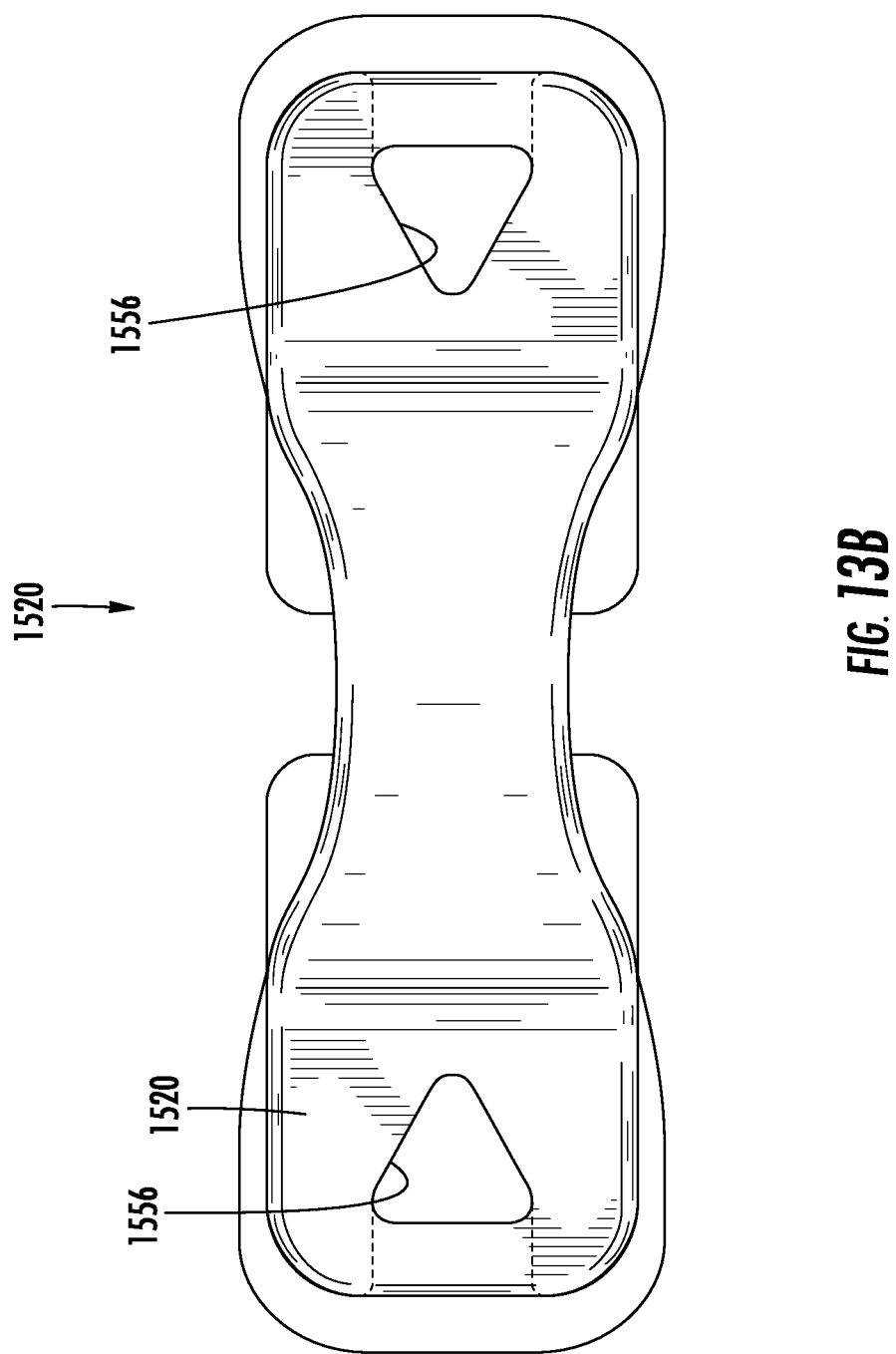

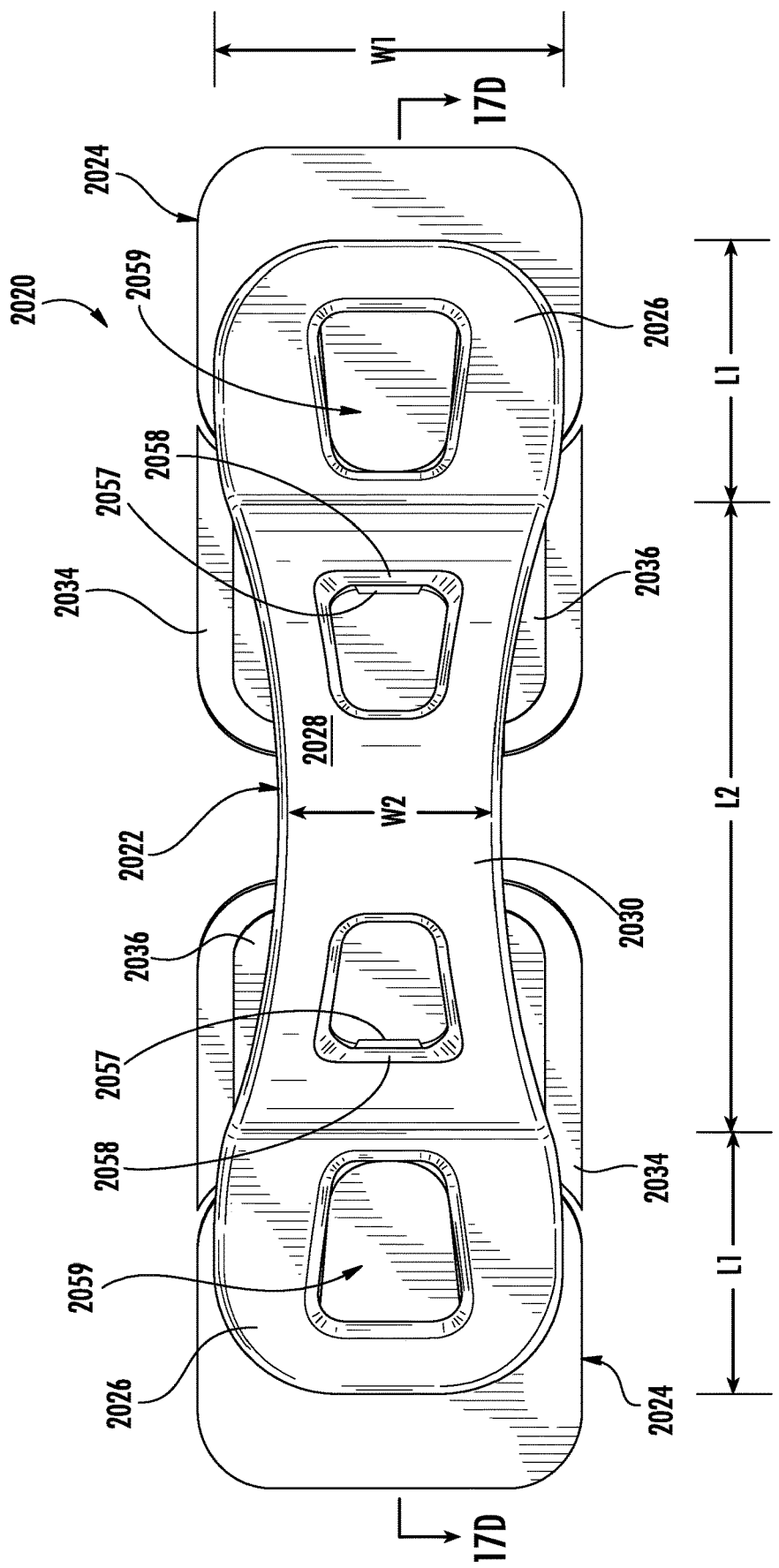

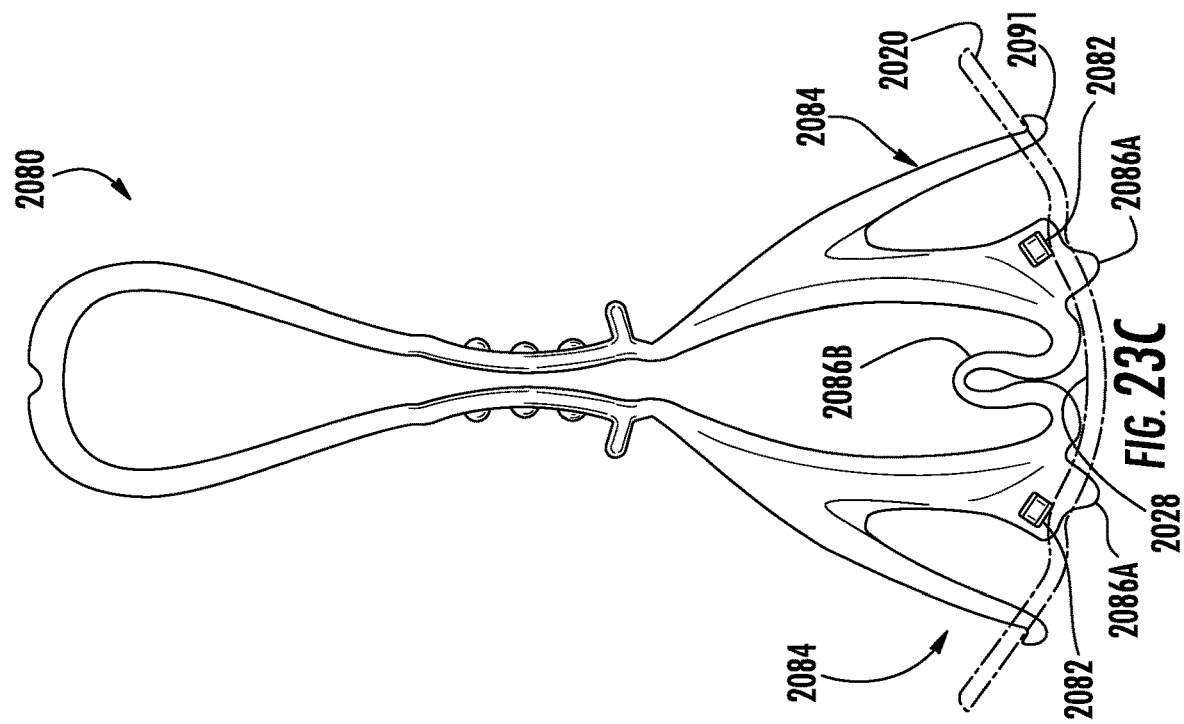
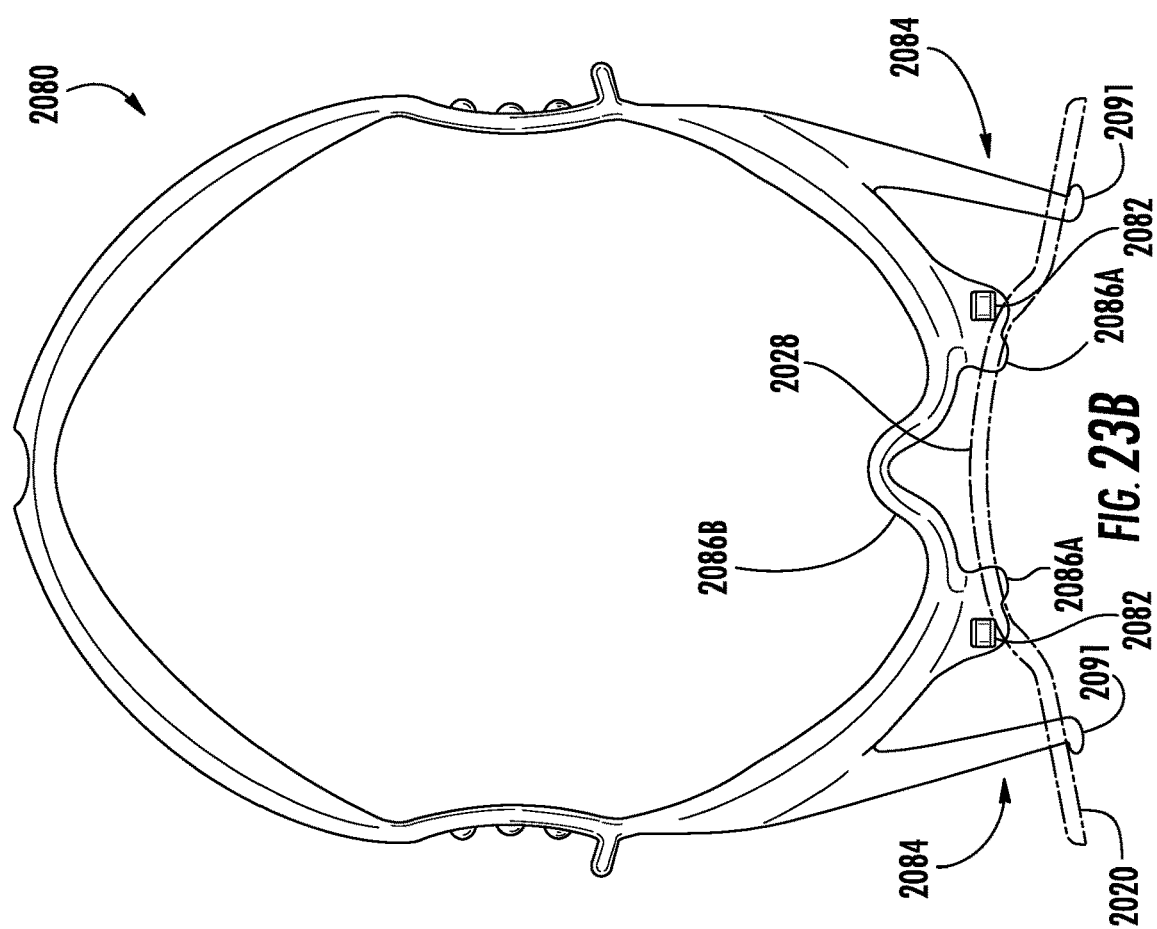

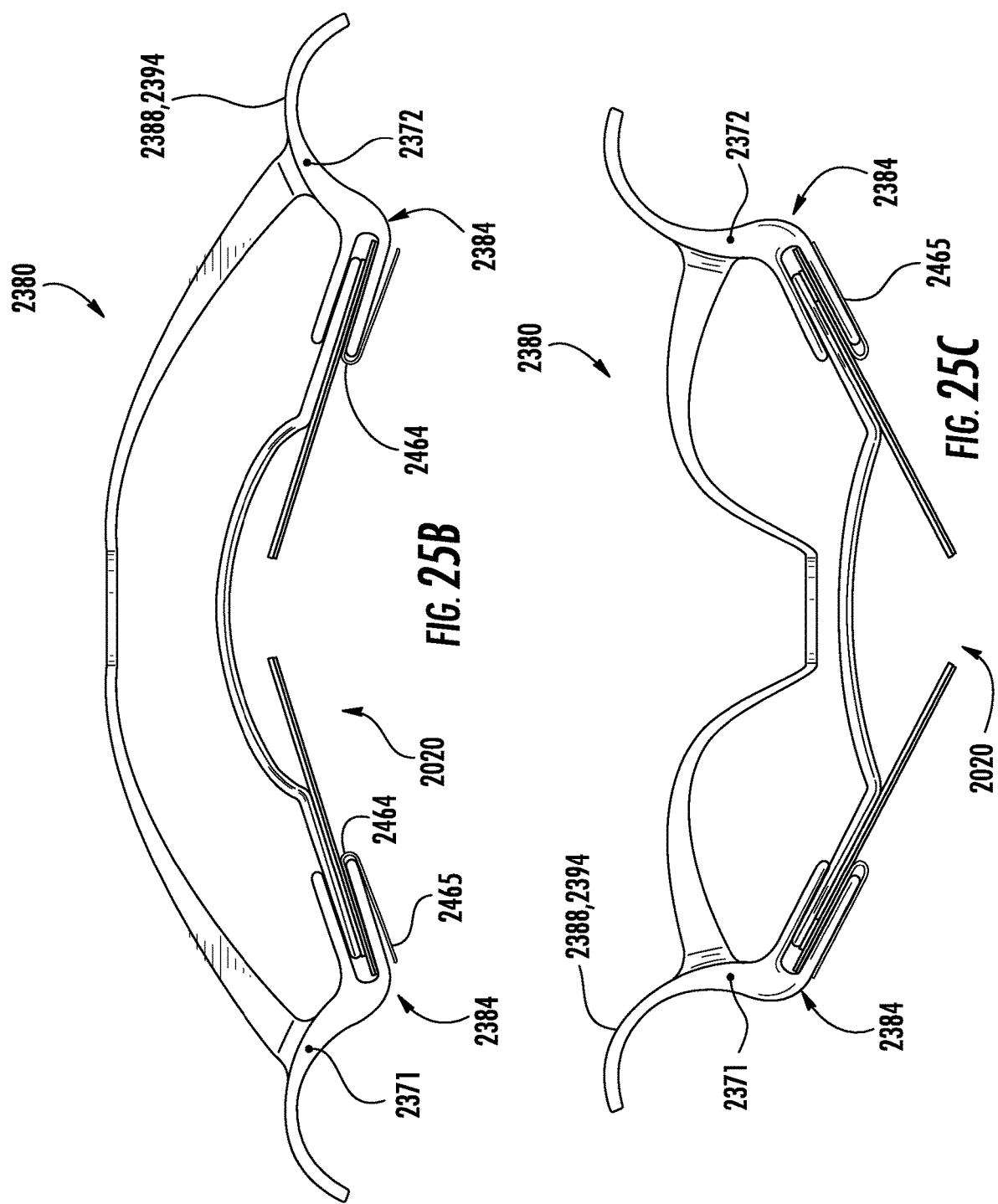

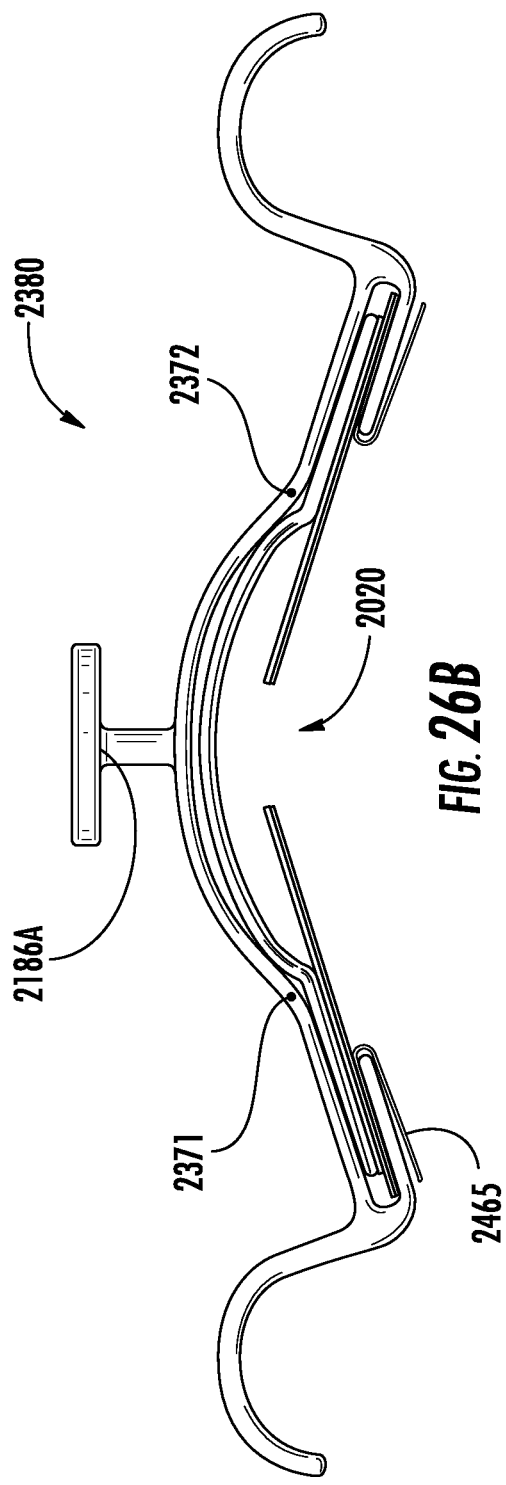
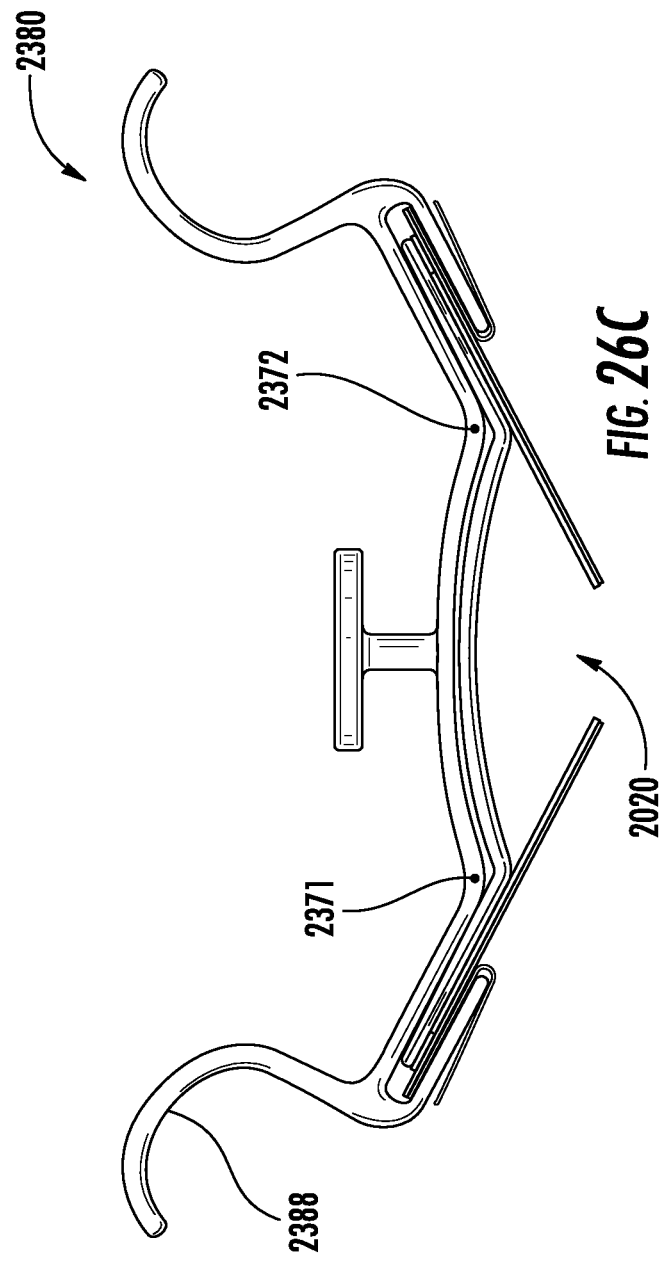

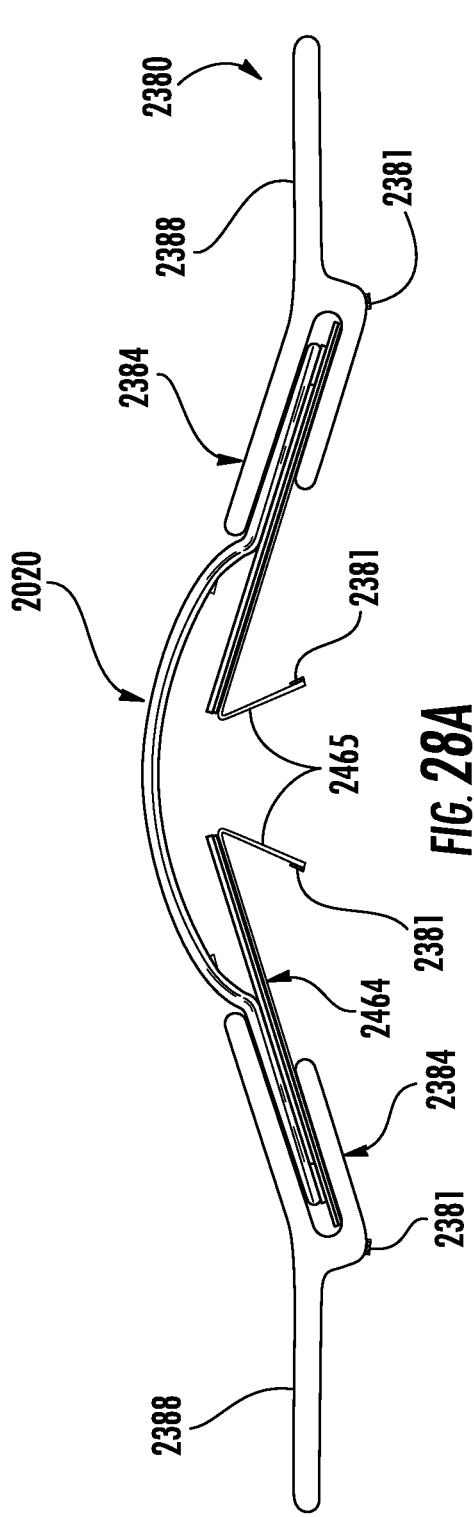
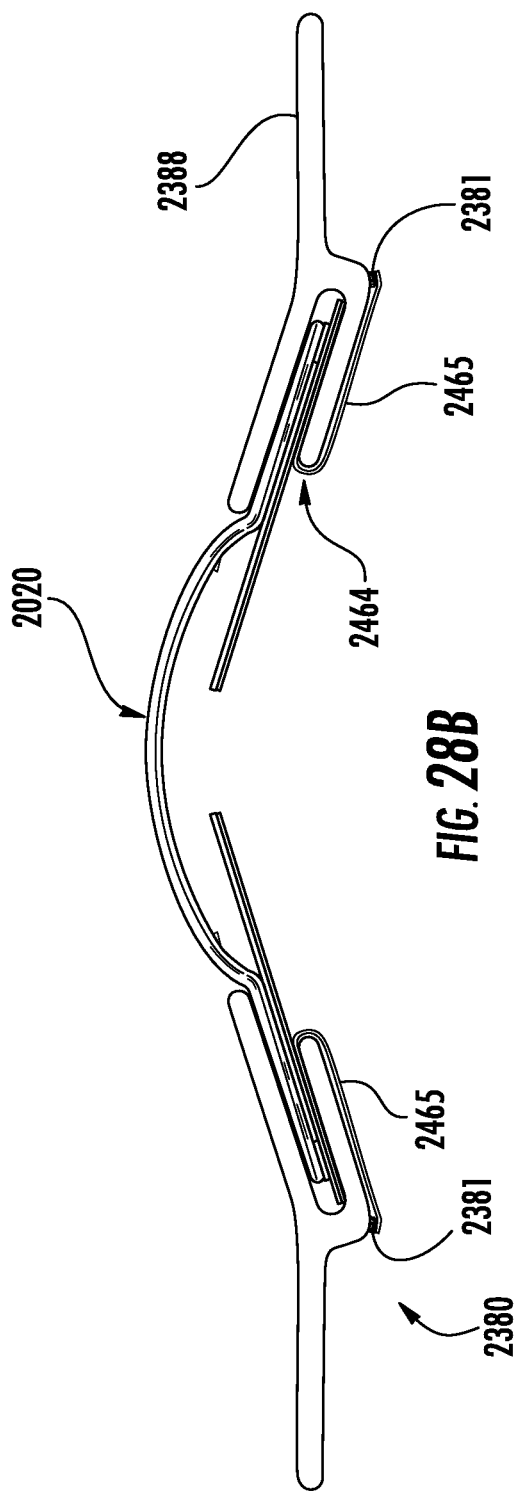

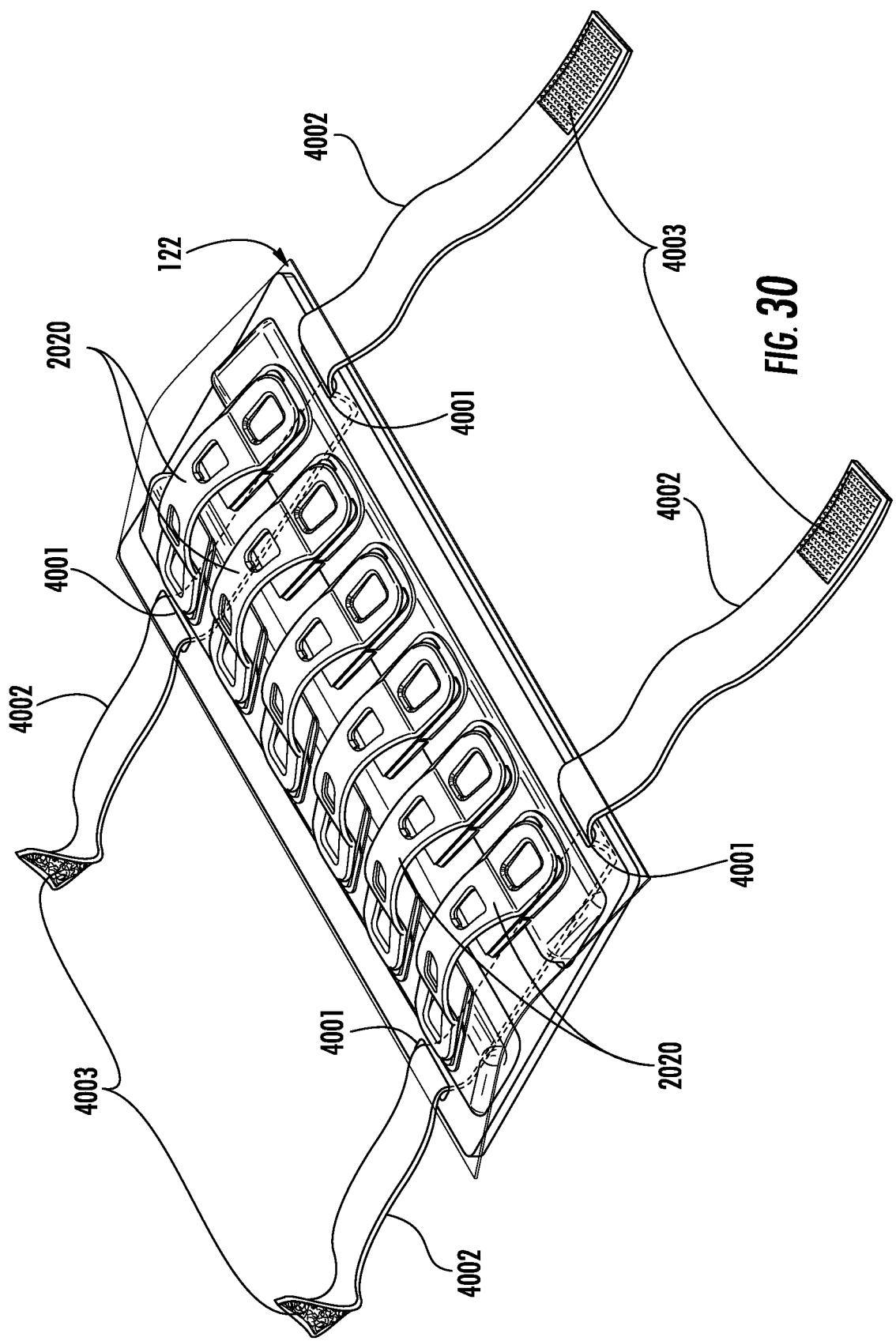

FORCE MODULATING TISSUE BRIDGES, ASSOCIATED TOOLS, KITS, AND METHODS

CROSS-REFERENCE TO RELATED APPLICATIONS

This application is a continuation of International Application No. PCT/US2017/057569 filed Oct. 20, 2017, which claims the benefit of U.S. Provisional Application No. 62/411,023, filed Oct. 21, 2016. Each of the above-referenced applications is incorporated herein by reference in its entirety.

FIELD OF THE INVENTION

The present invention generally relates to medical articles for covering wounds and/or scars, and, more particularly, to wound closure and/or reducing wound tension.

BACKGROUND

Traditional methods of wound closure typically do not adequately control wound tension, which is well known to be a primary stimulus of excess scar formation. In addition, tension reduction is known to decrease the size, discoloration, and poor appearance of scars when applied during the wound healing period.

Therefore, a need exists for force modulating tissue bridges that seek to allow wounds to be closed accurately, and further seeks to provide simultaneous reduction of tension on closed wounds and scars in the healing phases.

SUMMARY

An aspect of this disclosure is the provision of a medical article for at least partially covering a wound and/or scar tissue. The medical article can include a body comprising a central section extending over an area, and flanges respectively extending outwardly from opposite lower sections of the central section. At least the central section of the body can be elastically configured to be deformed from an at rest configuration to an extended configuration, so that at least the central section can return toward the at rest configuration in response to being released from the extended configuration. The lower sections are typically farther apart from one another in the extended configuration than in the at rest configuration. A first of the flanges can have opposite upper and lower surfaces that are each larger than a thickness defined between the upper and lower surfaces of the first flange. The medical article can further include a foot pad connected to the first flange for at least partially moving with the first flange. The foot pad can extend inwardly into the area over which the central section extends. The foot pad can have opposite upper and lower surfaces that are each larger than a thickness defined between the upper and lower surfaces of the foot pad. The upper surface of the foot pad and the lower surface of the first flange can face toward one another.

The central section can comprise an arch extending over the area over which the central section extends. The foot pad can be a first foot pad. A second of the flanges can have opposite upper and lower surfaces that are each larger than a thickness defined between the upper and lower surfaces of the second flange. The medical article can further comprise a second foot pad connected to the second flange for at least partially moving with the second flange. The second foot pad can extend inwardly into the area over which the central section extends. The second foot pad can have opposite upper and lower surfaces that are each larger than a thickness defined between the upper and lower surfaces of the second foot pad. The upper surface of the second foot pad and the lower surface of the second flange can face toward one another.

The body can be stiffer than at least one of the foot pads. At least one of the foot pads can include an extension (e.g., strut) extending inwardly into the area over which the central section extends. At least one of the foot pads can comprise an outer sheet configured to be attached to a patient's tissue, and an inner sheet positioned between the outer sheet and the first flange, wherein the inner sheet can be stiffer than the outer sheet. The outer sheet can be larger than the inner sheet. An extension of the outer sheet can extend outwardly past an outer edge of the inner sheet.

In accordance with another aspect of this disclosure, a medical article comprises an arch extending over an area, and a medial strut connected to the arch and extending into the area over which the arch extends. Optionally, the medial strut can comprise an outer layer configured to be attached to a patient's tissue, and an inner layer positioned between the outer layer and the arch. Optionally, the inner layer can be stiffer than the outer layer, or vise versa. The medial strut can be a first medial strut. A second medial strut can be connected to the arch and extend into the area over which the arch extends. The first and second medial struts can be positioned oppositely with respect to one another.

A medical article optionally can further comprise, or otherwise be associated with, at least one release liner adhered to the foot pad(s) and/or medial strut(s). A medical article optionally can include one or more features (e.g., a hole, receptacle, space between the body and at least a portion of a foot pad, and/or a catch part) configured for interacting with an applicator tool.

Another aspect of this disclosure is the provision of a tool configured for being used to manipulate a medical article. The tool can comprise first and second parts that are spaced apart from one another and each configured to releasably engage a medical article, a reconfigurable linkage connecting the first and second parts to one another, and levers (e.g., handles) extending from proximate the linkage. The linkage and levers can be cooperatively configured so that at least portions the first and second parts are moved away from one another in response to at least portions of the levers being moved toward one another.

The first and second parts can be first and second catch parts configured to releasably attach to the medical article. Each of the catch parts can comprise a shank and one or more protrusion extending outwardly from the shank. The tool optionally can further include a bearing surface that is: positioned between the first and second catch parts, connected to the first and second catch parts by the linkage, and optionally configured to engage the medical article while the first and second catch parts are engaged to the medical article.

In another aspect of this disclosure, a tool configured for being used to manipulate a medical article can comprise a reconfigurable linkage connecting first and second bodies to one another. The first body can comprise a first lever connected to a first part. The second body can comprise a second lever connected to a second part. The first and second parts can be configured to respectively engage (e.g., at least partially receive) opposite first and second ends of a medical article. The reconfigurable linkage can be configured so that: the first and second bodies are pivotable relative to one another about first and second axes, respectively, and the first and second axes are movable toward and away from one another.

An aspect of this disclosure is the provision of a package having a support comprising a central section and outer sections respectively extending outwardly and downwardly. A medical article can be at least partially supported by the support. Foot pads of the medical article can respectively be proximate the outer sections of the support. One or more gaps between the support and the medial article can be configured to receive a portion of a tool configured for being used to manipulate a medical article.

A liner can be positioned between the support and the medical article. The medical article can be releasably mounted to the liner. At least a portion of the liner can be fixedly mounted to the support. The liner can comprise a line of disruption for at least partially facilitating relative movement between the medical article and the support. The line of disruption can at least partially define a flap in the liner. Such flaps can be respectively associated with foot pads of the medical article(s).

An aspect of this disclosure is the provision of a method for at least deforming a medical article from an at rest configuration to an extended configuration. The deforming can be comprised of reconfiguring a tool while the tool and the medical article are engaged to one another. The tool and the medical article being engaged to one another can be comprised of a first part of the tool and a first part of the medical article being in engagement with one another, and a second part of the tool and a second part of the medical article being in engagement with one another. The reconfiguring of the tool can be comprised of moving levers of the tool toward one another so that the first and second parts of the tool move away from one another in response to the moving of the levers of the tool toward one another, and the first and second parts of the medical article move away from one another in response to the first and second parts of the tool moving away from one another.

In accordance with an aspect of this disclosure, a method comprises deforming a medical article from an at rest configuration to an extended configuration so that foot pads of the medical article are farther apart from one another in the extended configuration than in the at rest configuration. Each of the foot pads can comprise an inner portion (e.g., medial strut) extending inwardly from an outer portion of the foot pad, so that the inner portions are positioned between the outer portions of the foot pads. The inner portions can be adhesively mounted to a patient's tissue while the medical device is in its extended configuration. Then the medial article can reconfigure from the extended configuration to an intermediate configuration that is between the at rest configuration and the extended configuration. The outer portions of the pads can be adhesively mounted to the tissue while the medical device is in its intermediate configuration. Optionally, the adhesively mounting of the outer portions of the pads to the tissue can occur at least partially in response to the automatic/biased reconfiguring of the medial article.

The foregoing summary provides a few brief examples and is not exhaustive, and the present invention is not limited to the foregoing examples. The foregoing examples, as well as other examples, are further explained in the following detailed description with reference to accompanying drawings.

BRIEF DESCRIPTION OF THE DRAWINGS

FIGS. 1A through 1D depict various views of a medical article that may optionally be referred to as a force modulating tissue bridge, or simply tissue bridge, and which may be used to at least partially cover a wound and/or scar, for example to help facilitate wound closure and/or reduce wound tension, in accordance with a first embodiment of this disclosure.

FIGS. 4A through 4F depict a sequence of steps of a method of using the applicator tool to remove a tissue bridge from the tray, in accordance with the first embodiment.

FIGS. 5A through 5D depict various views of a medical article or tissue bridge having a central release liner and release liner mounting straps affixed thereto, in accordance with a second embodiment of this disclosure.

FIGS. 12A and 12B depict an applicator tool mounted to a tissue bridge, in accordance with an eighth embodiment.

FIGS. 13A and 13B depict a tissue bridge, in accordance with a ninth embodiment.

FIGS. 17A through 17C depict a tissue bridge in accordance with an eleventh embodiment.

FIGS. 23A through 23C depict an applicator tool in accordance with a twelfth embodiment.

FIGS. 25A through 25C depict an applicator tool in combination with a tissue bridge, in accordance with a fourteenth embodiment.

FIGS. 26A through 26C depict an applicator tool in combination with a tissue bridge, in accordance with a variation of the fourteenth embodiment.

FIGS. 28A and 28B depict an applicator tool in combination with a tissue bridge, an in accordance with a variation of the fourteenth embodiment.

FIG. 30 depicts a tray that is carrying a series of tissue bridges, and is equipped with fastening straps, in accordance with an embodiment of this disclosure.

DETAILED DESCRIPTION

Figure 1A:
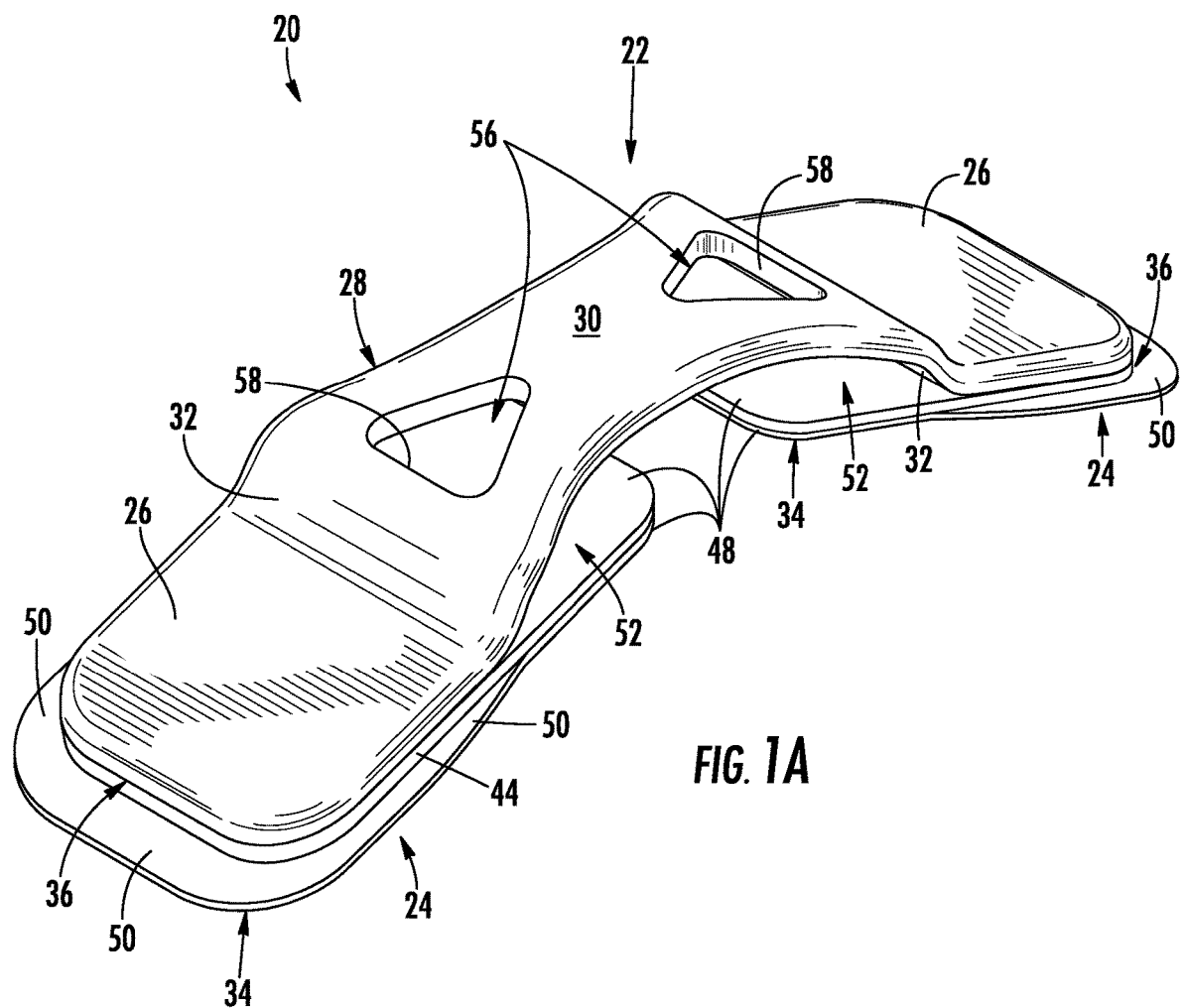

Numerous embodiments are described below and illustrated in the accompanying figures, in which like numerals refer to like parts throughout the several views. For convenience of description and ease of understanding, and not for the purpose of limiting the scope of this disclosure or the associated inventions, some embodiments may be referred to by number. The embodiments described provide examples and should not be interpreted as limiting the scope of the invention. Other embodiments, and modifications and improvements of the described embodiments, will occur to those skilled in the art and all such other embodiments, modifications and improvements are within the scope of the invention.

FIGS. 1A-1D depict an at least partially elastic (e.g., generally elastic) medical article 20 in its undeformed or at rest configuration (e.g., relaxed state), in accordance with a first embodiment. The medical article 20 may optionally be referred to as a force modulating tissue bridge 20, or simply tissue bridge 20, and throughout this disclosure the tissue bridge may be more generally referred to as a medical article. In the following, first an example of a method of using the tissue bridge 20 is very briefly described, and thereafter the tissue bridge and other aspects of this disclosure are described in greater detail.

The tissue bridge 20 can be mounted to tissue such as, but not limited to, a surface of a patient's skin, for example the outer surface of the patient's epidermis. The tissue bridge 20 is typically mounted so that it extends across and at least partially covers a wound and/or scar. In the first embodiment, the tissue bridge 20 comprises generally elastic material, and prior to the tissue bridge being mounted on the patient, the tissue bridge can be generally elastically deformed from its undeformed or at rest configuration to a strained, deformed, or extended configuration. The tissue bridge 20 can at least begin to be mounted to the tissue (e.g., skin tissue), so that a central section of the tissue bridge extends across a wound and/or scar, while the tissue bridge is maintained in its extended configuration. After being at least partially mounted in its extended configuration, the tissue bridge 20 can be allowed to generally elastically reconfigure from its extended configuration at least partially toward its at rest configuration, which may, for example, reduce tension in the tissue, help close the wound, help inhibit wound reopening, and/or inhibit scar disfiguring (e.g., widening), as will be discussed in greater detail below. In the first embodiment, the tissue bridge 20 comprises material that is at least generally elastic, so that the tissue bridge is biased toward its at rest configuration (e.g., relaxed state).

The tissue bridge 20 of the first embodiment comprises a generally elastic body 22 and one or more multi-layer foot pads 24 mounted to the body, although in some examples one or more of the foot pads and/or portions thereof can be omitted (e.g., a foot-pad may consist of, or consist essentially of, a single layer). The body 22 can be generally referred to as and/or generally function as a backbone or other suitable structure configured to movably connect two or more of the foot pads 24 to one another. In the embodiment shown in FIGS. 1A-1E, the body 22 includes at least two flanges 26 (e.g., feet) respectively extending obliquely, for example outwardly and downwardly, from opposite lower portions of a central section or arch 28 of the body. Each of the flanges 26 can be planar, or they can be substantially or about planar since it may not be critical that the flanges be exactly planar. The flanges 26 can extend divergently relative to one another, and obliquely relative to one another. The arch 28 can include a central spanning section 30, and lower sections 32 respectively extending downwardly from opposite portions of the spanning section. The lower sections 32 of the arch 28 can optionally be configured as and/or referred to as shoulders 32. The flanges 26 can respectively extend obliquely, for example outwardly and downwardly, from lower portions of the shoulders 32. The shoulders 32 can provide a smoothly curved transition between the spanning section 30 of the arch 28 and the flanges 26. In the embodiment shown in FIGS. 1A-1E, the spanning section 30 of the arch 28 has a relatively low profile and is at least generally arcuate, which can be advantageous for an active person having the tissue bridge 20 mounted on their skin. Alternatively, it is believed that in some situations the arch 28 can be at least more of a flat arch, or the spanning section 30 of the arch can be flat, or the arch or features thereof can be in any other suitable configurations that will allow the tissue bridge 20 to function generally or substantially as described herein.

Figure 1D:
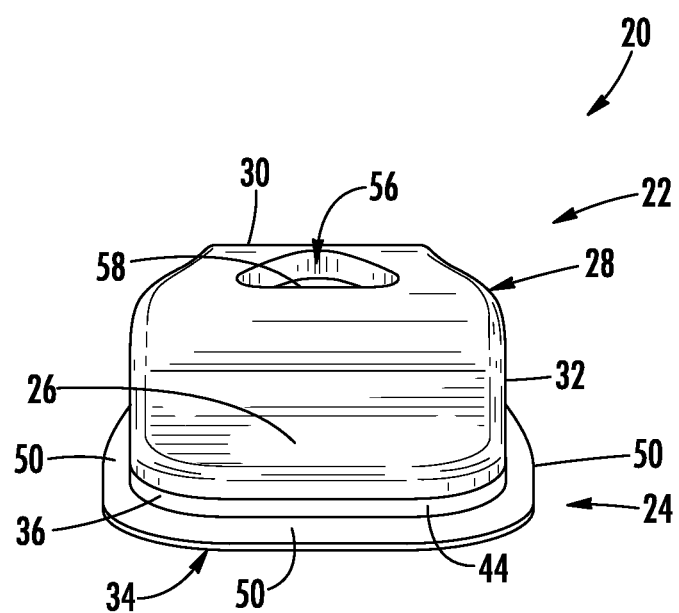

Each of the parts of the tissue bridge 20 will typically be constructed of suitable medical-grade materials. For example, the body 22 can be an injection-molded or mechanically thermoformed, unitary (e.g., single-piece) article such that the spanning section 30, shoulders 32 and flanges 26 can be formed together as a single article from an injection-moldable or formable, generally elastic material such as, but not limited to, polycarbonate, or any other suitable injection-moldable or formable material. Referring to FIG. 1C, each of the spanning section 30, shoulders 32, and flanges 26 can be about the same thickness, or alternatively the thickness of the body 22 can vary along its length. Referring to FIG. 1B, the width of the body 22 can, for example, taper along its length, so that the spanning section 30 is relatively narrow (e.g., has a narrowed waist) as compared to the shoulder 32 and flanges 26, so that the spanning section can be more readily deformed as compared to the shoulders and flanges. For example, the side edges of the spanning section 30 can be inwardly curved or concave, as shown in FIGS. 1A, 1B and 1D, or they may have a stepped or other suitable configurations. Alternatively, the side edges of the spanning section 30 can extend generally or substantially straight in a top plan view of the tissue bridge 20, or they can extend in any other suitable manner.

As shown in FIGS. 1A-1D, the foot pads 24 can be spaced apart from one another, and the foot pads can be fixedly mounted to the flanges 26. Each foot pad 24 can be or include be a mat, laminate or other suitable structure comprising one or more layers of material. For example, in the first embodiment, each foot pad 24 includes an outer layer or sheet 34 configured to be attached to tissue (e.g., skin tissue), and an inner layer or sheet 36 positioned between, and fixedly connected to each of, the outer sheet 34 and the respective flange 26.

Figure 1E:
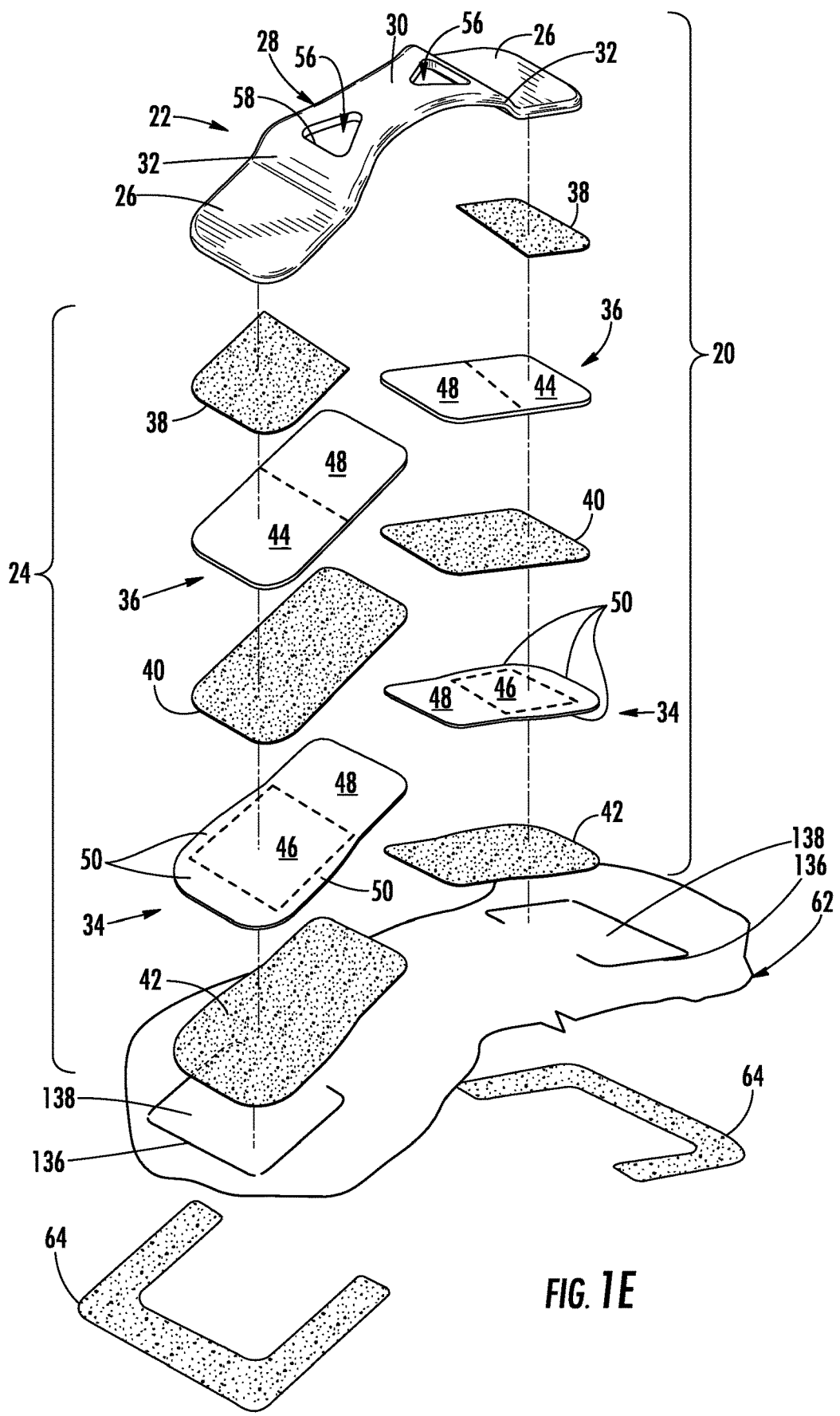
FIG. 1E is a pictorial exploded view of the tissue bridge of FIGS. 1A-1D, wherein FIG. 1E further depicts the tissue bridge exploded away from a schematically depicted section of a release liner and associated adhesive material, in accordance with the first embodiment.

Referring to the exploded view of FIG. 1E, the tissue bridge 20 can include inner, intermediate and outer adhesive layers 38, 40, 42. The inner adhesive layers 38 can be between and fixedly connect the inner sheets 36 to the flanges 26, the intermediate adhesive layers 40 can be between and fixedly connect the outer sheets 34 to the inner sheets, and the outer adhesive layers 42 can be on the outer sides of the outer sheets for attaching the tissue bridge 20 to tissue (e.g., a patient's skin), as will be discussed in greater detail below.

The outer and inner sheets 34, 36 can be provided, for example, by die cutting them from appropriate webs or larger sheets of material, such as fabric or cast microporous polymeric sheet for the outer sheets 34, and an extruded polymer or plastic sheet for the inner sheets 36. The outer sheets 34 can be made of suitable fabric materials, cast materials, films, or other materials of the type from which skin-contact layers of bandages or other wound dressings are formed, or any other suitable material. The plastic inner sheets 36 can be made of suitable materials such as, for example, polyethylene, polyethylene terephthalate, or any other suitable materials. The inner and intermediate adhesive layers 38, 40 can respectively comprise adhesive materials that are compatible with the materials being connected thereby. The outer adhesive layer 42 (e.g., patient contact adhesive) can be, for example, adhesive material of the type that is typically used as an adhesive backing for bandages or other wound dressings. In the first embodiment, the outer adhesive layer 42 can have a lower adhesive strength than the inner and intermediate adhesive layers 38, 40, such as when the tissue bridge 20 is to be removably mounted to tissue (e.g., a patient's skin).

In the first embodiment, both the body 22 and the inner sheet 36 have a higher modulus of elasticity (e.g., are formed from stiffer material) than the outer sheet 34. More generally, the body 22 and the inner sheet 36 can be stiffer than the outer sheet 34 because of a variety of factors, such as being larger, thicker, comprising material having a higher modulus of elasticity and/or being constructed to have an apparent modulus of elasticity. Similarly, the body 22 can have a higher modulus of elasticity than the foot pads 24.

As shown in FIG. 1C, the body 22, including its flanges 26, can be thicker than each of the outer and inner sheets 34, 36, and the arch 28 can extend over an area into which portions of the outer and inner sheets can optionally extend. The area over which the arch 28 extends may be referred to as a central area, a treatment area, an under-arch area, and/or the like. The thicknesses of the body 22 and sheets 34, 36 can be varied, for example, independently as necessary to produce tissue bridges 20 of different sizes and to function optimally in different anatomical areas and with different treatment tissue characteristics.

As shown in FIGS. 1A and 1E, at each end of the tissue bridge 20, the flange 26, outer sheet 34, inner sheet 36, and adhesive layers 38, 40, 42 can be at least partially superposed with one another and can have different configurations from one another. For example and as schematically illustrated in FIG. 1E by dashed boundary lines on the outer and inner sheets 34, 36, a congruent portion 44 of each inner sheet can be superposed with and coextensive with the respective flange 26, and a congruent portion 46 of the outer sheet 34 can be superposed with and coextensive with the respective inner sheet congruent portion 44. As other examples that are also at least partially schematically illustrated by the dashed boundary lines in FIG. 1E, inner extensions 48 of the outer and inner sheets 34, 36 can extend congruently with one another into the central area over which the arch 28 extends such that the inner extensions 48 are neither superposed by nor coextensive with the flanges 26. More generally, each foot pad 24 can include at least one extension 48 that extends into the central area over which the arch 28 extends such that the inner extension 48 can be neither superposed by nor coextensive with the flanges 26.

In the first embodiment, the inner extensions 48 may be referred to as medial extensions 48, for example since they extend toward the middle of the area over which the arch 28 extends. As another example and as will be discussed in greater detail below, the inner or medial extensions 48 can be configured so that they at least partially resist longitudinal compression when the tissue bridge 20 in its extended configuration is mounted to tissue (e.g., skin tissue) and then allowed to generally elastically reconfigure from its extended configuration at least partially toward its at rest configuration. Accordingly, the inner or medial extensions 48 can be referred to as medial struts 48. In the first embodiment, each medial strut 48 includes the inner extensions 48 of both sheets 34, 36, but one or more layers or sheets of the medial strut 48 can be omitted, such that each medial strut can be formed of one or more layers of material.

Referring to FIGS. 1A and 1E, one or more outer extensions 50 of the foot pads 24, or more specifically of the outer sheets 34, can extend outwardly such that they are neither superposed by nor coextensive with the flanges 26 or the medial struts 48. In the example shown in FIG. 1B, outer extensions 50 can extend outwardly past one or more of the peripheral edges (e.g., the outer end edges and side edges) of the flanges 26.

In the example shown in FIG. 1C, the medial struts 48 can be spaced apart from (e.g., at least partially spaced apart from) the arch 28 and extend into the central area over which the arch extends, so that gaps or receptacles 52 are at least partially defined between the medial struts and the arch. The receptacles 52 can at least partially define, or be at least part of, catch parts configured for interacting with corresponding features of an applicator tool that may be used, for example, in the mounting of the tissue bridge 20 to tissue (e.g., a patient's skin), wherein the applicator tool is discussed in greater detail below. For example, the tissue bridge 20 can include one or more catch parts, and the catch parts can respectively comprise the receptacles 52. A variety of differently configured catch parts are within the scope of this disclosure.

In the first embodiment, the body 22 includes at least two catch parts that further comprise holes 56 that extend through the body 22 and are open to the receptacles 52. The holes 56 can be defined in the arch 28, or more specifically the holes can be positioned in opposite end portions of the spanning section 30. In the example shown in FIG. 1B, the holes 56 can be open to the central area over which the arch 28 extends, or more specifically the holes can be open to the receptacles 52; and the medial struts 48 can extend beneath the holes.

As shown in FIGS. 1A and 1B, each of the holes 56 can be triangular, with a side of the triangle, or more specifically an edge 58 of the arch 28 that defines the triangle, extending crosswise to the length of the arch. The respective catch part can further include the edge 58. The edge 58 can extend parallel, or more generally substantially parallel or about parallel, to the boundary between the spanning section 30 and the respective shoulder 32. In other words, the edge can extend perpendicular to, or more generally substantially perpendicular to or about perpendicular to, the lengthwise or longitudinal axis of the body 22. In addition, the holes 56, when present, can reduce the area or volume of the outer portions of the spanning section 30 in a manner that enhances the deformability of the outer portions of the spanning section.

Each catch part can further include a portion 60 (FIG. 1C) of the lower surface of the arch 28, wherein the surface portion 60 extends outwardly from the edge 58. The catch parts, receptacles 52, holes 56 and associated edges 58, and surface portions 60, or the like, may be optional, and other positions and configurations of catch parts, receptacles, holes, or the like, are within the scope of this disclosure.

In a version of the first embodiment, the foot pads 24 can be described as including the flanges 26, so that the flanges can be respective layers of the foot pads, and the flanges can be referred to as foot plates 26, or the like. As another example, the first embodiment embraces configurations of the tissue bridge 20 in which the foot plates 26 are not integrally formed with the arch 28. For example, the foot plates 26 can be formed separately from the arch 28 and can be fixedly or movably connected to the arch, such as by way of pivots, hinges, or any other suitable features. Other variations are also with the scope of this disclosure. For example, the foot plates 26 can have one or more holes formed therein or therethrough, as discussed in greater detail below. As another example alluded to above, one or more layers of each foot pad 24 can be omitted. For example and for each foot plate 26, it may be suitable in some situations to omit the layers between the foot plate and outer adhesive layer 42, so that the outer adhesive layer, which is for use in mounting the tissue bridge 20 to tissue (e.g., a patient's skin), is mounted directly to the underside of the foot plate. It is also within the scope of the first embodiment for the medial struts 48 to be integrally formed with the arch 28, flanges 26 and/or foot plates 26. For example, the medial struts 48 can be extensions of the flanges 26 and/or foot plates 26.

As alluded to above, FIG. 1E depicts the tissue bridge 20 in an exploded configuration. Additionally, FIG. 1E depicts the tissue bridge 20 exploded away from a schematically depicted section of a release liner 62 and associated adhesive material 64. As an example, after a tissue bridge 20 is manufactured or as part of the manufacturing process for the tissue bridge, the tissue bridge, or more specifically the outer sheets 34 by way of the outer adhesive layers 42, can be releasably mounted on the upper surface of the release liner 62. In addition, the lower surface of a portion of the release liner 62 can be fixedly mounted to a support by way of the adhesive material 64, as will be discussed in greater detail below. The release liner 62 can be, for example, a paper or plastic-based film sheet coated with a release agent that is engaged against the outer adhesive layers 42 so that the tissue bridge 20 is releasably mounted on the release liner.

In accordance with the first embodiment, the tissue bridge 20 can be at least somewhat translucent, and the tissue bridge can optionally include indicia, visible design elements and/or other visual features comprising one or more of color, contrasting colors, decorations, aligning marks, pictures, logos, images, characters, words, or any other suitable features that can be printed matter, or the like, wherein the printed matter, or the like, can be embedded or encapsulated in the tissue bridge and visible through one or more exterior surfaces of the tissue bridge. For example, one or more of the components or layers of the tissue bridge 20 can be at least generally transparent and/or at least generally translucent, and the printed matter, or the like, can be interior of exterior surfaces of the tissue bridge 20 and seen by a user of the tissue bridge through at least one of the exterior surfaces of the tissue bridge. For example, the printed matter, or the like, can be on a layer or surface of the tissue bridge 20 that is internal to the tissue bridge (e.g., printed matter, or the like, can be positioned or "sandwiched" between the various layers of the tissue bridge). Referring to FIG. 1E and as an example, the body 22 and the inner sheets 36 can each be at least partially transparent, and the printed matter, or the like, can be on the top surface of at least one of the outer sheets 34 so that it is visible through the body 22 and the respective inner sheet 36. As another example, the body 22 can be at least partially transparent, and the printed matter, or the like, can be on the top surface of at least one inner sheet 36 so that it is visible through the body 22. Alternatively, it is believed that the printed matter, or the like, can be contained in one of more of the adhesive layers 38, 40, 42 and/or in any other suitable location, with the predetermined portion(s) of the tissue bridge 20 being least partially transparent and/or translucent for allowing the printed matter, or the like, to be visible through one or more exterior surfaces of the tissue bridge.

FIGS. 2A-2D depict an applicator mechanism in the form of an applicator tool 80 that can be used, for example, to manipulate the tissue bridge 20 or another suitable medical article, for example as part of a method of mounting the tissue bridge to tissue (e.g., a patient's skin), in accordance with the first embodiment. For example, the applicator tool 80 can include one or more parts or features that can be spaced apart from one another and can be configured to releasably engage the tissue bridge 20. In the first embodiment, the one or more parts or features of the applicator tool 80 that are configured to engage the tissue bridge 20 can comprise at least one bearing or contact surface 82 and/or one or more catch parts 84. For example, the contact surface 82 can be positioned between the catch parts 84. The applicator tool 80 can further include a reconfigurable frame connecting the contact surface 82 and catch parts 84 to one another. The applicator tool 80, and the like, can be more generally referred to as a tool. For example, the tool 80, or the like, may be used for more purposes than applying a tissue bridge 20.

The frame can include a reconfigurable linkage (e.g., one or more links 86A, 86B) connecting the contact surface 82 and catch parts 84 to one another, and one or more levers 88A, 88B extending upwardly from the links 86A, 86B. The applicator tool 80 can be configured so that when the bearing or contact surface 82 faces downwardly, the catch parts 84 extend downwardly from the linkage (e.g., link(s) 86A, 86B), and the levers 88A, 88B extend upwardly from the linkage. The links 86A, 86B and the levers 88A, 88B can be cooperatively configured so that at least portions of the catch parts 84 move away from one another, and the contact surface 82 moves toward a line between the catch parts 84, in response to at least portions of the levers 88A, 88B being moved toward one another, as will be discussed in greater detail below.

The links 86A, 86B can comprise several links, for example a central link 86A and outer links 86B. Similarly, the levers 88A, 88B can comprise several levers, for example inner levers 88A and outer levers 88B. In the example shown in FIGS. 2A-2D, the contact surface 82 can be a lower end face of the central link 86A, and the catch parts 84 can include shanks 90 extending from lower ends of the outer links 86B and/or outer levers 88B. Each catch part 84 can further include at least one protrusion 92 extending outwardly from the lower end of the shank 90 in a direction that is crosswise to the length of the shank. The protrusions 92 can face away from one another.

The outer links 86B can extend obliquely, outwardly and downwardly from opposite sides of an upper portion of the central link 86A respectively to upper portions of the shanks 90. The inner levers 88A can extend obliquely, outwardly and upwardly from opposite sides of an upper portion of the central link 86A. The outer levers 88B can extend obliquely, outwardly and upwardly respectively from upper portions of the shanks 90.

The levers 88A, 88B can be configured as and/or comprise handles 94. For example, in the embodiment depicted in FIGS. 2A and 2B, a handle 94 can include adjacent levers 88A, 88B that are connected to one another. These connections can comprise the adjacent levers 88A, 88B being directly connected to one another proximate their upper ends, and crossmembers 96 connected to and spanning between the adjacent levers.

The applicator tool 80 can be an injection-molded, unitary (e.g., single-piece) article formed from an injection-moldable, generally elastic material such as, but not limited to, polycarbonate, polyethylene, or any other suitable injection-moldable material. Alternatively, the applicator tool 80 can be made of metal, metal alloys, steel, or any other suitable materials that can allow for re-sterilization. For example, hinges or other suitable connections that allow for relative movements between subparts can be included in the applicator tools 80, such as when the applicator tools are made of relatively rigid materials. As additional examples, a variety of different linkages, levers 88A, 88B, and handles 94 are within the scope of this disclosure, as will be discussed in greater detail below.

Figure 2A:
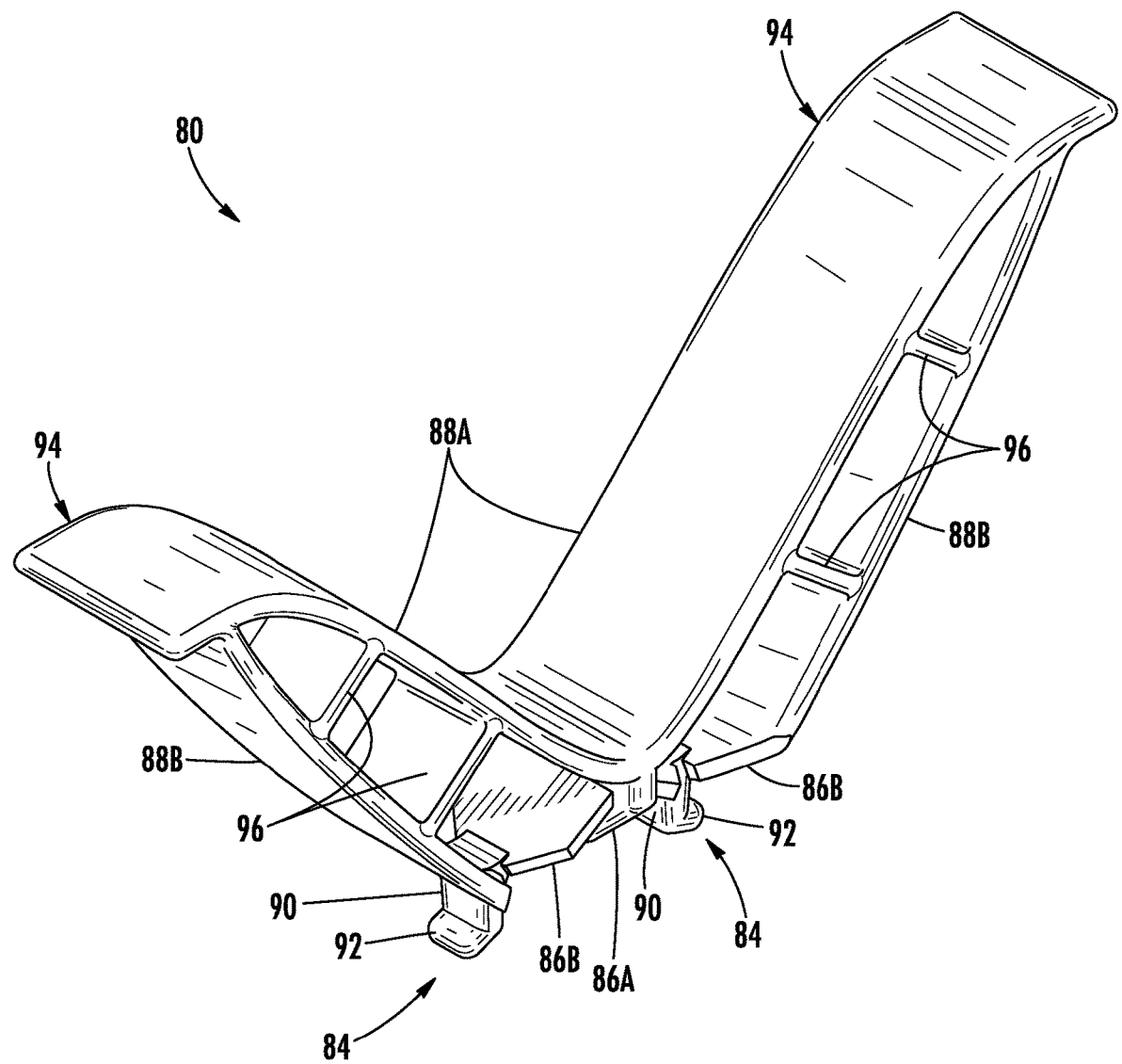
FIGS. 2A through 2D depict various views of a tool configured for being used to manipulate the medical article or tissue bridge of FIGS. 1A-1E, wherein the tool may optionally be referred to as an applicator tool, in accordance with the first embodiment.
Figure 2B:
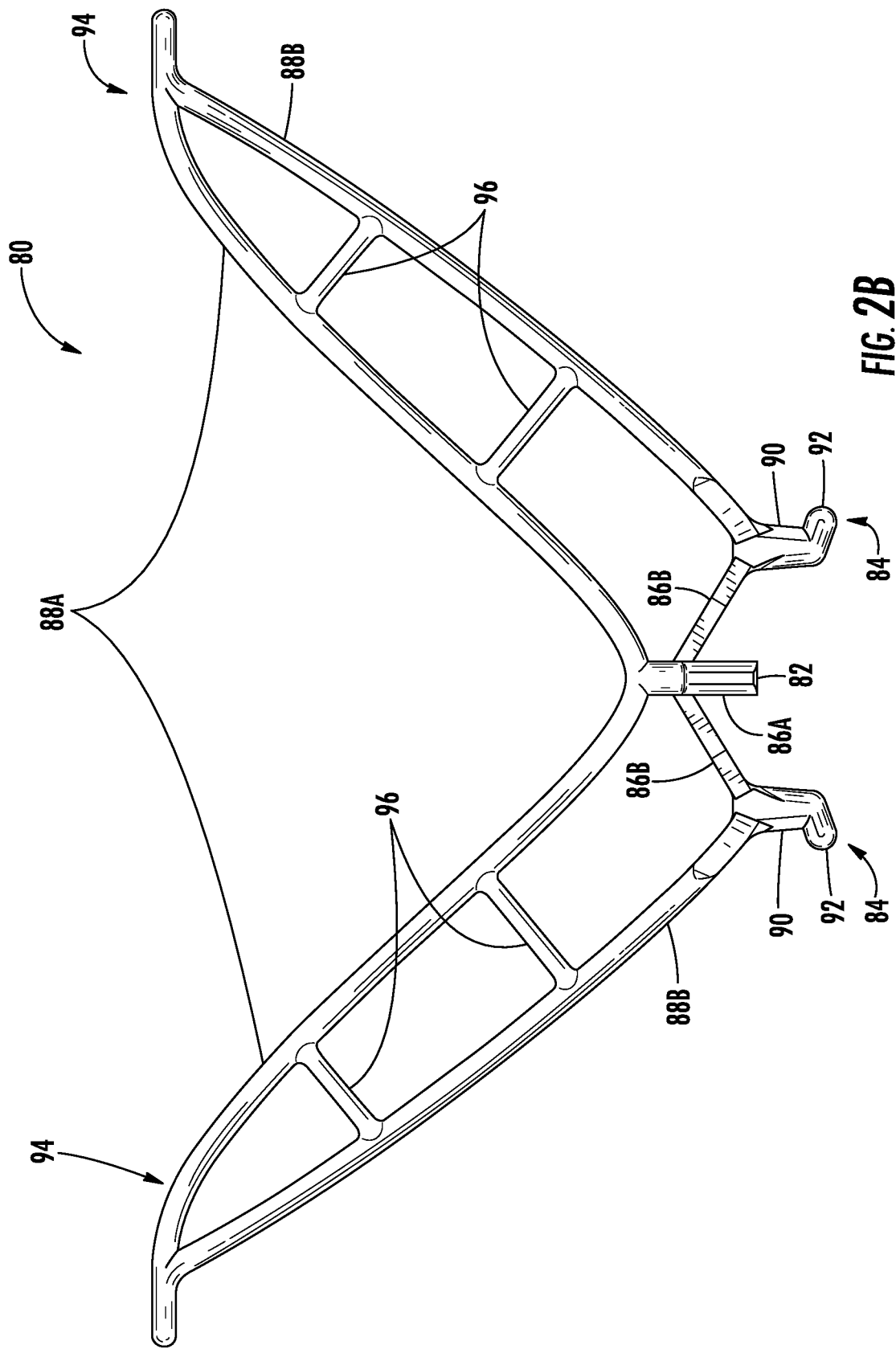
Figure 2C:
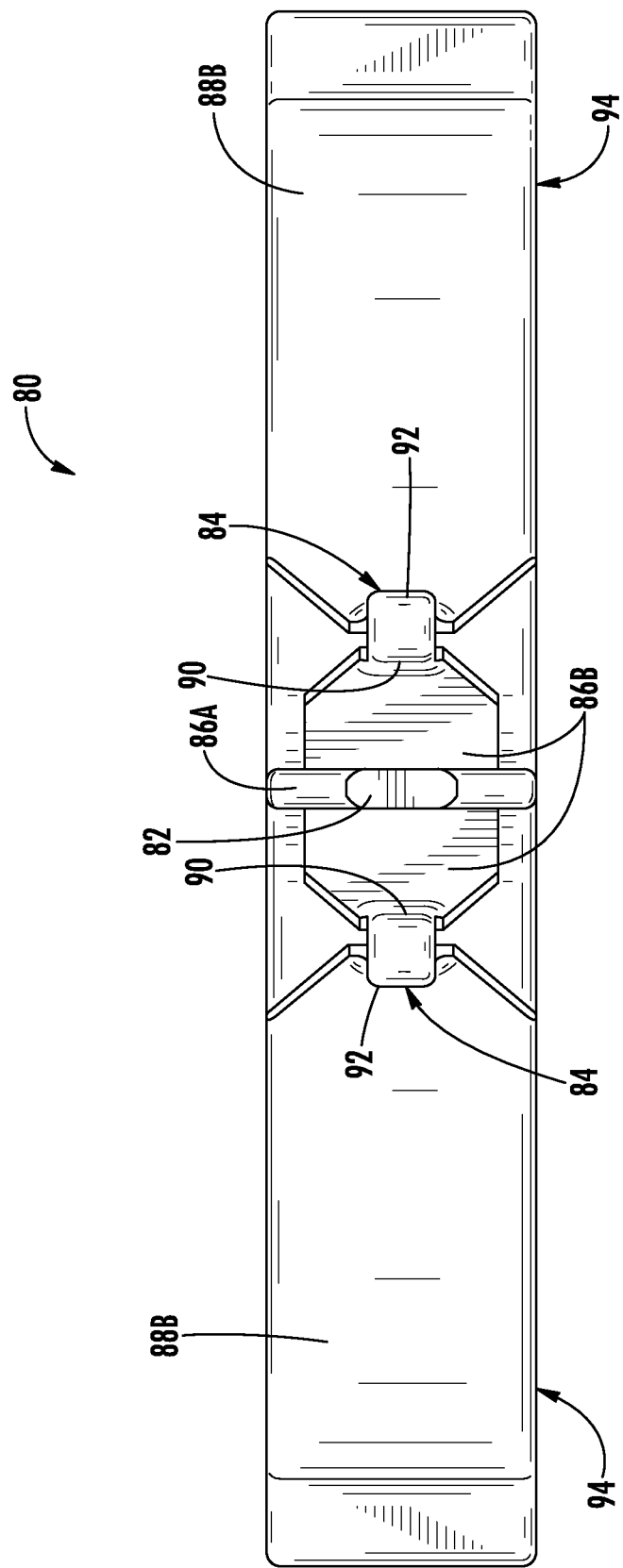
Figure 2D:
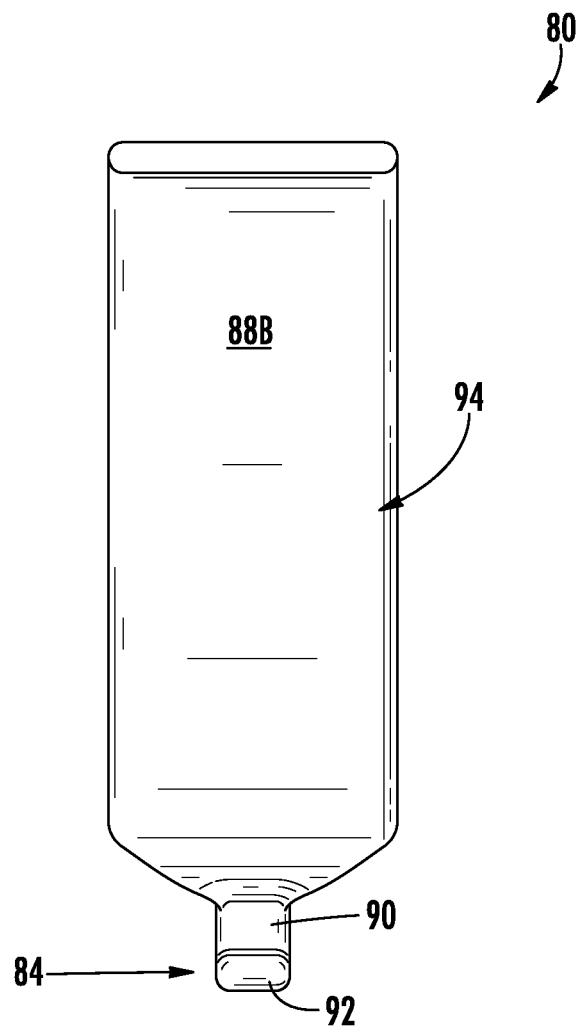
Figure 2E:
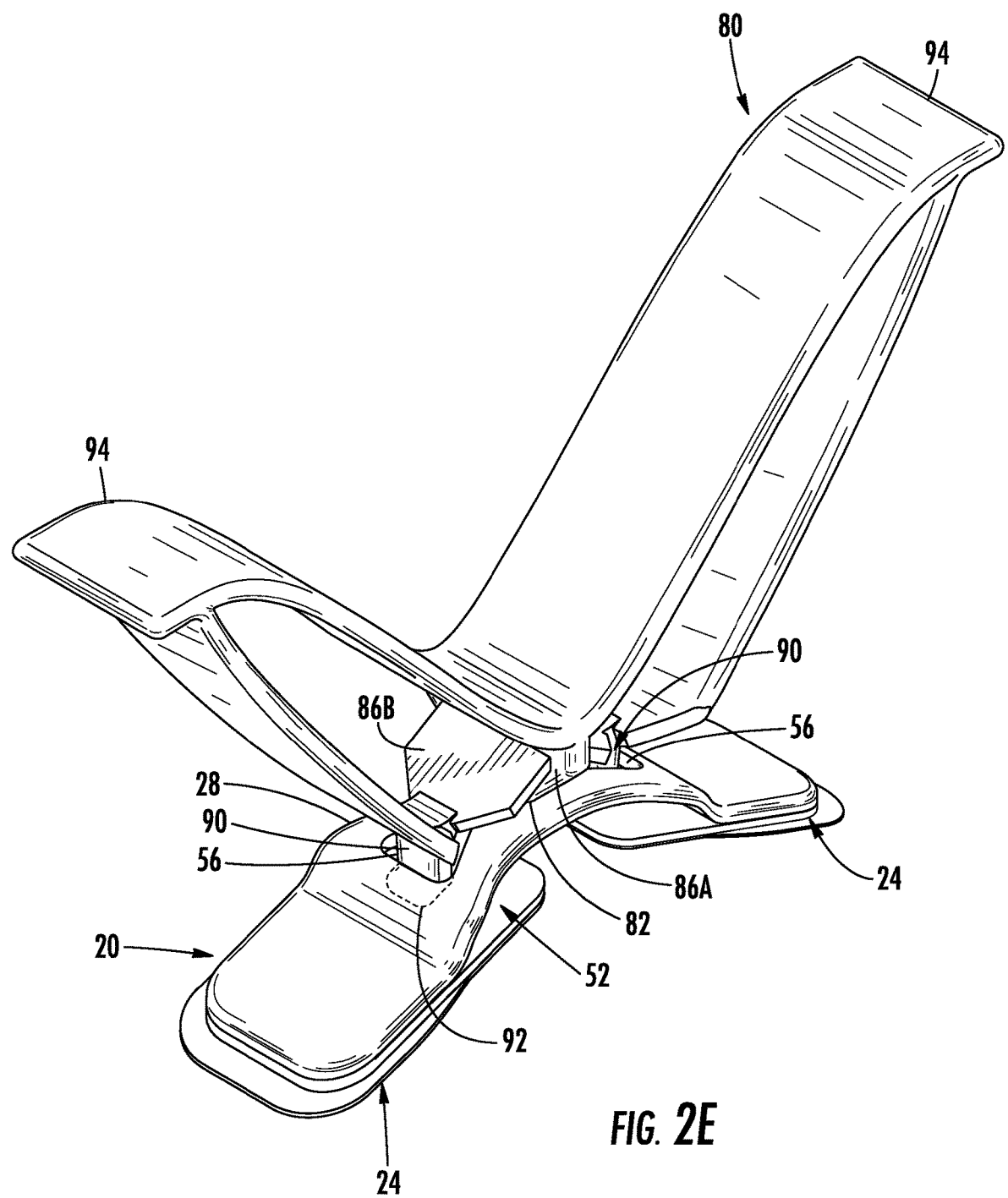
FIG. 2E is a pictorial view of the applicator tool of FIGS. 2A-2D mounted to the tissue bridge of FIGS. 1A-1E, in accordance with the first embodiment.

In accordance with an example of the first embodiment depicted in FIG. 2E, the tissue bridge 20 and applicator tool 80 are cooperatively configured so that the applicator tool can be releasably engaged to the tissue bridge, and the applicator tool can be used to manipulate the tissue bridge as part of a method of mounting the tissue bridge to tissue. For example, FIG. 2E depicts the bearing or contact surface 82 in opposing-face-to-face relation with an upper surface of the arch 28, and the shanks 90 extending through the holes 56. In the configuration of FIG. 2E, the protrusions 92 are hidden from view within the receptacles 52, as partially schematically illustrated by dashed lines. More generally, the above-discussed catch parts of the applicator tool 80 and tissue bridge 20 are respectively engaged to one another in FIG. 2E. However, a variety of differently configured catch parts are within the scope of this disclosure.

The applicator tool 80 can optionally further include one or more features for at least partially facilitating predetermined cooperative interaction between the applicator tool and the tissue bridge 20. For example, the levers 88A, 88B and/or handles 94, or features associated therewith, can be configured to come into contact with one another when the desired degree of deformation is reached in the tissue bridge 20, thereby seeking to prevent over distortion of the tissue bridge. In addition or alternatively, the levers 88A, 88B and/or handles 94, or features associated therewith, can be configured to (e.g., can include one or more catches, rows of catches, or the like, configured to) cause the applicator tool 80 to hold the tissue bridge 20 in one or more predetermined states of deformation (e.g., one or more predetermined strained, deformed, or extended configurations) without requiring the user to continually squeeze together the handles 94, or the like. For example, the applicator tool 80 can include mechanisms (e.g. rows of catches) that can be sequentially activated, similarly to such mechanisms of surgical clamps, so one click (e.g., a first predetermined engagement between the catches or the like) can cause a relatively low state of deformation in the tissue bridge, two clicks (e.g., a second predetermined engagement between the catches or the like) can cause a relatively medium state of deformation in the tissue bridge, and three clicks (e.g., a third predetermined engagement between the catches or the like) can cause a relatively large state of deformation in the tissue bridge (e.g., the full deformation). In addition, the levers 88A, 88B, handles 94 and/or other suitably associated features can have different shapes to assist in ergonomically optimized use, for example by comprising partial or complete rings, recesses shaped to accept the user's digit(s) and/or other suitable features. Cooperative interaction between the applicator tool 80 and tissue bridge 20, such as engagement between their catch parts, will be discussed in greater detail below, after a discussion of the option of the tissue bridges and applicator tools being conveniently provided as parts of kits.

Figure 3A:
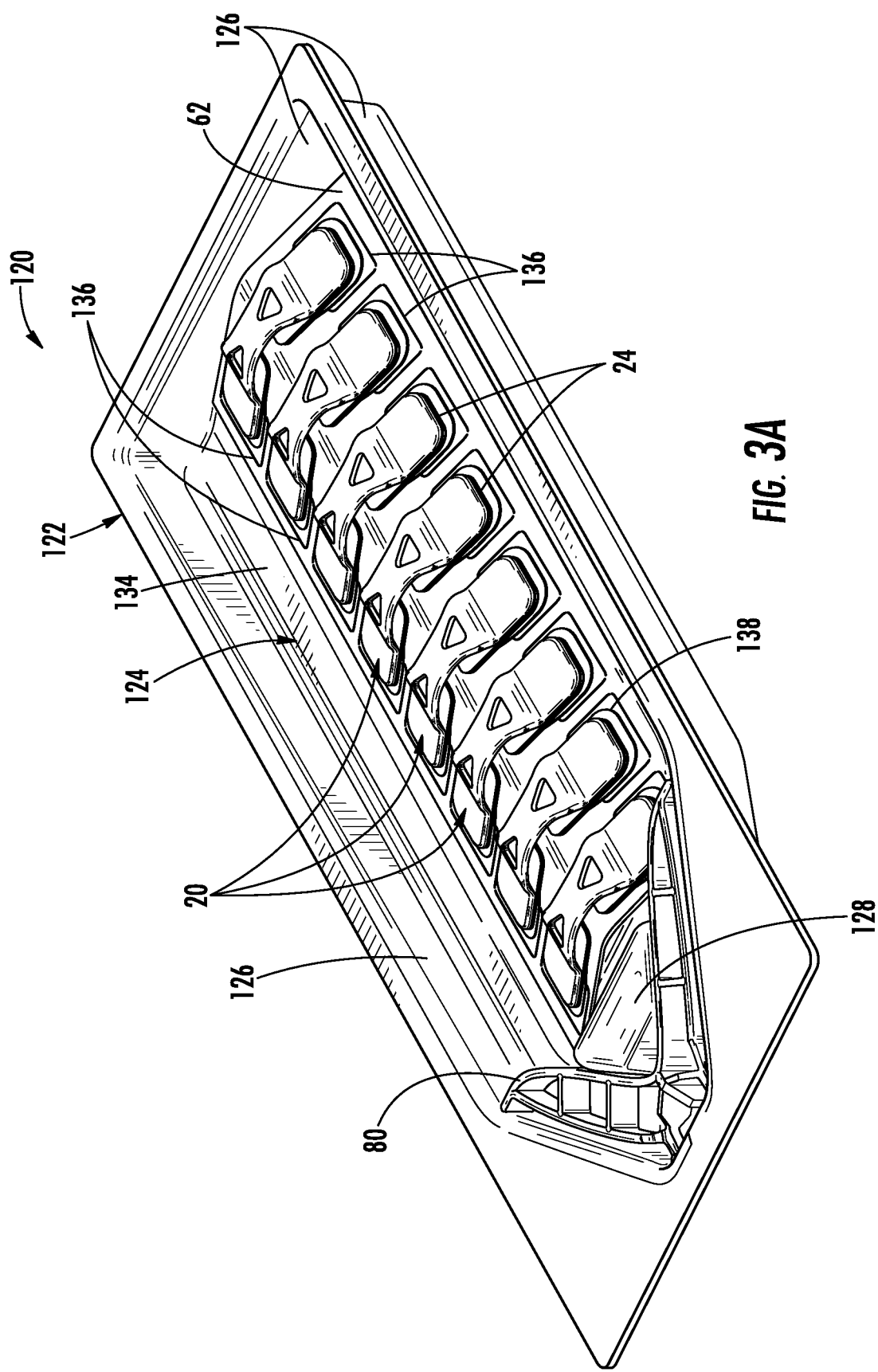
FIG. 3A is a top pictorial view of at least a portion of a kit or package comprising the applicator tool of FIGS. 2A-2D and several of the tissue bridges of FIGS. 1A-1E at least partially contained in a tray, in accordance with the first embodiment.

In accordance with the first embodiment, and as at least partially depicted in FIG. 3A, one or more of the tissue bridges 20 and optionally at least one applicator tool 80 can be provided as part of a kit or package 120 that can further include the release liner 62 and adhesive material 64 (FIG. 1E). In the example shown in FIGS. 3A-3C, the package 120 can include a container in the form of an injection molded or vacuum-formed tray 122, or the like. The tray 122 can have a base panel 124 and sidewalls 126 extending upwardly from the periphery of the base panel to define a cavity of the tray. Also, the package 120 and/or tray 122 can optionally include at least one divider 128 that extends upwardly from the base panel 124 and is positioned between and distant from opposite sidewalls 126 to at least partially divide the tray cavity into at least first and second compartments configured for respectively receiving the applicator tool 80 and one or more tissue bridges 20. The first compartment of the tray 122, or more specifically the divider 128 and the sidewalls 126 that at least partially define the first compartment of the tray, can define a shape that is complementary to the peripheral shape of, and about the same size as, the applicator tool 80, so that a releasable interference fit can be defined between the first compartment and the applicator tool within the first compartment. As another example, the first compartment of the tray 122, divider 128 and applicator tool 80 can be omitted from the tray 122. Any applicator tool 80 can be provided as part of a package that is separate from the package including the tray 122.

As an example, the tray 122 can be an inner tray that can be put in either an outer tray, a pouch and/or other suitable packaging. As other examples, the tray 122 can include other features, for example slots or other surface features that can be used to secure the tray to the user's body (e.g., non-dominant forearm), to a fixture (e.g., a mayo tray), or in other suitable configurations.

Figure 3B:
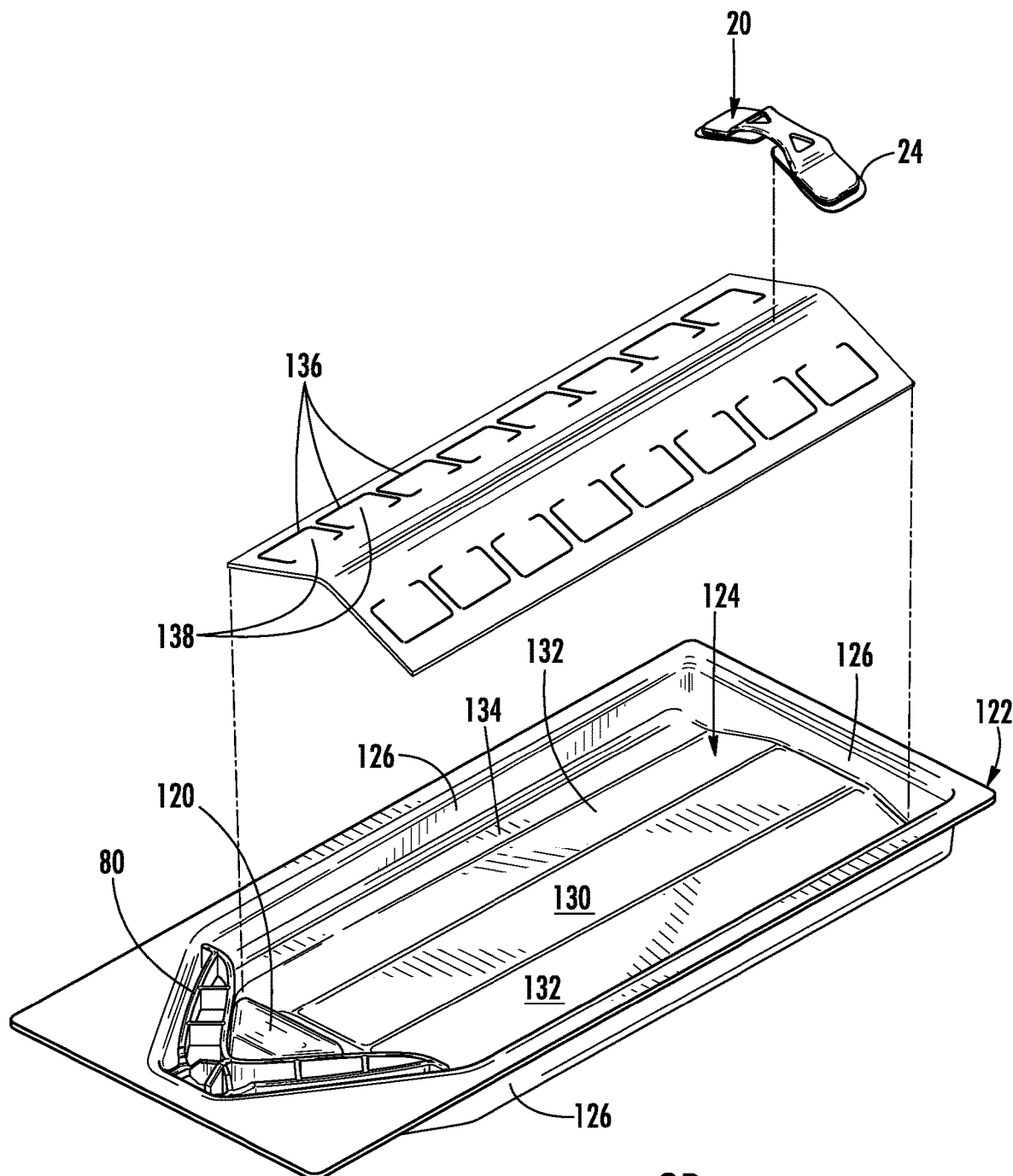
FIG. 3B is a partially exploded view of some of the objects of the package of FIG. 3A, in accordance with the first embodiment.
Figure 3C:
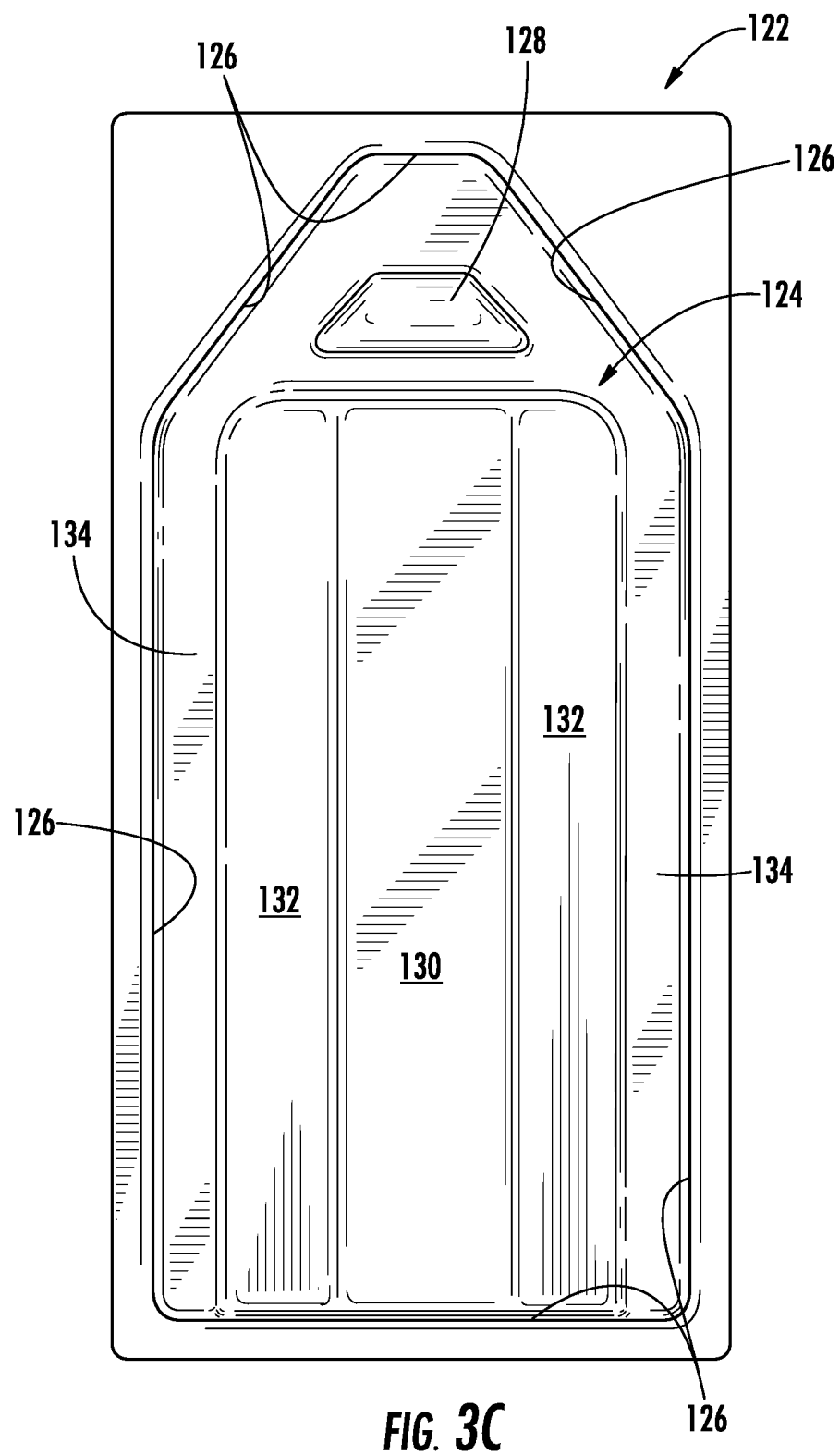
FIG. 3C is an isolated, top plan view of the tray of FIG. 3A, in accordance with the first embodiment.
Figure 3D:
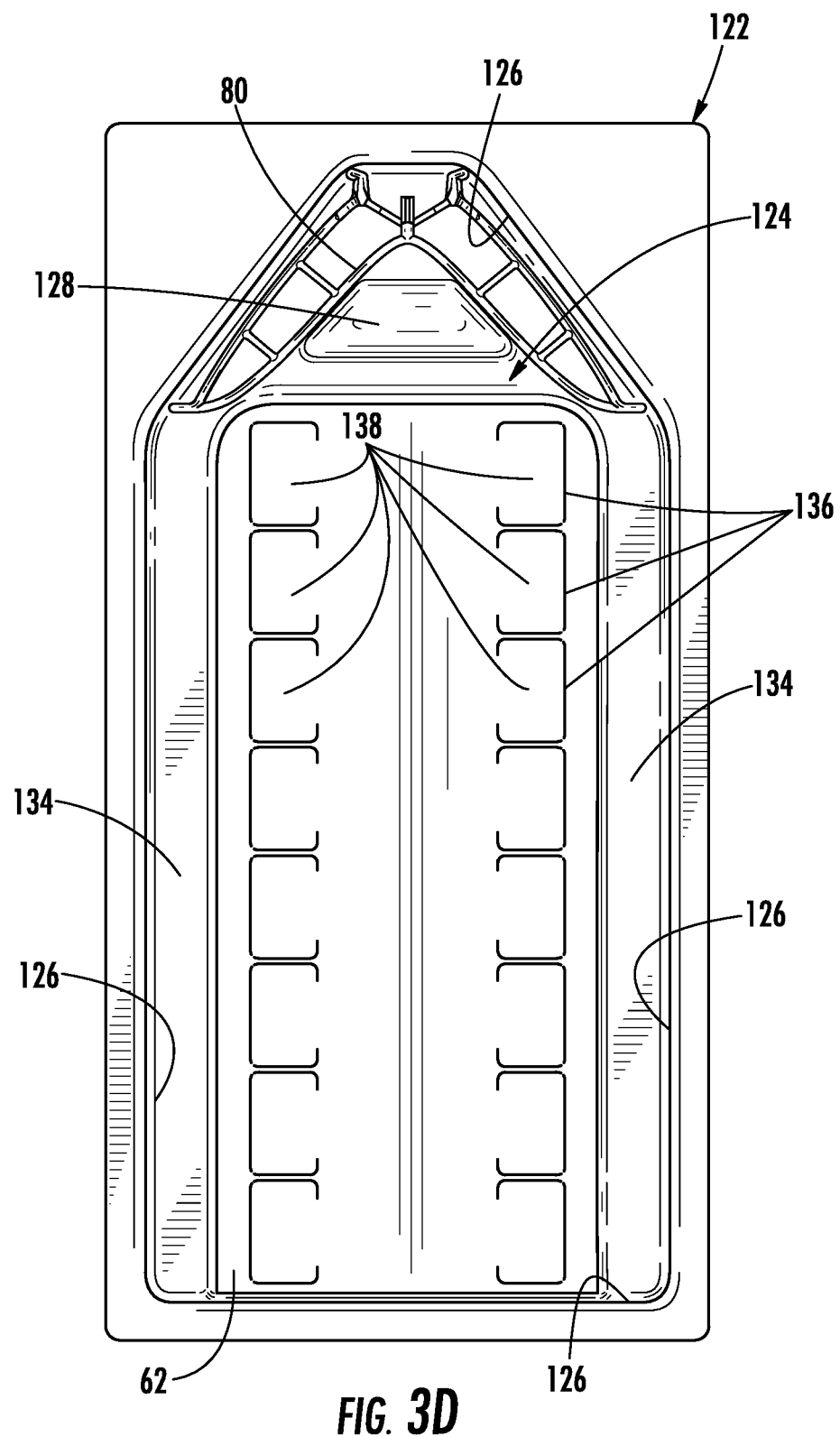
FIG. 3D is a top plan view of the tray of FIG. 3A containing the applicator tool and release liner, in accordance with the first embodiment.
Figure 3E:
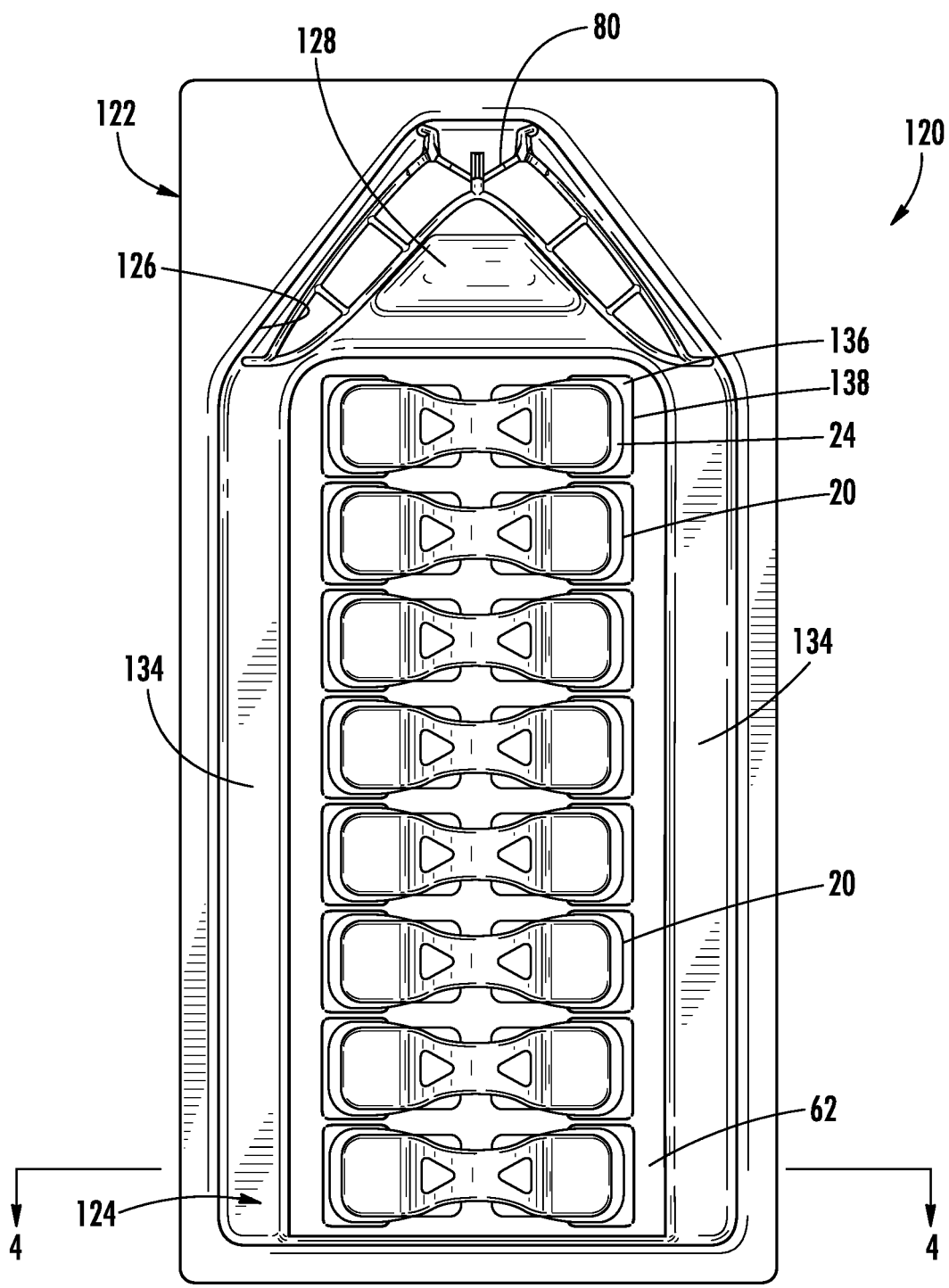
FIG. 3E is a top plan view of the package of FIG. 3A, in accordance with the first embodiment.

Referring to the exploded view of FIG. 3B, and the isolated top plan view of the tray 122 in FIG. 3C, the base panel 124 can be configured in the form of and/or to define a generally ridge-shaped support extending along at least a portion of the length of the tray. The ridge-shaped support can include an elevated central section 130 of the base panel and downwardly sloping outer sections 132 of the base panel. The central section 130 can be flat, although exact flatness may not be required such that the central section can be generally or substantially flat, or in any other suitable configuration. For example, the central section can be concave, or the like. The outer sections 132 can extend obliquely, or more specifically outwardly and downwardly, from opposite portions or edges of the raised central section 130. For example, the outer sections 132 can extend obliquely, inwardly and upwardly from lower, marginal portions 134 of the base panel 124. Two or more pairs of outer sections 132 can be included in each tray 122. Alternatively, the central section 130 can be recessed downwardly relative to inner portions of the outer sections 132.

Referring to FIGS. 1E, 3A, 3B, 3D and 3E, the release liner 62 can include a series of lines of disruption 136. Each line of disruption 136 can comprise one or more cuts, slits, breachable lines of disruption, perforations and/or overlapping and/or sequential combinations thereof, for at least partially defining flaps 138 in the release liner 62, as will be discussed in greater detail below. The lines of disruption 136 can be configured in a variety of patterns. In some examples, the pattern may be symmetrical in relationship to each associated (e.g., subsequently mounted) tissue bridge 20. In other examples, the lines of disruption 136 can be asymmetrical in relationship to each associated (e.g., subsequently mounted) tissue bridge 20. In the first embodiment, each line of disruption 136 extends partially around the foot pad 24 that is mounted to the flap 138 defined by the line of disruption, and opposite ends of the line of disruption extend beneath the food pad.

In accordance with the first embodiment, the tissue bridges 20 can be manually assembled and/or at least partially assembled by way of one or more automated coating, laminating and cutting processes. For example, the release liner 62 can be a base ply or layer of a laminate that is appropriately cut (e.g., die cut) and partially delaminated to at least partially form the foot pads 24 on the release liner, and thereafter the bodies 22 can be respectively mounted to the foot pads 24, or the like. The lines of disruption 136 can be formed by an appropriate one or more of the cutting (e.g., die cutting) steps, or the like, such that the lines of disruption (e.g., slits, perforations or other suitable cuts) may extend at least partially into one or more layers of the foot pad 24. As a more specific example, the lines of disruption 136, or extensions thereof, or the like, may extend into the outer adhesive layer 40 (FIG. 1E). At an appropriate time, typically after the die cutting, or the like, the underside of the release liner 62 can be fixedly secured to the surface of the outer sections 132 of the tray 122 by way of, for example, adhesive material 64 (FIG. 1E) arranged in a pattern such that the adhesive material is omitted from between the flaps 138 in the release liner and the respective portions (e.g., outer sections 132) of the tray, so that the flaps can be moved relative to the reminder of the release liner, as will be discussed in greater detail below. More generally, any adhesion or other suitable connection between the flaps 138 and the respective portions (e.g., outer sections 132) of the tray 122 is weaker than the adhesion or other suitable connection between the remainder of the release liner 62 and the tray, so that the flaps can be moved relative to the reminder of the release liner, as will be discussed in greater detail below.

Figure 4A:
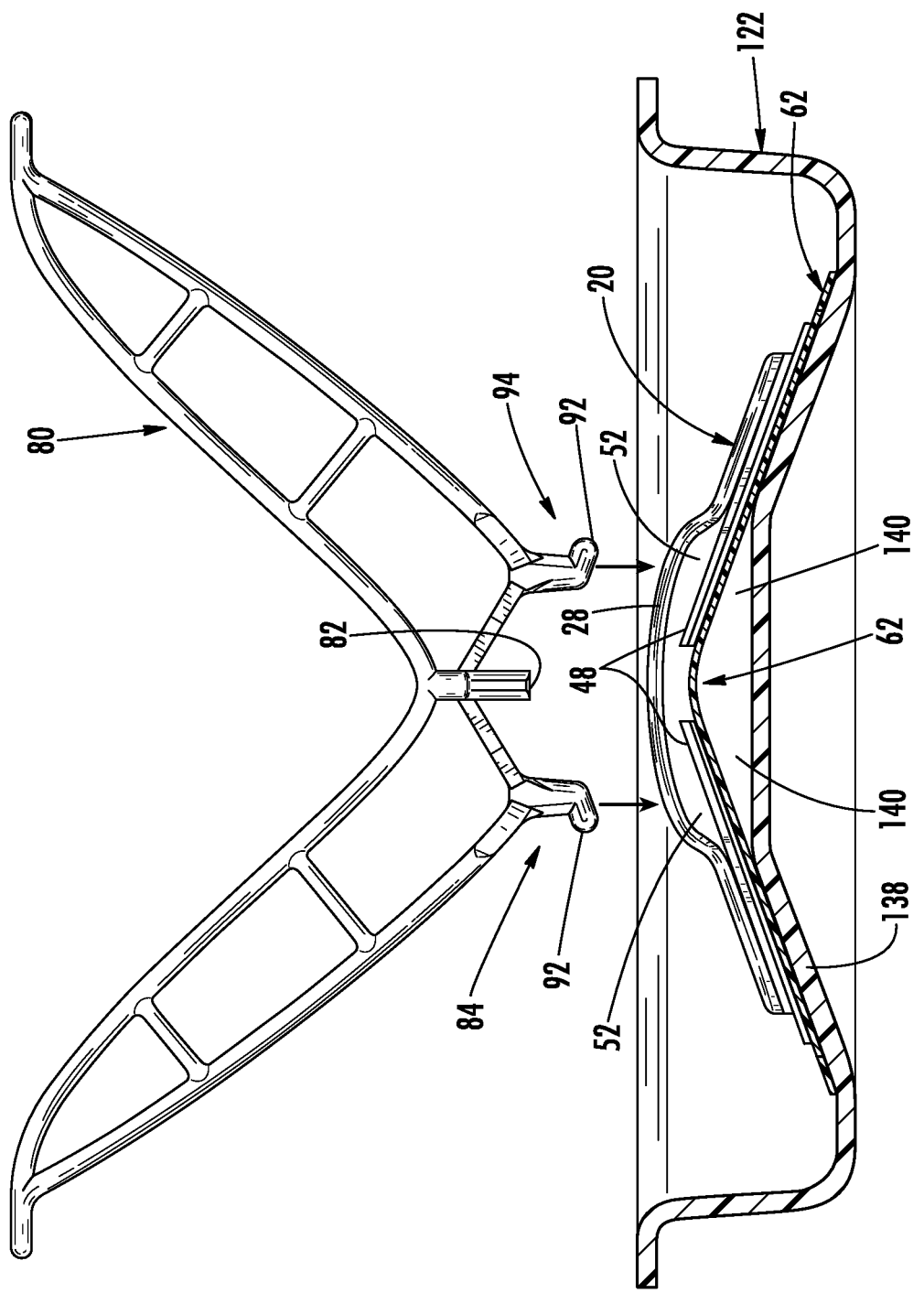

Referring to FIGS. 4A-4F, a method of using the applicator tool 80 to remove a tissue bridge 20 from the tray 122 is described in the following, in accordance with the first embodiment. In FIGS. 4A-4F, the tray 122 and release liner 62 are cross-sectioned along line 4-4 of FIG. 3E. Referring to FIG. 4A, initially, the applicator tool 80 (e.g., in its undeformed or at rest configuration) can be engaged against the tissue bridge 20 (e.g., in its undeformed or at rest configuration) by way of relative movement causing increased closeness between the applicator tool 80 and the tray 122 (e.g., movement of the applicator tool toward the tissue bridge mounted on the release liner 62 in the tray). Referring to FIGS. 4A and 4B, in response to the relative movement, the protrusions 92 of the tool catch parts 84 can enter the receptacles 52 by way of the holes 56 (FIGS. 1A and 1B). That is, the protrusions 92 can enter the receptacles 52 by traveling through the holes 56. For example, the applicator tool 80 can be pushed downwardly to engage the tissue bridge 20 in a manner so that the protrusions 92 of the tool catch parts 84 enter the receptacles 52 by way of the holes 56, and optionally also the tool contact surface 82 engages the central apex or any other suitable surface of the arch 28. The applicator tool 80 can be in its undeformed or at rest configuration throughout the step of the protrusions 92 of the tool catch parts 84 entering the receptacles 52 by way of the holes 56. As another example, the distance between the tips of the protrusions 92 can be greater than the distance between the hole edges 58 (FIGS. 1A and 1B) so that the protrusions "snap" into the holes 56 and/or receptacles 52 and are optionally releasably contained in the receptacles by way of an interference fit, or the like.

The relative movement causing increased closeness between the applicator tool 80 and the tray 122 may be facilitated by a user manually holding the handles 94 of the applicator tool and moving the applicator tool toward the tissue bridge 20 in the tray, or the tissue bridge may be supported by any other suitable surface. Referring to FIG. 4B, the protrusions 92 can engage respective surfaces of the medial struts 48 in response to the relative movement causing increased closeness between the applicator tool 80 and the tray 122.

Figure 4D:
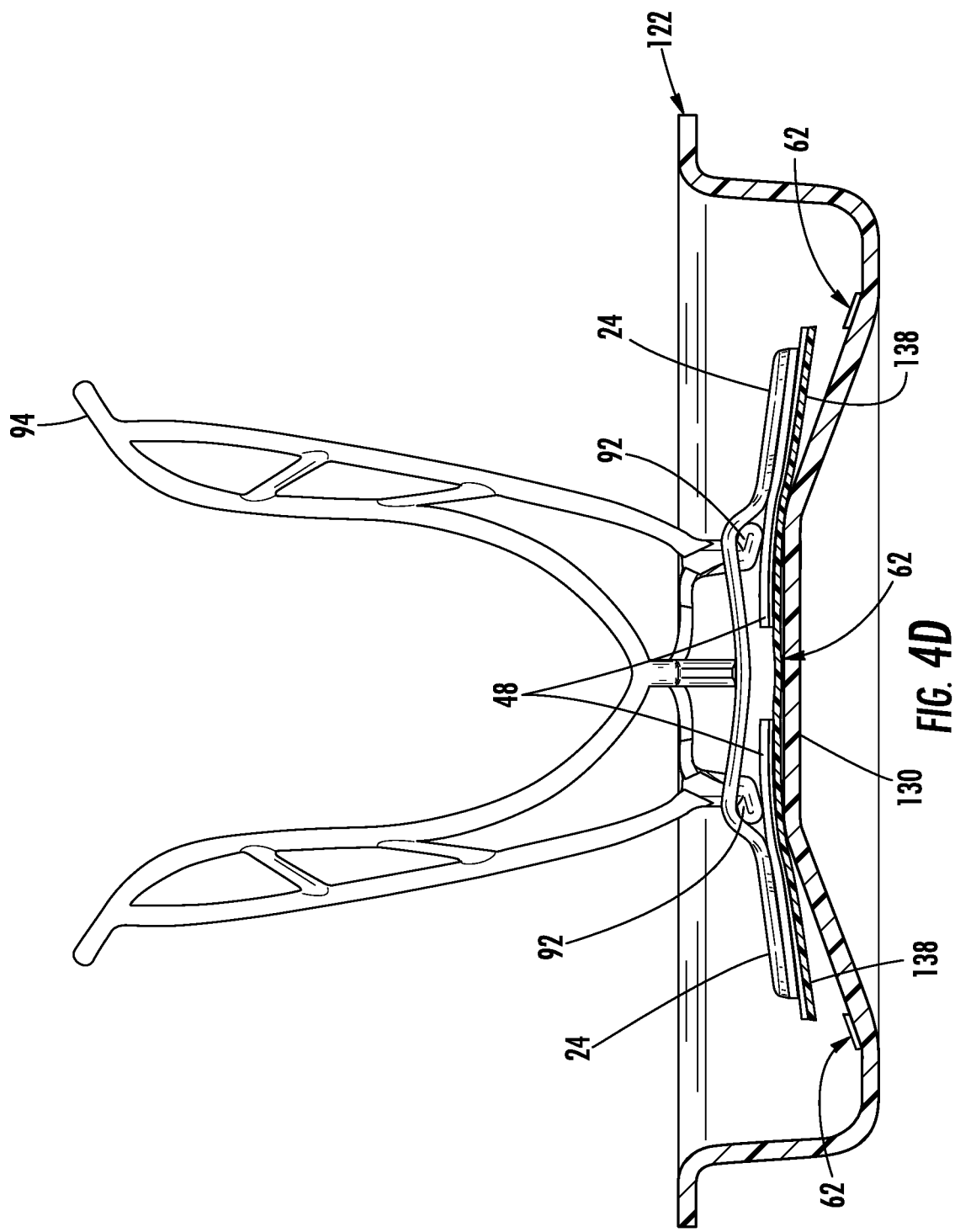

For serially achieving the configurations of FIG. 4C and FIG. 4D, simultaneously and/or in series, the relative movement causing increased closeness between the applicator tool 80 and the tray 122 can continue, and the handles 94 can be manually squeezed together (e.g., pushed toward one another) so that the applicator tool reconfigures toward its actuated or deformed configuration and applies deforming forces on the tissue bridge 20. As the applicator tool 80 is, for example, simultaneously pushed with greater force against the tissue bridge 20 and caused to deform farther toward its deformed configuration, the applicator tool applies forces against the tissue bridge 20 so that the tissue bridge is responsively deformed toward its strained, deformed, or extended configuration. For example, the applicator tool 80 can simultaneously apply a downward force via the contact surface 82 and laterally outward forces via the catch parts 84.

In the transition from the configuration of FIG. 4C to the configuration of FIG. 4D, the outer portions of the foot pads 24 have moved, or more specifically pivoted, away from the tray outer sections 132. As discussed above, the flaps 138 can be attached to the outer portions of the foot pads 24 by way of the outer adhesive layer 42 (FIG. 1E). Therefore, the flaps 138 can be carried by, and pivot with, the outer portions of the foot pads 24. Therefore, the flaps 138 pivot outwardly relative to a reminder of the release liner 62 that remains fixedly mounted to the tray base panel 124. That is, the flaps 138 can pivot outwardly relative to (e.g., at least partially delaminate from) a reminder of the release liner 62 and the tray 122 in response to respective movement, reconfiguring, and/or the like of the tissue bridge 20 and applicator tool 80. In the first embodiment, the release liner 62 is a support that supports the tissue bridge, and each flap 138 can be referred to as a first section of the support, and the reminder of the release liner 62 and/or the tray 122 can be referred to as a second section of the support, or the like.

As another example, in the transition from the configuration of FIG. 4C to the configuration of FIG. 4D, the protrusions 92 have pushed (e.g., deflected) the medial struts 48 downwardly toward the recessed central section 130 of the tray 122 to close one or more gaps 140 (FIGS. 4A and 4B) positioned between the medial struts and the tray central section. However, such strut deflection and/or closure of the gaps 140 can be optional and may not occur. As other examples, the gaps 140 may be at least partially closed, only partially closed and/or it is believed that it may be possible in some situations to omit the gaps 140. That is, in an example, the medial struts 48 can pivot downwardly relative to a reminder of the foot pads 24 in response to respective movement, reconfiguring, and/or the like of the tissue bridge 20 and applicator tool 80.

Referring to FIG. 4C-4F, the applicator tool 80 and tissue bridge 20 can be cooperatively configured and engaged to one another in a predetermined manner so that, in response to the handles 94 being manually squeezed or pushed closer to one another, at least lower portions of the tool catch parts 84 are moved farther away from one another and the contact surface 82 moves toward a line between the catch parts 84, and this movement of the applicator tool 80 forces the tissue bridge 20 into its fully deformed or extended configuration, an example of which is shown in FIG. 4F. For example, the manual inward force applied to the opposite sides of the handles 94 to achieve this configuration can be in a range of from more than 0.2 pounds force (0.89 newtons) to less than 2 pounds force (8.9 newtons).

In the transition from the configuration of FIG. 4E to the configuration of FIG. 4F, the release liner 62 typically fully separates from the tissue bridge 20, and the flaps 138 can pivot/fall back into their original positions in response to relative movement causing increased distance between the applicator tool 80 and the tray 122. The release liner 62 typically fully separates from the tissue bridge 20 in a manner that fully exposes the outer adhesive layer 42 (FIG. 1E) (e.g., patient contact adhesive), so that there are no remnants of the release liner stuck to the tissue bridge and the outer adhesive layer is ready for being used to secure the tissue bridge to tissue, such as the skin of a patient.

For example, in FIG. 4F the tissue bridge 20 and applicator tool 80 are engaged to one another, and both the tissue bridge and the applicator tool are in their deformed configurations so that the tissue bridge is securely grasped or otherwise held by the applicator tool, so that as the applicator tool is manually moved away from the tray 122 the applicator tool carries the tissue bridge away from the tray. While the tissue bridge 20 is securely held by the applicator tool 80, the applicator tool can be used to apply the tissue bridge to tissue, such as the skin of a patient.

Figure 4G:
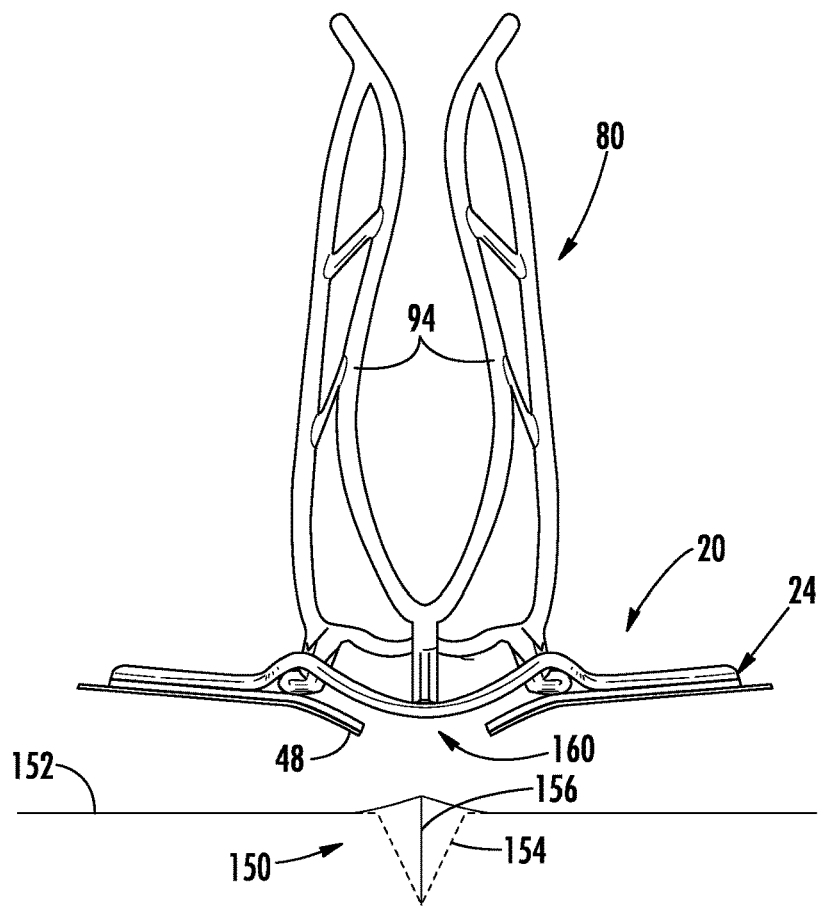
FIGS. 4G through 4K depict a sequence of steps of a method of using the applicator tool to apply the tissue bridge to a wound, in accordance with the first embodiment.
Figure 4H:
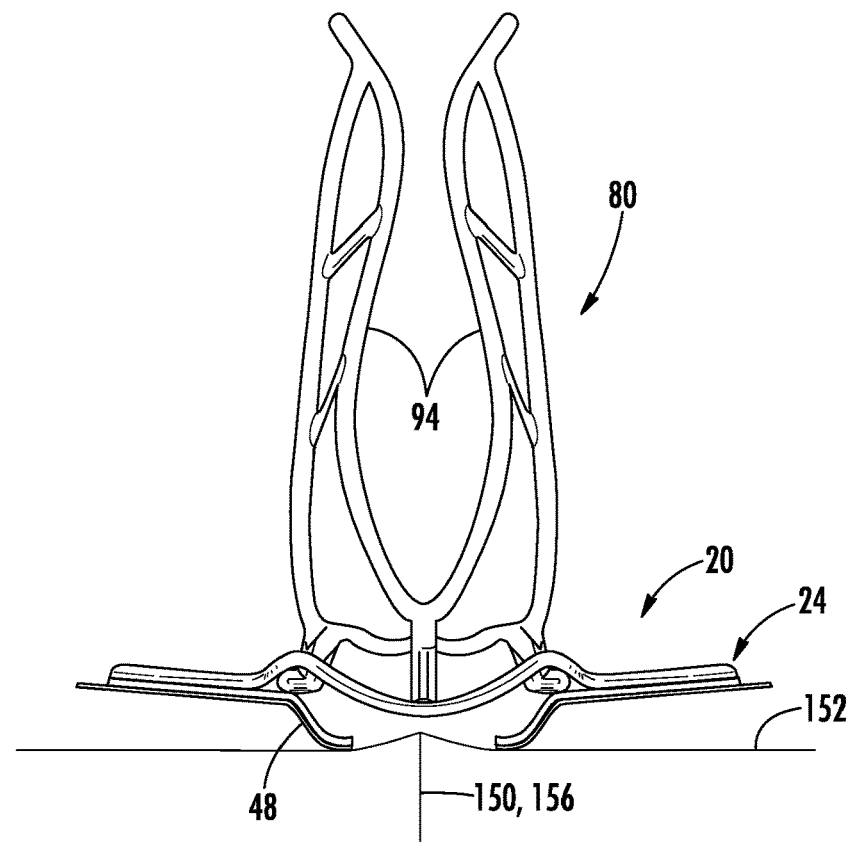
Figure 4I:
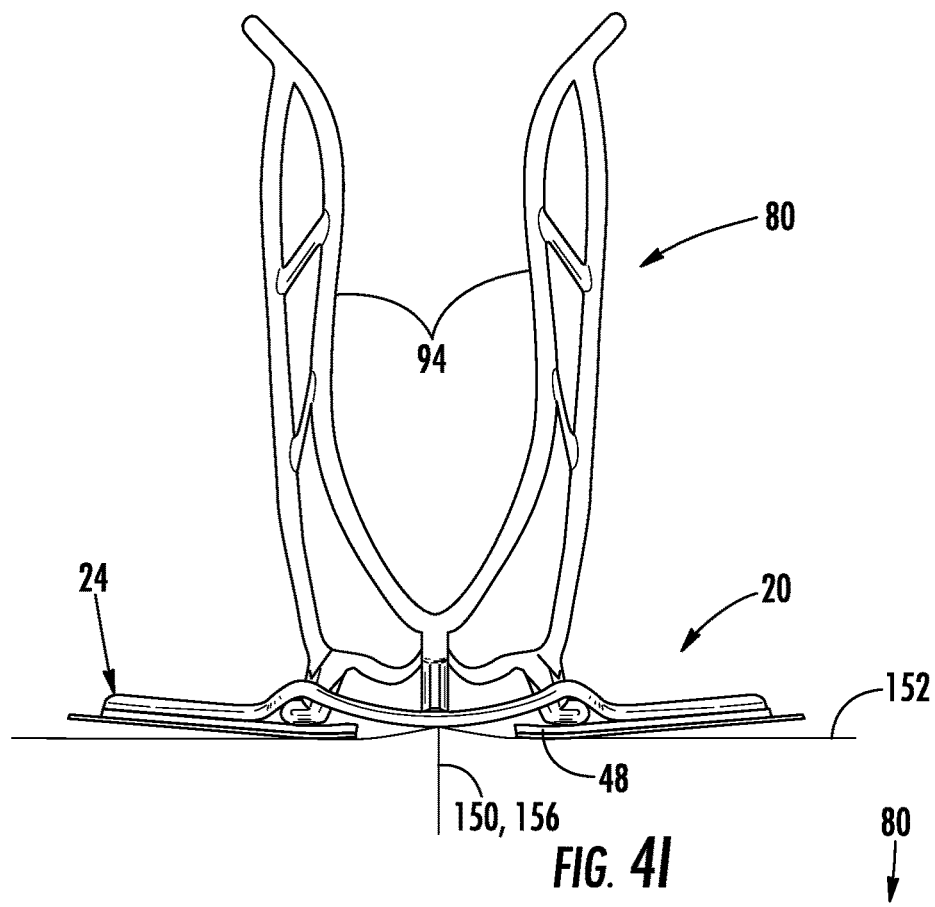
Figure 4J:
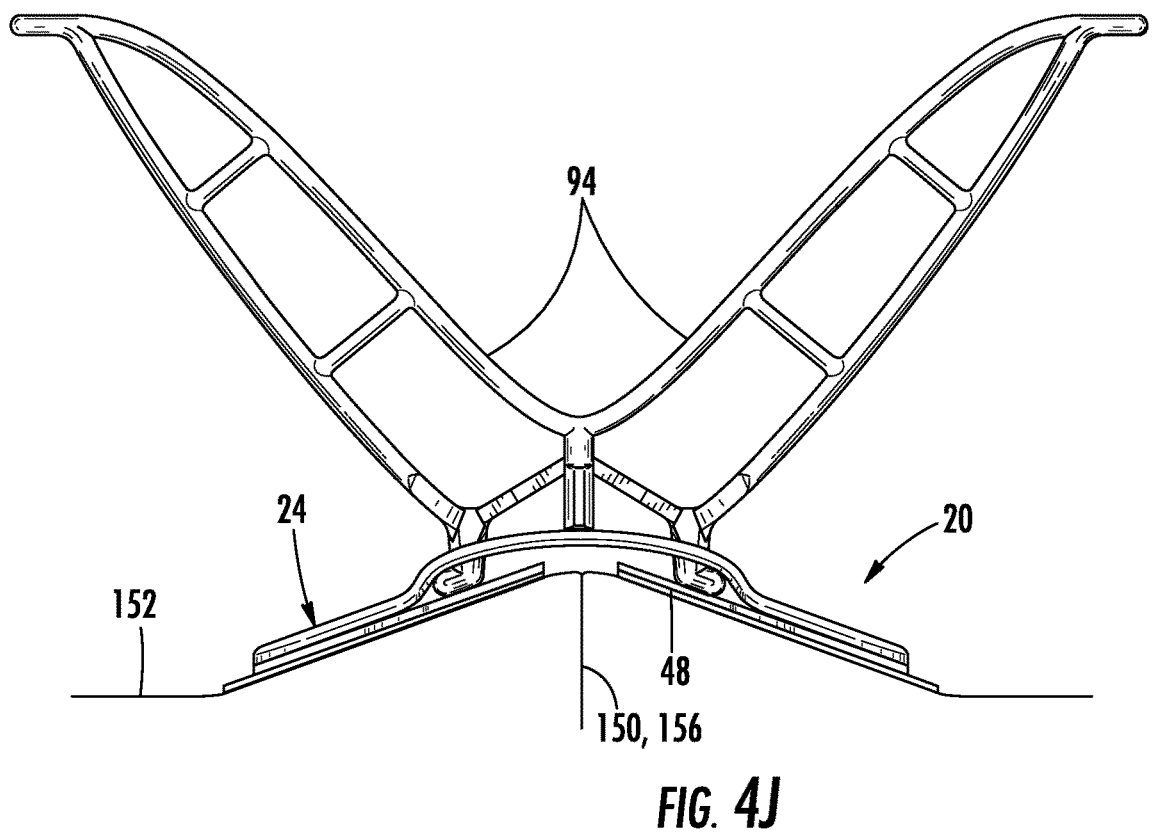

Referring to FIGS. 4G-4K, a method of using the applicator tool 80 to apply a tissue bridge 20 to tissue 152 on either side of a cut 150 in a patient's skin 152 is described in the following, in accordance with the first embodiment. FIG. 4G schematically depicts with dashed lines 154 the originally spaced apart edges of the cut 150, and a solid line 156 schematically depicts that the edges of the cut may be manually pushed together prior to applying the tissue bridge 20 over the cut. The applicator tool 80 holding the tissue bridge 20 can be moved toward the cut 150 so that the tissue bridge 20 extends crosswise to, or more specifically substantially perpendicular to, the length of the cut 150, and the first contact between the tissue bridge and the tissue or skin 152 occurs at the inner end sections or portions of the medial struts 48 on either side of the cut. Referring to FIGS. 4H and 4I, the applicator tool 80 can continue to be pushed closer to the cut 150 so that the inner portions of medial struts 48 begin to become adhered to the skin 152 by the outer adhesive layer 42 (FIG. 1E) (e.g., patient contact adhesive). For example, the transmission of force from the applicator tool 80, by way of the catch parts 84, against the medial struts 48 can cause the pressure-sensitive adhesive layer 42 to be engaged against the tissue 152 with sufficient force to cause the inner portions of medial struts 48 to become adhered to the tissue 152 at opposite sides of the cut 150.

Then, the manual force on the handles 94 of the applicator tool 80 can be reduced, so that the tissue bridge 20 returns toward its at rest configuration, and the medial struts 48 become closer together and push the portions of the tissue 152 to which they are adhered toward one another. Then, in response to the tissue bridge 20 returning farther toward its at rest configuration, the reconfiguring of the tissue bridge causes the outer portions of the foot pads 24 to move or pivot downwardly into contact with the tissue 152 at opposite sides of the cut 150. In one example, this contact between the outer portions of the foot pads 24 and the tissue 152 at opposite sides of the cut 150 may occur with sufficient force to cause the pressure-sensitive adhesive layer 42 to securely adhere the outer portions of the foot pads 24 to the tissue 152 at opposite sides of the cut 150.

In accordance with the first embodiment, the inner portions of the medial struts 48 are adhesively mounting to the tissue 152 while the tissue bridge 20 is in its deformed or extended configuration; and thereafter as the tissue bridge 20 returns toward its at rest configuration and reaches an intermediate configuration that is between the extended and at rest configurations, the remainder or outer portions of the foot pads 24 are adhesively mounted to the tissue. When the tissue bridge 20 is first engaged against the tissue 152, the point of first contact and adhesive mounting to the tissue can be at the inner end sections or portions of the medial struts 48, and this mounting can occur while the medial struts are being pushed downwardly by way of the applicator tool 80. In the first embodiment, as the deforming force being applied on the tissue bridge 20 by the applicator tool 80 is reduced, the medial struts 48 move or rotate inwards, thus centrally pulling the tissues 152 to which they are adhesively mounted, and this action by the medial struts 48 occurs before the outer portions of the foot pads 24 are adhesively attached to the tissue. At this intermediate point, in which the medial struts 48 are at least partially attached to the tissue 152 and have moved inwards, and the outer portions of the foot pads 24 are not yet attached to the tissue, the shear stress and/or strain on predetermined tissue (i.e., tissue that is lateral to the lateral-most contact point between the medial strut and the tissue) is distributed laterally and in a gradual manner. Then, when the lateral or outer portions of the foot pads 24 are pressed down and adhered to the tissue 152, the predetermined tissue underneath and at the lateral edges or outer edges of the foot pads 24 is secured (e.g., adhered to the foot pads) in its state in which the stress and/or strain in the predetermined tissue is distributed laterally and in a gradual manner, which seeks to prevent sudden, high sheer stress at the lateral edges (e.g., opposite ends) of the tissue bridge 20.

Figure 4K:
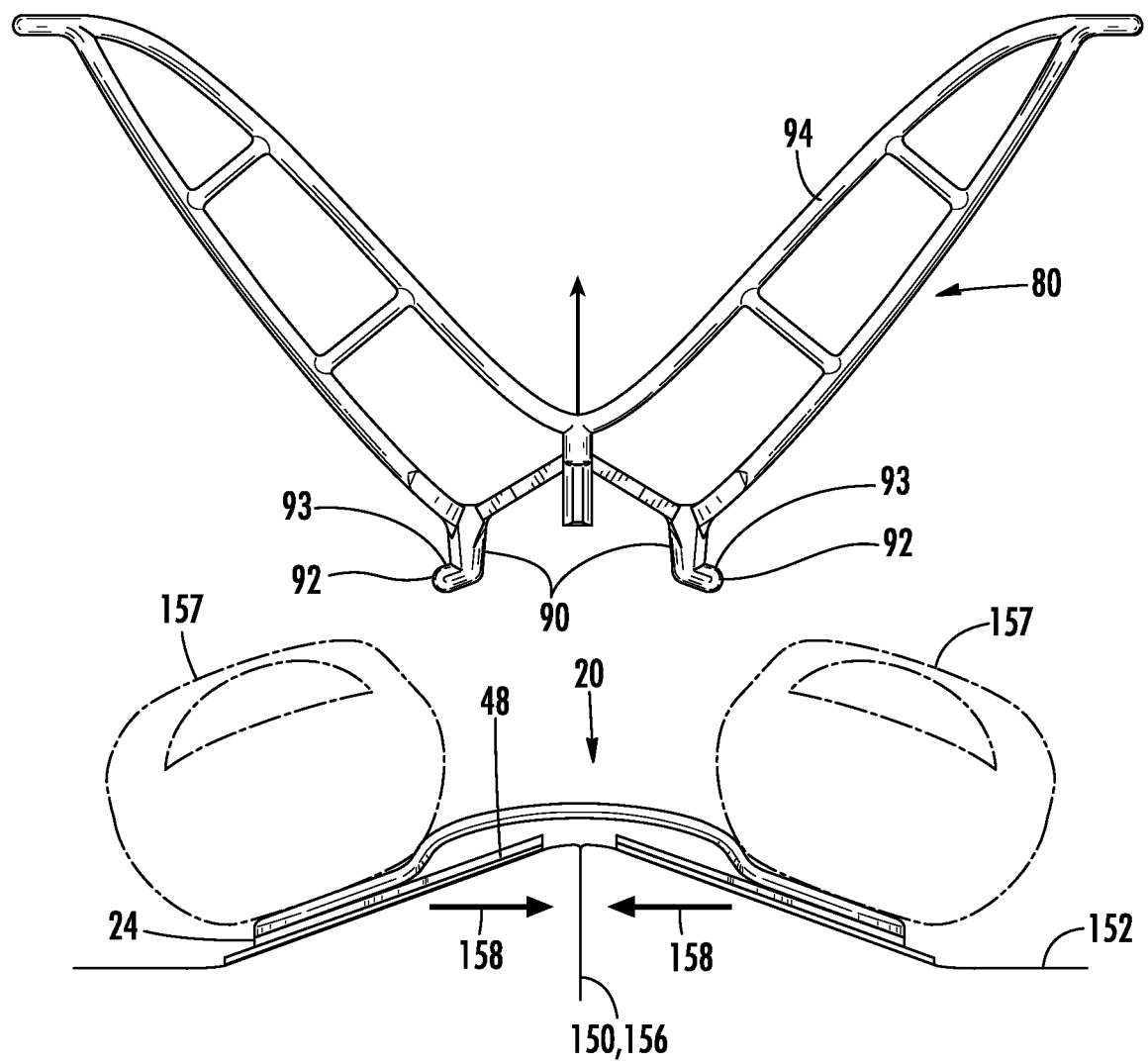
Figure 5A:
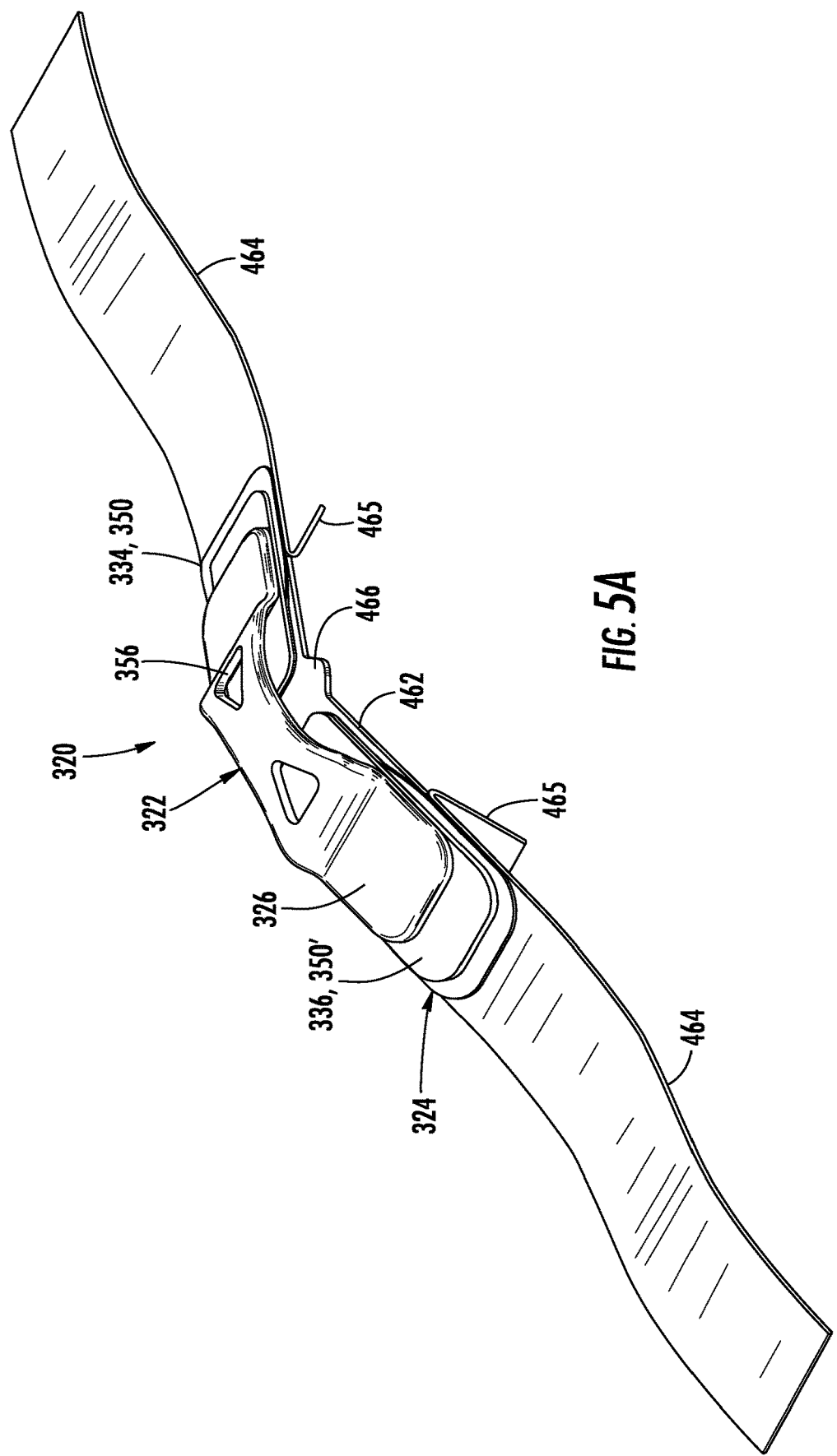

Referring to FIG. 4K, the applicator tool 80 can then be removed from the tissue bridge 20 so that the tissue bridge remains mounted over the cut 150; then the applicator tool may be used to install another tissue bridge. As an example, the distance between the tips of the protrusions 92 can be greater than the distance between the hole edges 58 (FIGS. 1A and 1B). In such an example, upper surfaces or engagement shoulders 93 of the catch parts 84 can extend obliquely downwardly from the shanks 90, so that there can be relative sliding between the shoulders 93 and the edges 83 when the applicator tool 80 is withdrawn from the tissue bridge. In response to such sliding, the catch parts 84 can pivot toward one another and, thus, be freed from the holes 56. Alternatively, the catch parts 84 can be moved toward one another in any other suitable manner as part of the catch parts 84 being freed from the holes 56. As another example, after a tissue bridge 20 is mounted to a patient and the applicator tool 80 is allowed to return to its relaxed configuration, the tissue bridge 20 may reconfigure toward its relaxed configuration without fully reaching its relaxed configuration, so that the protrusions 92 can freely pass through the holes 56.

A user can push down manually with their fingers 157 on the foot pads 24, for example with sufficient force to ensure that the pressure-sensitive adhesive layer 42 securely adheres the foot pads 24 to the tissue 152 at opposite sides of the cut 150. In accordance with the first embodiment, the tissue bridge 20 can be mounted to the tissue 152 in a manner such that the tissue bridge and tissue apply force against one another, and the force applied by the tissue typically restricts the tissue bridge from fully returning to its at rest configuration. As a result, the tissue bridge 20 applies compressive force to the tissue 152 by way of the foot pads 24, as schematically depicted in FIG. 4K by arrows 158, in a manner that can, for example, reduce tension in the tissue, help close the wound 150, help inhibit wound reopening and/or inhibit scar disfiguring (e.g., widening). In the example shown in FIG. 4K, the tissue 152 proximate the scar and/or wound 150 bulges into the central area over which the arch 28 extends.

In association with the forces being applied against one another by the tissue 152 and the tissue bridge 20 when the tissue bridge is mounted, for example, as shown in FIG. 4K, the medial struts 48 are typically under longitudinal compression. In addition, the medial struts 48 can be configured in a manner that seeks to allow the arch 28 and medial struts to move in a manner that provides a wide opening 160 (FIG. 4G) for at least partially enveloping the subject tissue 152, wound 150, scar, or the like, so that the tissue bridge 20 can function to substantially inhibit any tension in the tissue, wound reopening, and/or scar disfiguring (e.g., widening). In addition, the medial struts 48 can advantageously reach inwardly toward the margins of the wound (or scar). In addition, the medial struts 48 can flex upwards or downwards independently to compensate for changes in tissue tension (e.g. due to swelling) or for off-centered placement of the tissue bridge; therefore, the medial struts may help align the margins of the wound (or scar) to the same vertical height.

In alternative embodiments, the applicator tool 80 may be replaced with one or more other suitable tools or features configured for providing one or more forces corresponding to the downward force provided via the contact surface 82 and the laterally outward forces provided via the catch parts 84. Such alternative tools may comprise a plunger mechanism, a side-directed pliers mechanism, a cam-activated mechanism, and/or any other suitable features, and such alternative tools may be multi-piece tools. As another example, the tissue bridges 20 may be applied to tissue 152 using one or more straps, or the like, as will be discussed in greater detail below.

Numerous other embodiments are within the scope of this disclosure. For example, other embodiments (e.g., embodiments two through fourteen) of this disclosure can be configured and/or function at least generally like the first embodiment, except for variations noted and variations that will be reasonably apparent to those of ordinary skill in the art. Accordingly, some of the drawing reference numerals used in the foregoing are used in the following and/or reference numerals for similarly configured and/or similarly functioning features may be incremented by two hundred, or other amounts, in the following.

Referring to FIGS. 5A-5D regarding a tissue bridge 320 of a second embodiment, the outer extension(s) 350' of the outer sheets 334 extend farther outwardly as compared to the corresponding features of the first embodiment. In addition, the inner sheets 336 include outer extensions 350' that extend outwardly past the outer edges of the respective foot plate or flange 326, and are recessed inwardly relative to the outer edge of the respective outer extension 350. The holes 356 can be included in the bodies 322, or these holes can be omitted, since the tissue bridge 320 may be mounted using features other than the applicator tool 80 of the first embodiment.

As shown in FIGS. 5A-5D, by way of the outer adhesive layer 42 (FIG. 1E) (e.g., patient contact adhesive), at least one central release or peel liner 462 and one or more release or peel liner mounting straps 464 are respectively mounted to the foot pads 324. Inner ends of the mounting straps 464 can include at least one folded over flap 465. The central release liner 462 can define or include at least one tab 466, and the tab can extend from the side of the central release liner. In the second embodiment, the mounting straps 464 are longer than the central release liner 462 and configured so that they can be used as an applicator tool for mounting the tissue bridge 320 to tissue 452. Each of the release liners 462, 464 can be, for example, a release liner in the form of a paper or plastic-based film sheet coated with a release agent that is engaged against the outer adhesive layers 42 so that the tissue bridge 320 is releasably mounted on the release liners 462, 464.

Figure 6A:
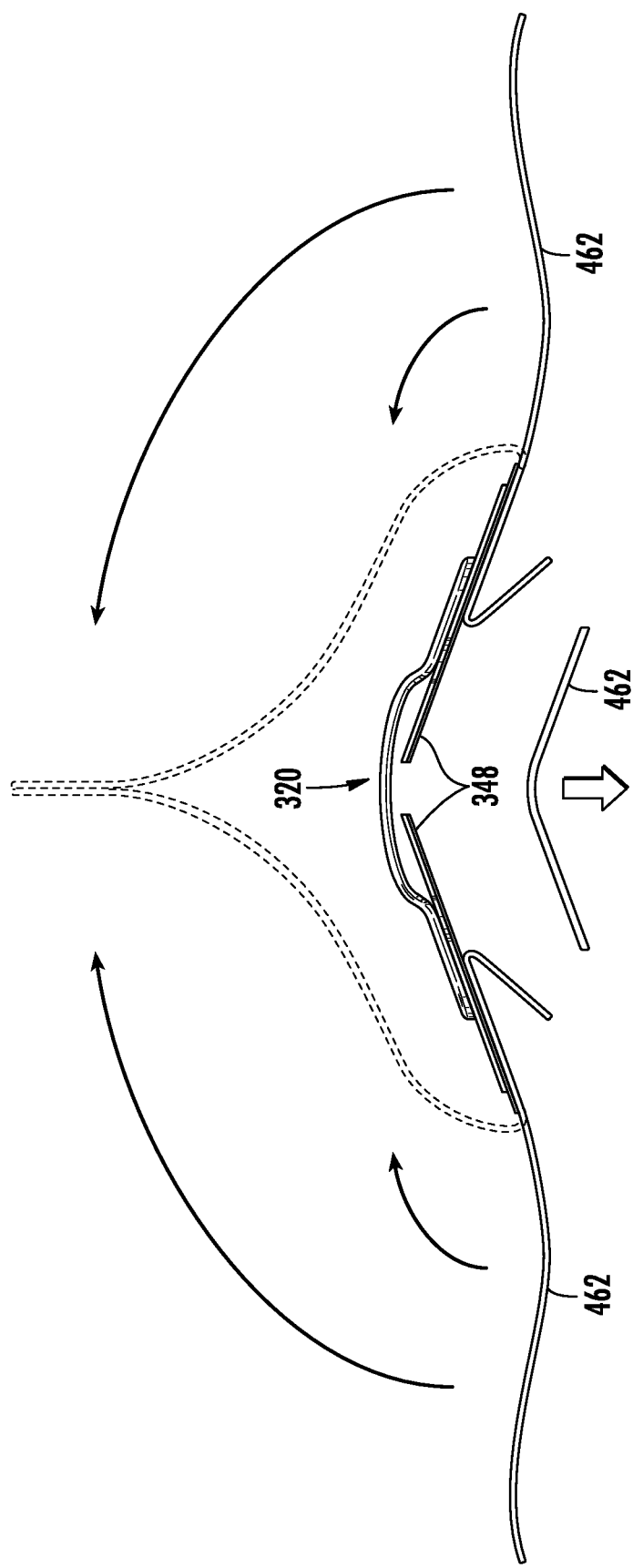
FIGS. 6A through 6F depict a sequence of steps of a method of applying the tissue bridge of FIGS. 5A-5D to a wound, in accordance with the second embodiment.
Figure 6B:
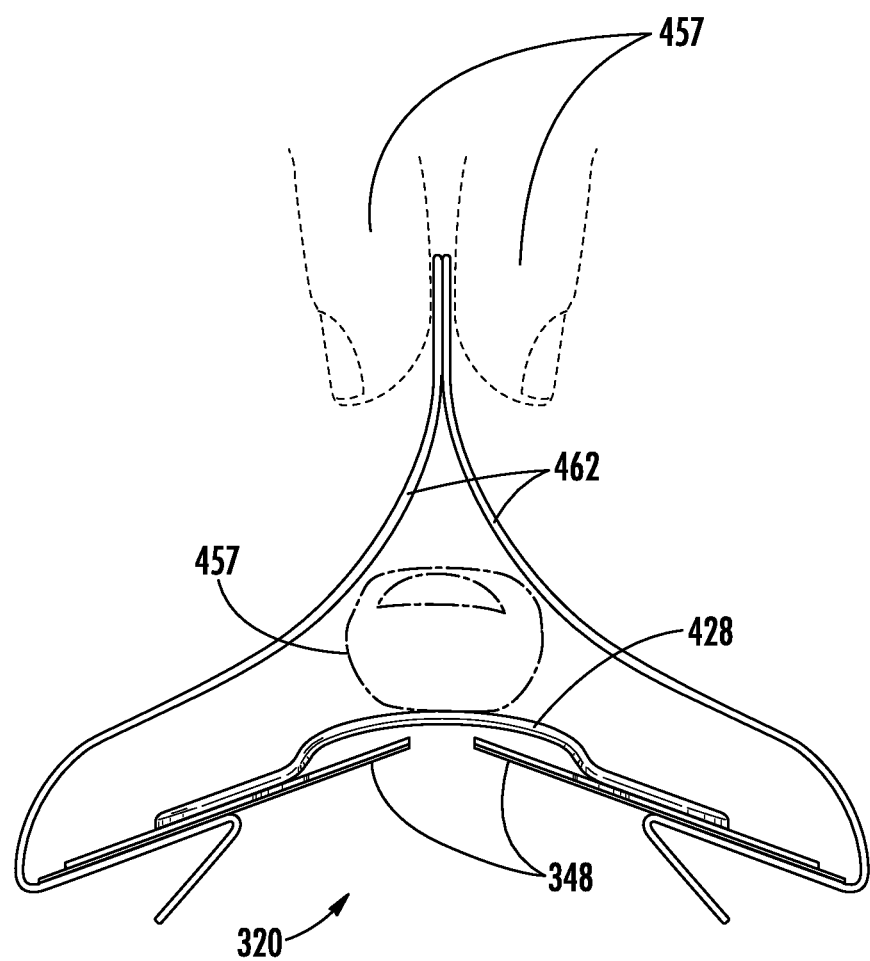

Referring to FIGS. 6A-6F, a method applying the tissue bridge 320 onto tissue 452 including a wound 450 is described in the following, in accordance with the second embodiment. Referring to FIG. 6A and then FIGS. 6B-6D, the tab 466 (FIGS. 5A-5C) can be manually grasped and pulled to remove the central release liner 462 and expose the outer adhesive layer 42 on at least the medial struts 348. Then, the free ends of the release liner mounting straps 464 may be drawn together and pulled, such as by fingers 457, while another finger 457 pushes downwardly on the arch 328 so that deforming forces are applied on the tissue bridge 320, and the inner portions of the medial struts 348 begin to become adhered to the tissue 452 by the outer adhesive layer 42 (FIG. 1E) (e.g., patient contact adhesive). In the second embodiment, the mounting of the tissue bridge 320 onto the tissue 452 can be carried out at least generally similarly to the first embodiment, so that after the medial struts 348 are at least partially attached to the tissue 452 and have moved inwards, and the outer portions of the foot pads 324 are not yet attached to the tissue, the shear stress and/or strain on predetermined tissue (i.e., tissue that is lateral to the lateralmost contact point between the medial strut and the tissue) is distributed laterally and in a gradual manner; and then, when the lateral or outer portions of the foot pads 324 are pressed down and adhered to the tissue 452, the predetermined tissue underneath and at the lateral edges or outer edges of the foot pads 324 is secured (e.g., adhered to the foot pads) in its state in which the stress and/or strain in the predetermined tissue is distributed laterally and in a gradual manner, which seeks to prevent sudden, high sheer stress at the lateral edges (e.g., opposite ends) of the tissue bridge 320.

Figure 6C:
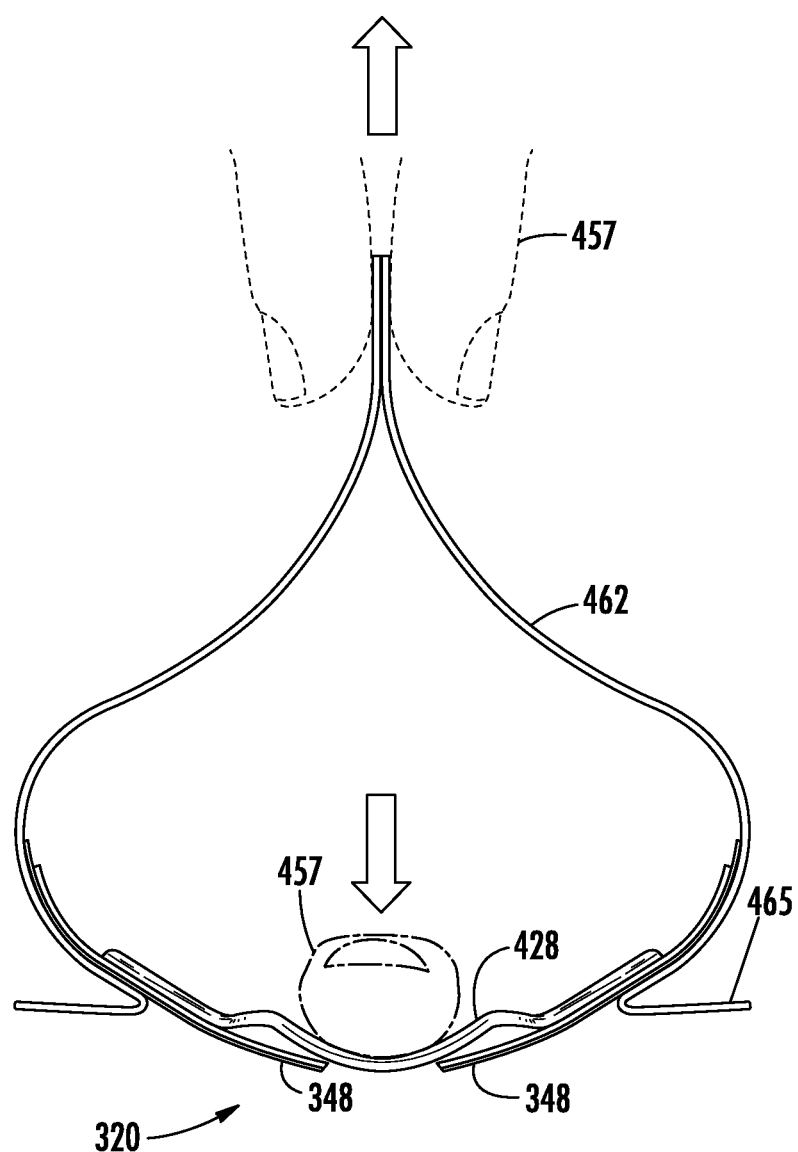
Figure 6D:
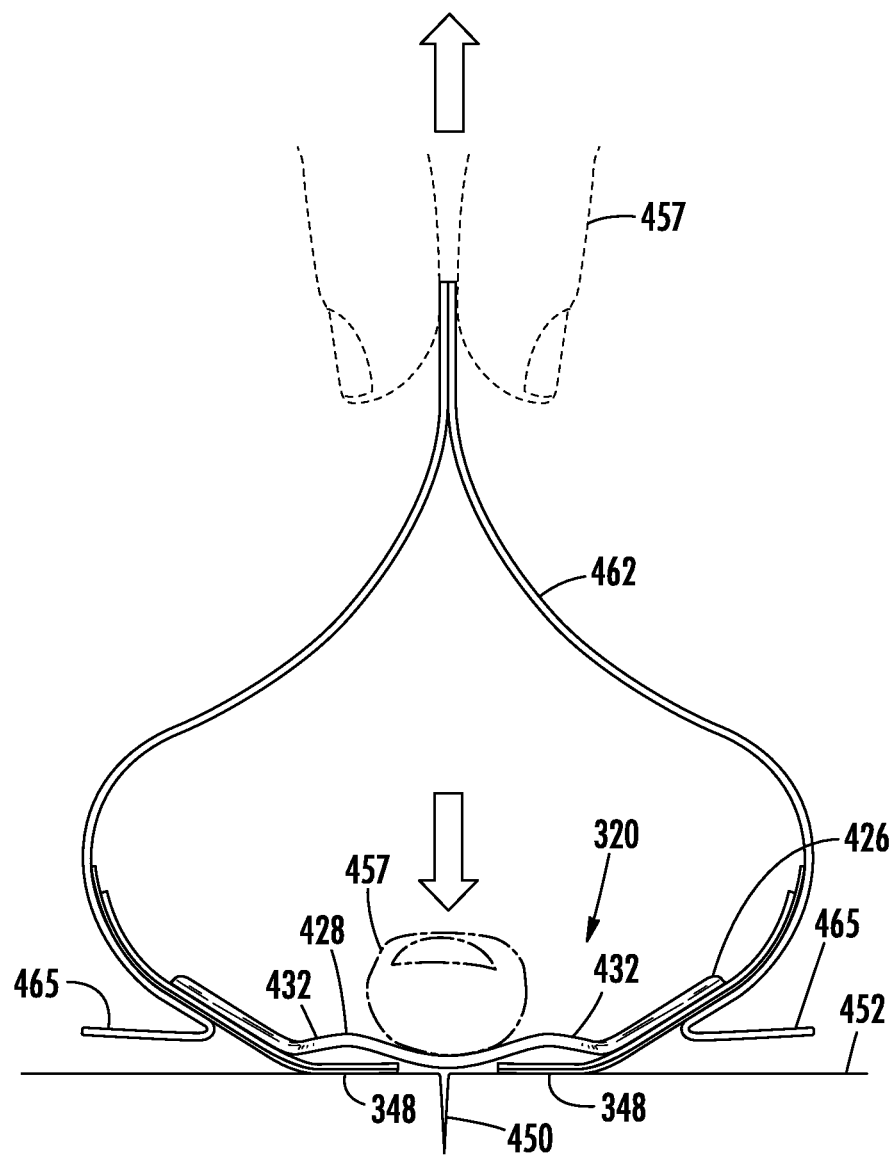
Figure 6E:
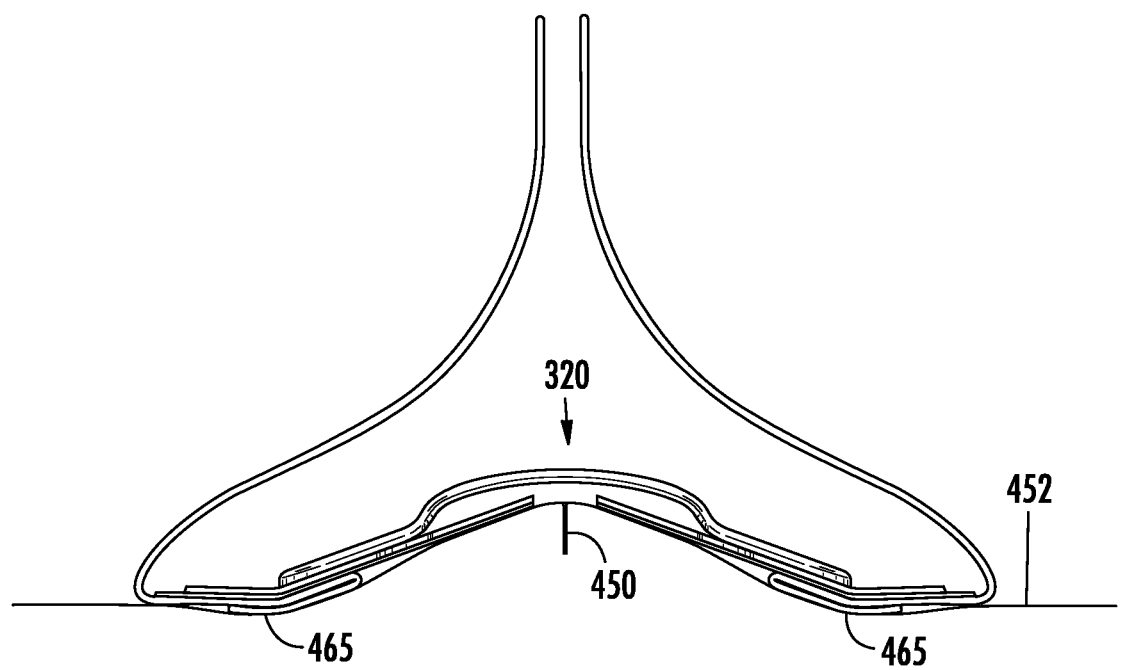
Figure 6F:
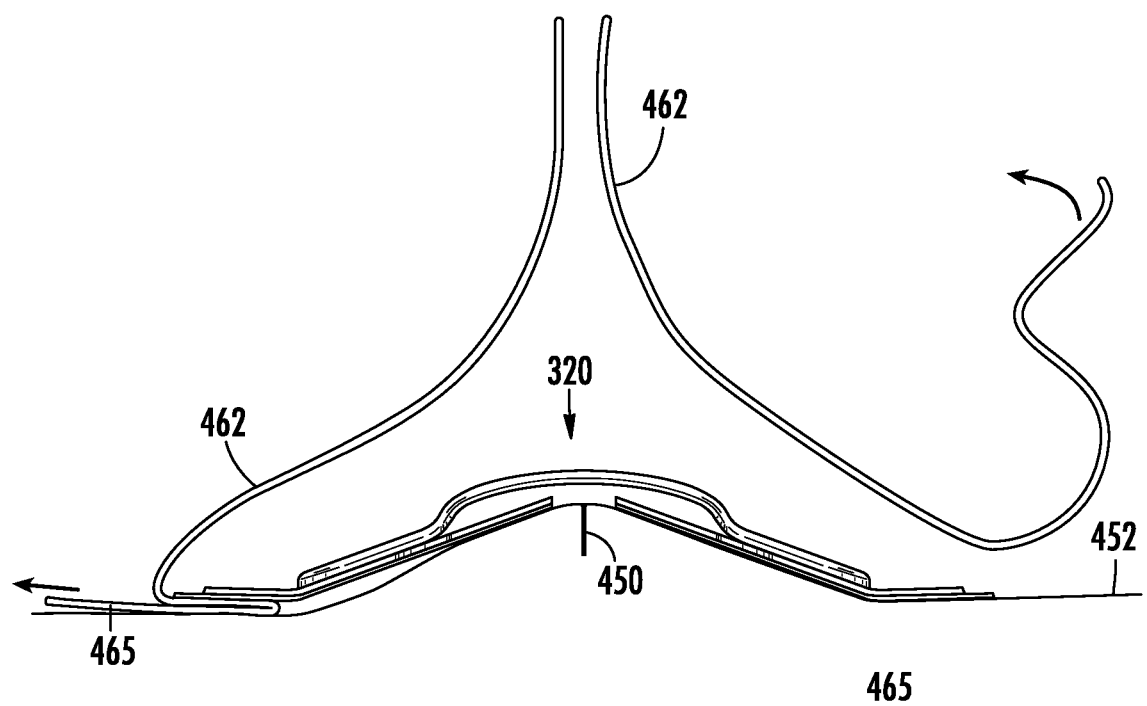

Referring to FIGS. 6E and 6F, the mounting straps 464 can be removed from the tissue bridge 320 by manually grasping and pulling the flaps 465. Then, a user can push down manually on the foot pads 324 with sufficient force to ensure that the pressure-sensitive adhesive layer 42 securely adheres the foot pads to the tissue 452 at opposite sides of the scar or wound 150.

Figure 7:
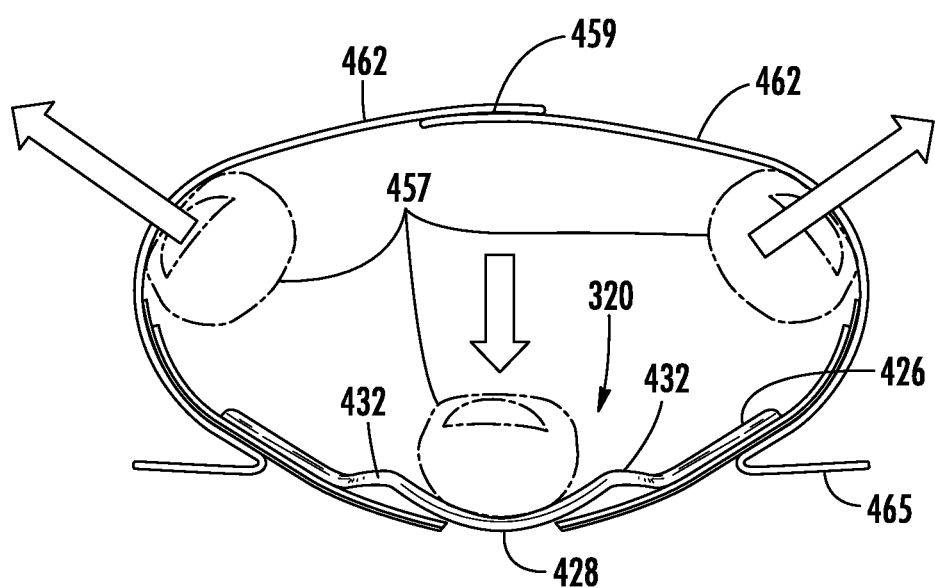
FIG. 7 depicts a step of a method of applying the tissue bridge to a wound, in accordance with a third embodiment of this disclosure.

Referring to FIG. 7, in a third embodiment, the outer ends of the mounting straps 464 can be fixedly connected to one another by way of any suitable mechanical fasteners 459, adhesive material 459, or the like, so that a user may apply the tissue bridge using the fingers 457 of a single hand. Referring to FIGS. 6C and 7, joining the outer ends of the mounting straps 464 together, for example manually and/or with one or more fasteners 459 and/or adhesive material 459, can cause not only the arch 328 to flex, but also the shoulders 432 and foot plates or flanges 426 to flex when the tissue bridge 320 is in its deformed or extended configuration.

Figure 8A:
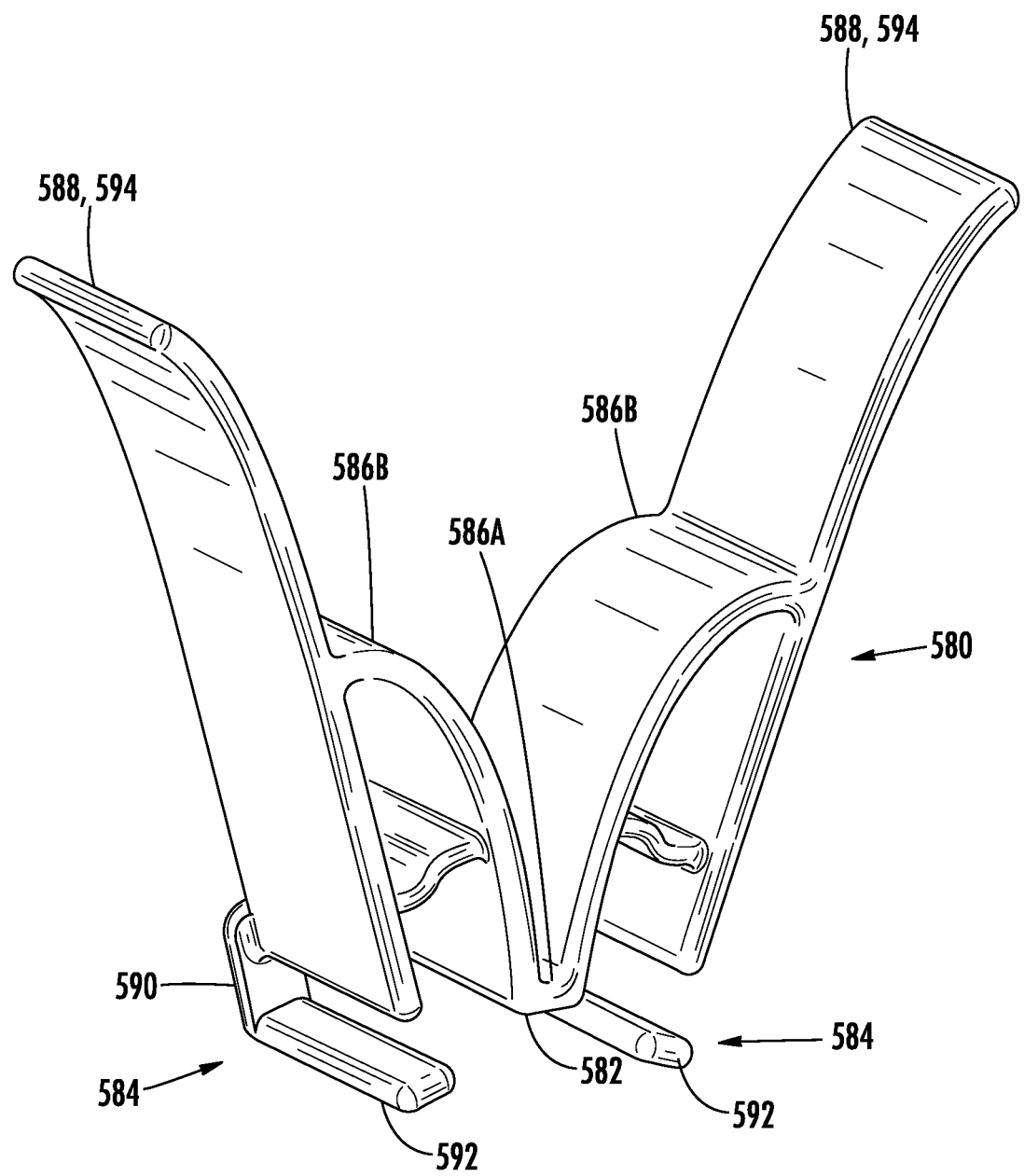
FIG. 8A is an isolated, pictorial view of an applicator tool, in accordance with a fourth embodiment of this disclosure.
Figure 8B:
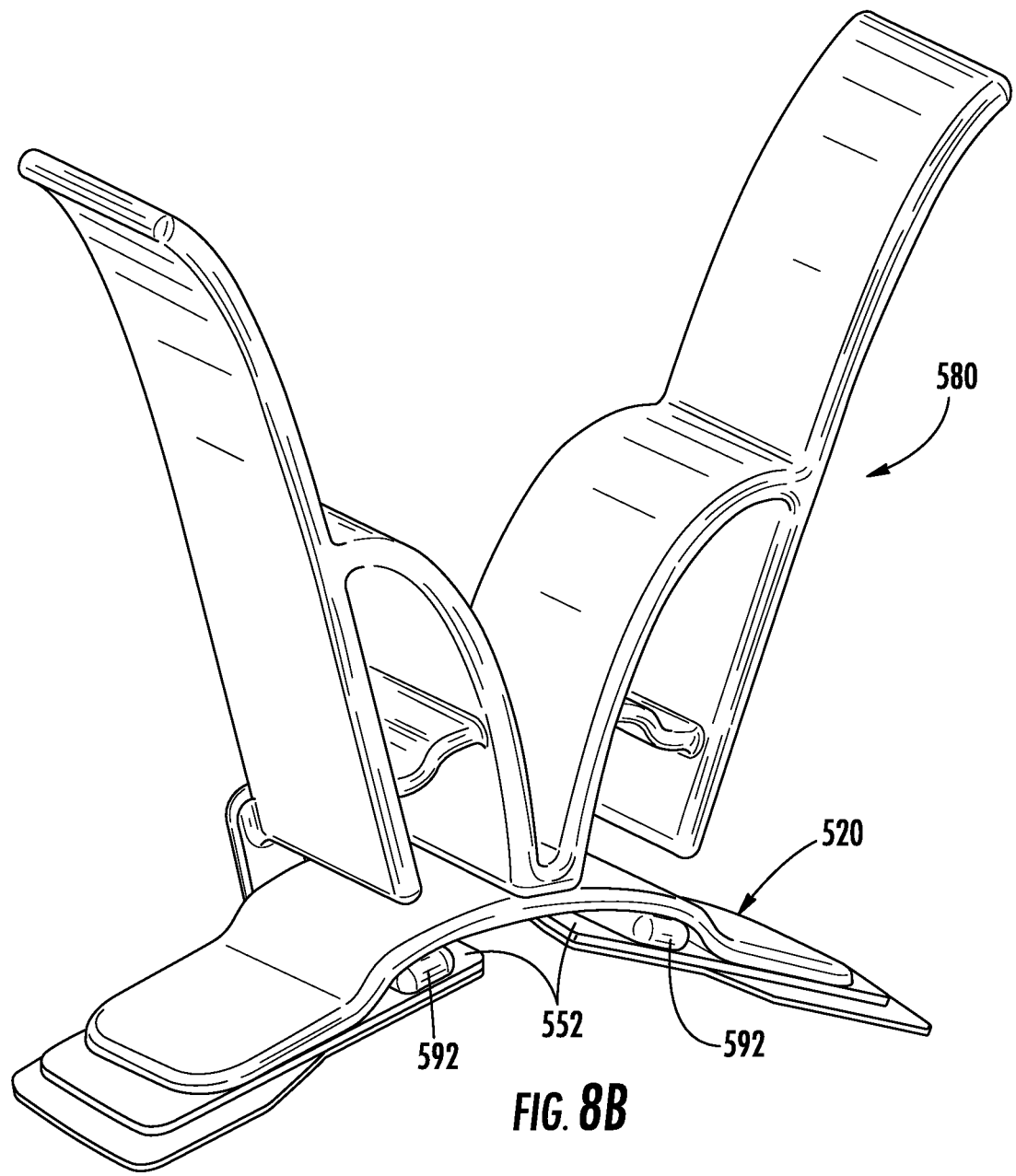
FIG. 8B is a pictorial view of the applicator tool of FIG. 8A mounted to a tissue bridge, in accordance with the fourth embodiment.
Figure 8C:
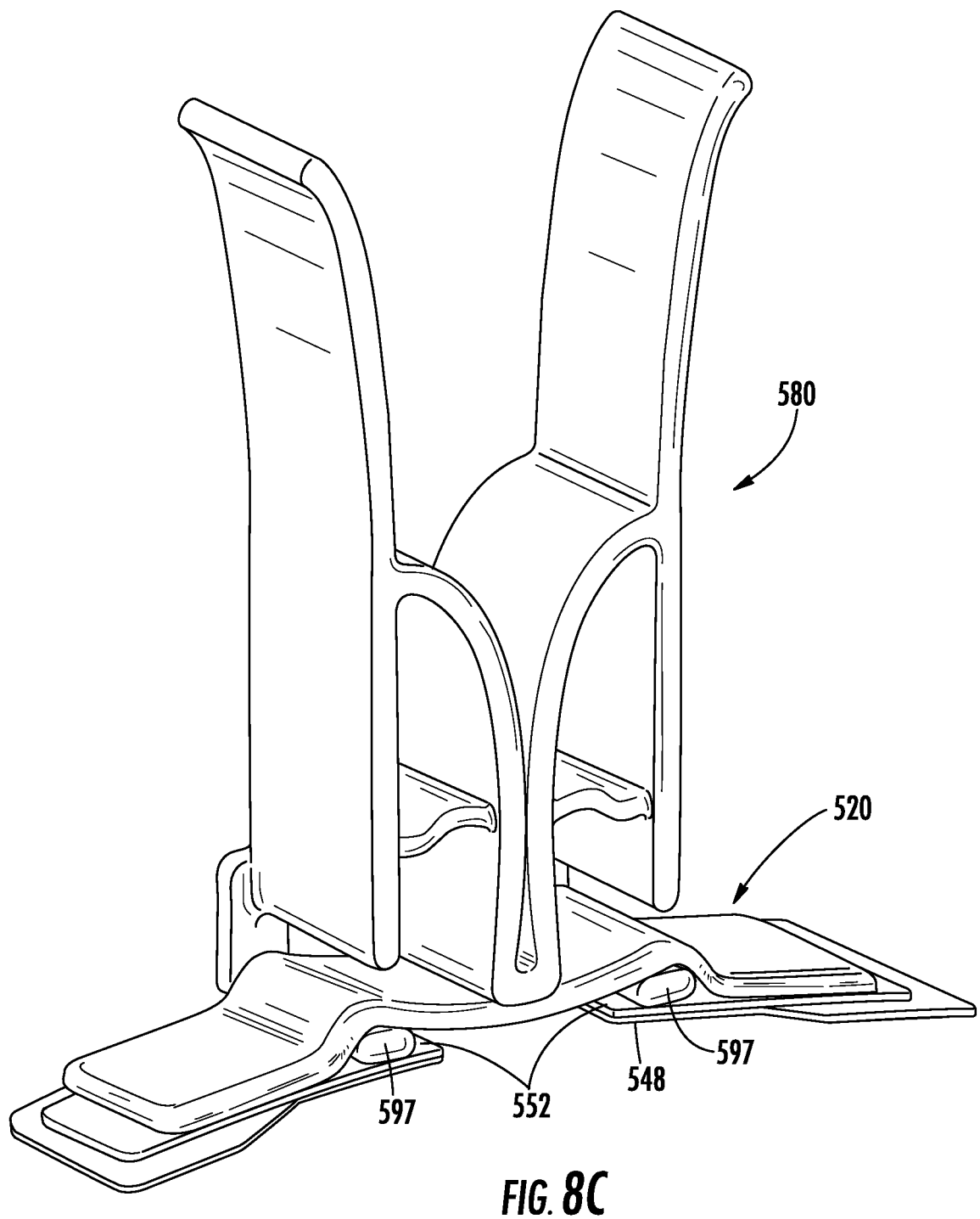
FIG. 8C depicts a step of a method of applying the tissue bridge to a wound, in accordance with the fourth embodiment.

FIG. 8A depicts an applicator tool 580; FIG. 8B depicts the applicator tool 580 in receipt of a tissue bridge 520; and FIG. 8C depicts that the tissue bridge 520 and applicator tool 580 are engaged to one another, and both the tissue bridge and the applicator tool are in their deformed configurations so that the tissue bridge is securely grasped or otherwise held by the applicator tool, in accordance with a fourth embodiment. Referring to FIG. 8A, the contact surface 582 can be a lower end face of a central link 586A, and outer links 586B can extend obliquely upward from the central link 586A to levers 588 or handles 594. The catch parts 584 can include shanks 590 extending downwardly from lower ends of the levers 588 or handles 594. Each catch part 584 can further include at least one protrusion 592 extending outwardly from the lower end of the shank 590 in a direction that can be crosswise to the length of the shank. The protrusions 592 can extend along, or more specifically parallel to, the length of the contact surface 582. Referring to FIGS. 8B and 8C, the protrusions 592 can enter the receptacles 552 (which are partially defined by the medial struts 548) through side openings of the receptacles 552.

Figure 9A:
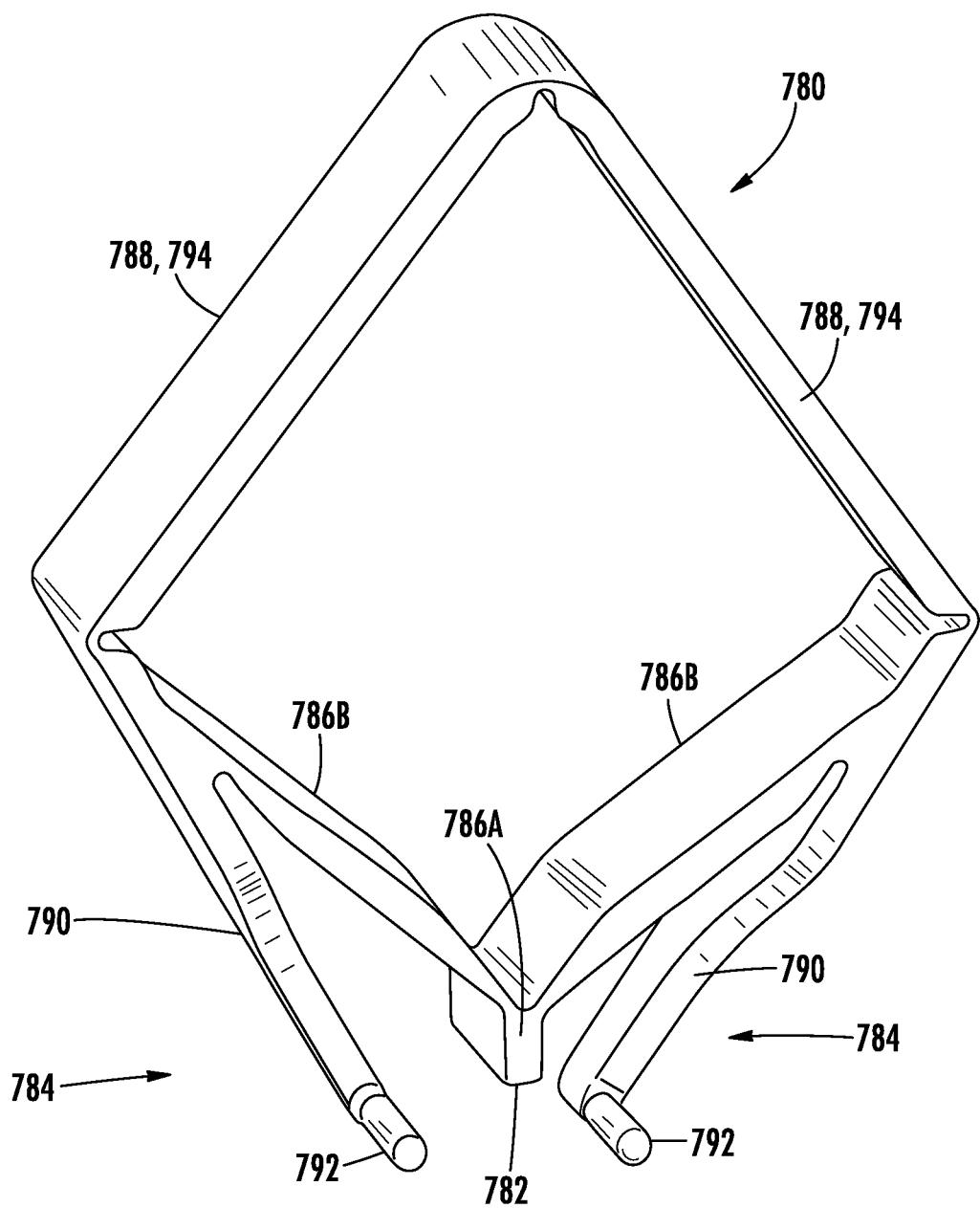
FIG. 9A is an isolated, pictorial view of an applicator tool, in accordance with a fifth embodiment of this disclosure.
Figure 9B:
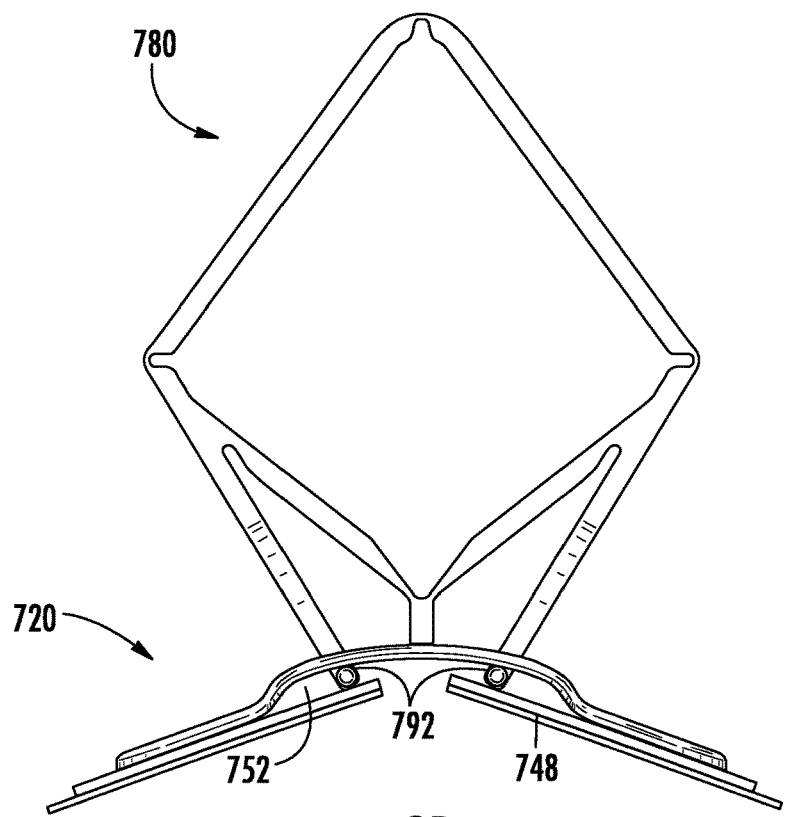
FIG. 9B is a pictorial view of the applicator tool of FIG. 9A mounted to a tissue bridge, in accordance with the fifth embodiment.
Figure 9C:
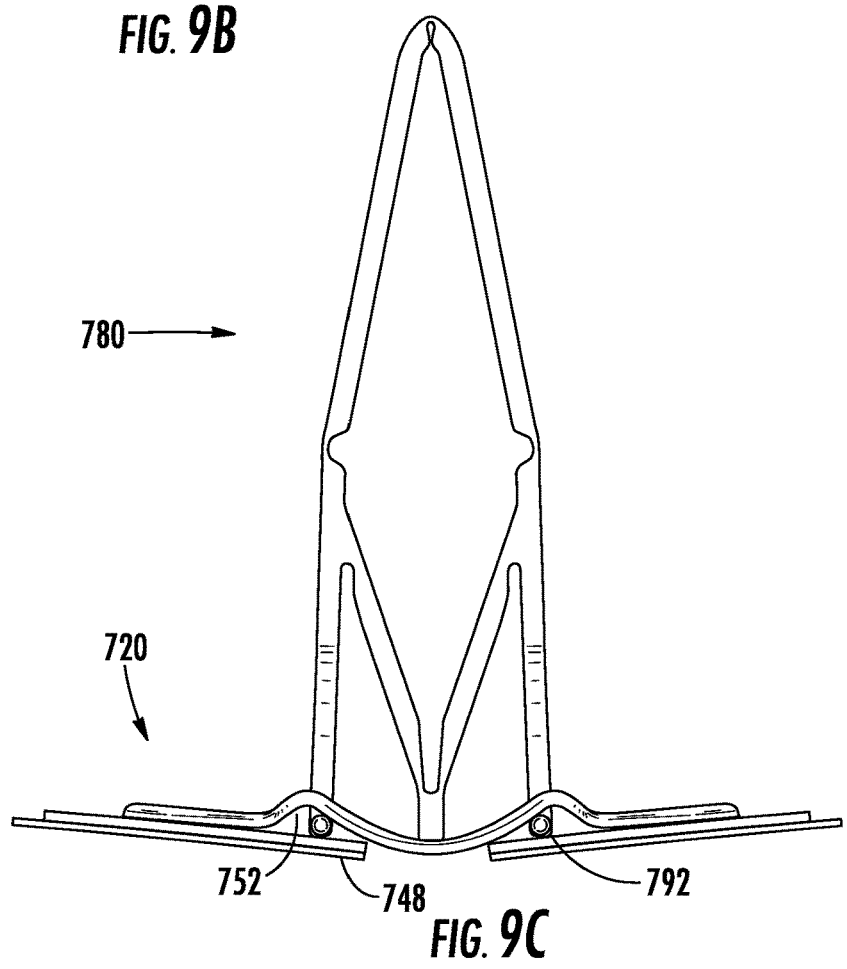
FIGS. 9C and 9D depict a step of a method of applying the tissue bridge to a wound, in accordance with the fifth embodiment.
Figure 9D:
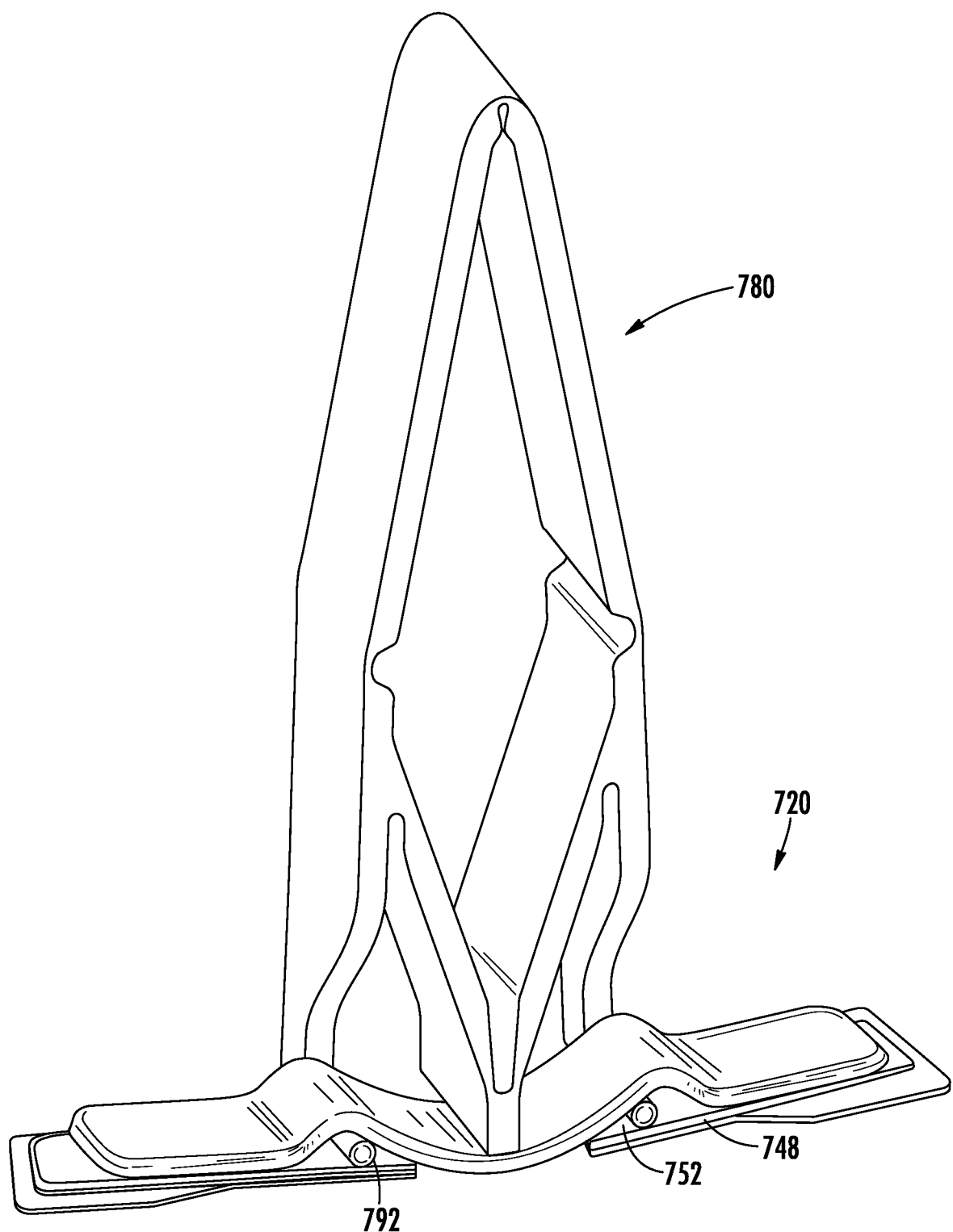

FIG. 9A depicts an applicator tool 780; FIG. 9B depicts the applicator tool 780 in receipt of a tissue bridge 720; and FIGS. 9C and 9D depict that the tissue bridge 720 and applicator tool 780 are engaged to one another, and both the tissue bridge and the applicator tool are in their deformed configurations so that the tissue bridge is securely grasped or otherwise held by the applicator tool, in accordance with a fifth embodiment. Referring to FIG. 9A, the contact surface 782 can be a lower end face of a central link 786A, and outer links 786B can extend obliquely upward from the central link 786A to levers 788 or handles 794 joined to one another at their upper ends. The catch parts 784 can include shanks 790 extending downwardly from lower ends of the levers 788 or handles 794. Each catch part 784 can further include at least one protrusion 792 extending outwardly from the lower end of the shank 790 in a direction that can be crosswise to the length of the shank. The protrusions 792 can extend along, or more specifically parallel to, the length of the contact surface 782. Referring to FIGS. 9B-9D, the protrusions 792 can enter the receptacles 752 (which are partially defined by the medial struts 748) through side openings of the receptacles 752.

Figure 10A:
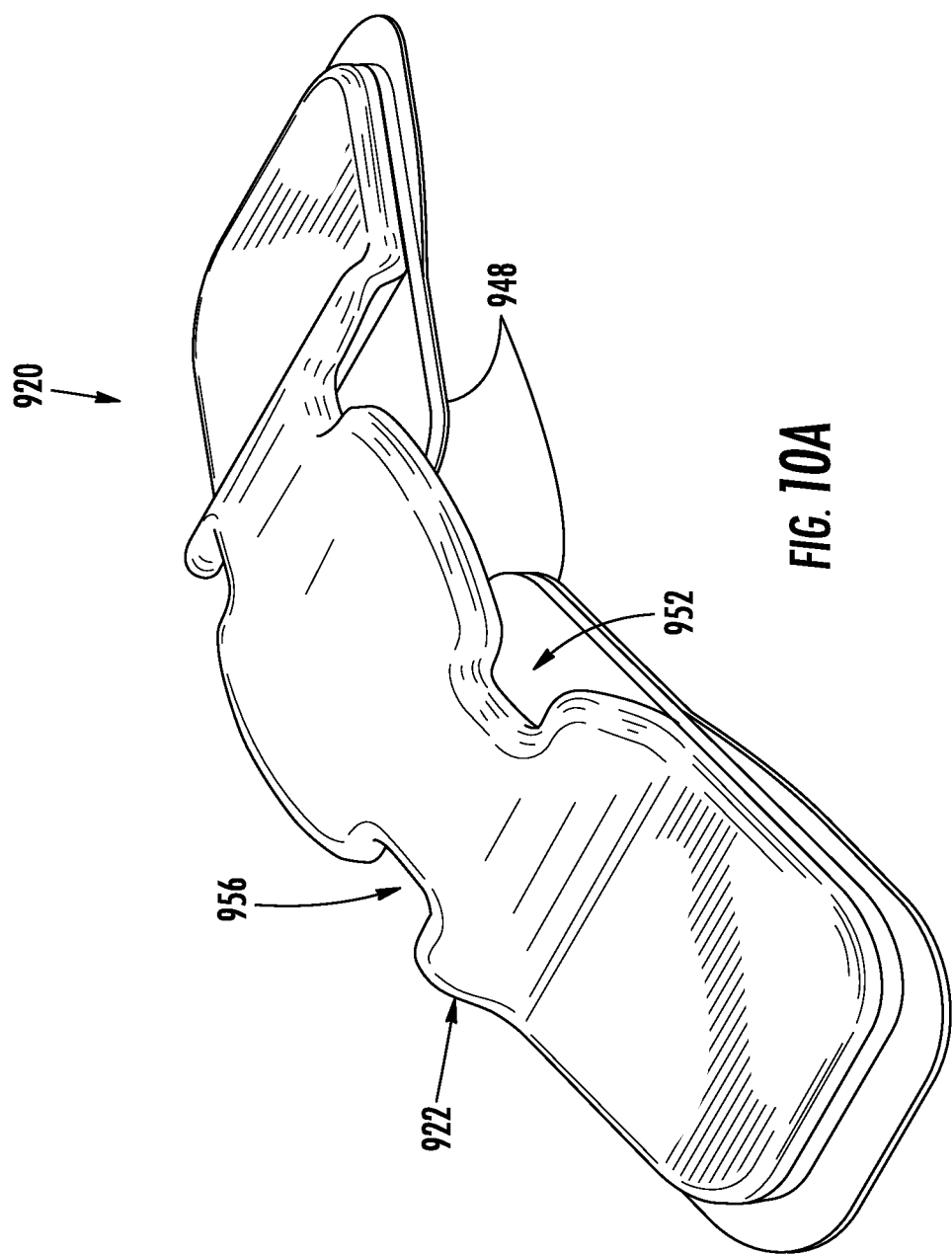
FIG. 10A is a pictorial view of a tissue bridge, in accordance with a sixth embodiment of this disclosure.
Figure 10B:
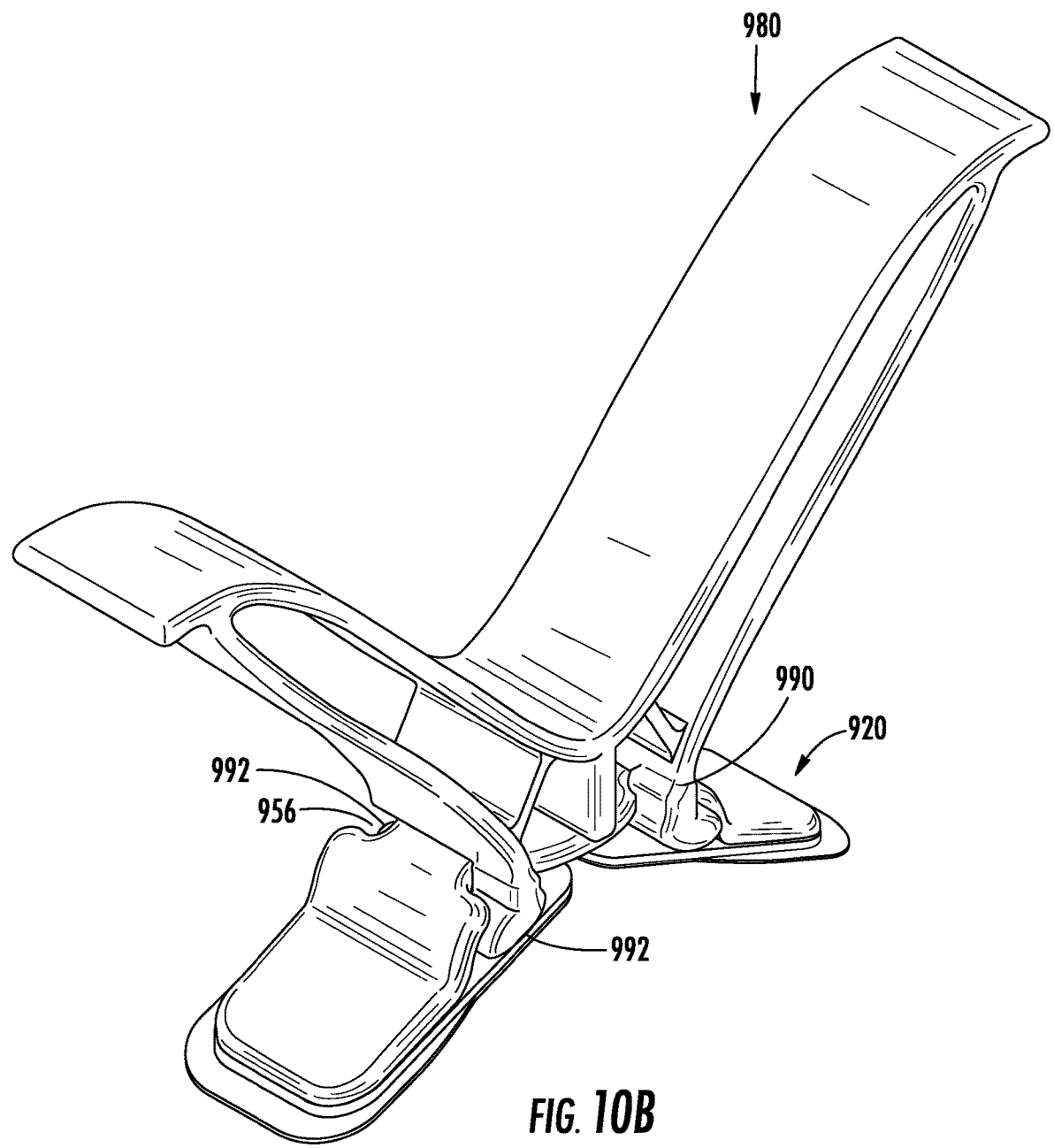
FIGS. 10B and 10C depict an applicator tool mounted to the tissue bridge of FIG. 10A, in accordance with the sixth embodiment.
Figure 10C:
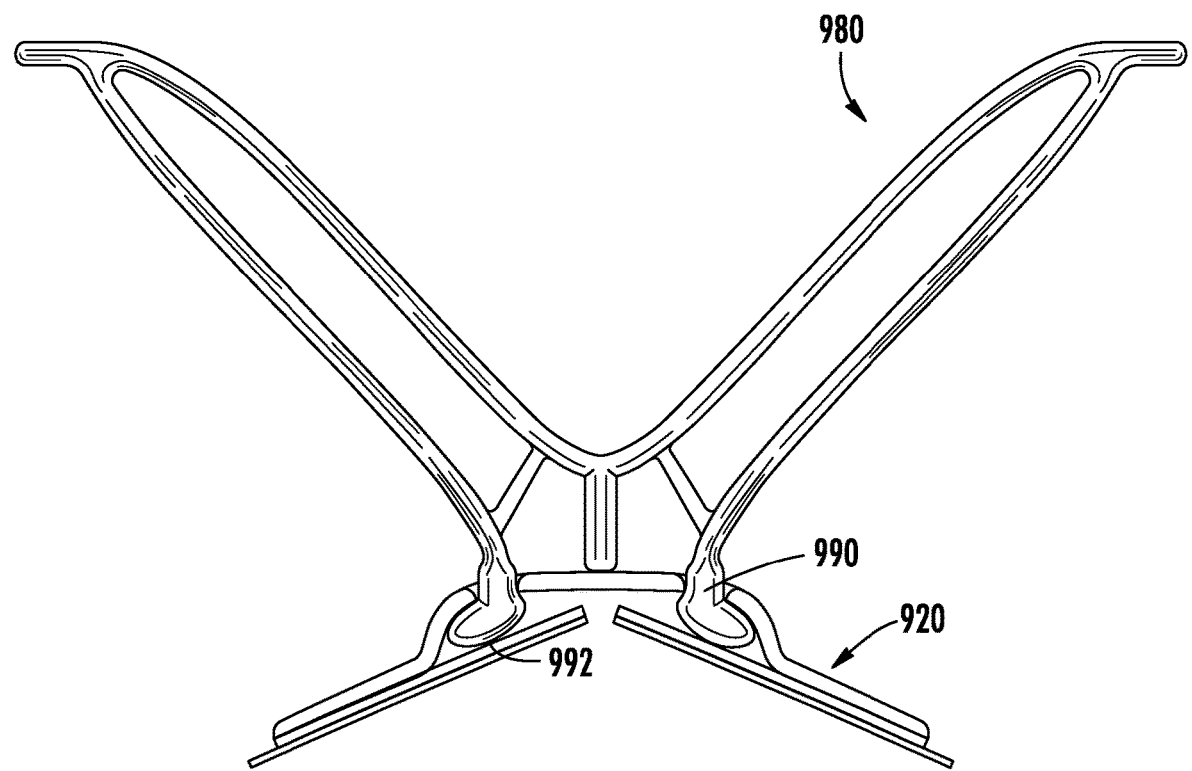
Figure 10D:
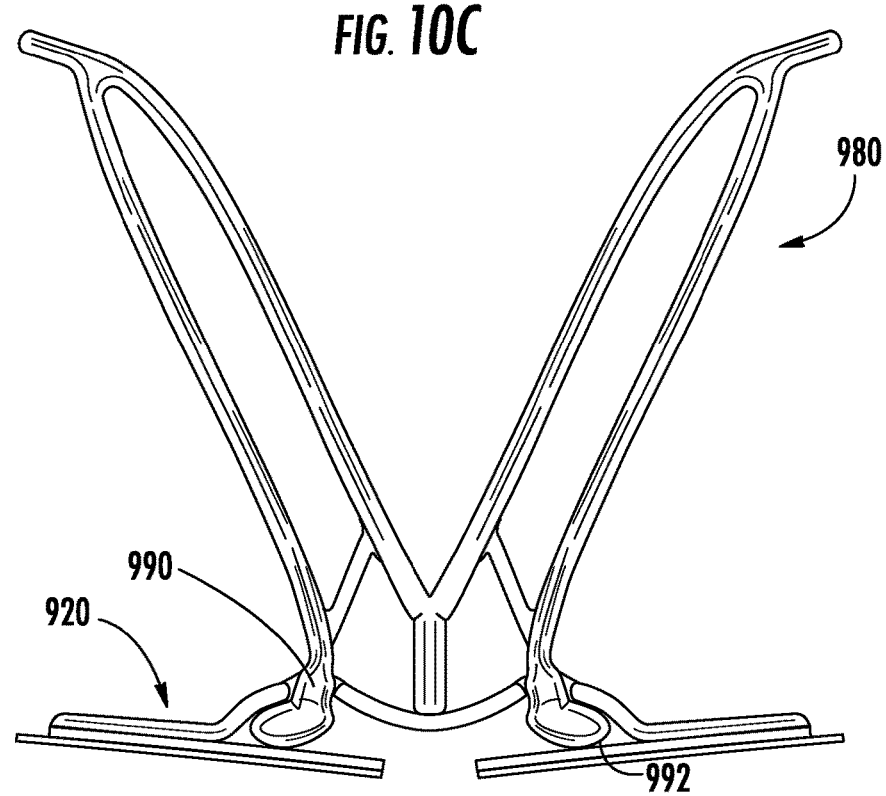
FIGS. 10D and 10E depict a step of a method of applying the tissue bridge to a wound, in accordance with the sixth embodiment.
Figure 10E:
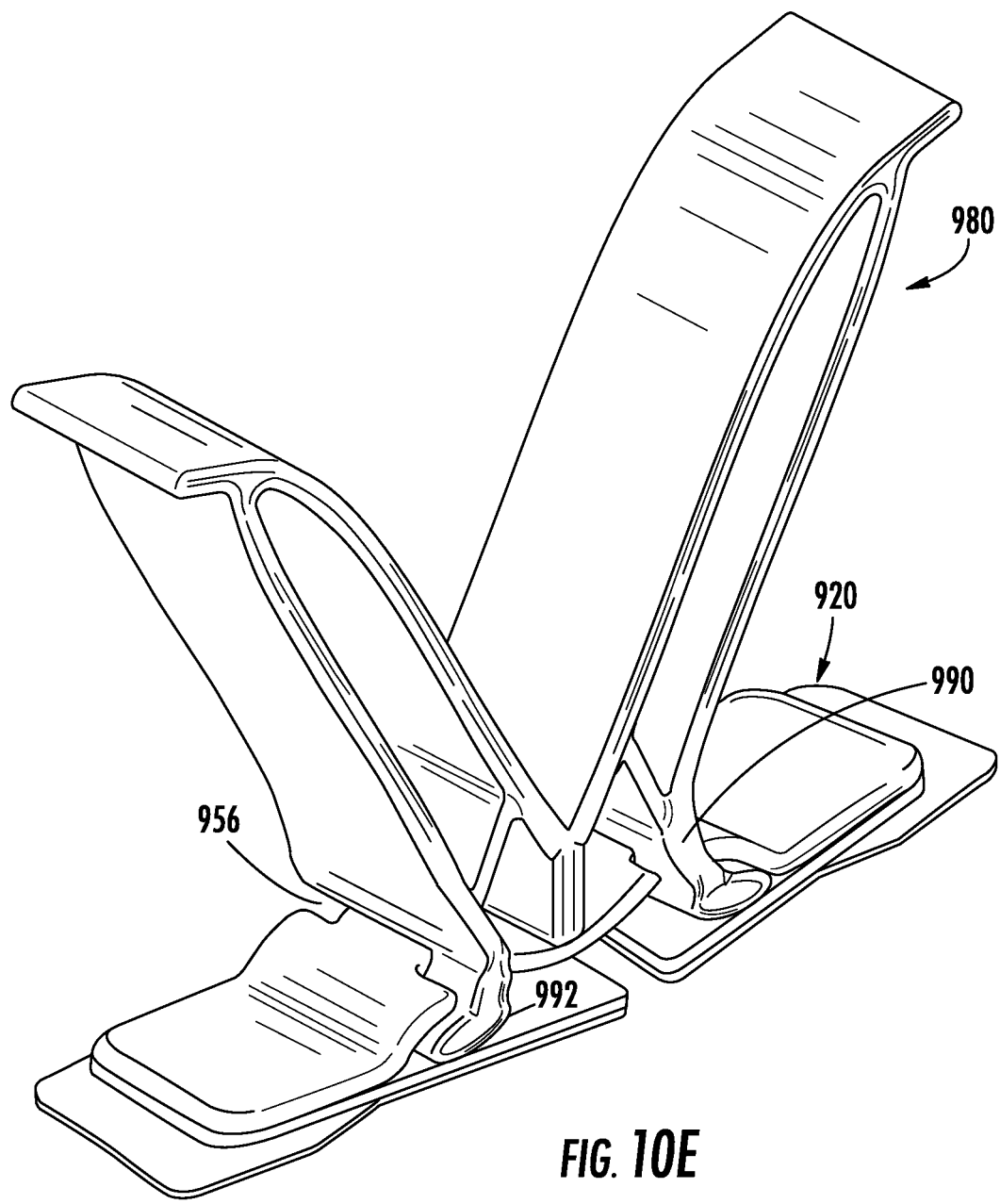

FIG. 10A depicts a tissue bridge 920, in accordance with a sixth embodiment. The catch holes 956, which extend through the body 922 and are open to the receptacles 952, can also be open at the side edges of the body. FIGS. 10B and 10C depict an applicator tool 980 in receipt of the tissue bridge 920; and FIGS. 10D and 10E depict that the engaged together tissue bridge 920 and applicator tool 980 are both in their deformed configurations so that the tissue bridge is securely grasped or otherwise held by the applicator tool, in accordance with the sixth embodiment. The catch part shanks 990 can enter respective catch holes 956 from the side, and the catch part protrusions 992 can enter the receptacles 952 (which are partially defined by the medial struts 948) through side openings of the receptacles 952.

Figure 11A:
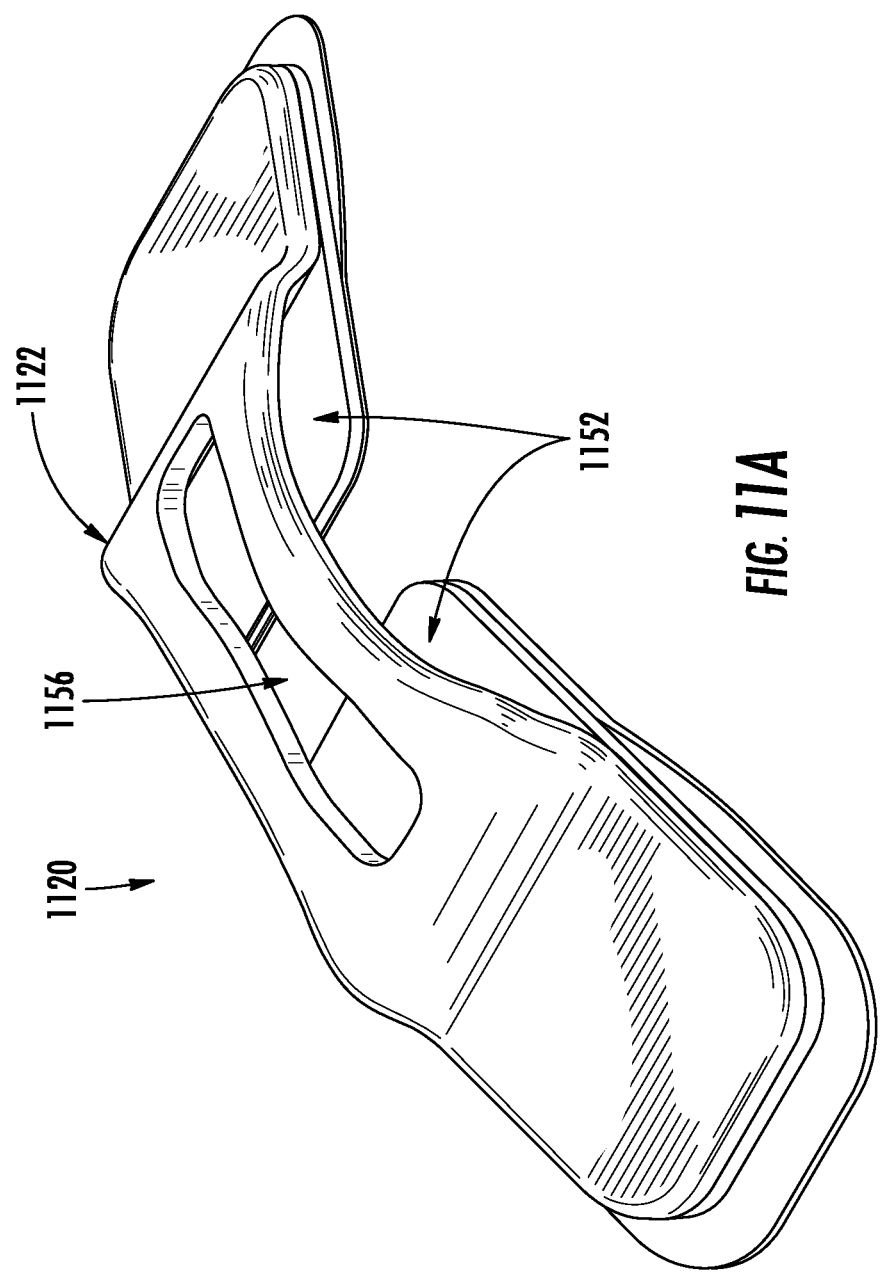
FIG. 11A is a pictorial view of a tissue bridge, in accordance with a seventh embodiment of this disclosure.
Figure 11B:
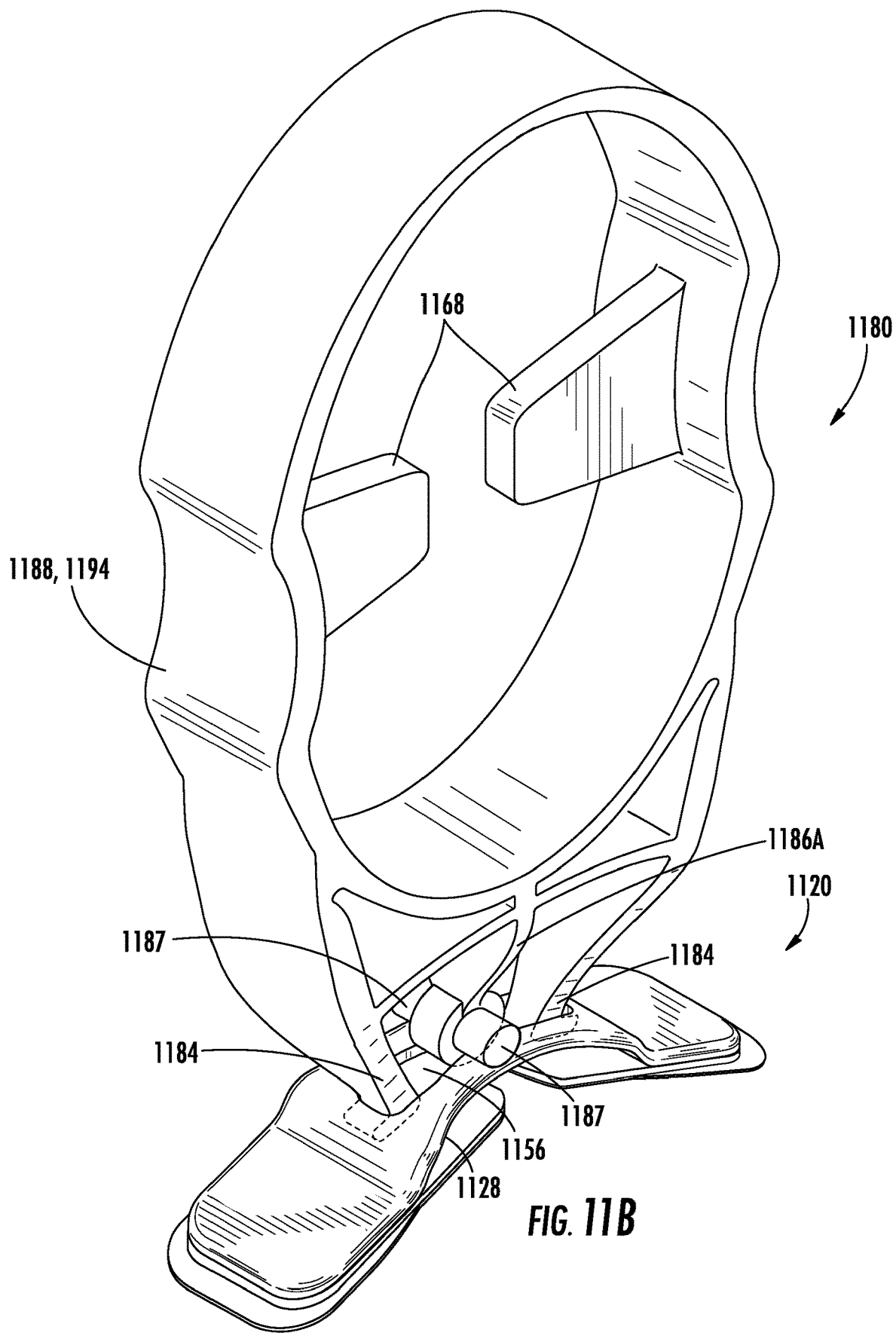
FIGS. 11B and 11C depict an applicator tool mounted to the tissue bridge of FIG. 11A, in accordance with the seventh embodiment.
Figure 11C:
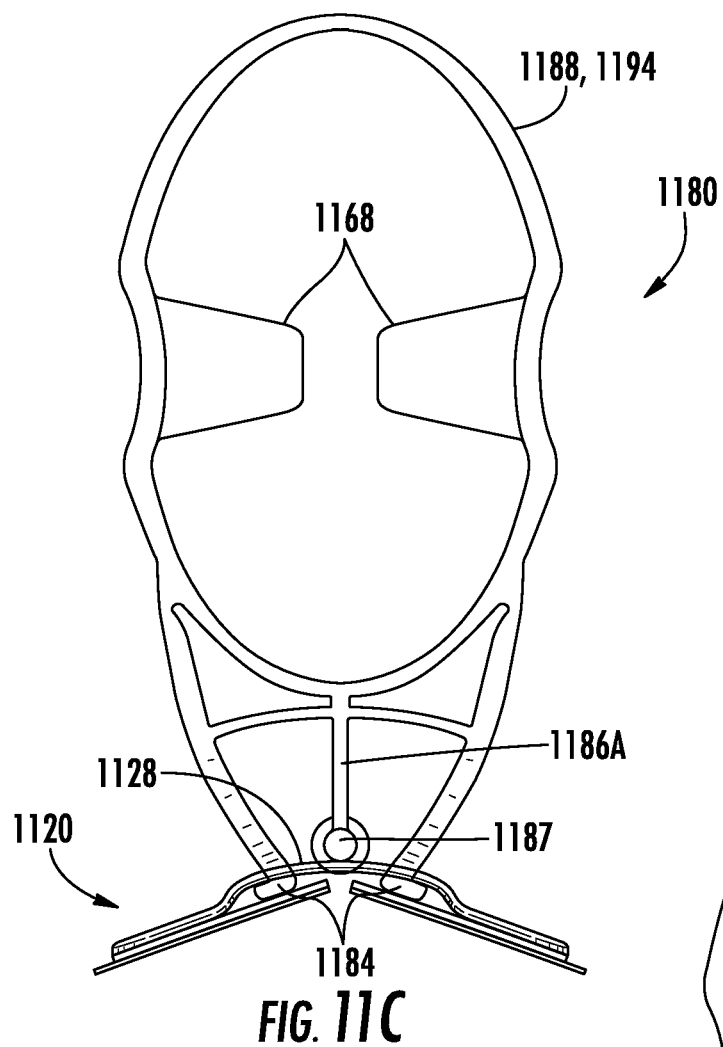
Figure 11D:
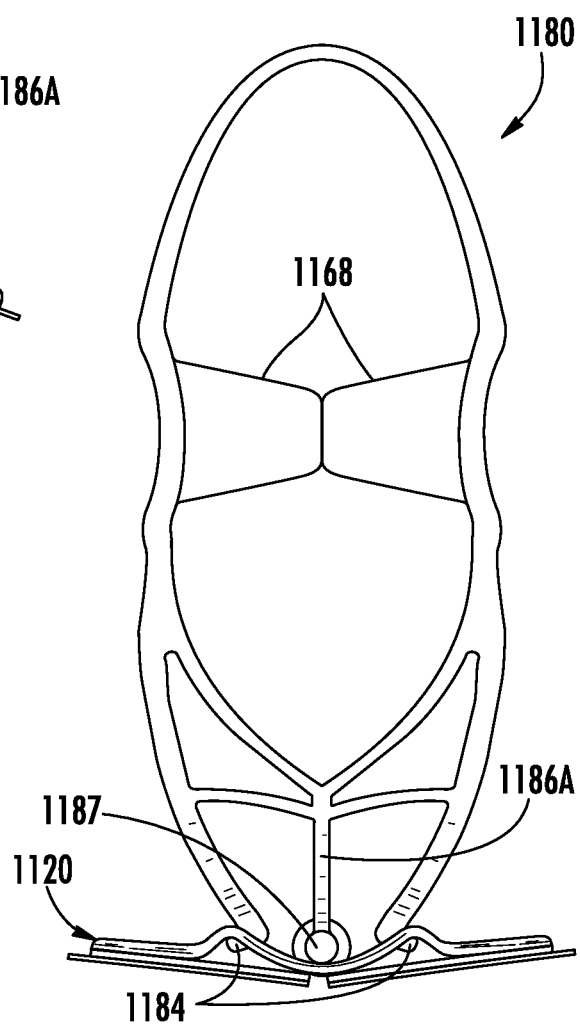
FIGS. 11D and 11E depict a step of a method of applying the tissue bridge to a wound, in accordance with the seventh embodiment.
Figure 11E:
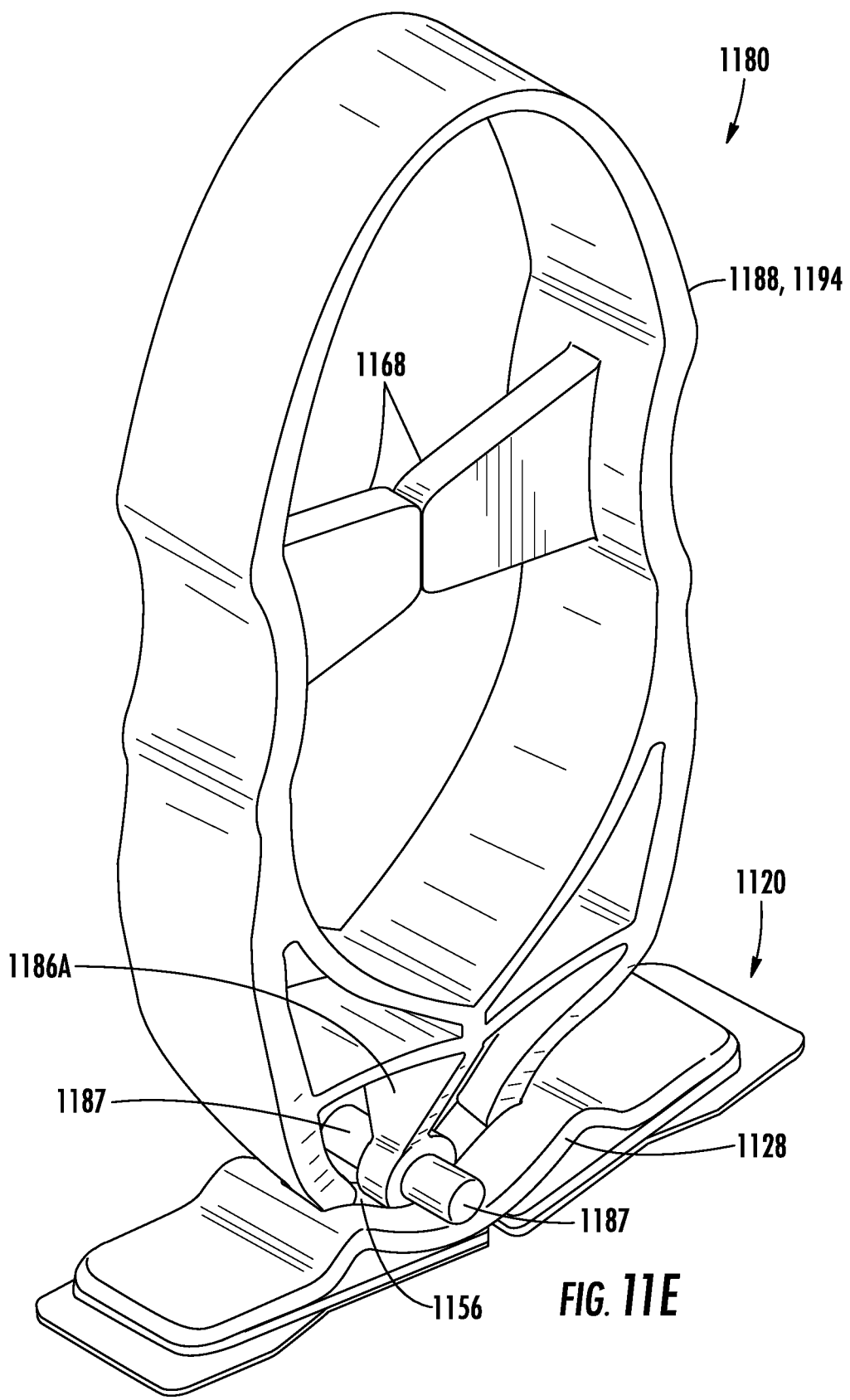

FIG. 11A depicts a tissue bridge 1120 of a seventh embodiment. In the seventh embodiment, the catch holes 1156 are in the form of a slot 1156 that extends through the body 1122 and is open to the receptacles 1152. FIGS. 11B and 11C depict an applicator tool 1180 in receipt of the tissue bridge 1120; and FIGS. 11D and 11E depict that the engaged together tissue bridge 1120 and applicator tool 1180 are both in their deformed configurations so that the tissue bridge is securely grasped or otherwise held by the applicator tool, in accordance with the seventh embodiment. The catch parts 1184 extend downwardly through the slot 1156. An enlarged section of the lower end of the applicator tool's central link 1186A fits into the slot 1156, and protrusions 1187 extending from opposite sides of the lower end of the central link 1186A engage against the upper surfaces of the arch 1128 at opposite sides of the slot 1156. The levers 1188 or handles 1194 can be joined to one another at their upper ends, and tabs 1168 or other suitable structures extending inwardly from the levers 1188 or handles 1194 can engage one another to restrict any further inward movement of the levers 1188 or handles 1194 when the engaged together tissue bridge 1120 and applicator tool 1180 are both in their deformed configurations. For example, the tabs 1168 and or other suitable features can be configured to come into contact with one another when the desired degree of deformation is reached in the tissue bridge 1120, thereby seeking to prevent over distortion of the tissue bridge.

As at least alluded to above, the tissue bridges and applicator tools of the third through seventh embodiments can be cooperatively configured with respect to one another at least generally like the tissue bridges and applicator tools of first embodiment. For example and referring back to FIGS. 4C and 4D, the tissue bridges and applicator tools of the third through seventh embodiments can be cooperatively configured to function like tissue bridges and applicator tools of the first embodiment with regard to the catches or protrusions 92 engaging and pushing (e.g., deflecting) the medial struts 48 downwardly.

Figure 12B:
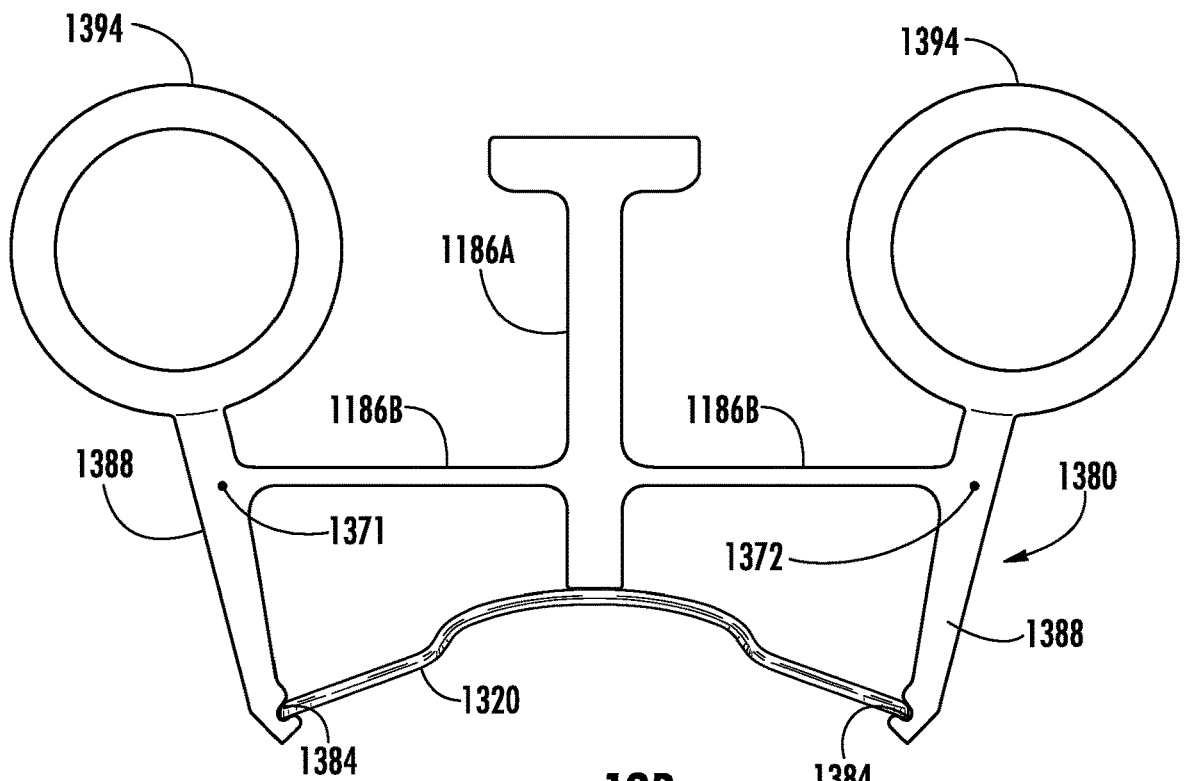
Figure 12C:
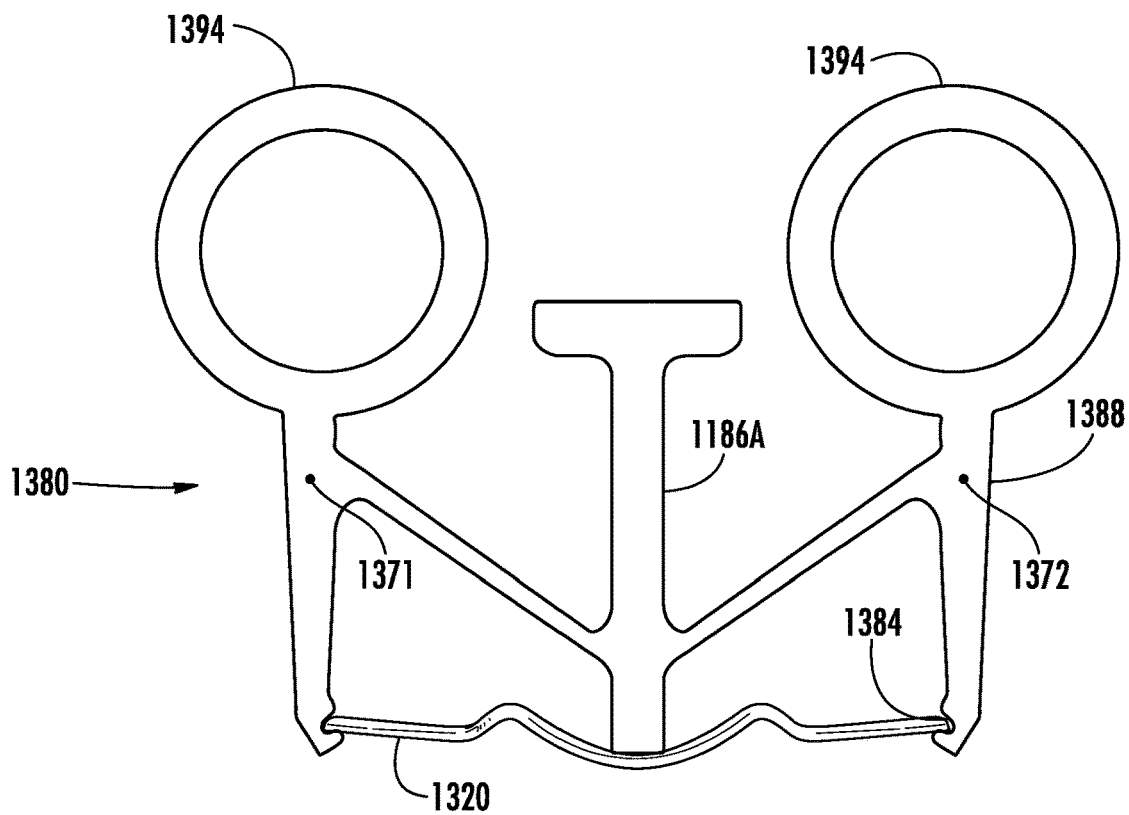
FIGS. 12C and 12D depict a step of a method of applying the tissue bridge to a wound, in accordance with the eighth embodiment.
Figure 12D:
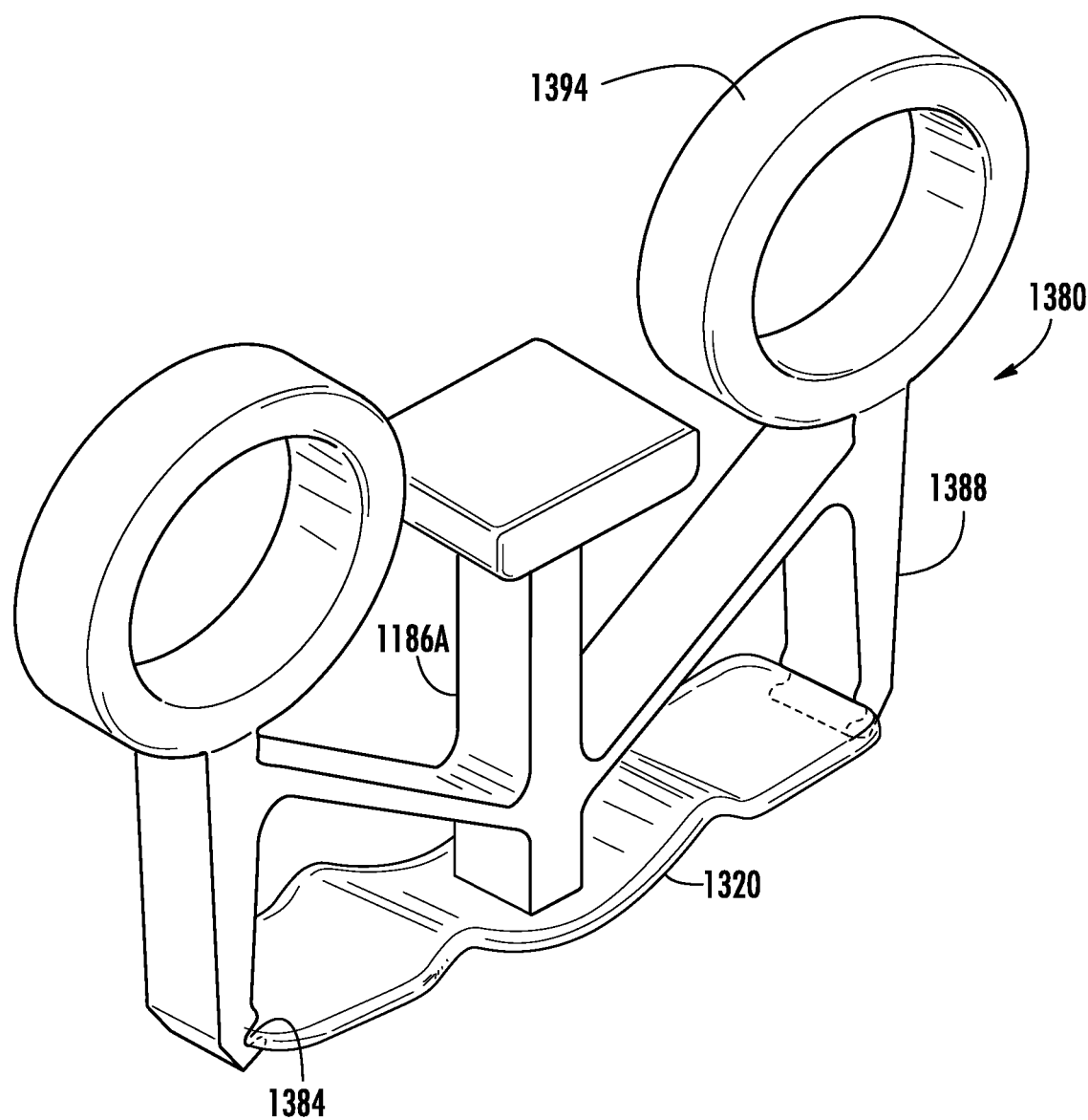

FIGS. 12A and 12B depict an applicator tool 1380 in receipt of a tissue bridge body 1320; and FIGS. 12C and 12D depict that the engaged together applicator tool 1380 and tissue bridge body 1320 are both in their deformed configurations so that the tissue bridge body is securely grasped or otherwise held by the applicator tool, in accordance with an eighth embodiment. The catch parts 1384 can comprise receptacles, or more specifically slots, into which opposite ends of the tissue bridge body 1320 respectively extend. The levers 1388 or handles 1394 can have loops, partial loops, handles and/or other suitable features fixedly connected at their upper ends or therealong for receiving fingers of an operator of the tool 1380, and another finger can be pressed downwardly on a platform and/or other suitable features at the upper end of the central link 1186A.

The applicator tool 1380 can have a first body comprising a first lever 1388 connected to a first catch part 1384, and a second body comprising a second lever 1388 connected to a second catch part 1384. Referring to FIGS. 12B and 12C, the reconfigurable linkage (e.g., linkages 1186A, 1186B) can connect the first and second bodies to one another, and be configured so that (e.g., simultaneously): the first and second bodies are pivotable relative to one another about first and second axes 1371, 1372, respectively; and the first and second axes 1371, 1372 are movable toward and away from one another. The levers 1388, handles 1394, linkage (e.g., linkages 1186A, 1186B) and/or other suitably associated features can have a variety of different configurations to assist in ergonomically optimized use, for example by comprising partial or complete rings, recesses shaped to accept the user's digit(s) and/or other suitable features.

Figure 13A:
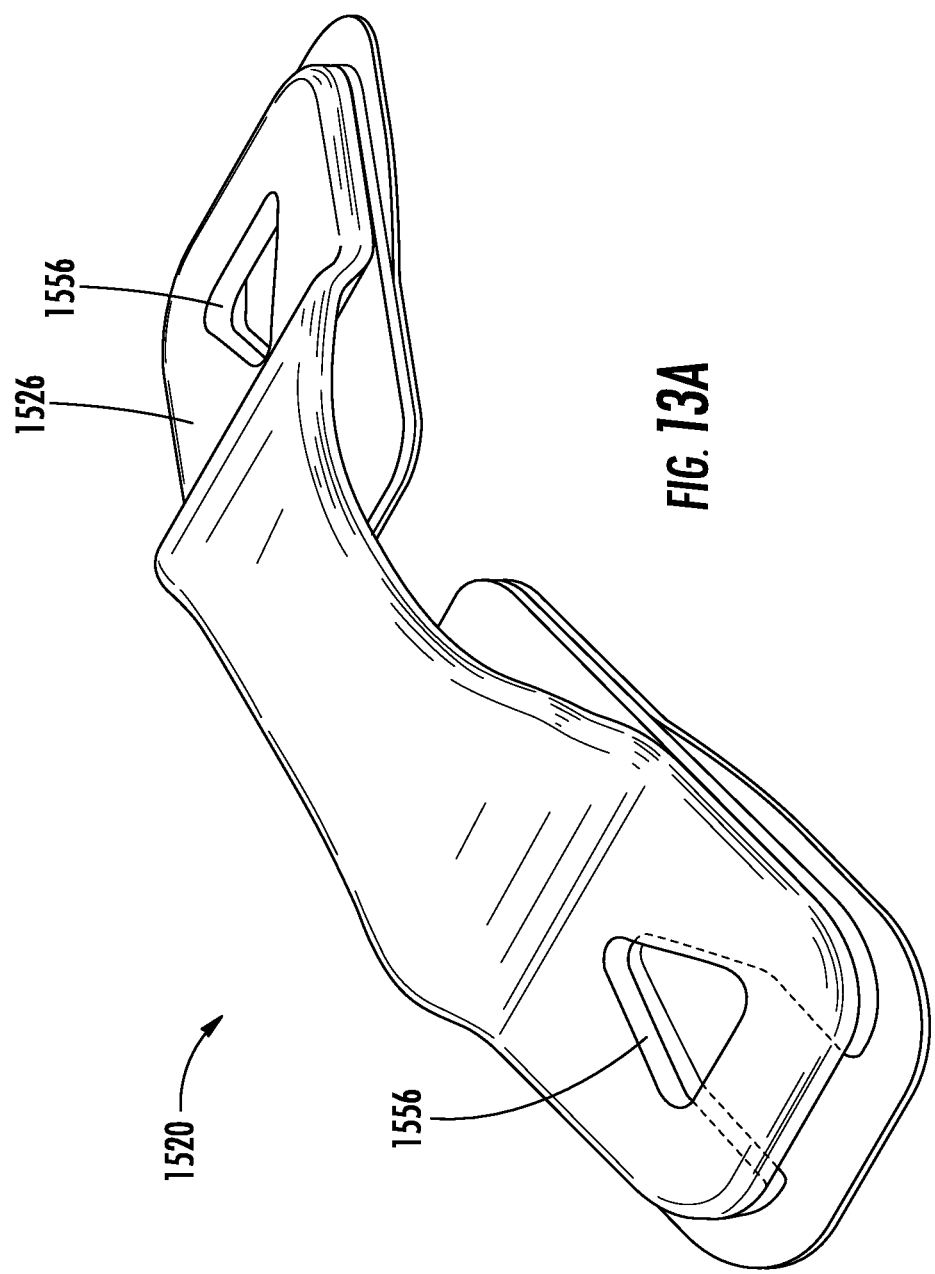
Figure 13C:
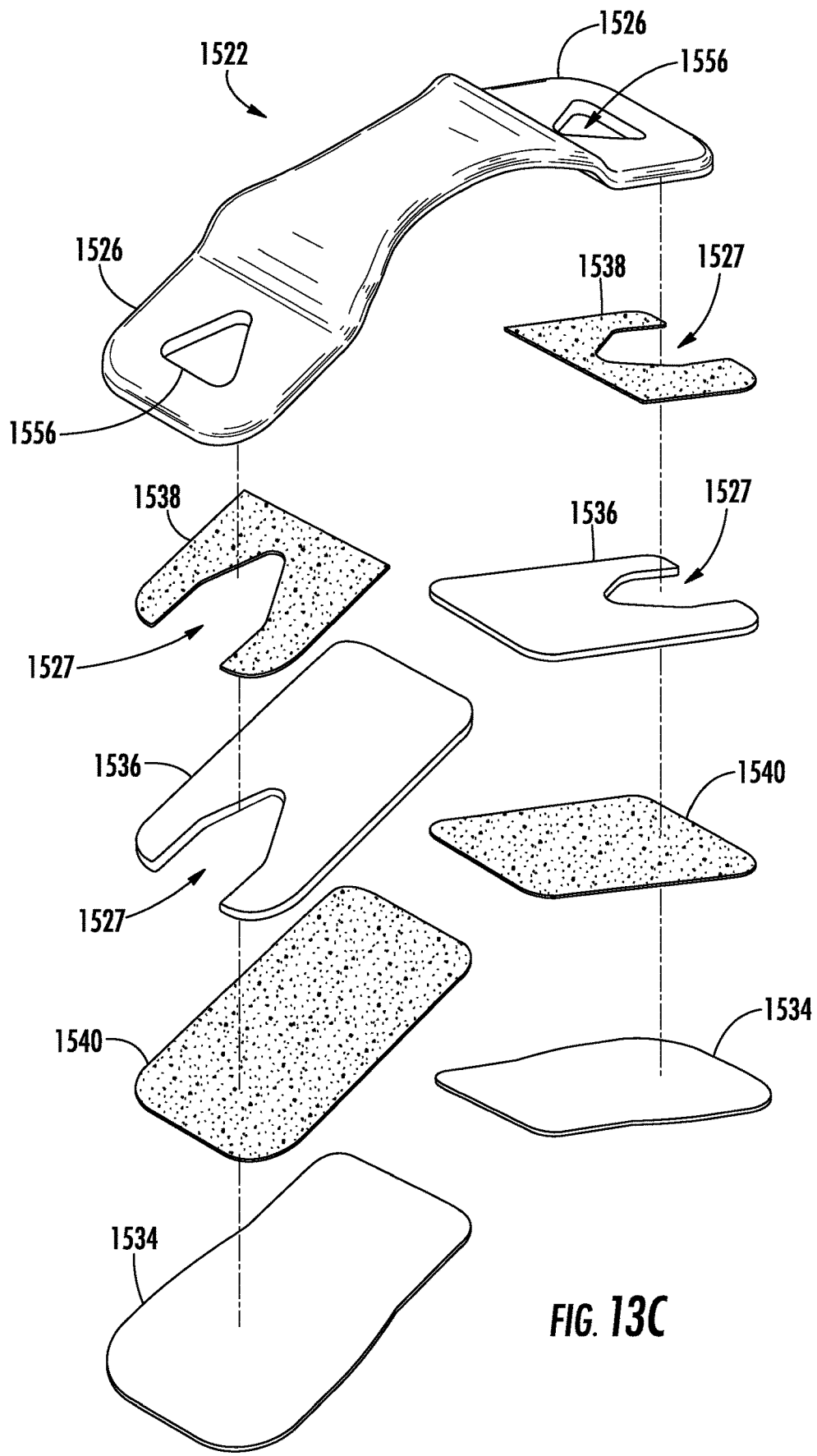
FIG. 13C is an exploded view of the tissue bridge, in accordance with the ninth embodiment.

FIGS. 13A and 13B depict a tissue bridge 1520 of a ninth embodiment. As shown in FIG. 13A-13C, the catch holes 1556 can extend through the foot plates or flanges 1526. Referring to the exploded view of FIG. 13C, the tissue bridge 1520 includes inner and intermediate adhesive layers 1538, 1540 respectively between and fixedly connecting the inner sheets 1536 to the flanges 1526, and the outer sheets 1534 to the inner sheets. The tissue bridge 1520 can further include lower holes 1527 in the inner adhesive layers 1538 and inner sheets 1536. The lower holes 1527 can be open to the catch holes 1556, and the lower holes 1527 can also extend outwardly to be open at the outer edges of the inner adhesive layers 1538 and inner sheets 1536. As discussed in greater detail below, the catch holes 1556 can mate with respective portions of applicator tools. In addition and/or alternatively, the holes 1527, 1556 (e.g., open widows) can provide pathways for ventilation/moisture transmission.

Figure 13D:
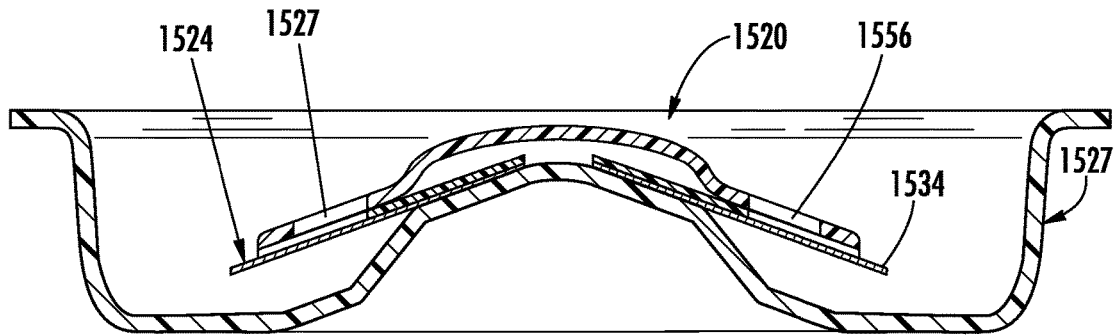
FIG. 13D is a cross-sectional view of at least a portion of a kit or package comprising the tissue bridge at least partially contained in a tray, in accordance with the ninth embodiment.
Figure 13E:
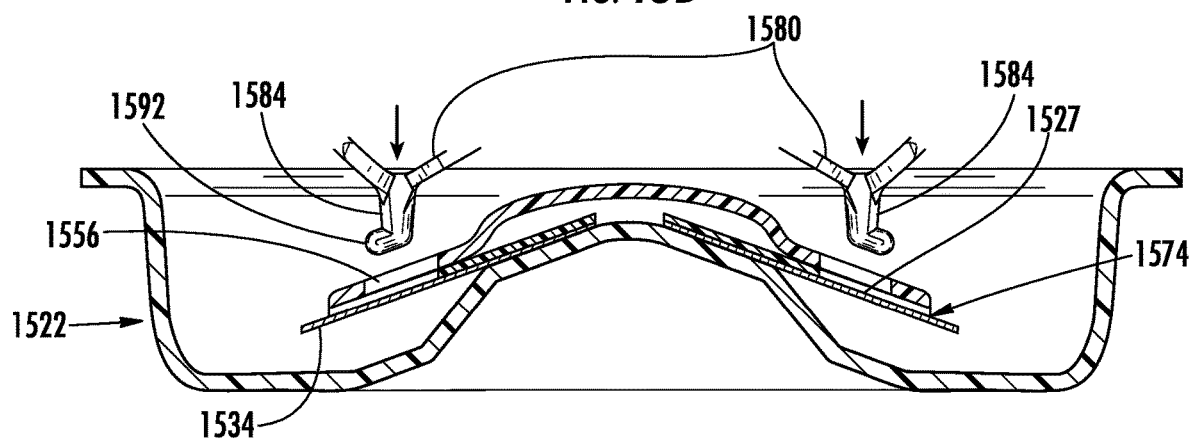
FIGS. 13E and 13F depict a sequence of steps of a method of using an applicator tool to remove a tissue bridge from the tray, in accordance with the ninth embodiment.
Figure 13F:
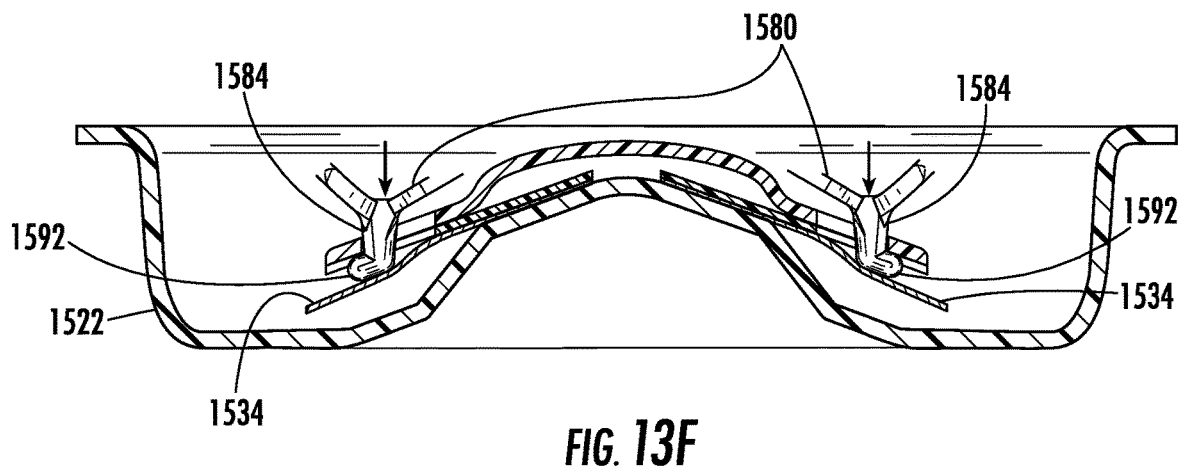

FIG. 13D depicts the tissue bridge 1520 mounted in a tray 1622, and FIGS. 13E and 13F depict some of the steps of a method of using the applicator tool 1580 to remove the tissue bridge from the tray 1622, in accordance with the ninth embodiment. For example, in response to relative movement causing increased closeness between the applicator tool 1580 and the tray 1622, or more specifically movement of the applicator tool toward the tissue bridge 1520 mounted in the tray, the tool catch parts 1584 can enter the inner lower holes 1527 by way of the outer holes 1556, so that respective portions of the outer sheets 1534 can be engaged by, and pushed (e.g., stretched) outwardly by, the protrusions 1592; and the catch parts 84 become releasably connected to the tissue bridge 1520. The inner lower holes 1527 can further extend through other layers of the foot pads 1524. In the ninth embodiment, when the applicator tool 1580 is operated to cause the both the applicator tool and the tissue bridge 1520 to be in their deformed configurations so that the tissue bridge is securely grasped or otherwise held by the applicator tool, not only the arch 1528 flexes, but also the shoulders 1532 and foot plates or flanges 1526 flex, similarly to as shown in FIGS. 6C and 7.

Figure 14:
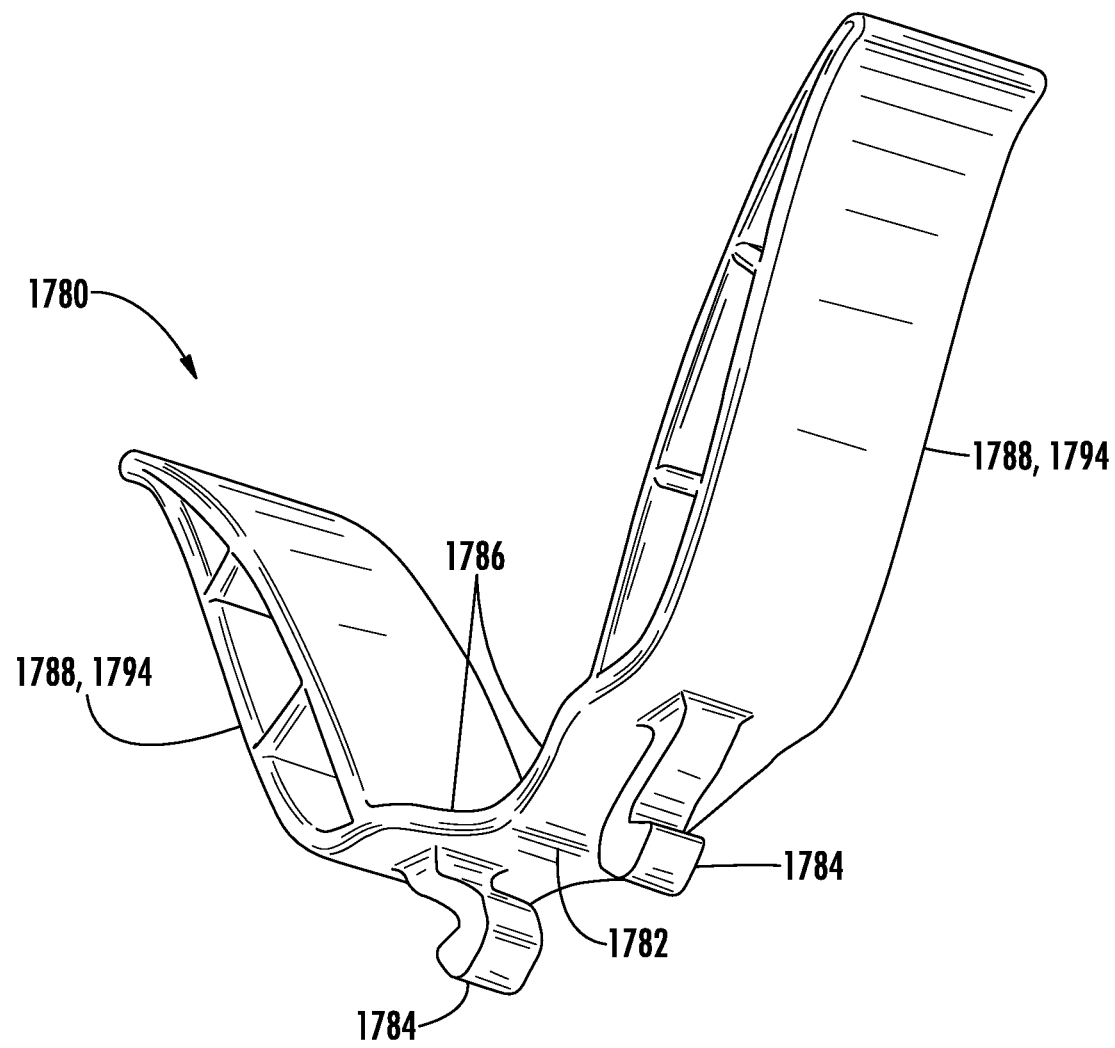
FIG. 14 is a bottom pictorial view of an applicator tool, in accordance with a tenth embodiment.
Figure 15:
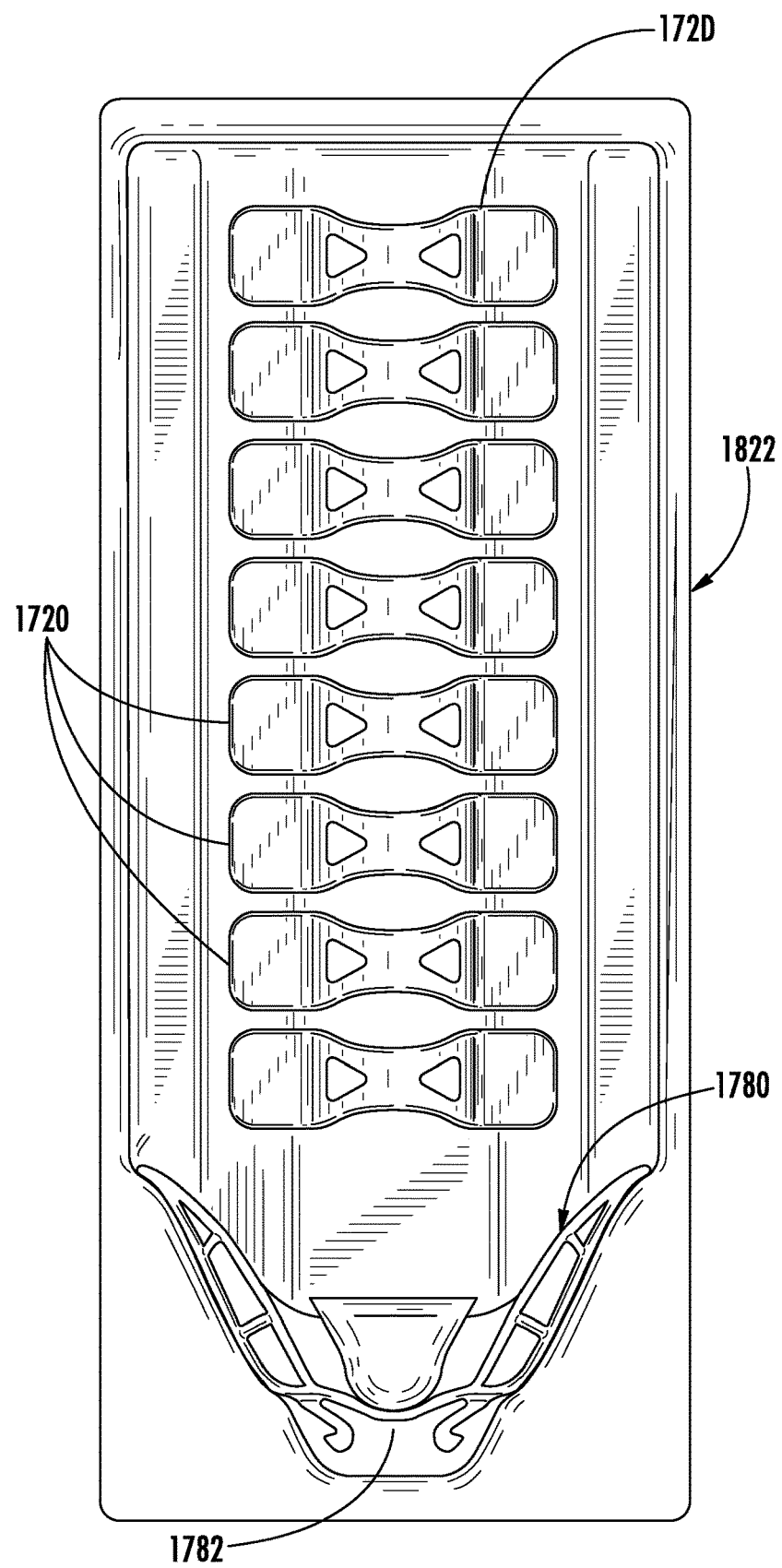
FIG. 15 is a top plan view of a tray at least partially containing the applicator tool and a series of tissue bridges, in accordance with the tenth embodiment.

FIG. 14 is a bottom pictorial view of an applicator tool 1780, in accordance with a tenth embodiment. In the tenth embodiment, the bearing or contact surface 1782, which is positioned between the catch parts 1784 for pressing against the apex of the arch of a tissue bridge, is defined at the juncture between links 1786 and/or at the lower point of at least one link 1786. The one or more links 1786 can extend obliquely upward from the contact surface 1782 to the levers 1788 or handle 1794. FIG. 15 is a top plan view of a tray 1822 at least partially containing the applicator tool 1780 and a series of tissue bridges 1720.

Other embodiments are also within the scope of this disclosure. For example, catch parts of the tissue bridges can include hook-shaped members, shelves, shoulders or other catch-like features extending upwardly from the foot plates or flanges for engaging with catches of the applicator tools. In another example, the shoulders and foot plates or flanges may be omitted from the body of a tissue bridge, and curved foot pads, which can comprise curved medial struts, can be connected either directly or indirectly to the arch of such a tissue bridge.

As another example, one or more therapeutic agents can optionally be included in any of the above-described kits, packages, and/or in or on the tissue bridges. For example, a medicinal, a biologic (e.g. amnion or chorion), growth factors, wound healing factors, drugs (wound modulators, steroids, antibiotics), and/or other suitable therapeutic agents can be included in the kits, packages, and/or in or on the tissue bridges in a manner that seeks to improve wound healing, reduce scars, and/or reduce complications. As one specific example, an element or medium that is in addition to or an additional part of a tissue bridge may comprise the therapeutic agent, and such a medium may be associated with any of the above-descried tissue bridges.

Figure 16A:
FIG. 16A is a schematic top plan view of an elongate scar or wound in tissue.
Figure 16B:
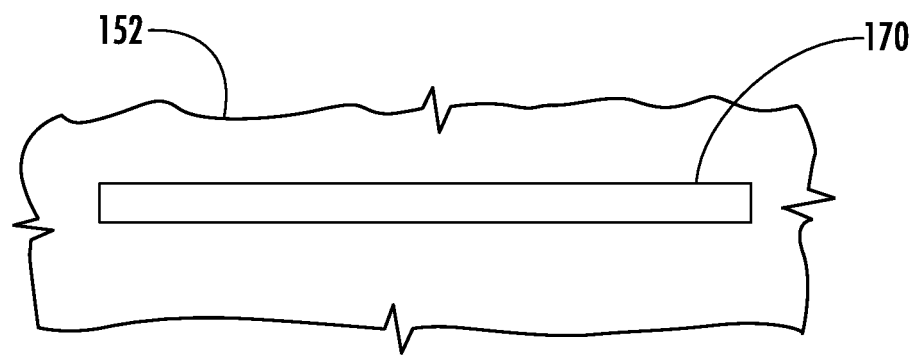
FIG. 16B is like FIG. 16A, except that the scar or wound is covered by a strip.
Figure 16C:
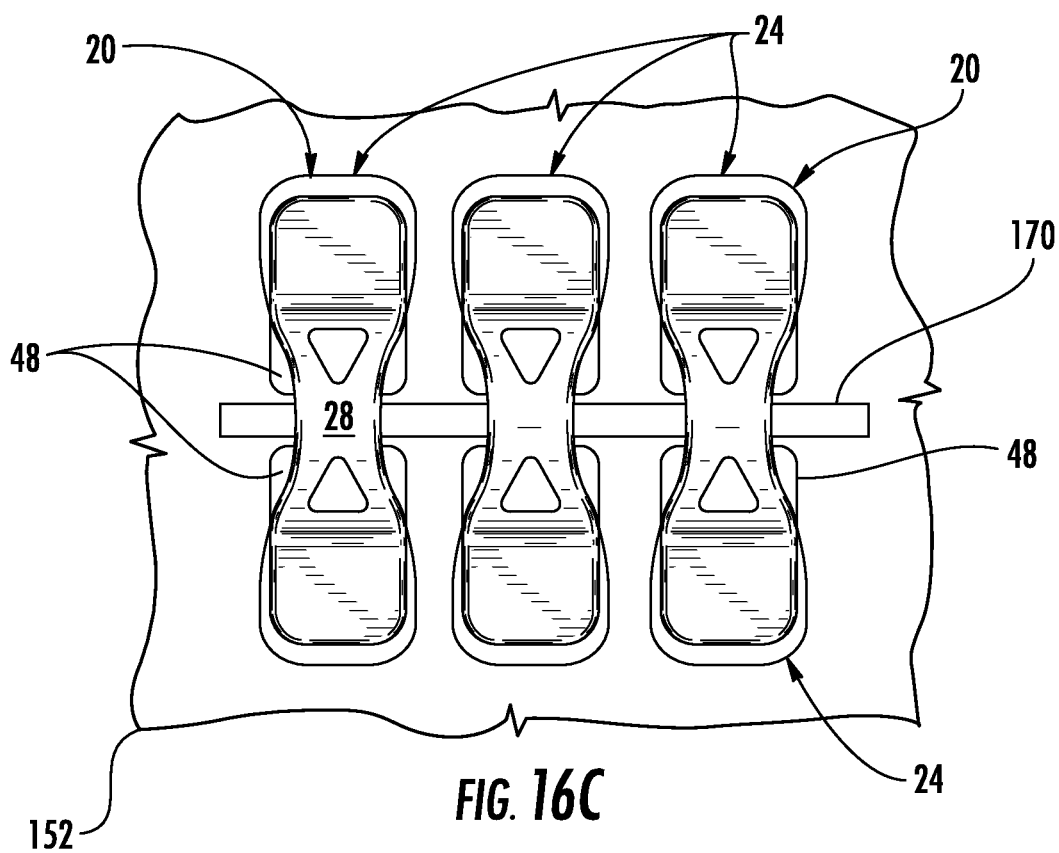
FIG. 16C is like FIG. 16B, except that tissue bridges have been mounted over the strip, in accordance with an embodiment of this disclosure.
Figure 16D:
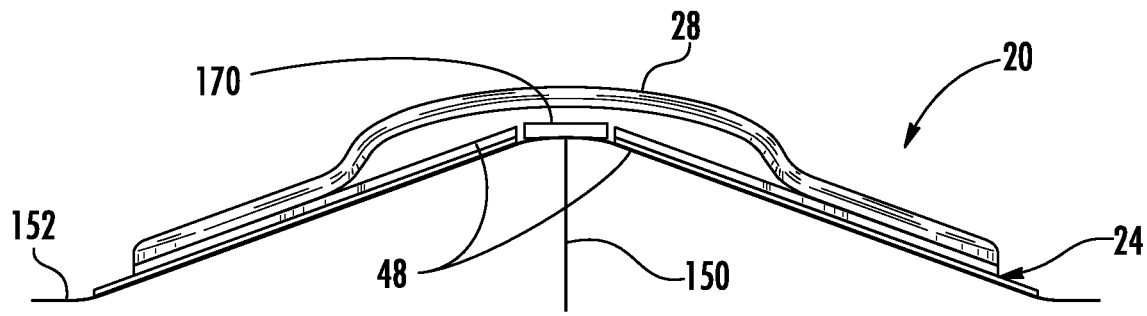
FIG. 16D is a side elevation view of a first version of the assembly of 16C.

FIGS. 16A-16C depict some of the steps of a method of associating a medium with one or more of the tissue bridges 20 of the first embodiment, although the method may be carried out with any other suitable tissue bridges, or the like. The medium can be in the form of a strip 170 of material such as, but not limited to, silicone tape. FIG. 16A depicts an elongate scar or wound 150 in tissue 152, for example the outer surface of a patient's epidermis. Referring also to FIG. 16B, the scar or wound 150 can be covered with the strip 170, wherein the covering strip typically extends along the scar or wound. Referring to FIGS. 16C and 16D, one or more of the tissue bridges 20 can be mounted to the tissue 152 so that the tissue bridges extend across the strip 170, and for each tissue bridge the strip extends between the inner edges of the foot pads 24, or more specifically the strip extends between the inner edges of the medial struts 48.

Figure 16E:
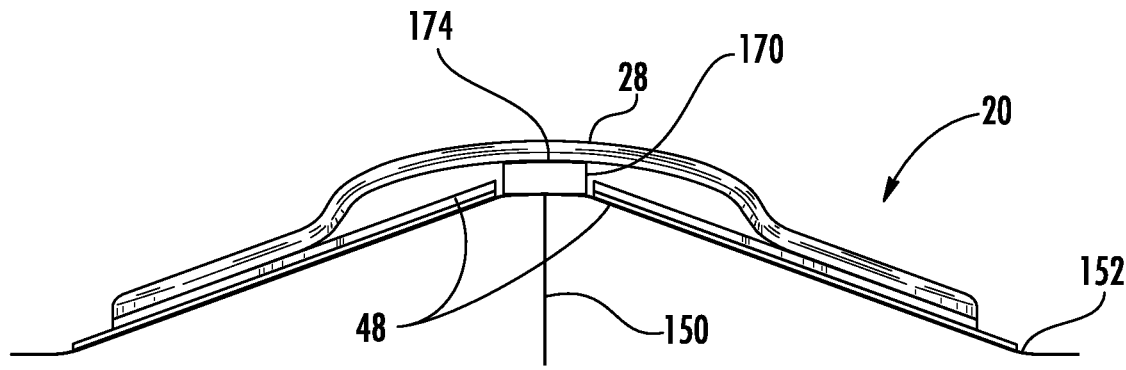
FIG. 16E is a side elevation view of a second version of the assembly of FIG. 16D, and FIG. 16E also depicts a tissue bridge in accordance with another embodiment of this disclosure.

In the example shown in FIG. 16D, the strip 170 is not fixedly connected to the tissue bridges 20, but can optionally be connected to the tissue 152 with releasable adhesive material 172. Alternatively, in the example shown in FIG. 16E, the strip 170 can be fixedly connected to the arch 28 with adhesive material 174. Referring to FIG. 16E, the relative sizes of features can be such that strip 170 can be engaged to both the underside of the arch 28 and the scar or wound 150, for example in a manner that seeks to holed the strip in place, whether or not the adhesive material 174 is present. For example, the strip or medium 170 can be a foam of such a thickness that the one or more tissue bridges 20 slightly push down on the foam to maintain good contact between the foam and scar or wound 150, wherein the foam is or can optionally include one or more therapeutic agents, such as silicone.

In addition or alternatively, the strip can be mounted to the arch 28. For example, regarding a method related to FIG. 16E, the underside of one or more of the arches 28 can be fixedly connected to the strip 170 by adhesive material 174 during original manufacture of the one or more tissue bridge, so that the strip 170 is originally engaged against the scar or wound 150 in the tissue 152 at the same time that the one or more tissue bridges are mounted to the tissue. That is, multiple tissue bridges 20 may be fixedly mounted to a single strip 170 and/or each tissue bridge may be mounted to a separate strip. For the latter example, for each tissue bridge 20, the strip 170 can be wider than the width of the tissue bridge, so that end sections of adjacent the strips abut and/or overlap one another when a series of the tissue bridges are applied adjacent to one another.

Figure 16F:
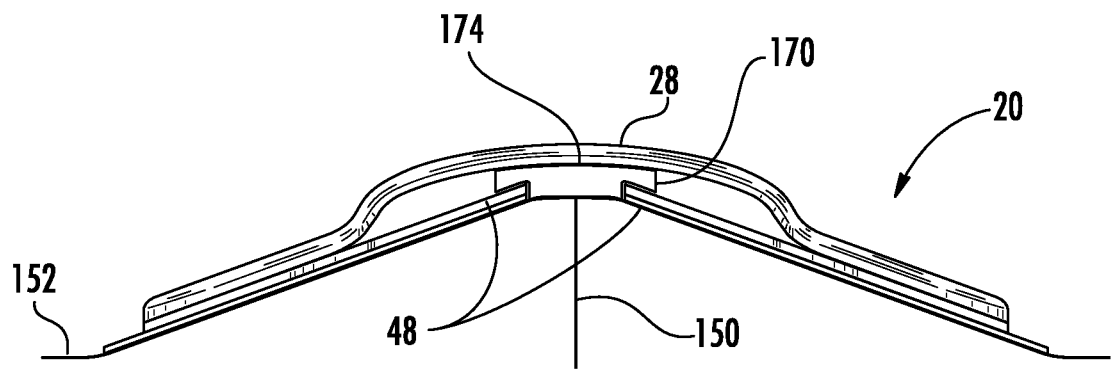
FIG. 16F is similar to FIG. 16E, in accordance with another embodiment of this disclosure.
Figure 16G:
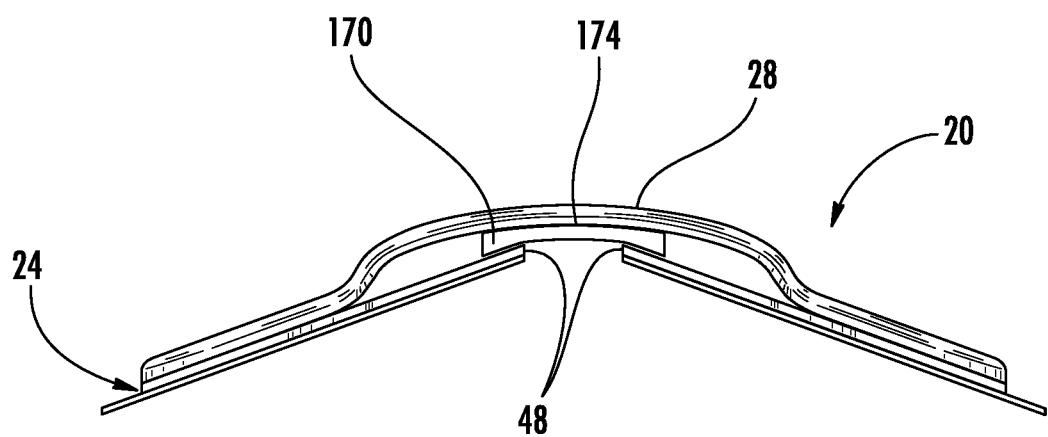
FIG. 16G is a side elevation view of a tissue bridge in accordance with an embodiment of this disclosure.

Referring to FIG. 16F, in addition to the strip or medium 170 being positioned between the inner edges of the foot pads 24 or medial struts 48, the strip or medium can also extend at least partially over the medial struts, such as, for example, to accommodate a relatively larger area of the adhesive material 174. In one aspect of this disclosure, the strip or medium 170 may or may not extend lateral to the level of the medial edges of the medial struts 48 in the at rest configuration of the tissue bridge 20. For example, FIG. 16G depicts a side view of a tissue bridge 20 in its at rest configuration, wherein the strip or medium 170 is fixedly connected to the underside of the arch by the adhesive material 174, and the strip or medium 170 is configured to be positioned at least partially between the foot pads 24 and/or medial struts 48 when the tissue bridge is mounted to tissue 152, for example as shown in one or more of FIGS. 16D-F.

Reiterating from above, in one example the strip 170 can comprise silicone, or be a silicone strip. As other examples, the strip 170 can be any suitable medium comprising one or more therapeutic agents, examples of which are mentioned above. As additional examples, the strips or mediums 170 can comprise or otherwise embrace other materials and various geometries/forms of materials such as, but limited to, foams, fabrics (wovens, non-wovens, and/or felts) laminations of same/differing materials, and the like, that can carry and/or comprise one or more therapeutic agents. The materials can have one or more properties that work with or enable the therapeutic agents. As another example, the strips or mediums 170 can comprise biodegradable materials such as, but not limited to, polymers that can be "doped" with therapeutic agents so that as the polymers break down the therapeutic agents are released. Alternatively, the strip or medium 170 may not contain or otherwise carry any therapeutic agent, and can be, or can function as, a dressing, tape or other suitable medical covering for engaging the scar or wound 150. As another example, one or more therapeutic agents can be applied to the scar or wound 150 in a conventional manner, and thereafter the strip or medium 170 and tissue bridge 20 may be mounted over the one or more therapeutic agents on the scar or wound.

An eleventh embodiment of this disclosure is the same as the first and ninth embodiments discussed above, except for variations noted, and variations that will be apparent to those of ordinary skill in the art. Accordingly and for example, like drawing reference numerals are used for the first and eleventh embodiments, except that the reference numerals for the eleventh embodiment are typically incremented by two thousand as compared to the first embodiment.

FIGS. 17A-17E depict the at least partially elastic (e.g., generally elastic) medical article 2020 in its undeformed or at rest configuration, in accordance with the eleventh embodiment. At least partially reiterating from above, the medical article 2020 may optionally be referred to as a force modulating tissue bridge 2020, or simply tissue bridge 2020, and throughout this disclosure the tissue bridge may be more generally referred to as a medical article.

Figure 17A:
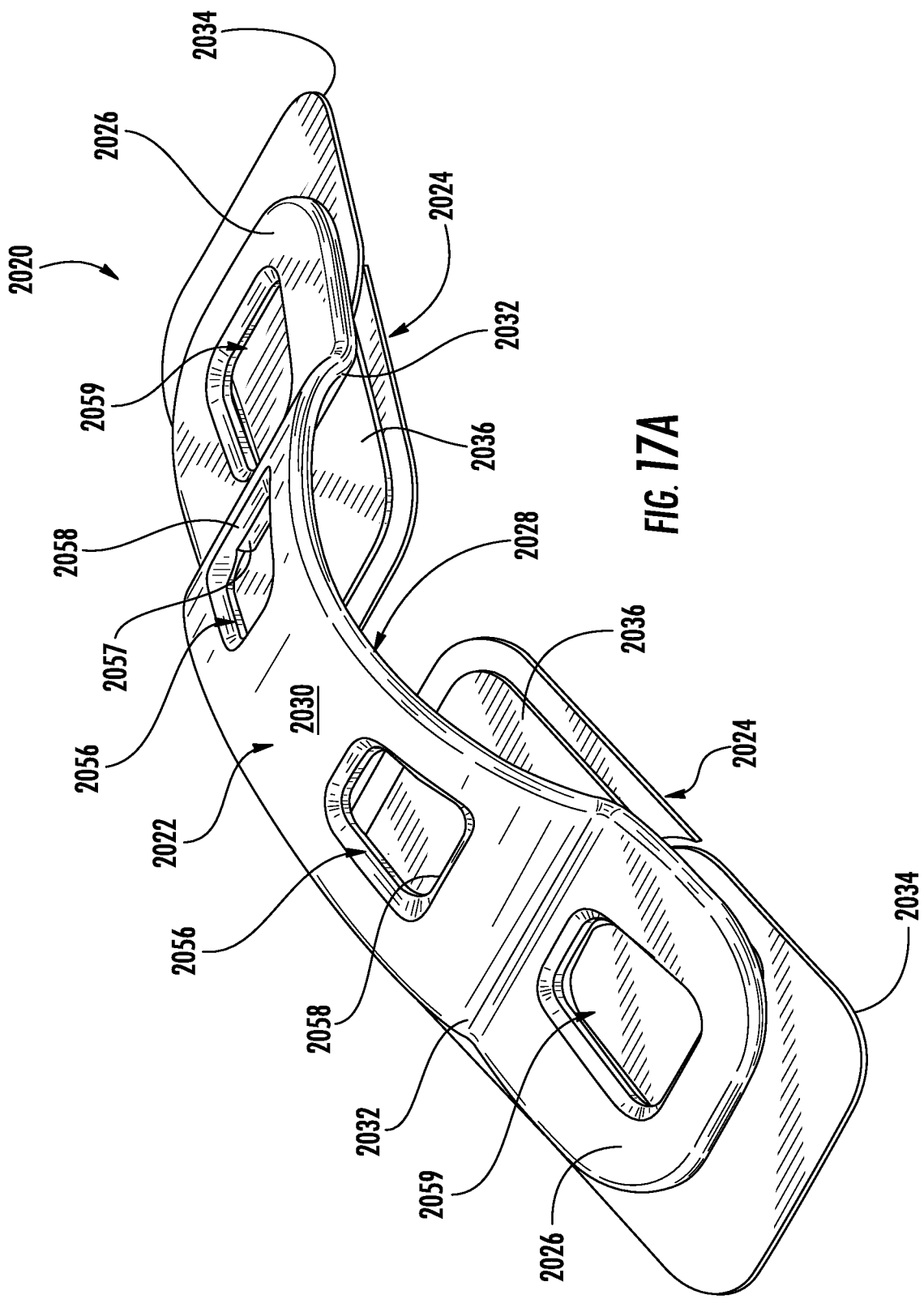

Referring primarily to FIG. 17A, the tissue bridge 2020 of the eleventh embodiment comprises a generally elastic body 2022 and one or more multi-layer foot pads 2024 mounted to the body, although in some examples one or more of the foot pads and/or portions thereof can be omitted (e.g., a foot-pad may consist of, or consist essentially of, a single layer). The body 2022 can be generally referred to as and/or generally function as a backbone or other suitable structure configured to movably connect two or more of the foot pads 2024 to one another. The body 2022 can include at least two flanges 2026 (e.g., feet) respectively extending obliquely, for example outwardly and downwardly, from opposite lower portions of a central section or arch 2028 of the body. Each of the flanges 2026 can be planar, or they can be substantially or about planar since it may not be critical that the flanges be exactly planar. The flanges 2026 can extend divergently relative to one another, and obliquely relative to one another. The arch 2028 can include a central spanning section 2030, and lower sections 2032 respectively extending downwardly from opposite portions of the spanning section. The lower sections 2032 of the arch 2028 can optionally be configured as and/or referred to as shoulders 2032. The flanges 2026 can respectively extend obliquely, for example outwardly and downwardly, from lower portions of the shoulders 2032. The shoulders 2032 can provide a smoothly curved transition between the spanning section 2030 of the arch 2028 and the flanges 2026.

In one example, the arch's central spanning section 2030 can be thicker than the flanges 2026, and other variations are within the scope of this disclosure. For example, whereas the arch 2028 is typically depicted in the drawings as being at least generally arcuate, it is believed that in some situations the arch 2028 can be at least more of a flat arch, or the spanning section 2030 of the arch can be flat, or the arch or features thereof can be in any other suitable configurations that will allow the tissue bridge 2020 to function generally or substantially as described herein.

Each of the parts of the tissue bridge 2020 will typically be constructed of suitable medical-grade materials. For example, the body 2022 can be an injection-molded or mechanically thermoformed, unitary (e.g., single-piece) article such that the spanning section 2030, shoulders 2032 and flanges 2026 can be formed together as a single article from an injection-moldable or formable, generally elastic material such as, but not limited to, polycarbonate, or any other suitable injection-moldable or formable material. Each of the spanning section 2030, shoulders 2032, and flanges 2026 can be about the same thickness, or alternatively the thickness of the body 2022 can vary along its length. The width of the body 2022 can, for example, taper along its length, so that the spanning section 2030 is relatively narrow (e.g., has a narrowed waist) as compared to the shoulder 2032 and flanges 2026, so that the spanning section can be more readily deformed as compared to the shoulders and flanges. For example, the side edges of the spanning section 2030 can be inwardly curved or concave, or they may have a stepped or other suitable configurations. Alternatively, the side edges of the spanning section 2030 can extend generally or substantially straight in a top plan view of the tissue bridge 2020, or they can extend in any other suitable manner.

The foot pads 2024 can be spaced apart from one another, and the foot pads can be fixedly mounted to the flanges 2026. Each foot pad 2024 can be or include be a mat, laminate or other suitable structure comprising one or more layers of material. For example, each foot pad 2024 can include an outer layer or sheet 2034 configured to be attached to tissue (e.g., skin tissue), and an inner layer or sheet 2036 positioned between, and fixedly connected to each of, the outer sheet 2034 and the respective flange 2026.

Figure 17C:
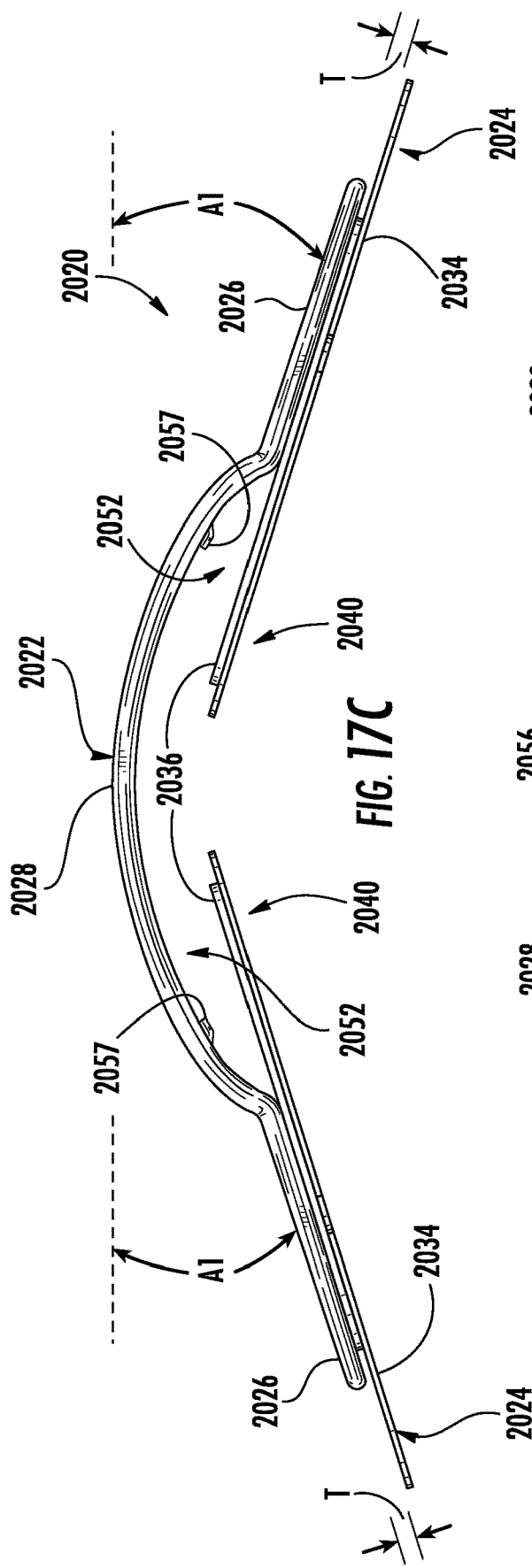
Figure 17D:
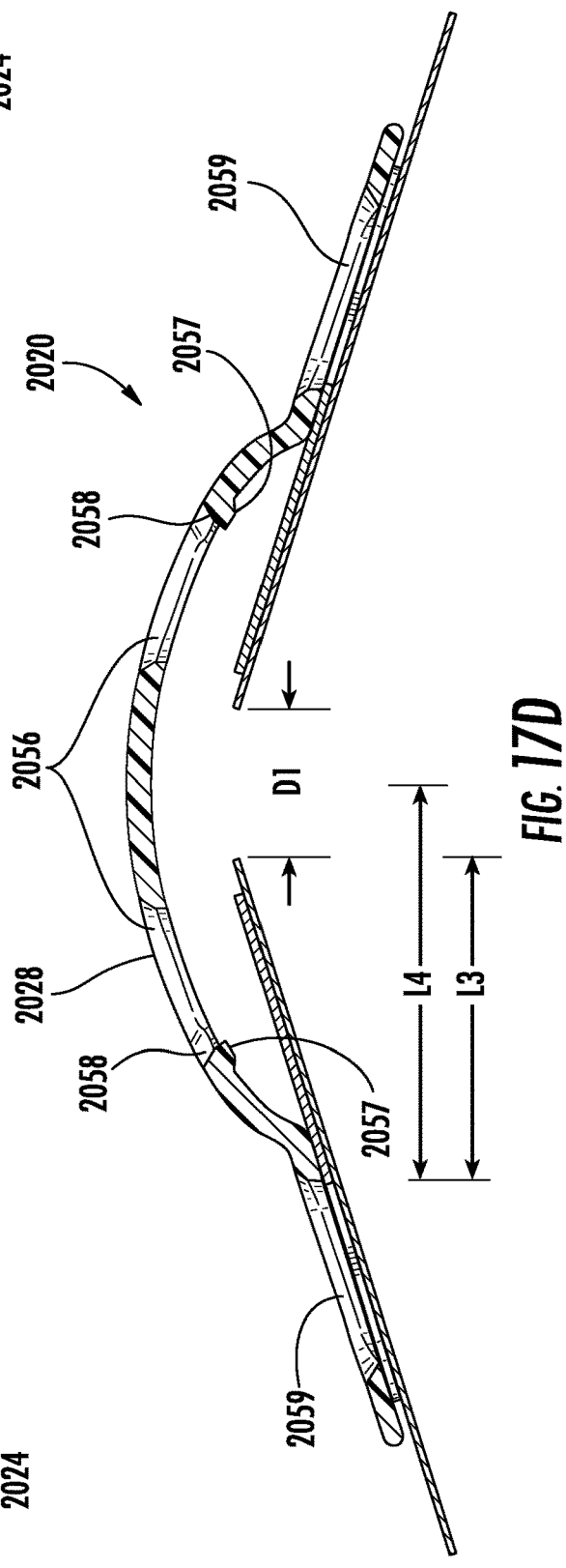
FIG. 17D is a cross-sectional view taken along line 17D-17D of FIG. 17B.
Figure 17E:
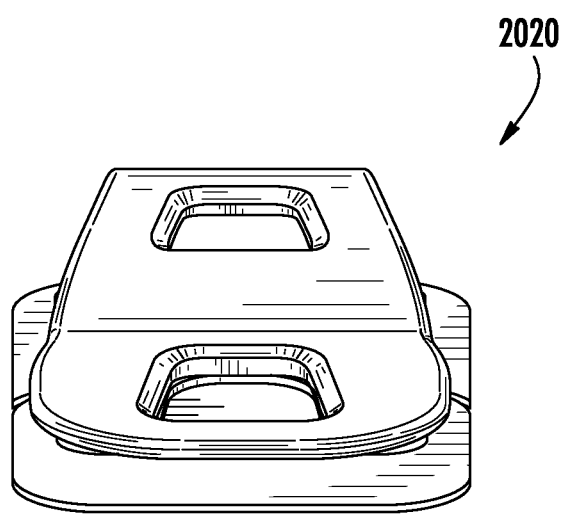
FIG. 17E is an end elevation view of the tissue bridge of the eleventh embodiment.
Figure 17F:
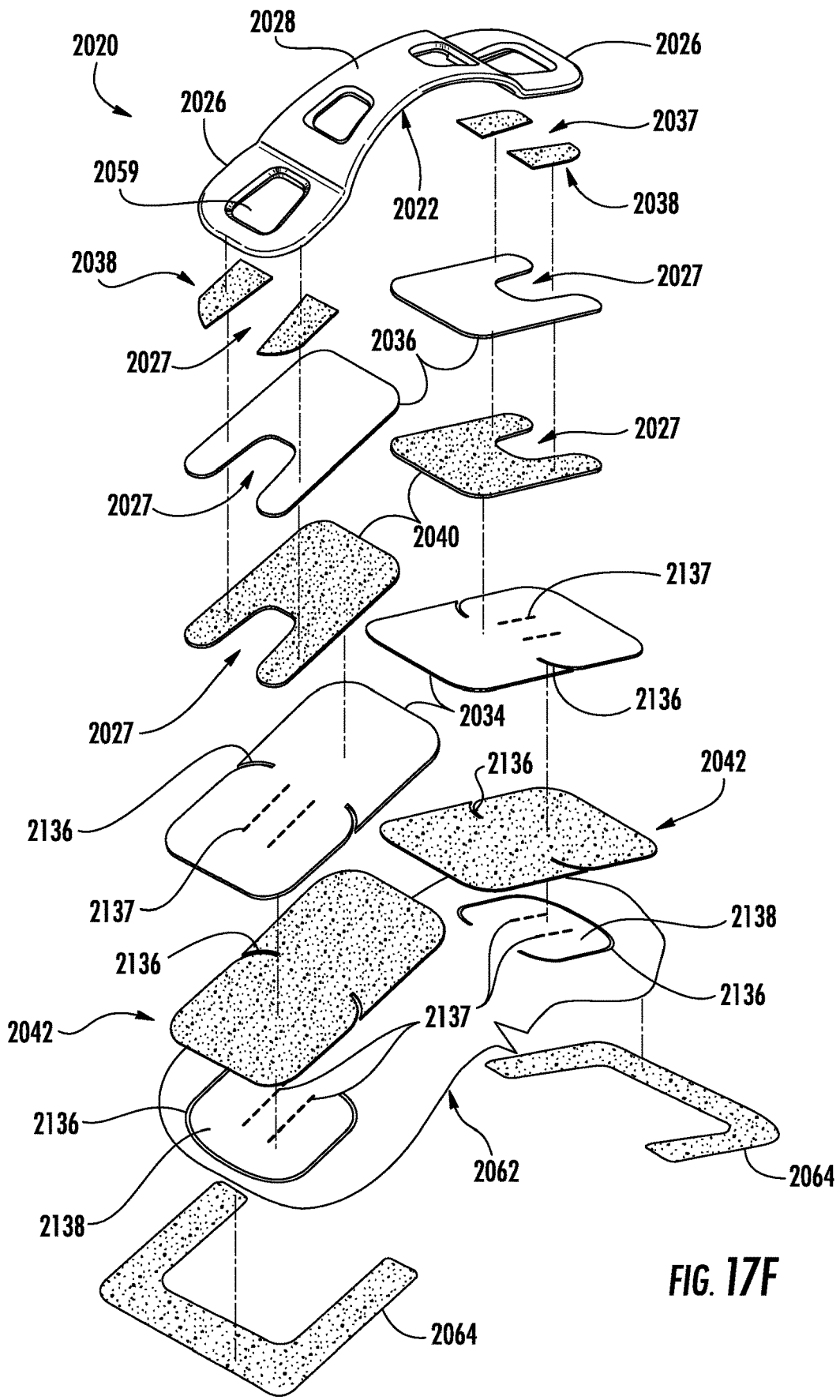
FIG. 17F is a top pictorial exploded view of the tissue bridge of the eleventh embodiment, wherein FIG. 17F further depicts the tissue bridge exploded away from a schematically depicted section of a release liner and associated adhesive material, in accordance with the eleventh embodiment.
Figure 17G:
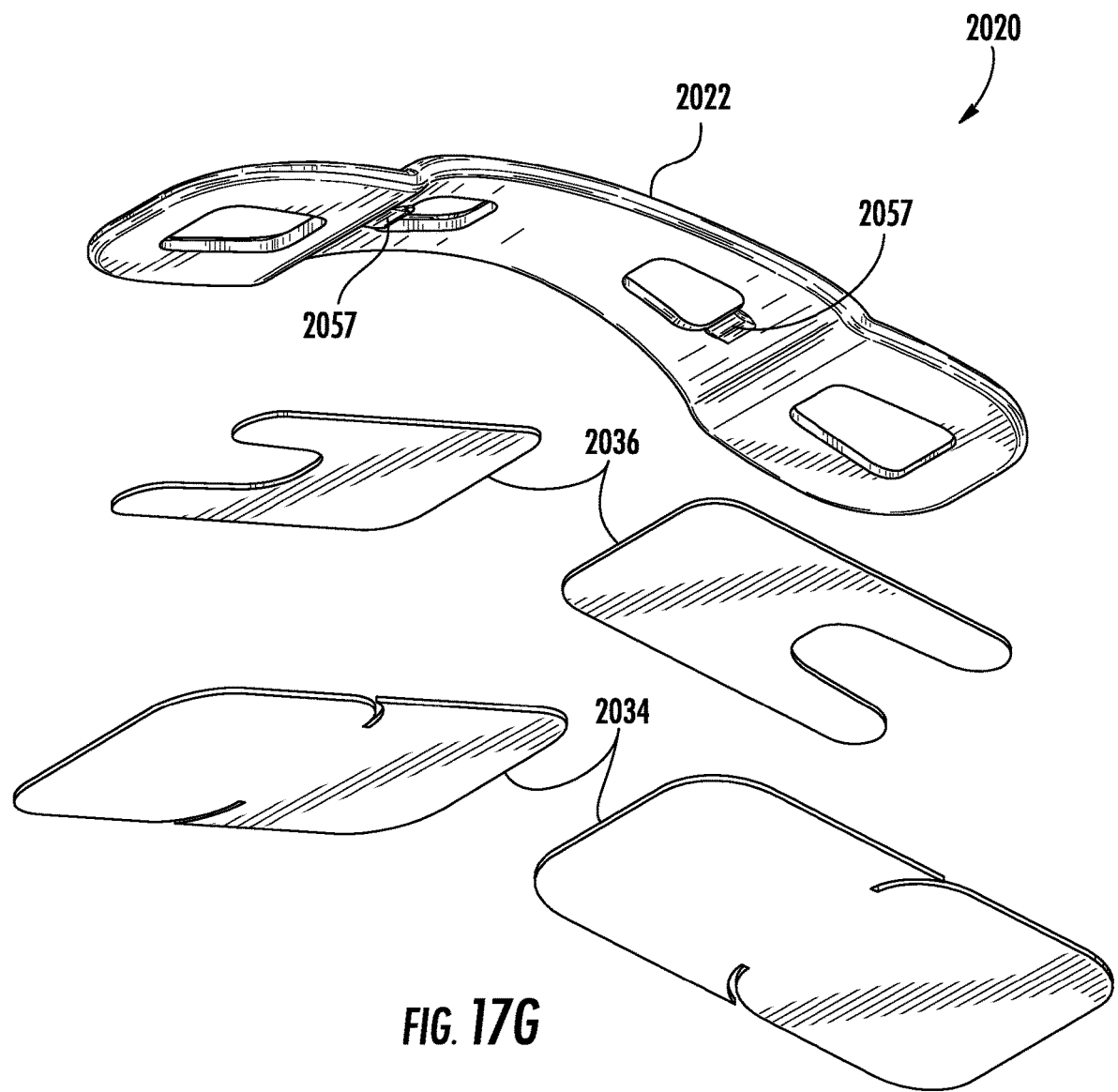
FIG. 17G is a bottom pictorial exploded view of selected layers of the tissue bridge of the eleventh embodiment

Referring to the exploded view of FIG. 17F, the tissue bridge 2020 can include inner, intermediate and outer adhesive layers 2038, 2040, 2042. The inner adhesive layers 2038 can be between and fixedly connect the inner sheets 2036 to the flanges 2026, the intermediate adhesive layers 2040 can be between and fixedly connect the outer sheets 2034 to the inner sheets, and the outer adhesive layers 2042 can be on the outer sides of the outer sheets for attaching the tissue bridge 2020 to tissue (e.g., a patient's skin).

The outer and inner sheets 2034, 2036 can be provided by die cutting them from appropriate webs or larger sheets of material, such as fabric or cast microporous polymeric sheet for the outer sheets 2034, and an extruded polymer or plastic sheet for the inner sheets 2036. The outer sheets 2034 can be made of suitable fabric materials, cast materials, films, or other materials of the type from which skin-contact layers of bandages or other wound dressings are formed, or any other suitable material. The plastic inner sheets 2036 can be made of suitable materials such as, for example, polyethylene, polyethylene terephthalate, or any other suitable materials. The outer adhesive layer 2042 can have a lower adhesive strength than the inner and intermediate adhesive layers 2038, 2040, such as when the tissue bridge 2020 is to be removably mounted to tissue (e.g., a patient's skin).

Both the body 2022 and the inner sheet 2036 can have a higher modulus of elasticity (e.g., are formed from stiffer material) than the outer sheet 2034. More generally, the body 2022 and the inner sheet 2036 can be stiffer than the outer sheet 2034 because of a variety of factors, such as being larger, thicker and/or comprising material having a higher modulus of elasticity. The body 2022, including its flanges 2026, can be thicker than each of the outer and inner sheets 2034, 2036, although the thicknesses can be varied. The arch 2028 can extend over an area into which portions of the outer and inner sheets can optionally extend. The area over which the arch 2028 extends may be referred to as a central area, a treatment area, an under-arch area, and/or the like.

Referring to FIG. 17C, inner extensions 2048 of the outer and inner sheets 2034, 2036 can extend congruently with one another into the central area over which the arch 2028 extends such that the inner extensions 2048 are neither superposed by nor coextensive with the flanges 2026. More generally, each foot pad 2024 can include at least one extension 2048 that extends into the central area over which the arch 2028 extends such that the inner extension 2048 can be neither superposed by nor coextensive with the flanges 2026. The inner extensions 2048 may be referred to as medial extensions 2048, for example since they extend toward the middle of the area over which the arch 2028 extends. The inner or medial extensions 2048 can be configured so that they at least partially resist longitudinal compression when the tissue bridge 2020 in its extended configuration is mounted to tissue (e.g., skin tissue) and then allowed to generally elastically reconfigure from its extended configuration at least partially toward its at rest configuration. Accordingly, the inner or medial extensions 2048 can be referred to as medial struts 2048. A gap can be defined between adjacent ends of the medial extensions 2048, and the gap can be configured, for example, so that the adjacent ends of the medial extensions 2048 are spaced apart from one another and do not contact one another.

Referring to FIG. 17B, for each foot pad 2024, one or more (e.g., four) margins or outer extensions of the outer sheets 2034 can extend outwardly beyond the inner sheet 2036 such that they are neither superposed by nor coextensive with the inner sheet 2036. In the eleventh embodiment, each medial strut 2048 includes the inner extensions 2048 of both sheets 2034, 2036, but one or more layers or sheets of the medial strut 2048 can be omitted, such that each medial strut can be formed of one or more layers of material.

Referring to FIG. 17C, the medial struts 2048 can be spaced apart from (e.g., at least partially spaced apart from) the arch 2028 and extend into the central area over which the arch extends, so that gaps or receptacles 2052 are at least partially defined between the medial struts and the arch. The receptacles 2052 can at least partially define, or be at least part of, catch parts configured for interacting with corresponding features of an applicator tool that may be used, for example, in the mounting of the tissue bridge 2020 to tissue (e.g., a patient's skin). For example, the tissue bridge 2020 can include one or more catch parts that respectively comprise the receptacles 2052. A variety of differently configured catch parts are within the scope of this disclosure.

The body 2022 can include at least two catch parts that further comprise inner holes 2056 that extend through the body 2022 and are open to the receptacles 2052. The inner holes 2056 can be defined in the arch 2028, or more specifically the inner holes 2056 can be positioned in opposite end portions of the spanning section 2030. The inner holes 2056 can be open to the central area over which the arch 28 extends, or more specifically the inner holes can be open to the receptacles 2052; and the medial struts 2048 can extend beneath the inner holes. The inner holes 2056 can have any suitable shape. For example, they can be generally polygonal, or generally rectangular, with an edge 2058 of the arch 2028 that defines the inner hole 2056 extending crosswise to the length of the arch.

The respective catch part can further include the edge 2058 and a protrusion or rib 2057 extending downwardly from (e.g., downwardly from proximate) the edge 2058. The edge 2058 and rib 2057 can extend parallel, or more generally substantially parallel or about parallel, to the boundary between the spanning section 2030 and the respective shoulder 2032. In other words, the edge 2058 and rib 2057 can extend perpendicular to, or more generally substantially perpendicular to or about perpendicular to, the lengthwise or longitudinal axis of the body 2022. In addition, the inner holes 2056, when present, can reduce the area or volume of the outer portions of the spanning section 2030 in a manner that enhances the deformability of the outer portions of the spanning section. At least partially reiterating from above, each catch part can include a protruding portion 2057 of the lower surface of the arch 2028, wherein the protruding portion or rib 2060 extends outwardly from, or adjacent to, the edge 2058.

The inner holes 2056 can be omitted and/or the body 2022 can have one or more other holes formed therein or therethrough. For example, outer holes 2059 can extend through the foot plates or flanges 2026. Referring to the exploded view of FIG. 17F, the adhesive layers 2038, 2040 and inner sheets 2036 can further include lower holes 2027. The lower holes 2027 can be open to the outer holes 2059, and the lower holes 2027 can also extend outwardly to be open at the outer edges of the adhesive layers 2038, 2040 and inner sheets 1536. The outer holes 2059 can have any suitable shape. For example, the outer holes 2059 can be generally polygonal, or generally rectangular. The lower holes 2027 can be shaped complementary to the outer holes 2059.

FIG. 17F, in addition to depicting the tissue bridge 2020 in an exploded configuration, further depicts the tissue bridge 2020 exploded away from a schematically depicted section of a release liner 2062 and associated adhesive material 2064. As an example, after a tissue bridge 2020 is manufactured or as part of the manufacturing process for the tissue bridge, the tissue bridge, or more specifically the outer sheets 2034 by way of the outer adhesive layers 2042, can be releasably mounted on the upper surface of the release liner 2062. In addition, the lower surface of a portion of the release liner 2062 can be fixedly mounted to a support (e.g., tray) by way of the adhesive material 2064. The release liner 2062 can be, for example, a paper or plastic-based film sheet coated with a release agent that is engaged against the outer adhesive layers 2042 so that the tissue bridge 2020 is releasably mounted on the release liner. The release liner 2062 can include a series of lines of disruption 2136. Each line of disruption 2136 can comprise one or more cuts, slits, breachable lines of disruption, perforations and/or overlapping and/or sequential combinations thereof, for at least partially defining flaps 2138 in the release liner 2062. The lines of disruption 2136 can be configured in a variety of patterns. In the eleventh embodiment, each line of disruption 2136 extends partially around the foot pad 2024 that is mounted to the flap 2138 defined by the line of disruption 2136, and opposite ends of the line of disruption 2136 extend beneath the food pad. The lines of disruption 2136 can be formed as part of a cutting (e.g., die cutting) step, or the like, such that the lines of disruption 2136 (e.g., slits, perforations or other suitable cuts) may extend at least partially into one or more layers of the foot pad 2024. As a more specific example, the lines of disruption 2136, or extensions thereof, or the like, may extend into the outer adhesive layer 2040 and outer sheet 2034. Similarly, perforations or additional lines of disruption 2137 (e.g., perforations arranged in series) can be defined in the outer sheet 2034 and/or release liner 2062. The adhesive material 2064 is typically arranged in a pattern such that the adhesive material is omitted from between the flaps 2138 in the release liner 2062 and the respective portions of the tray, so that the flaps can be moved relative to the reminder of the release liner. In this regard, the adhesive material 2064 can be applied in any suitable pattern. For example, for a representative flap 2138, the adhesive material 2064 can extend along at least one of the edges of the flap without adhering the flap to the associated tray, or the like.

For example and like the first embodiment and at least some of the other embodiments, the tissue bridge 2020 of the eleventh embodiment can be configured so that each flange 2026 has opposite upper and lower surfaces that are each larger than a thickness defined between the upper and lower surfaces of the flange; each foot pad 2024 has opposite upper and lower surfaces that are each larger than a thickness defined between the upper and lower surfaces of the foot pad; and for each flange 2026 and the respective foot pad 2024 connected thereto, the upper surface of the foot pad and the lower surface of the flange: can face toward one another, can be superposed with one another, can be parallel (e.g., substantially parallel) to one another, and/or can be directly connected to one another by the inner adhesive layers 2038 positioned therebetween.

It is believed that the configuration (e.g., size) of the tissue bridge 2020 can be adjusted so that the tissue bridge can be well suited for a variety of different situations. Notwithstanding, for promoting ease of understanding, and not for the purpose of limiting the scope of the present invention, a few examples of dimensions and ratios are provided in this Detailed Description section of this disclosure. For example, in FIG. 17B, the lengths "L1" and widths "W1" of the upper and lower surfaces of the flanges 2026 are designated. In FIG. 17C the thicknesses "T" defined between the upper and lower surfaces of the flanges 2026 is designated. The flange thicknesses T are smaller than the flange lengths L1 and widths W1. Also in FIG. 17B, a width "W2" of the central spanning section 2030 of the arch 2028 is designated, and it is narrower than the widths W1 of the flanges 2026. As one example, the overall length of the tissue bridge 2020 in its relaxed state (i.e., in its at rest configuration) can be in a range of from about 1 inch (about 25 mm) to about 1.6 inches (about 41 mm), or more specifically about 1.3 inches (about 33 mm); the lengths L1 of the upper and lower surfaces of the flanges 2026 can be in a range of from about 0.22 inches (about 5.6 mm) to about 0.35 inches (about 8.9 mm), or more specifically about 0.28 inches (about 7.1 mm); the widths W1 of the upper and lower surfaces of the flanges 2026 can be in a range of from about 0.3 inches (about 7.6 mm) to about 0.5 inches (about 12.7 mm), or more specifically about 0.4 inches (about 10.2 mm); the flange thicknesses T defined between the upper and lower surfaces of the flanges 2026 can be in a range of from about 0.016 inches (about 0.41 mm) to about 0.024 inches (about 0.61 mm), or more specifically about 0.02 inches (about 0.51 mm); and the width W2 of the arch central spanning section 2030 can be in a range of from about 0.2 inches (about 5.1 mm) to about 0.3 inches (about 7.6 mm), or more specifically about 0.25 inches (about 6.3 mm). Accordingly, the upper and lower surfaces of the flanges 2026 (e.g., the flange lengths L1 and/or widths W1) can be at least two, several or many times larger than the thickness T defined between the upper and lower surfaces of the flange. Other dimensions and/or ratios are within the scope of this disclosure.

In other examples, the overall length of the tissue bridge 2020 in its relaxed state (i.e., in its at rest configuration) can be in a range of from about 0.65 inch (about 16 mm) to about 3.5 inches (about 88 mm), or more specifically about 1.3 inches (about 33 mm); the lengths L1 of the upper and lower surfaces of the flanges 2026 can be in a range of from about 0.14 inches (about 3.6 mm) to about 0.66 inches (about 16.7 mm), or more specifically about 0.28 inches (about 7.1 mm); the widths W1 of the upper and lower surfaces of the flanges 2026 can be in a range of from about 0.2 inches (about 4.9 mm) to about 0.9 inches (about 23.8 mm), or more specifically about 0.4 inches (about 10.2 mm); the flange thicknesses T defined between the upper and lower surfaces of the flanges 2026 can be in a range of from about 0.010 inches (about 0.27 mm) to about 0.045 inches (about 1.14 mm), or more specifically about 0.02 inches (about 0.51 mm); and the width W2 of the arch central spanning section 2030 can be in a range of from about 0.13 inches (about 3.3 mm) to about 0.56 inches (about 14.3 mm), or more specifically about 0.25 inches (about 6.3 mm). Other dimensions and/or ratios are within the scope of this disclosure.

With continued reference to FIG. 17B, the arch 2028 can have a length "L2" of about 0.7 inches (about 17.8 mm), while the tissue bridge 2020 is in its relaxed state. In the relaxed state of the tissue bridge 2020, the ratio of the arch length L2 to the tissue bridge's overall length (L1 plus L2 plus L1) (i.e. L2 divided by (L1 plus L2 plus L1)) can range of from greater than 0.35 to less than 0.75, or more specifically can be about 0.3. In the relaxed state of the tissue bridge 2020, the ratio of the arch length L2 to the flange length L1 (i.e. L2 divided by L1) can range of from greater than 1 to less than 5, or more specifically can be about 0.23. The ratio of the flange length L1 to the flange width W1 (i.e. L1 divided by W1) can range of from greater than 0.5 to less than 3, or more specifically can be about 0.77. Other dimensions and/or ratios are within the scope of this disclosure.

Similarly (e.g., measuring in the same directions as indicated by lengths L1, L2, widths W1, W2 and thicknesses T designated in FIGS. 17B and 17C), the tissue bridge 2020 of the eleventh embodiment can be configured so that each foot pad 2024 has opposite upper and lower surfaces that are each larger than a thickness defined between the upper and lower surfaces of the foot pad. As one example, the thicknesses defined between the upper and lower surfaces of each foot pad 2024 can be in a range of from about 0.01 inches (about 0.25 mm) to about 0.014 inches (about 0.36 mm), or more specifically can be about 0.012 inches (about 0.3 mm). The upper and lower surfaces of each foot pad 2024 can be at least two, several or many times larger than the thickness defined between the upper and lower surfaces of the foot pad. In one example, each inner sheet 2036 can be biaxially oriented polyethylene terephthalate film having a thickness in a range of from about 0.0025 inches (about 0.063 mm) to about 0.015 inches (about 0.38 mm), or more specifically can be about 0.005 inches (about 0.13 mm). With regard to the lengthwise and widthwise directions shown in FIG. 17B, in one example, for each inner sheet 2036, its length is at least twice its width, although there can be other ratios. A variety of other configurations (e.g., dimensions and/or ratios) are within the scope of this disclosure.

Referring to FIG. 17B, in a top plan view of the tissue bridge 2020, the ratio of the area of an outer hole 2059 (if present) to the area of the flange 2026 not counting the hole (i.e. the area of the outer hole 2059 divided by the area of the flange 2026 not counting the hole) can range of from greater than 1 to less than 3. Other dimensions and/or ratios are within the scope of this disclosure.

Referring to FIG. 17C, for a tissue bridge 2020 to be used on an area of skin where skin curvature is minimal, angles "A1" between a plane tangent to the top of the arch 2028 and the flanges 2026 can be within a range of from about 15 degrees to about 19 degrees, or more specifically can be about 17 degrees, while the tissue bridge is in its relaxed state. In another example, angles A1 can be within a range of from about 7 degrees to about 27 degrees, or more specifically can be about 17 degrees, while the tissue bridge is in its relaxed state. For areas of skin with greater or lesser curvature, the angles A1 can be adjusted to obtain a desired level of skin eversion. Other angles are within the scope of this disclosure.

Referring to FIG. 17D, for each medial strut 2048, the length "L3" of the medial strut can be less than the length "L4" of half of the arch 2028 in its relaxed state. More specifically, the ratio of the length L3 of the medial strut 2048 to the length L4 of half of the arch 2028 (i.e. L3 divided by L4) can be in a range of from greater than 0.3 to less than one, while the tissue bridge 2020 is in its relaxed state. Other dimensions and/or ratios are within the scope of this disclosure.

Referring to FIG. 17B, in a top plan view of the tissue bridge 2020, each of the side edges of the arch 2028 can have a radius of curvature of about 0.375 inches (about 9.5 mm). The ratio of this radius of curvature of the arch 2028 to the length L3 (FIG. 17D) of the medial strut 2048 (i.e. the radius of curvature of the arch 2028 divided by the length L3) can range of from greater than 0.18 to less than 0.6, or more specifically can be about 0.3. Other dimensions and/or ratios are within the scope of this disclosure.

Referring to FIG. 17D, the distance "D1" between adjacent ends of the medial struts 2048 can be in a range of from about 0.04 inches (about 1 mm) to about 0.7 inches (about 18 mm), or more specifically can be about 0.16 inches (about 4 mm). Other dimensions and/or ratios are within the scope of this disclosure.

FIGS. 18A-18D depict an applicator mechanism in the form of an applicator tool 2080 that can be used, for example, to manipulate a tissue bridge 2020 or another suitable medical article, for example as part of a method of mounting the tissue bridge to tissue (e.g., a patient's skin), in accordance with the eleventh embodiment. For example, the applicator tool 2080 can include one or more parts or features that can be spaced apart from one another and can be configured to releasably engage the tissue bridge 2020. In the eleventh embodiment, the one or more parts or features of the applicator tool 2080 that are configured to engage the tissue bridge 2020 can comprise at least one bearing or contact surface 2082 and/or one or more catch parts 2084. For example, the contact surface 2082 can be positioned between the catch parts 2084. The applicator tool 2080 can further include a reconfigurable frame connecting the contact surface 2082 and catch parts 2084 to one another.

The frame of the applicator tool 2080 can include a reconfigurable linkage (e.g., one or more links 2086) connecting the contact surface 2082 and catch parts 2084 to one another. The frame of the applicator tool 2080 can further include one or more levers 2088 comprising and/or extending upwardly from the links 2086. The applicator tool 2080 can be configured so that when the bearing or contact surface 2082 faces downwardly, the catch parts 2084 extend downwardly from the linkage (e.g., link(s) 2086), and the levers 2088 extend upwardly from the linkage. The links 2086 and the levers 2088 can be cooperatively configured so that at least portions of the catch parts 2084 move away from one another, and the contact surface 2082 moves toward a line extending from one to the other of the catch parts 2084, in response to at least portions of the levers 2088 being moved toward one another, as will be discussed in greater detail below.

The contact surface 2082 can be a lower end face of a pivotable junction (e.g., flexible joint, living hinge (e.g., area of reduced thickness), or the like) between the links 2086. The catch parts 2084 can include shanks 2090 extending from upper ends of the links 2086 and/or lower ends of the levers 2088. The links 2086 can be referred to as lower sections of the levers 2088. Each catch part 2084 can further include at least one outer protrusion 2092 extending outwardly from the lower end of the shank 2090 in a direction that is crosswise to the length of the shank. The outer protrusions 2092 can face away from one another. Each outer protrusion 2092 can be generally rectangular, and include an outer tip 2091 and an engagement shoulder 2093. An acute angle can be defined between the engagement surfaces 2093 and the shanks 2090. The links 2086 and the levers 2088 can be cooperatively configured so that the outer protrusion 2092 move away from one another in response to at least portions of the levers 2088 being moved toward one another.

The applicator tool 2080 can optionally include additional protrusions 2095 (e.g., stabilizing and/or alignment protrusions) extending outwardly from opposite sides of the shanks 2090. A distance between the engagement shoulder 2093 and the most adjacent shoulders of the stabilizing and/or alignment protrusions 2095 can be about equal to, or slightly larger than, a thickness of the spanning section 2030 of the tissue bridge 2020. As another example, the distance between the engagement shoulder 2093 and the most adjacent shoulders/the lower surfaces of the stabilizing and/or alignment protrusions 2095 can be in a range of from about 1 times to about 3.5 times the thickness of the spanning section 2030 of the tissue bridge 2020.

The links 2086 can extend obliquely, outwardly and upwardly from the contact surface 2082 respectively to upper portions of the shanks 2090. The levers 2088 can extend obliquely, outwardly and upwardly respectively from upper portions of the shanks 2090.

Figure 18A:
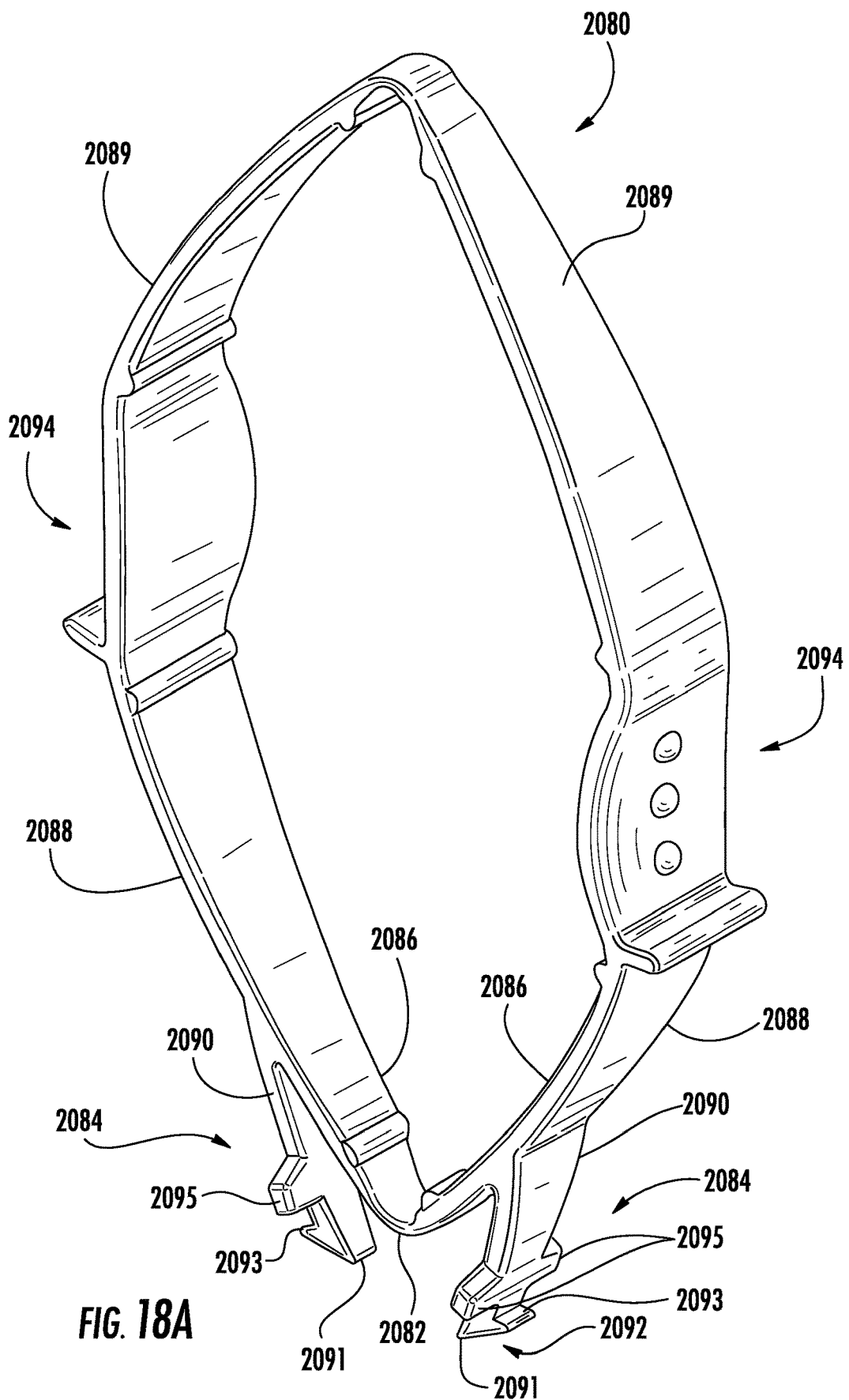
FIGS. 18A through 18C depict various views of an applicator tool in accordance with the eleventh embodiment.
Figure 18B:
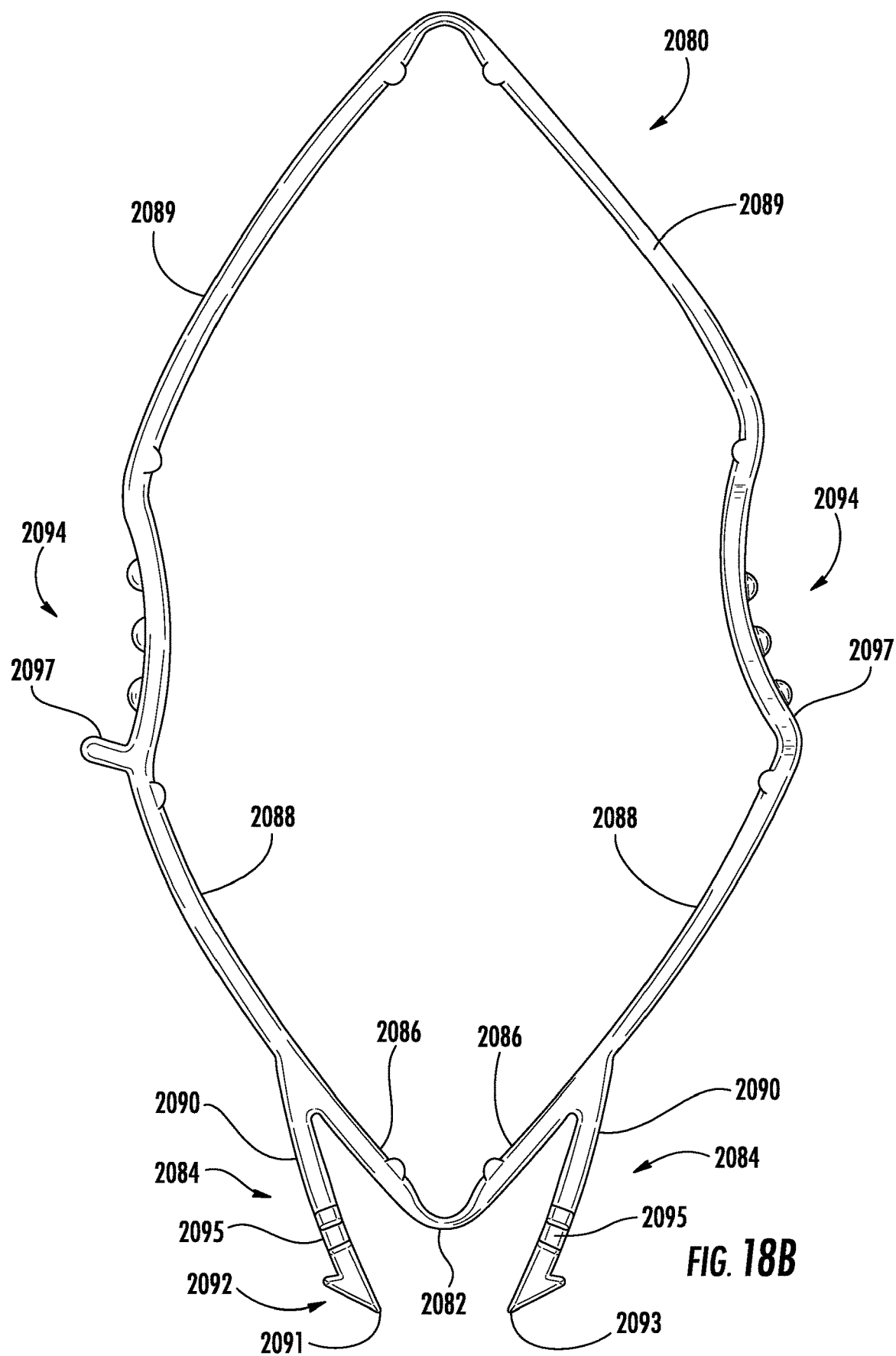
Figure 18C:
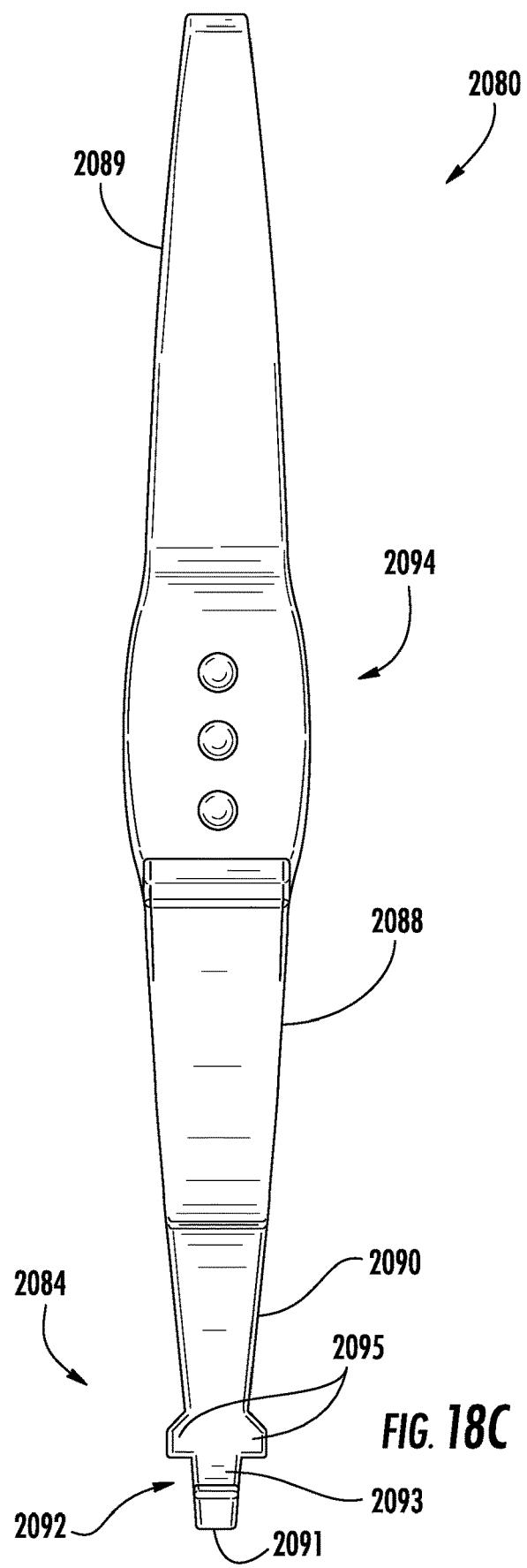

The levers 2088 can define or comprise handles 2094. For example, in the embodiment depicted in FIGS. 18A-18D, the handles 2094 can be an inwardly recessed, arcuate and/or concave sections of the levers 2088, although differently configured handles are within the scope of this disclosure. As an example, FIG. 18B depicts two differently configured handles 2094, each having an outer stop surface 2097 extending crosswise to the length of the applicator tool 2080 in a manner that seeks to restrict a user's fingers from inadvertently sliding downwardly out of the handle. The stop surface 2097 can be an upper surface of a post or other suitable protrusion. As another example, the stop surface 2097 can be a lower portion of a concave, arcuate or otherwise suitable curved surface. The handles 2094 can also include, for example, knurling configured in a manner that seeks to restrict a user's fingers from inadvertently sliding downwardly out of the handle. As depicted in FIGS. 18A-18D, the knurling can be in the form of protrusions or hemispherical bumps, although other features can be included for restricting a user's fingers from inadvertently sliding downwardly out of the handle.

Optionally, the levers 2088 can be lower levers 2088 that extend obliquely upward from (e.g., from proximate) the contact surface 2082 and/or catch parts 2084 to upper levers 2089. The upper levers 2089 can be joined to one another at their upper ends. The upper connection between the upper levers 2089 can be a pivotable junction (e.g., flexible joint, living hinge (e.g., area of reduced thickness), or the like) between the upper levers 2089. Alternatively, the upper levers 2089 may be omitted.

The applicator tool 2080 can be an injection-molded, unitary (e.g., single-piece) article formed from an injection-moldable, generally elastic material such as, but not limited to, polycarbonate, polyethylene, or any other suitable injection-moldable material. Alternatively, the applicator tool 2080 can be made of metal, metal alloys, steel, or any other suitable materials that can allow for re-sterilization. For example, hinges (e.g., at the junctions between respective portions of the levers 2088, 2089 and/or links 2086) or other suitable connections that allow for relative movements between subparts can be included in the applicator tools 2080, such as when the applicator tools are made of relatively rigid materials. As additional examples, a variety of different linkages, levers, and handles of the applicator tool 2088 are within the scope of this disclosure.

Figure 18D:
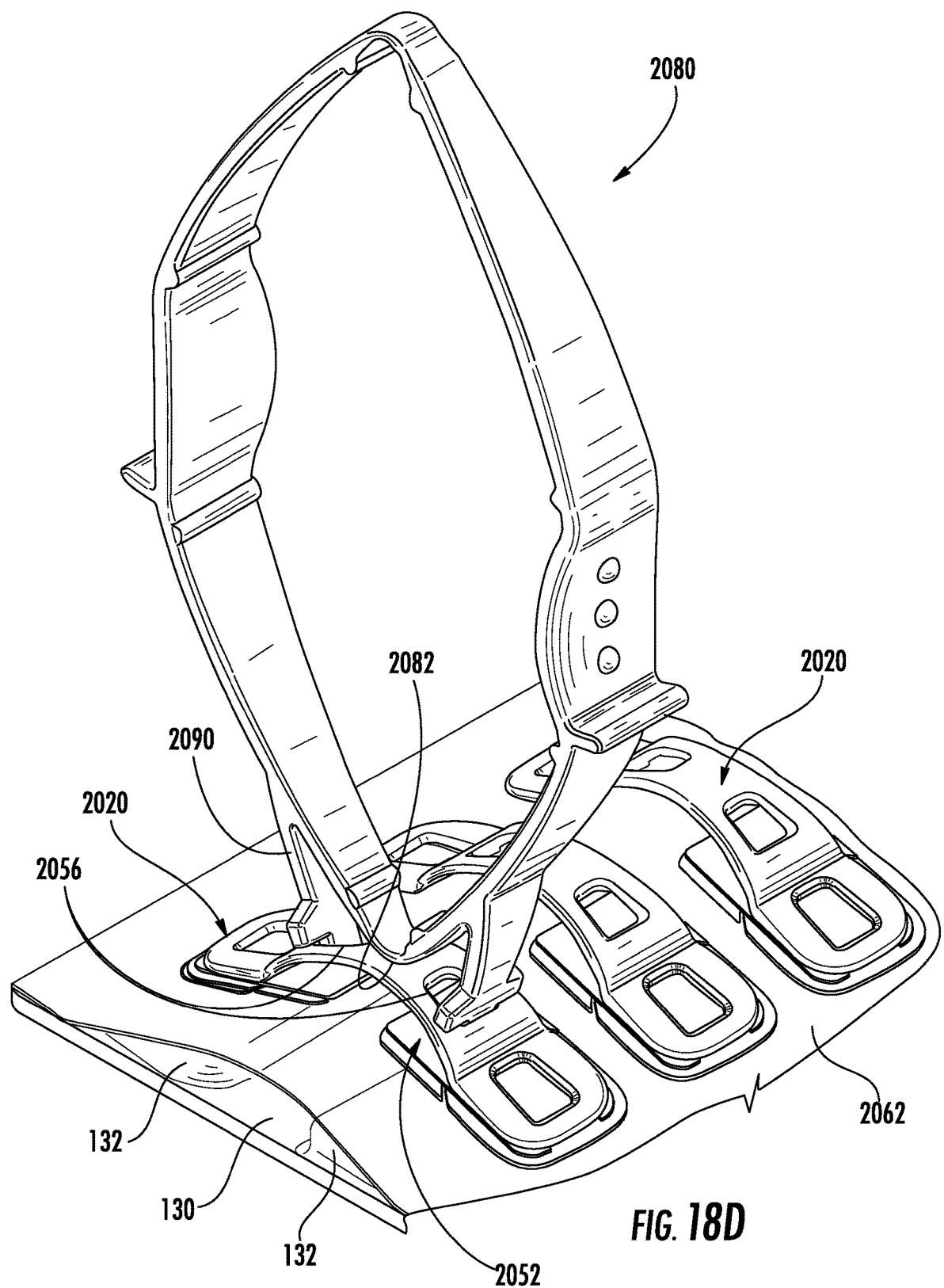
FIG. 18D depicts the applicator tool mated to a tissue bridge of a package including a tray and series of tissue bridges, in accordance with the eleventh embodiment.

In accordance with examples of the eleventh embodiment depicted in FIGS. 18D-20L, the tissue bridge 2020 and applicator tool 2080 are cooperatively configured so that the applicator tool can be releasably engaged to the tissue bridge, and the applicator tool can be used to manipulate the tissue bridge as part of a method of mounting the tissue bridge to tissue. For example, FIG. 18D depicts the bearing or contact surface 2082 in opposing-face-to-face relation with an upper surface of the arch 2028, and the shanks 2090 extending through the inner holes 2056. In the configuration of FIG. 18D, the outer protrusions 2092 (FIGS. 18A-18C) are hidden from view within the receptacles 2052. More generally, the catch parts of the applicator tool 2080 and tissue bridge 2020 are respectively engaged to one another in FIG. 18D. However, a variety of differently configured catch parts are within the scope of this disclosure.

Figure 19A:
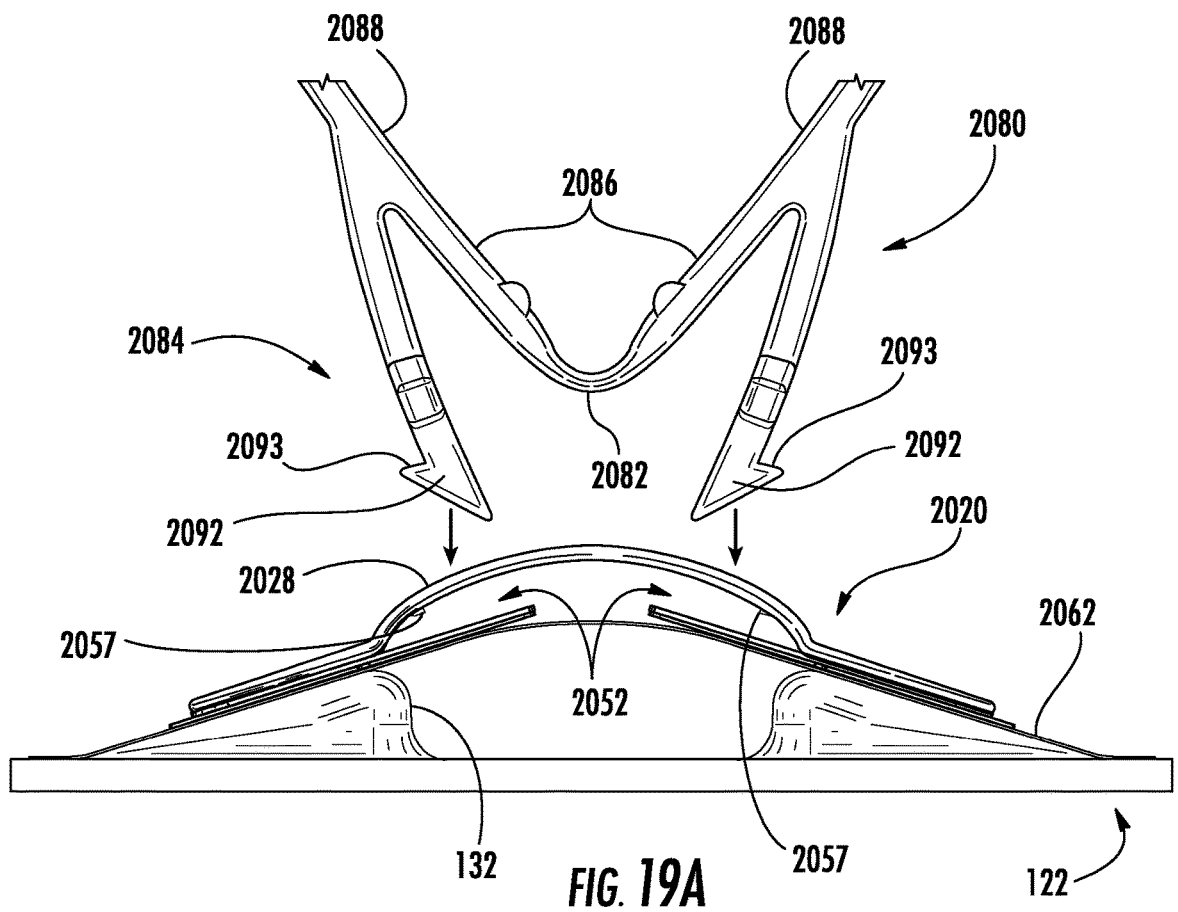
FIGS. 19A through 19F depict a sequence of steps of a method of using the applicator tool to remove a tissue bridge from the tray, in accordance with the eleventh embodiment.

Referring to FIGS. 19A-19F, a method of using the applicator tool 2080 to remove a tissue bridge 2020 from the tray 122 is described in the following, in accordance with the eleventh embodiment. Referring to FIG. 19A, initially, the applicator tool 2080 (e.g., in its undeformed or at rest configuration) can be engaged against the tissue bridge 2020 (e.g., in its undeformed or at rest configuration) by way of relative movement causing increased closeness between the applicator tool 2080 and the tray 122 (e.g., movement of the applicator tool toward the tissue bridge mounted on the release liner 2062 in the tray). In the eleventh embodiment, the applicator tool 2080 is elastic and, thus, biased toward its undeformed or at rest configuration.

Figure 19B:
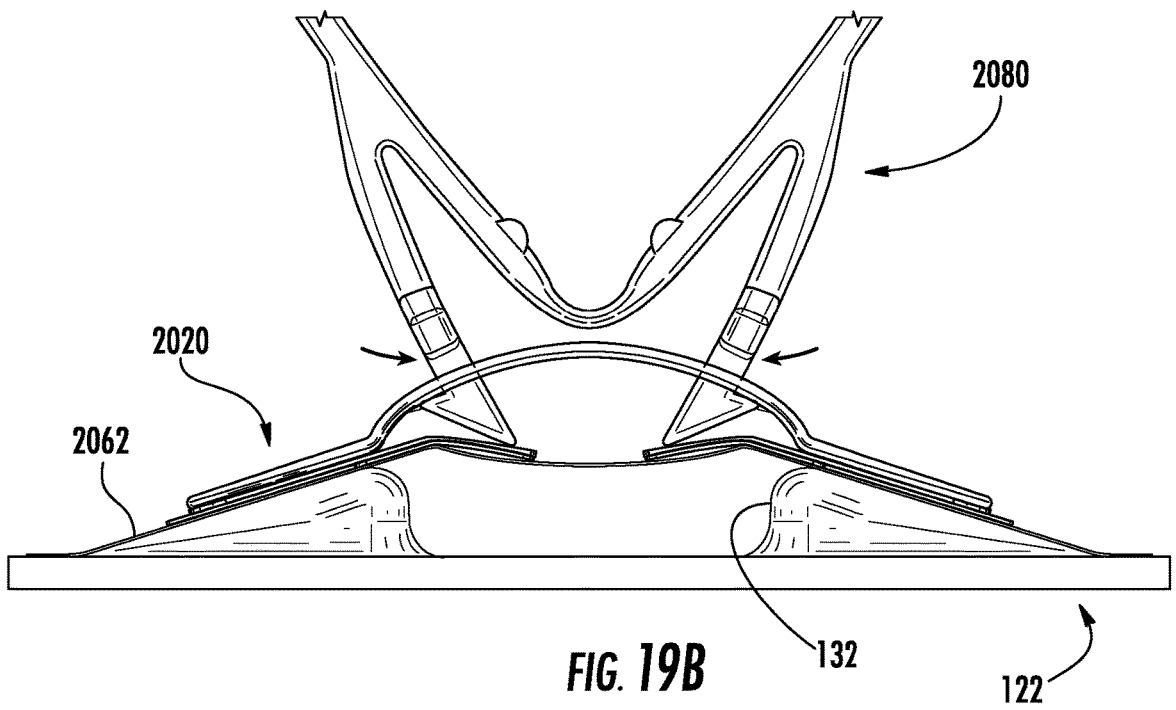

Referring to FIGS. 19A and 19B, in response to the relative movement, the outer protrusions 2092 of the tool catch parts 2084 can enter the receptacles 2052 by way of the inner holes 2056 (FIG. 17A). That is, the outer protrusions 2092 can enter the receptacles 2052 by traveling through the inner holes 2056. For example, the applicator tool 2080 can be pushed downwardly to engage the tissue bridge 2020 in a manner so that the outer protrusions 2092 of the tool catch parts 2084 enter the receptacles 2052 by way of the inner holes 2056, and optionally also the tool contact surface 2082 engages, or at least becomes more proximate to, the central apex or any other suitable surface of the arch 2028. In some embodiments, the tool contact surface 2082 may not (e.g., may never) engage the tissue bridge 2020.

The applicator tool 2080 can be in its undeformed or at rest configuration throughout the step of the outer protrusions 2092 of the tool catch parts 2084 entering the receptacles 2052 by way of the inner holes 2056. As another example, the distance between the tips of the outer protrusions 2092 can be greater than the distance between the hole edges 2058 (FIG. 17B) so that the protrusions outer protrusions 2092 "snap" into the inner holes 2056 and/or receptacles 2052 and are optionally releasably contained in the receptacles by way of an interference fit, or the like. The outward movement of the outer protrusions 2092 relative to one another associated with the "snap" is schematically represented by a pair of arrows in FIG. 19C.

In the eleventh embodiment, the inner holes 2056 are larger than the outer protrusion 2092 so that the outer protrusions can pass through the inner holes. Measuring in the same directions as indicated by widths W1, W2 in FIG. 17B, the widths of the outer protrusions 2092 (e.g., the widths of the engagement shoulders 2093) can be within a range of from less than about 1 times to about 0.4 times the width (or length) of the edges 2058 of the arch 2028 that partially define the inner holes 2056.

The relative movement causing increased closeness between the applicator tool 2080 and the tray 122 may be facilitated by a user manually holding the levers 2088 and/or handles 2094 (FIGS. 18A-18C) of the applicator tool and moving the applicator tool toward the tissue bridge 2020 in the tray, or the tissue bridge may be supported by any other suitable surface. Referring to FIG. 19B, the outer protrusions 2092 can engage respective surfaces of the medial struts 2048 in response to the relative movement causing increased closeness between the applicator tool 2080 and the tray 122. As a more specific example depicted in FIG. 19C, the engagement shoulders or surfaces 2093 of the tool 2080 can engage the engagement surfaces or ribs 2057 of the tissue bridge 2020.

Figure 19C:
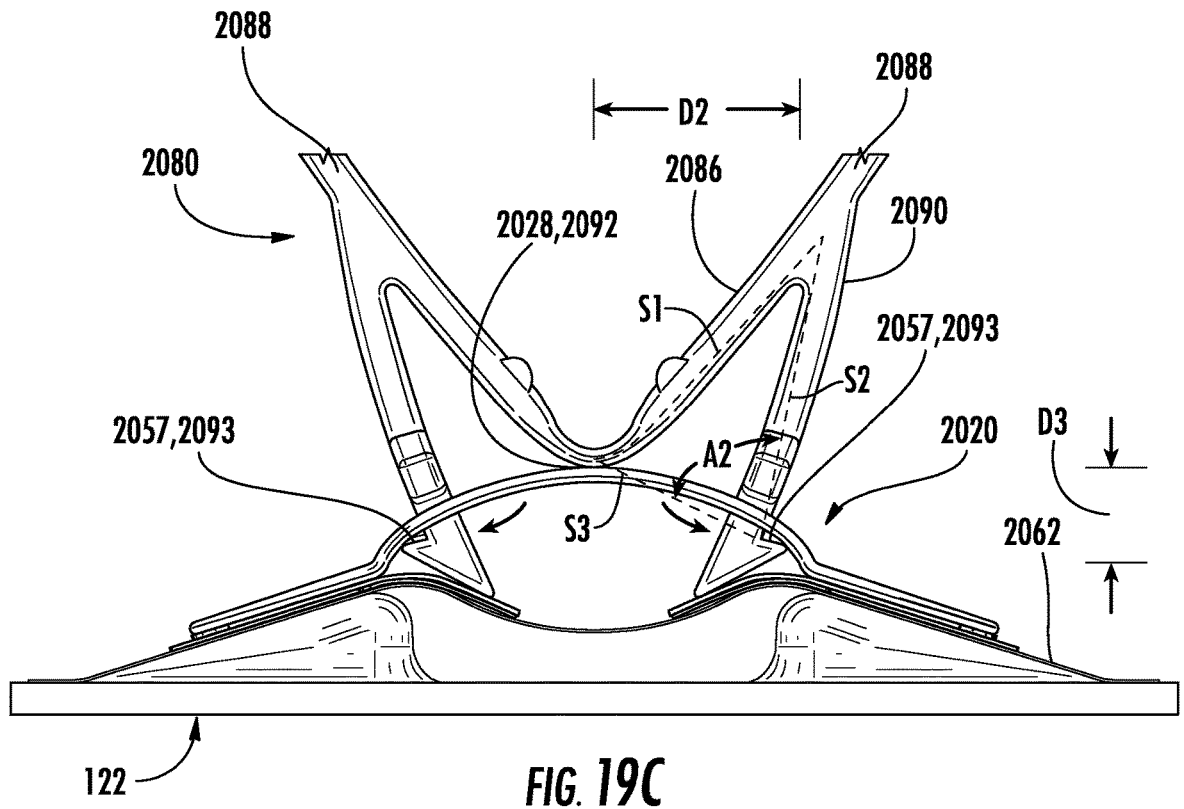
Figure 19D:
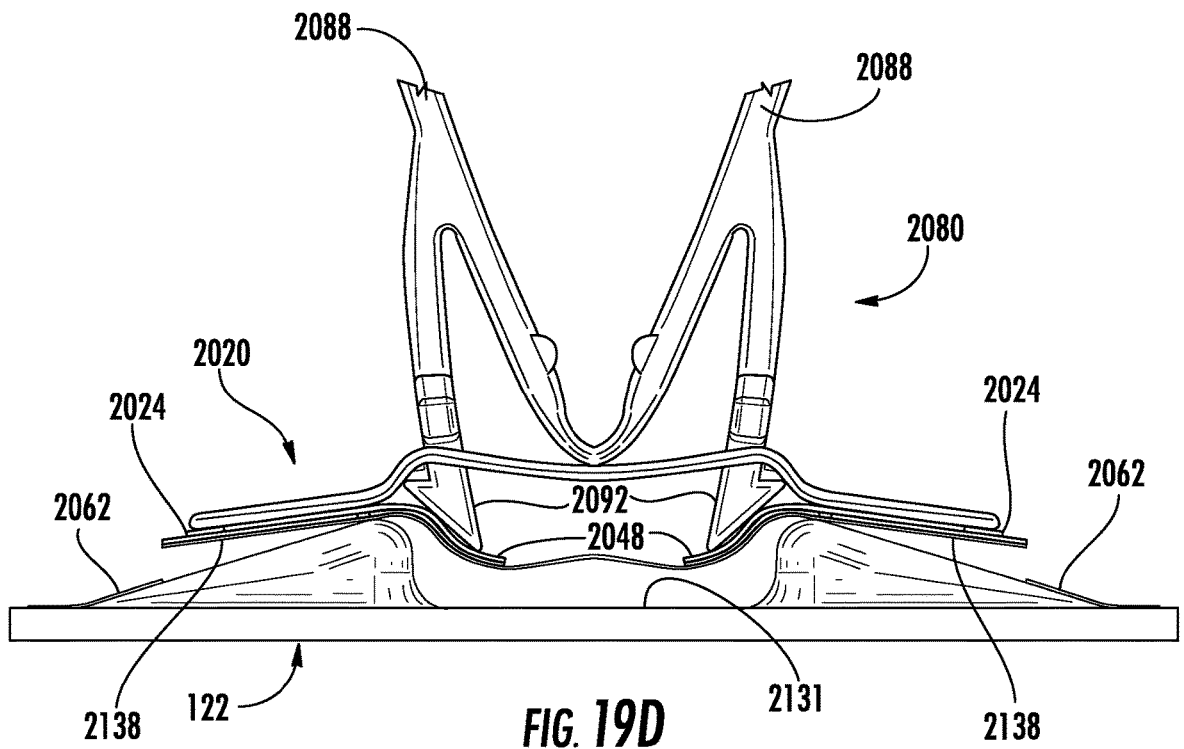

Then, for serially achieving the configurations of FIG. 19C and FIG. 19D, simultaneously and/or in series, the relative movement causing increased closeness between the applicator tool 2080 and the tray 122 can continue, and the handles 2094 can be manually squeezed together (e.g., pushed toward one another) so that the applicator tool reconfigures toward its actuated or deformed configuration and applies deforming forces on the tissue bridge 2020. As the applicator tool 2080 is, for example, simultaneously pushed with greater force against the tissue bridge 2020 and caused to deform farther toward its deformed configuration, the applicator tool applies forces against the tissue bridge 2020 so that the tissue bridge is responsively deformed toward its strained, deformed, or extended configuration. For example, the applicator tool 2080 can simultaneously apply a downward force via the contact surface 2082 and laterally outward forces via the catch parts 2084.

Referring to FIG. 19C, the distance between the medial struts 2048 and the inner holes 2056 (FIG. 17A) can be about the same as, or smaller than, the distance between the engagement shoulders 2093 and the outer tips 2091 of the outer protrusions 2092. As a result, the outer protrusions 2092 (e.g., the outer tips 2091) can engage the medial struts 2048 and cause them to deflect outwardly/downwardly, for example as shown in FIG. 19C. As another example, the distance between the engagement shoulders 2093 and the outer tips 2091 of the outer protrusions 2092 can be in a range of from about one to two times the distance between the medial struts 2048 and the inner holes 2056 in the relaxed configuration of the tissue bridge 2020.

Continuing to refer to FIG. 19C, as the applicator tool 2080 of the eleventh embodiment is transitioned from its undeformed or at rest configuration (e.g., FIG. 19C) to its actuated or deformed configuration (e.g., FIG. 19E), each side of the applicator tool and the associated tissue bridge 2020 can deform substantially symmetrically. For example, in FIG. 19C, the distance "D2" schematically depicts the span of travel of the junction between the adjacent link 2086 and shank 2090 that occurs during in the transition of the applicator tool 2080 from its undeformed or at rest configuration to its actuated or deformed configuration, and vice versa, and the span of travel D2 can be about 0.45 inches (11.5 mm). As another example, the distance "D3" schematically depicts how far the contact point or area between the engagement rib 2057 and engagement shoulder 2093 travels during in the transition of the applicator tool 2080 from its undeformed or at rest configuration to its actuated or deformed configuration, and vice versa, and the distance D3 can be about 2.1 inches (5.4 mm).

As schematically depicted in FIG. 19C, a side of a triangle or distance "S1" is defined between the central point of the top surface of the tissue bridge arch 2028 and the junction of the link 2086 and shank 2090. A side of the triangle or distance "S2" is defined between the junction of the link 2086 and shank 2090 and the contact point or area between the engagement rib 2057 and engagement shoulder 2093. An angle "A2" defined between a triangle side "S3" and triangle side S2 can be less than 120 degrees, or more specifically about 93 degrees. The ratio of the distance S1 to the distance S2 (i.e. S1 divided by S2) can range of from about 1.0 to about 1.4, or can range of from about 1.1 to about 1.2, or more specifically can be about 1.14.

In the transition from the configuration of FIG. 19C to the configuration of FIG. 19D, the outer portions of the foot pads 2024 have moved, or more specifically pivoted, away from the tray outer sections 132. As discussed above, the release liner flaps 2138 can be attached to the outer portions of the foot pads 2024 by way of the outer adhesive layer 2042. Therefore, the flaps 2138 can be carried by, and pivot with, the outer portions of the foot pads 2024. Therefore, the flaps 2138 pivot outwardly relative to a reminder of the release liner 2062 that remains fixedly mounted to the tray base panel 2124. That is, the flaps 2138 can pivot outwardly relative to (e.g., at least partially delaminate from) a reminder of the release liner 2062 and the tray 122 in response to respective movement, reconfiguring, and/or the like of the tissue bridge 2020 and applicator tool 2080. In the eleventh embodiment, the release liner 2062 is a support that supports the tissue bridge 2020, and each flap 2138 can be referred to as a first section of the support, and the reminder of the release liner 2062 and/or the tray 122 can be referred to as a second section of the support, or the like.

As another example, in the transition from the configuration of FIG. 19C to the configuration of FIG. 19D, the outer protrusions 2092 have pushed (e.g., deflected) the medial struts 2048 downwardly toward the recessed central section 2130 of the tray 122. That is, in an example, the medial struts 2048 can pivot downwardly relative to a reminder of the foot pads 2024 in response to respective movement, reconfiguring, and/or the like of the tissue bridge 2020 and applicator tool 2080.

Figure 19E:
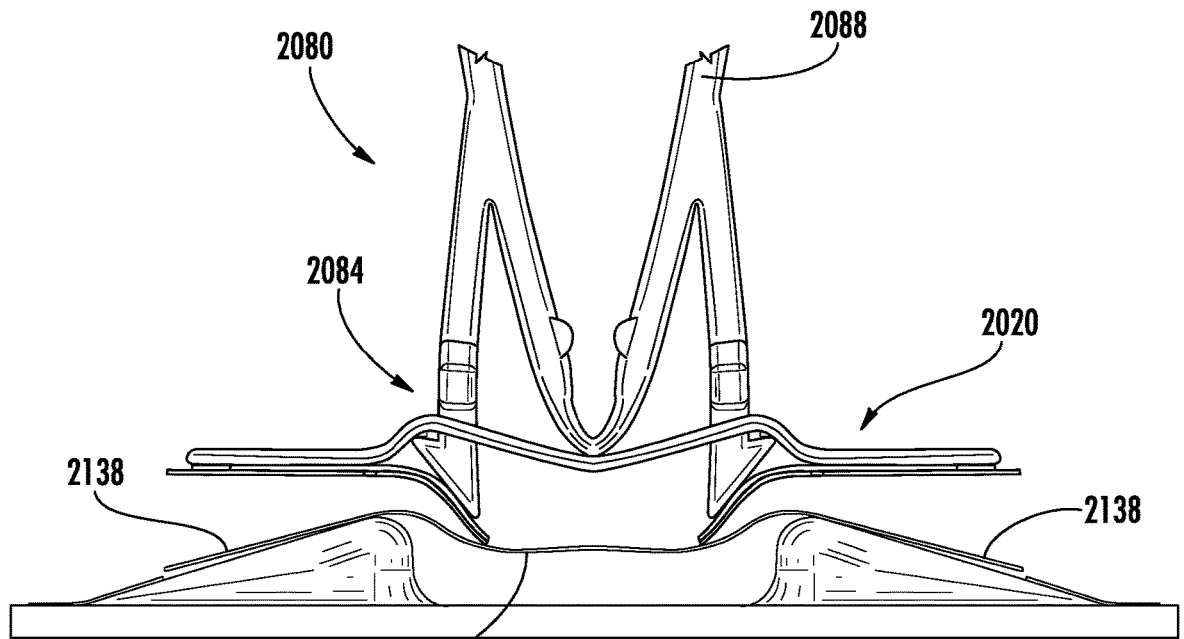
Figure 19F:
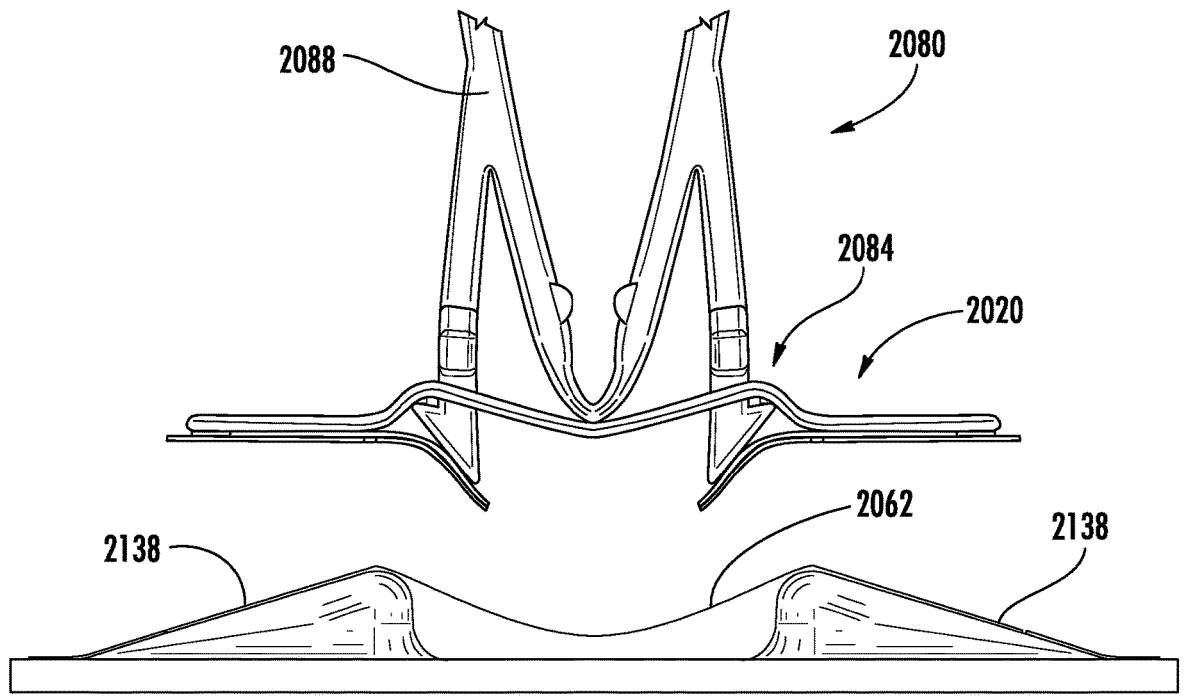

Referring to FIG. 19C-19F, the applicator tool 2080 and tissue bridge 2020 can be cooperatively configured and engaged to one another in a predetermined manner so that, in response to the handles 2094 being manually squeezed or pushed closer to one another, at least lower portions of the tool catch parts 2084 are moved farther away from one another and the contact surface 2082 moves toward a line between the catch parts 2084, and this movement of the applicator tool 2080 forces the tissue bridge 2020 into its fully deformed or extended configuration, an example of which is shown in FIG. 19F. For example, the manual inward force applied to the opposite sides of the handles 2094 to achieve this configuration can be in a range of from more than 0.2 pounds force (0.89 newtons) to less than 2 pounds force (8.9 newtons).

In the transition from the configuration of FIG. 19D to the configuration of FIG. 19E, the release liner 2062 typically fully separates from the tissue bridge 2020, and the flaps 2138 can pivot/fall back into their original positions in response to relative movement causing increased distance between the applicator tool 2080 and the tray 122. The release liner 2062 typically fully separates from the tissue bridge 2020 in a manner that fully exposes the outer adhesive layer 2042 (e.g., patient contact adhesive), so that there are no remnants of the release liner 2062 stuck to the tissue bridge and the outer adhesive layer is ready for being used to secure the tissue bridge to tissue, such as the skin of a patient.

For example, in FIG. 19F the tissue bridge 2020 and applicator tool 2080 are engaged to one another, and both the tissue bridge and the applicator tool are in their deformed configurations so that the tissue bridge is securely grasped or otherwise held by the applicator tool, so that as the applicator tool is manually moved away from the tray 122 the applicator tool carries the tissue bridge away from the tray. While the tissue bridge 2020 is securely held by the applicator tool 2080, the applicator tool can be used to apply the tissue bridge to tissue, such as the skin of a patient.

Figure 19G:
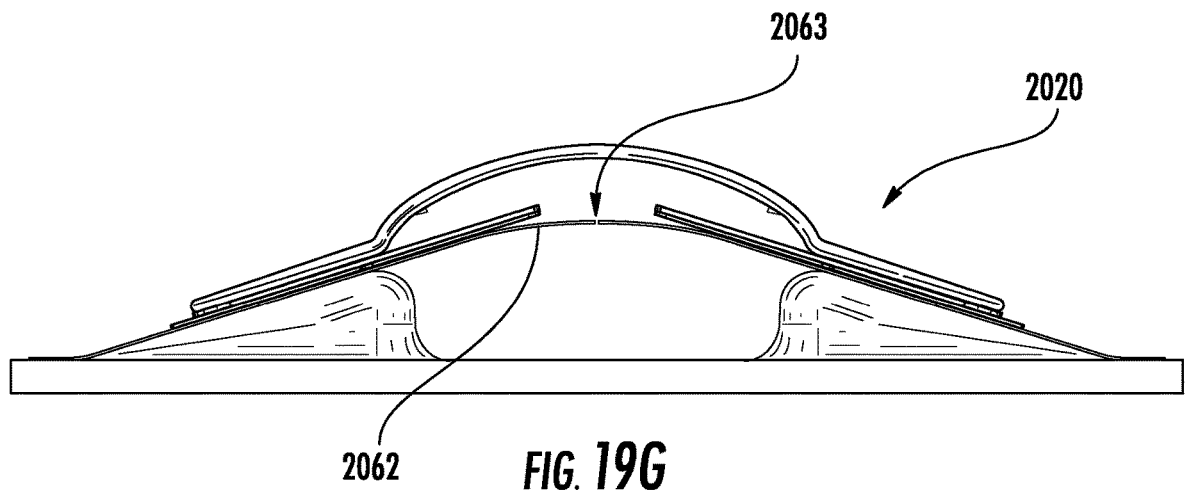
FIGS. 19G and 19H depict different confirmations of a release liner associated with a tissue bridge and tray, in accordance with the eleventh embodiment.
Figure 19H:
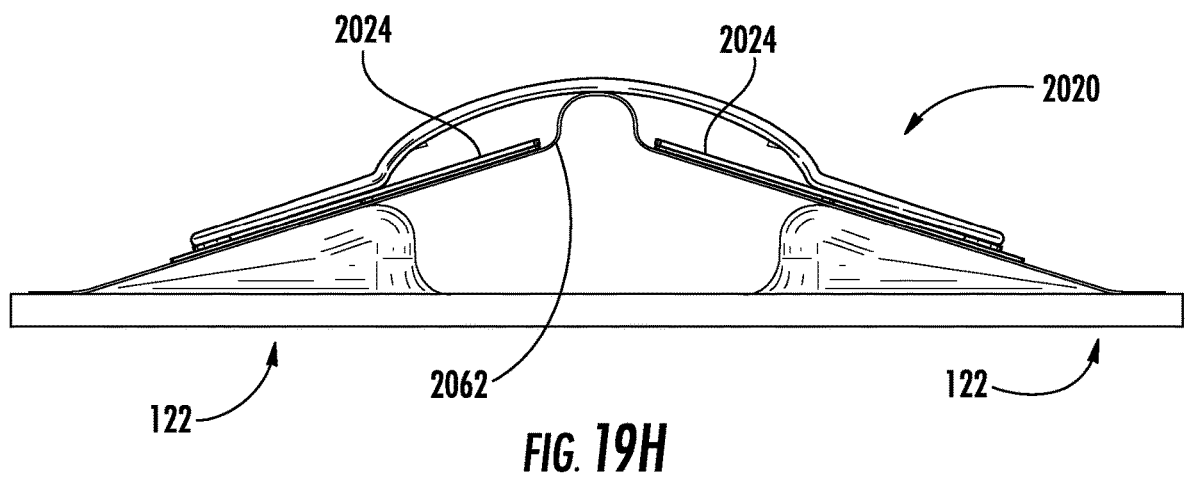

At least FIGS. 19C-19E may be characterized as schematically depicting stretching of the release liner 2062. However, any of such stretching can be avoided, for example as shown in FIG. 19G, by including a line of disruption 2063 (e.g., cut, slit or tear line) between respective sections of the release liner 2062. As another example depicted in FIG. 19H, a length of the portion of the release liner 2062 positioned between the inner ends of the foot pads 2024 can be greater than the distance between the inner ends of the foot pads 2024. The excess length of the portion of the release liner 2062 between the inner ends of the foot pads 2024 can be in the form of a bulge or overlapping section of the release liner 2062, or the like.

Figure 19I:
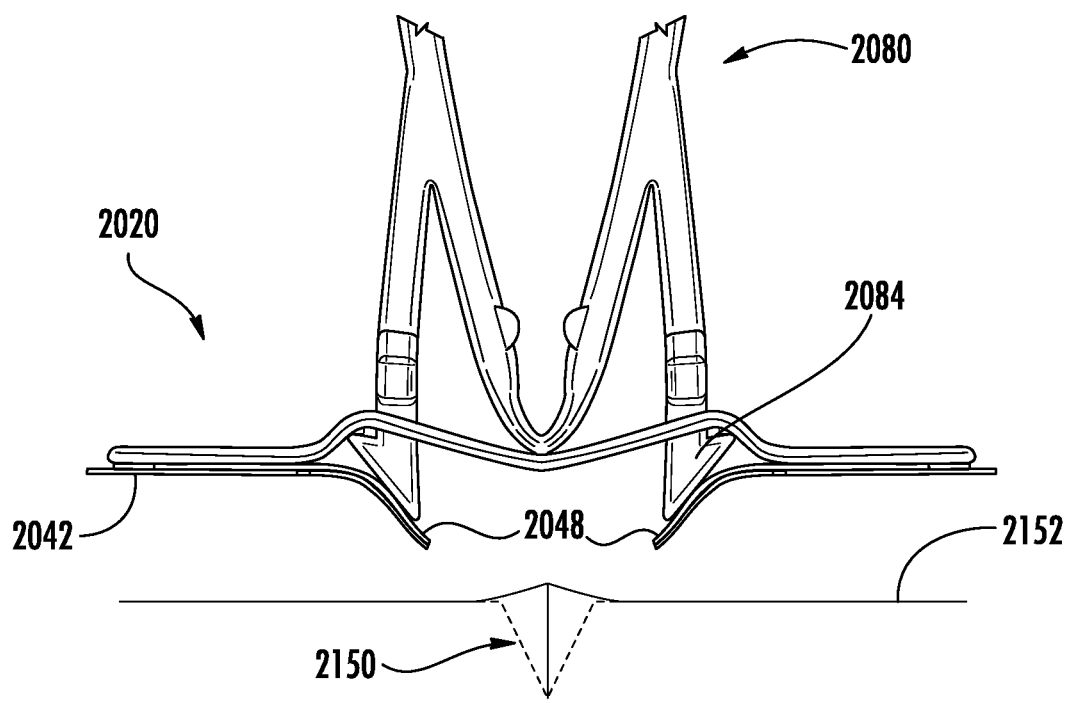
FIGS. 19I through 19L depict a sequence of steps of a method of using the applicator tool to apply the tissue bridge to a wound, in accordance with the eleventh embodiment.
Figure 19J:
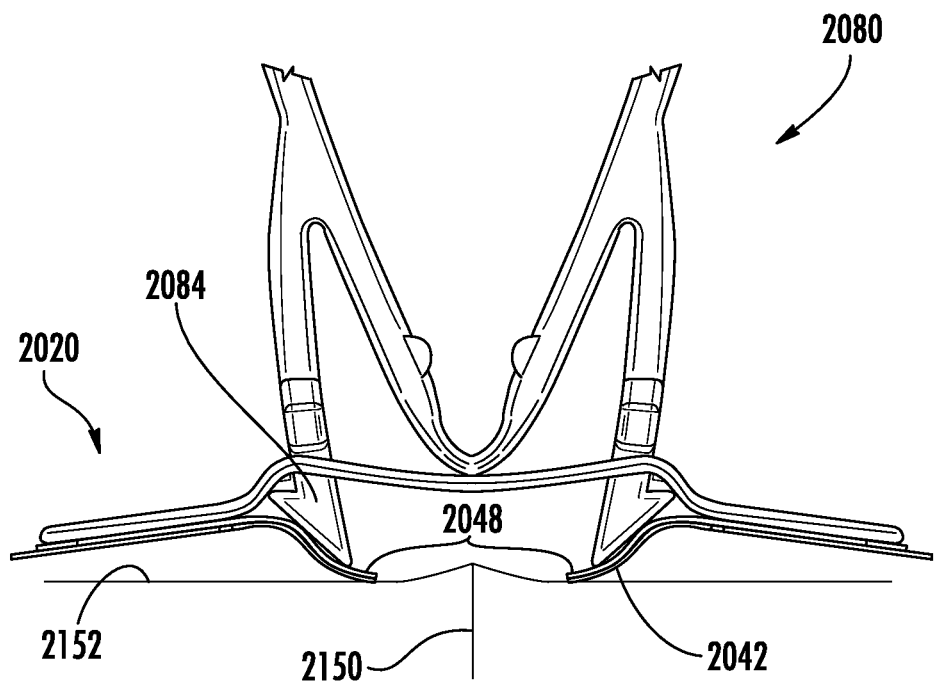
Figure 19K:
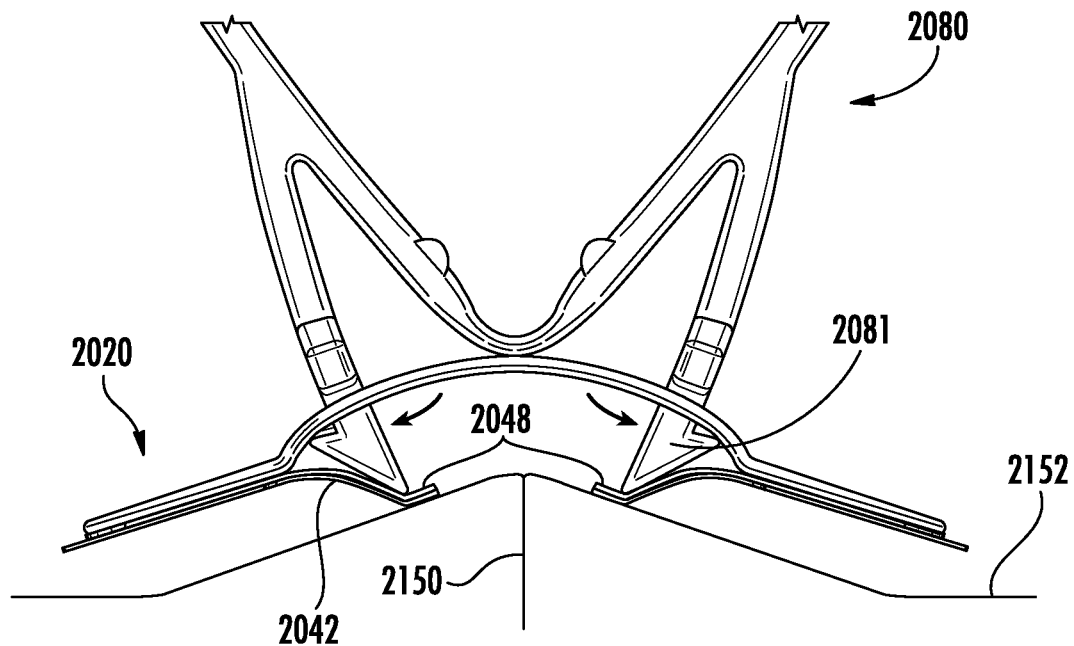

Referring to FIGS. 19I-19L, a method of using the applicator tool 2080 to apply a tissue bridge 2020 to tissue 2152 on either side of a cut 2150 in a patient's skin 2152 is described in the following, in accordance with the eleventh embodiment. FIG. 19I schematically depicts with dashed lines 2154 the originally spaced apart edges of the cut 2150, and a solid line 2156 schematically depicts that the edges of the cut may be manually pushed together prior to applying the tissue bridge 220 over the cut. The applicator tool 2080 holding the tissue bridge 2020 can be moved toward the cut 2150 so that the tissue bridge 2020 extends crosswise to, or more specifically substantially perpendicular to, the length of the cut 2150, and the first contact between the tissue bridge and the tissue or skin 2152 occurs at the inner end sections or portions of the medial struts 2048 on either side of the cut. Referring to FIG. 19J, the applicator tool 2080 can continue to be pushed closer to the cut 2150 so that the inner portions of medial struts 2048 begin to become adhered to the skin 152 by the outer adhesive layer 2042 (e.g., patient contact adhesive). For example, the transmission of force from the applicator tool 2080, by way of the catch parts 2084, against the medial struts 2048 can cause the pressure-sensitive adhesive layer 2042 to be engaged against the tissue 2152 with sufficient force to cause the inner portions of medial struts 2048 to become adhered to the tissue 2152 at opposite sides of the cut 2150. Then, for example as at least partially depicted in FIG. 19K, the manual force on the handles 2094 of the applicator tool 2080 can be reduced, so that the tissue bridge 2020 returns toward its at rest configuration, and the medial struts 2048 become closer together and push the portions of the tissue 2152 to which they are adhered toward one another. Then, in response to the tissue bridge 2020 returning farther toward its at rest configuration, the reconfiguring of the tissue bridge causes the outer portions of the foot pads 2024 to move or pivot downwardly into contact with the tissue 2152 at opposite sides of the cut 2150. In one example, this contact between the outer portions of the foot pads 2024 and the tissue 2152 at opposite sides of the cut 2150 may occur with sufficient force to cause the pressure-sensitive adhesive layer 2042 to securely adhere the outer portions of the foot pads 2024 to the tissue 2152 at opposite sides of the cut 2150.

In accordance with the eleventh embodiment, the inner portions of the medial struts 2048 are adhesively mounting to the tissue 2152 while the tissue bridge 2020 is in its deformed or extended configuration; and thereafter as the tissue bridge 2020 returns toward its at rest configuration and reaches an intermediate configuration that is between the extended and at rest configurations, the remainder or outer portions of the foot pads 2024 are adhesively mounted to the tissue. When the tissue bridge 2020 is first engaged against the tissue 2152, the point of first contact and adhesive mounting to the tissue can be at the inner end sections or portions of the medial struts 2048, and this mounting can occur while the medial struts are being pushed downwardly by way of the applicator tool 2080. In the eleventh embodiment, as the deforming force being applied on the tissue bridge 2020 by the applicator tool 2080 is reduced, the medial struts 2048 move or rotate inwards, thus centrally pulling the tissues 2152 to which they are adhesively mounted, and this action by the medial struts 2048 occurs before the outer portions of the foot pads 2024 are adhesively attached to the tissue. At this intermediate point, in which the medial struts 2048 are at least partially attached to the tissue 2152 and have moved inwards, and the outer portions of the foot pads 2024 are not yet attached to the tissue, the shear stress and/or strain on predetermined tissue (i.e., tissue that is lateral to the lateral-most contact point between the medial strut and the tissue) is distributed laterally and in a gradual manner. Then, when the lateral or outer portions of the foot pads 2024 are pressed down and adhered to the tissue 2152, the predetermined tissue underneath and at the lateral edges or outer edges of the foot pads 2024 is secured (e.g., adhered to the foot pads) in its state in which the stress and/or strain in the predetermined tissue is distributed laterally and in a gradual manner, which seeks to prevent sudden, high sheer stress at the lateral edges (e.g., opposite ends) of the tissue bridge 2020.

Figure 19L:
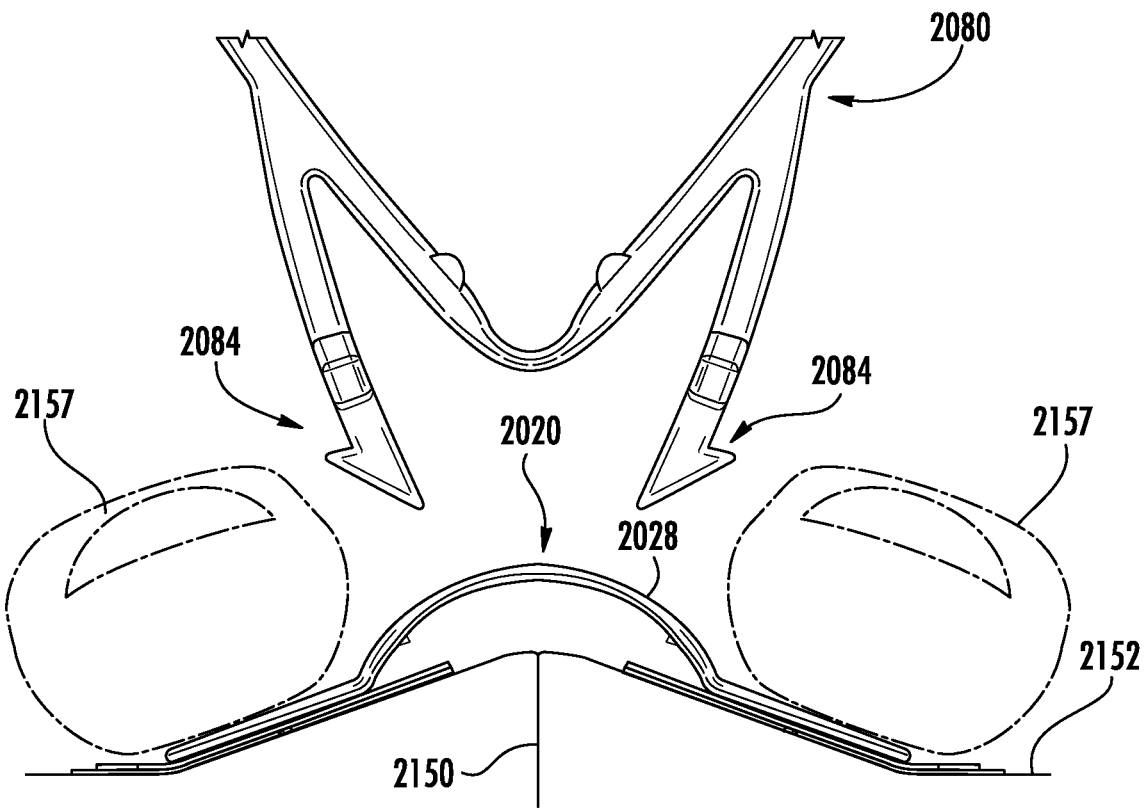

Referring to FIG. 19L, the applicator tool 2080 can then be removed from the tissue bridge 2020 so that the tissue bridge remains mounted over the cut 2150; then the applicator tool may be used to install another tissue bridge. In addition, a user can push down manually with their fingers 2157 on the foot pads 2024, for example with sufficient force to ensure that the pressure-sensitive adhesive layer 2042 securely adheres the foot pads 2024 to the tissue 2152 at opposite sides of the cut 2150. In accordance with the eleventh embodiment, the tissue bridge 2020 can be mounted to the tissue 2152 in a manner such that the tissue bridge and tissue apply force against one another, and the force applied by the tissue typically restricts the tissue bridge from fully returning to its at rest configuration. As a result, the tissue bridge 2020 applies compressive force to the tissue 2152 by way of the foot pads 2024 in a manner that can, for example, reduce tension in the tissue, help close the wound 2150, help inhibit wound reopening and/or inhibit scar disfiguring (e.g., widening). In the example shown in FIG. 19*l*, the tissue 2152 proximate the scar and/or wound 2150 bulges into the central area over which the arch 2028 extends.

The tissue bridge 2020, release liner 2062 and applicator tool 2080 can be configured differently than discussed above. For example, one or more of the layers of the tissue bridge 2020 can be configured differently than discussed above. As a more specific example, in the variation of the tissue bridge 2020 depicted in FIGS. 20A-20D, each of the inner sheets 2036 and the intermediate adhesive layers 2040 can include opposite, outwardly extending lateral extensions 2037, 2041. Accordingly, the inner sheets 2036, the intermediate adhesive layers 2040 and foot pads 2024 become wider in the inward direction, and taper in the outward direction, such the medial strut 2048 sections of the foot pads are wider than the outer sections of the foot pads. Each of the outer sheets 2034 and outer adhesive layers 2042 can be generally in the form of a quadrilateral, trapezoid, isosceles trapezoid, or any other suitable shapes.

Figure 20A:
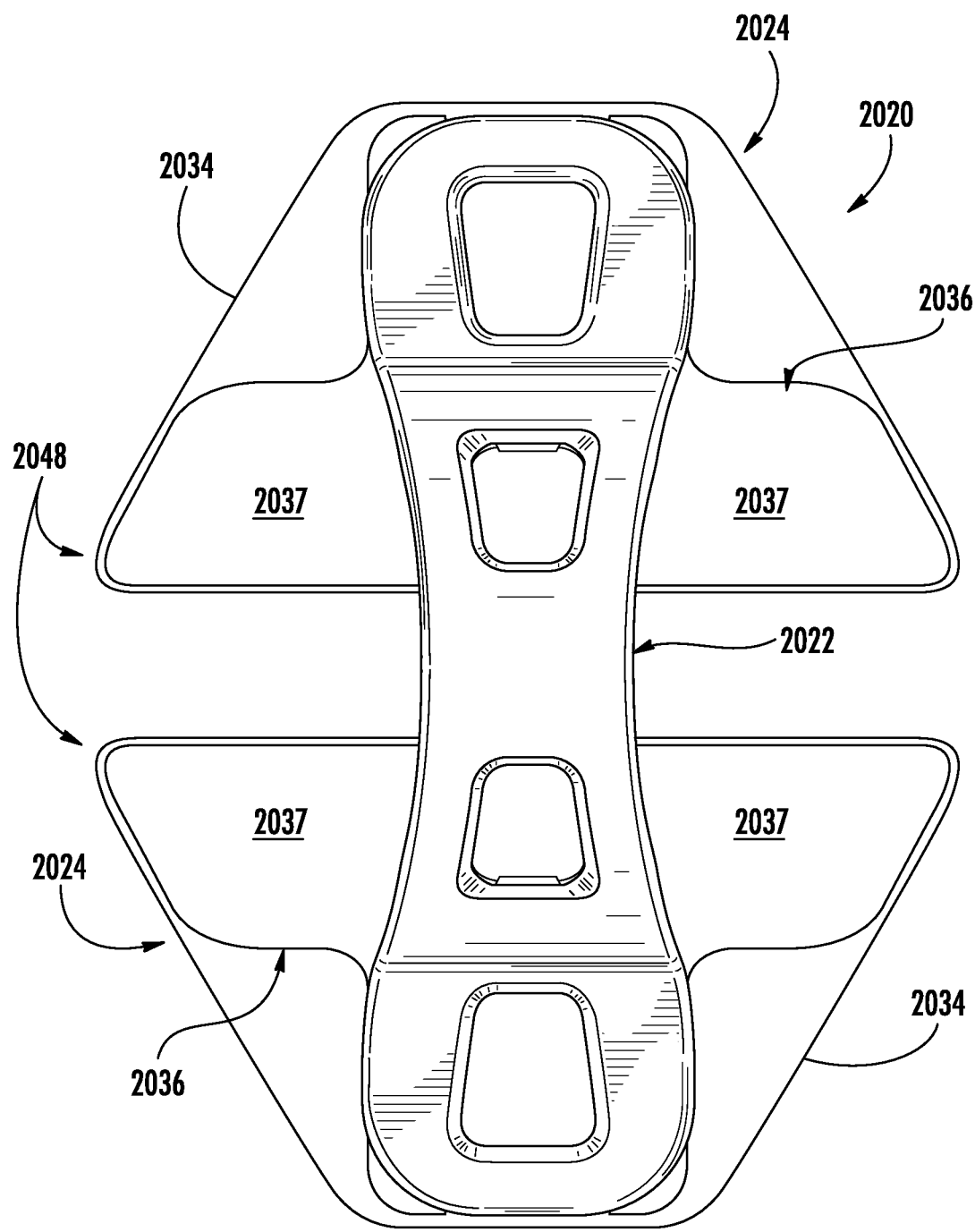
FIG. 20A is top plan view of a tissue bridge of a variation of the eleventh embodiment.
Figure 20B:
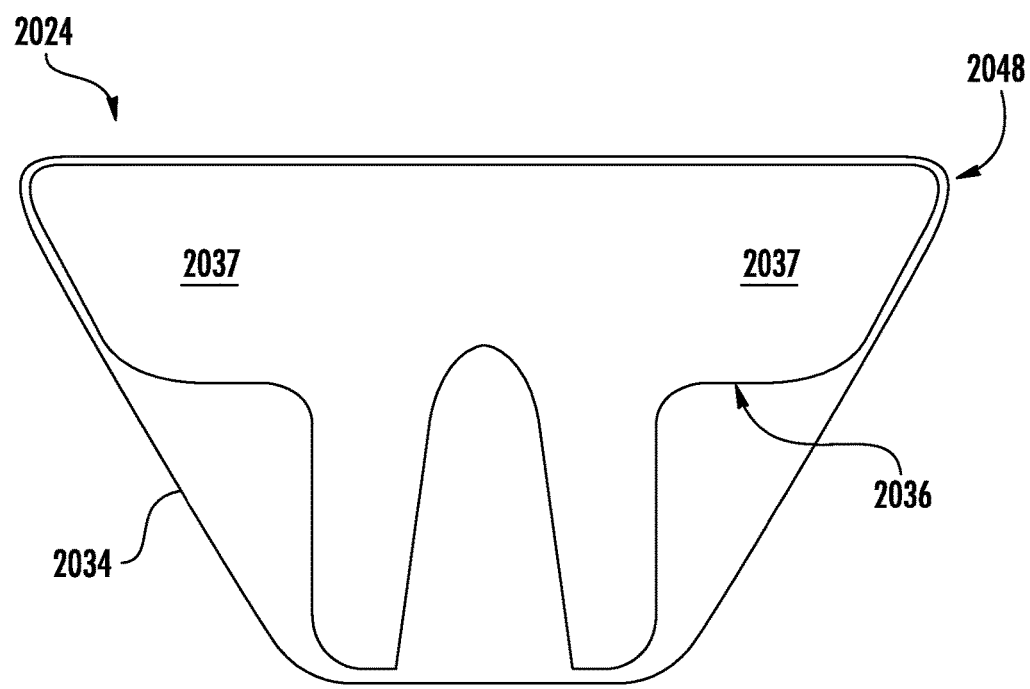
FIG. 20B is an isolated, top plan view of a footpad of the tissue bridge of the variation of the eleventh embodiment.
Figure 20C:
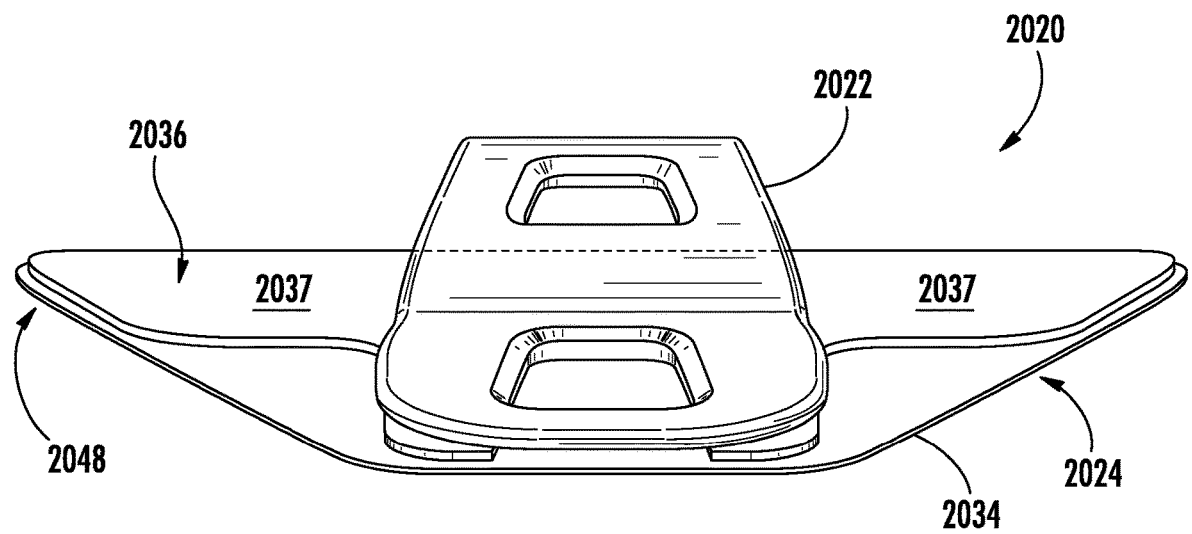
FIG. 20C is an end elevation view of the tissue bridge of the variation of the eleventh embodiment.
Figure 20D:
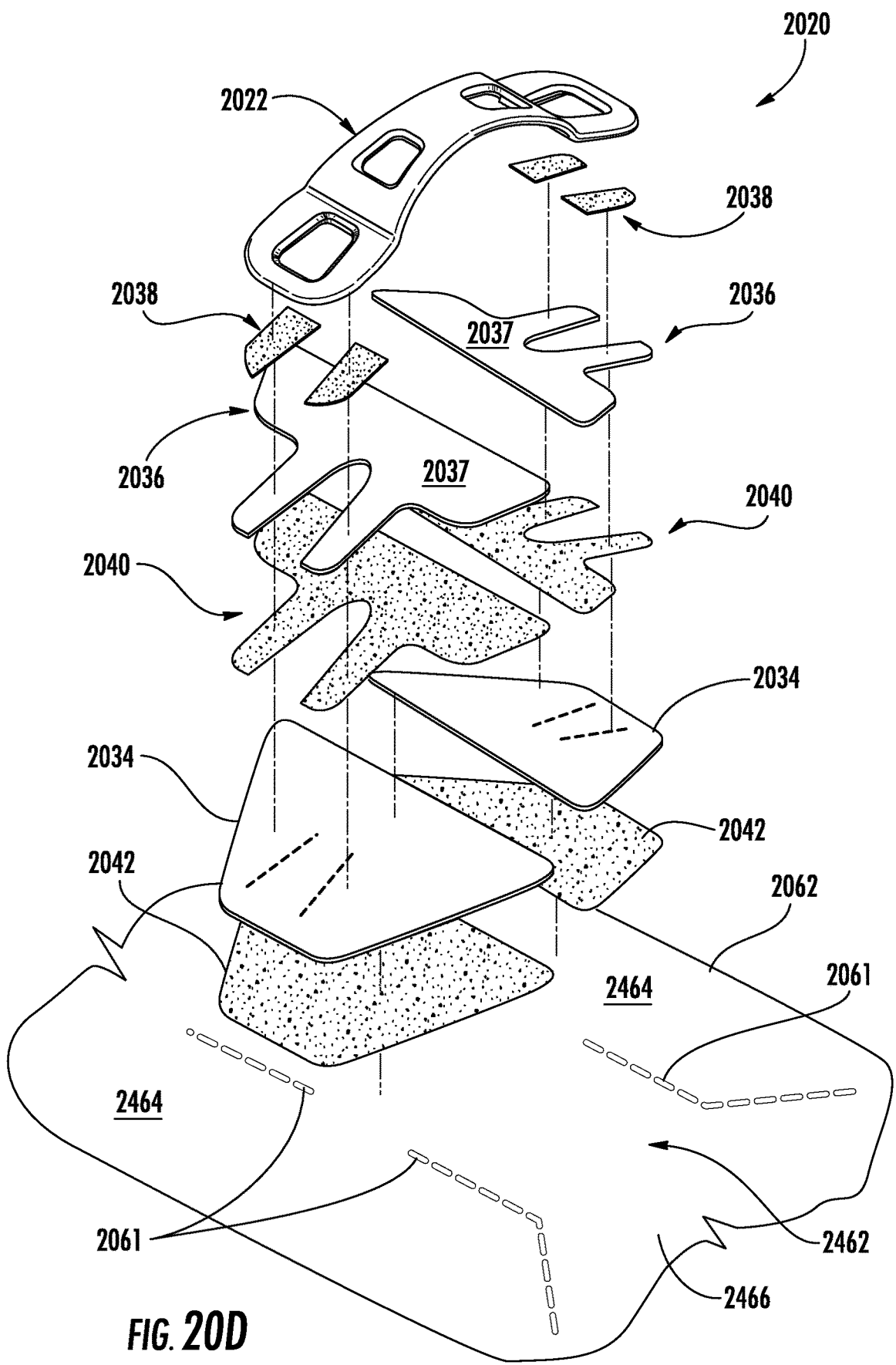
FIG. 20D is a top pictorial exploded view of the tissue bridge of the variation of the eleventh embodiment, wherein FIG. 20D further depicts the tissue bridge exploded away from a section of a release liner, in accordance with the variation of the eleventh embodiment.

Referring to FIG. 20D and in an example of some versions of this disclosure, the release liner 2062 may not be associated with (e.g., mounted to) any tray 122 (FIGS. 18A-18D). For example, for the version depicted in FIG. 20D, when the tissue bridge 2020 is fully assembled on the release liner 2062, thereafter at least a portion of the release liner may be removed, and then the tissue bridge 2020 may be applied by hand (e.g., not using an applicator). In this example, a user can manually grasp and pull a tab 2466 defined in the release liner 2062 between a pair of breachable lines of disruption (e.g., tear lines). The tab 2466 can be part of a central a central section 2462 of the release liner 2062 that is at least partially defined between the lines of disruption. Outer release liner portions 2464 can be manually grasped and used for mounting the tissue bridge 2020 to tissue.

Figure 21:
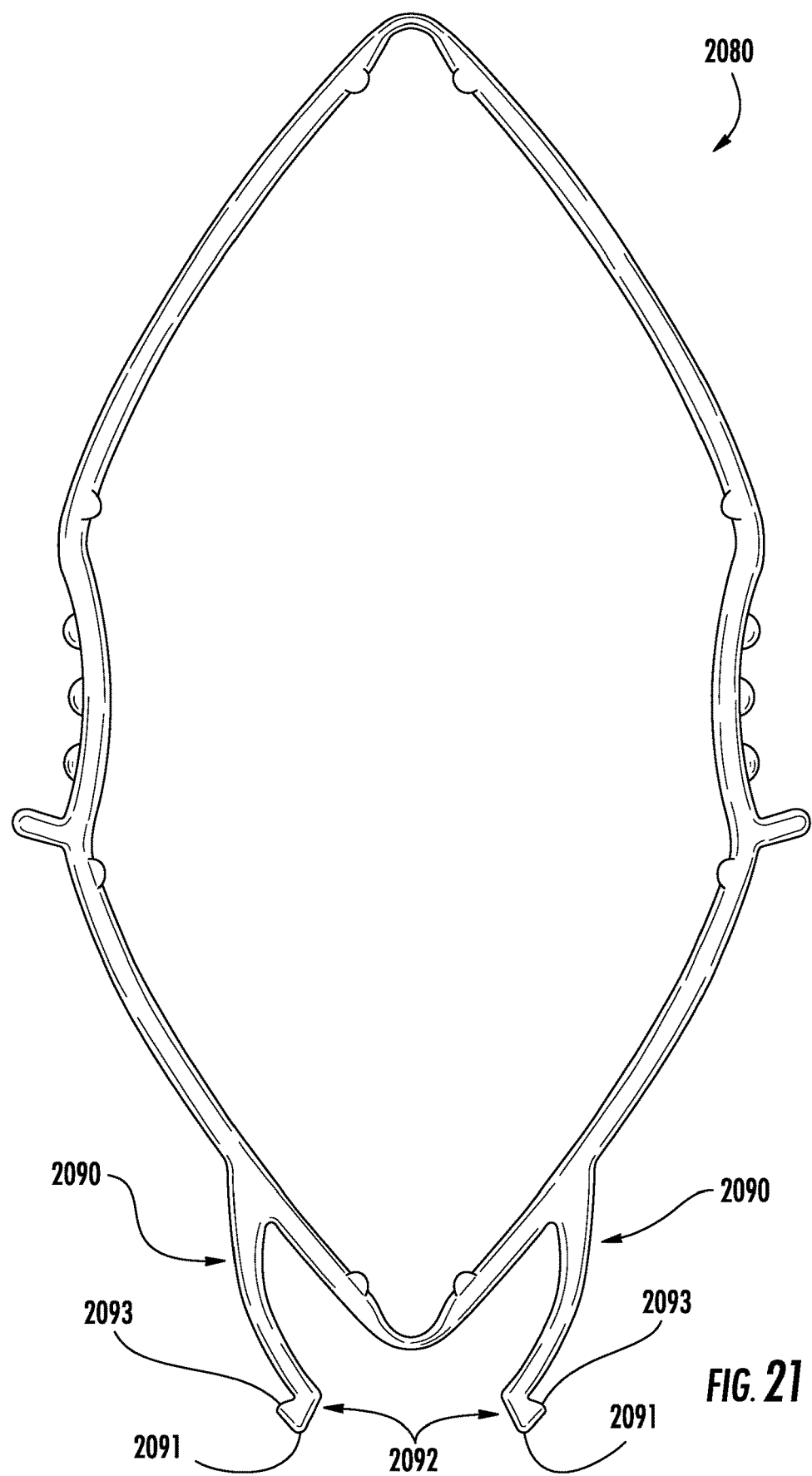
FIG. 21 depicts a variation of the applicator tool of the eleventh embodiment.
Figure 22:
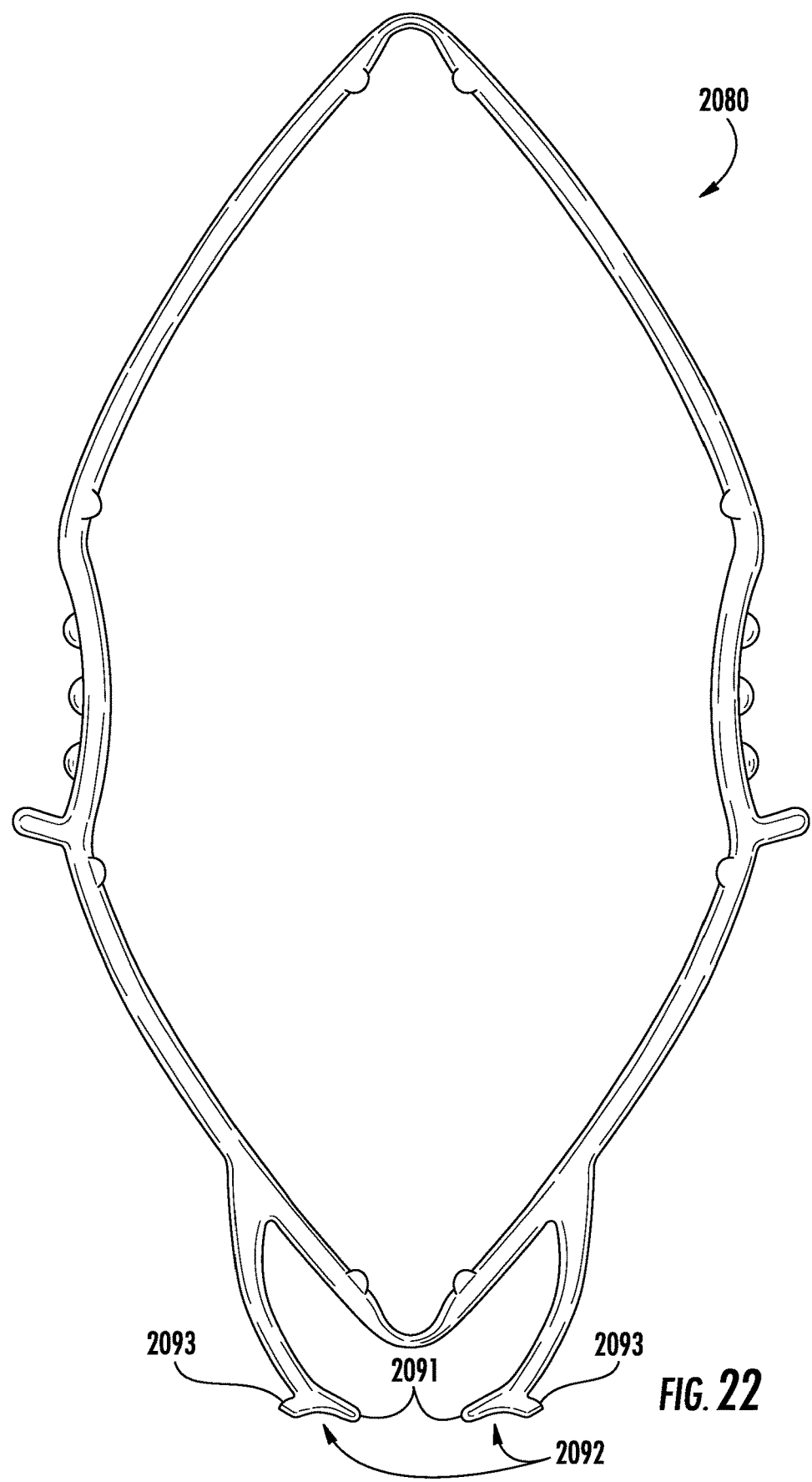
FIG. 22 depicts another variation of the applicator tool of the eleventh embodiment.

As additional examples, FIGS. 21 and 22 depict variations of the applicator tool 2080, wherein the outer protrusions 2092 are configured differently and the stabilizing and/or alignment protrusions 2095 can optionally be omitted. For example, in FIG. 21, the engagement shoulder 2093 can be at least partially defined by a bend in the shank 2090. As another example, in FIG. 22 the outer tip 2091 and engagement shoulder 2093 are relatively rounded.

Figure 23A:
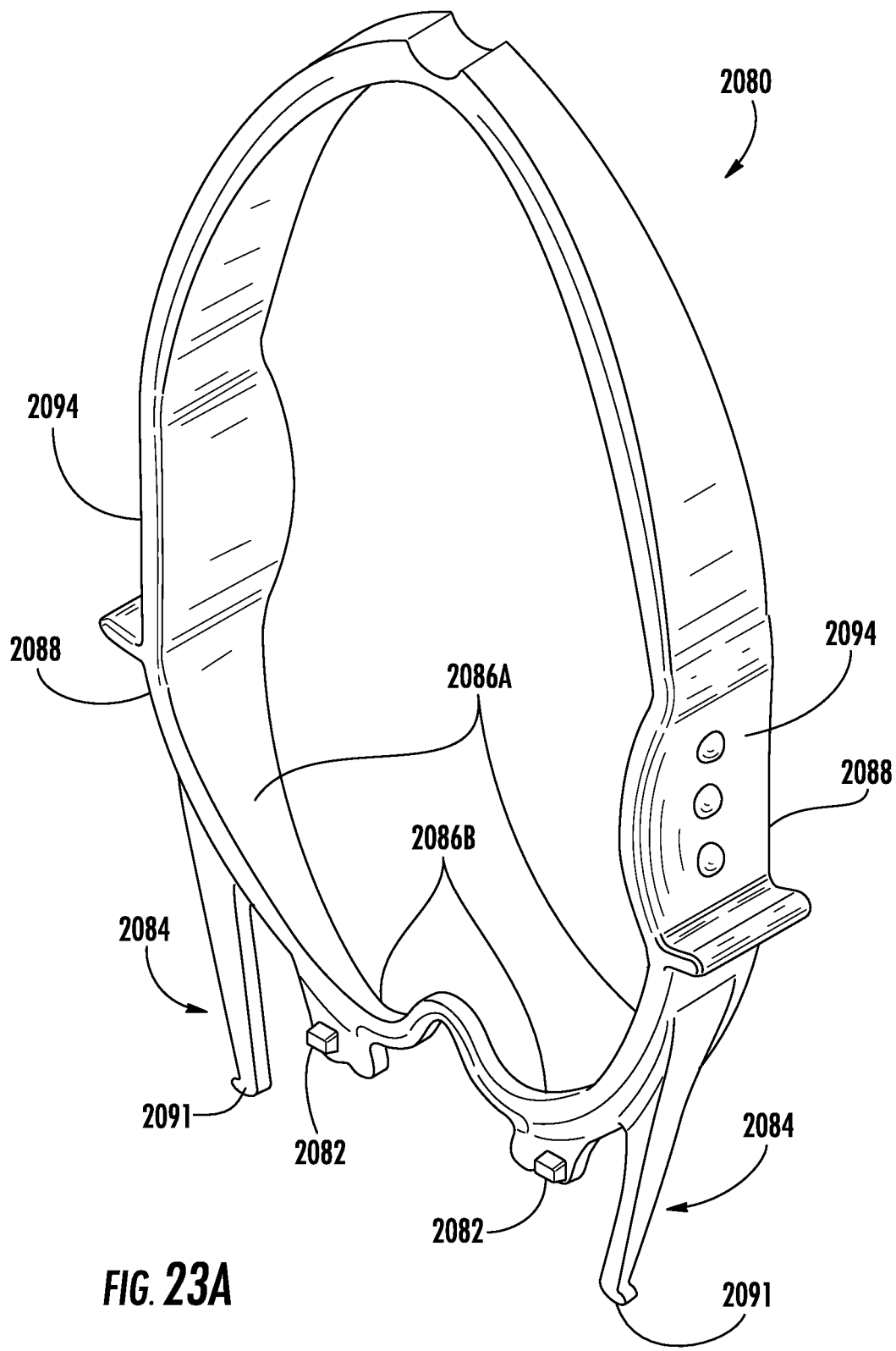

FIGS. 23A-23C depict an applicator tool 2080 in accordance with a twelfth embodiment, wherein the tissue bridge 2020 is schematically depicted in dashed lines in FIGS. 23B and 23C. The twelfth embodiment applicator tool 2080 includes parts or features that are spaced apart from one another and configured to releasably engage the tissue bridge 2020. In the twelfth embodiment, the parts or features of the applicator tool 2080 that are configured to engage the tissue bridge 2020 include bearing or contact surfaces 2082 and catch parts 2084. For example, the contact surfaces 2082 can be positioned between the catch parts 2084. The twelfth embodiment applicator tool 2080 further includes a reconfigurable frame connecting the contact surfaces 2082 and catch parts 2084 to one another.

Referring to FIG. 23A, the frame of the twelfth embodiment applicator tool 2080 include a reconfigurable linkage (e.g., links 2086A, 2086B) connecting the contact surfaces 2082 and catch parts 2084 to one another. The catch parts 2084 extend downwardly from the levers 2088 and/or handles 2094 and/or linkage (e.g., links 2086A), and the levers 2088 and/or handles 2094 extend upwardly from at least some of the linkage. The links 2086A are connected to one another by way of one or more additional links, for example the links 2086B, which form a hinge or hinge-like member (e.g., a pivotable junction, flexible joint, living hinge (e.g., area of reduced thickness), or the like). The contact surfaces 2082 can be lower surfaces of protrusions extending outwardly from lower end sections of the links 2086A. The links 2086A, 2086B and levers 2088 and/or handles 2094 can be cooperatively configured so that at least lower portions of the catch parts 2084 move away from one another and the contact surfaces 2082 move toward a line extending from one to the other of the catch parts 2084 in response to at least portions of the levers 2088 and/or handles 2094 being moved toward one another.

Figure 24A:
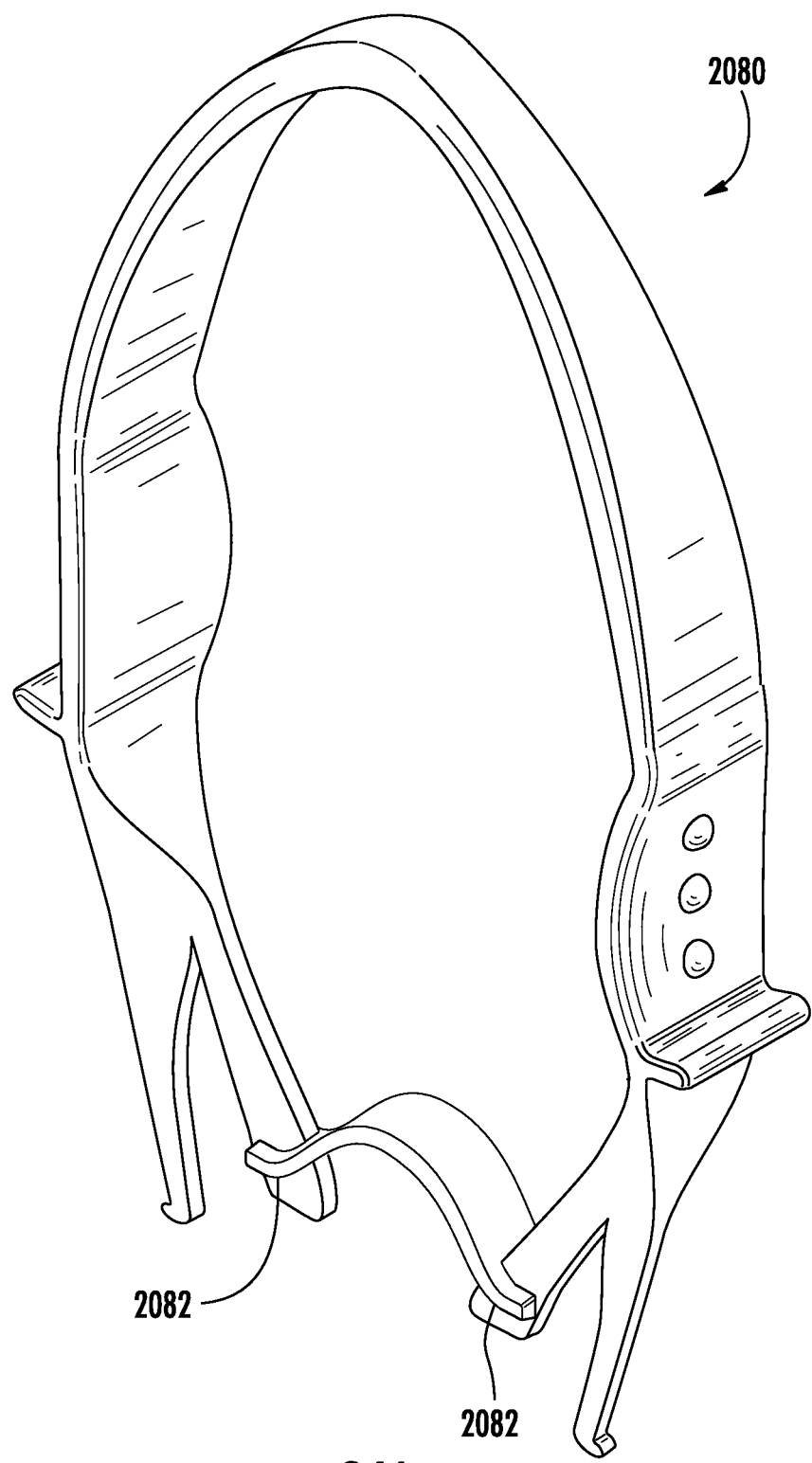
FIGS. 24A through 24C depict an applicator tool in accordance with a thirteenth embodiment.
Figure 24C:
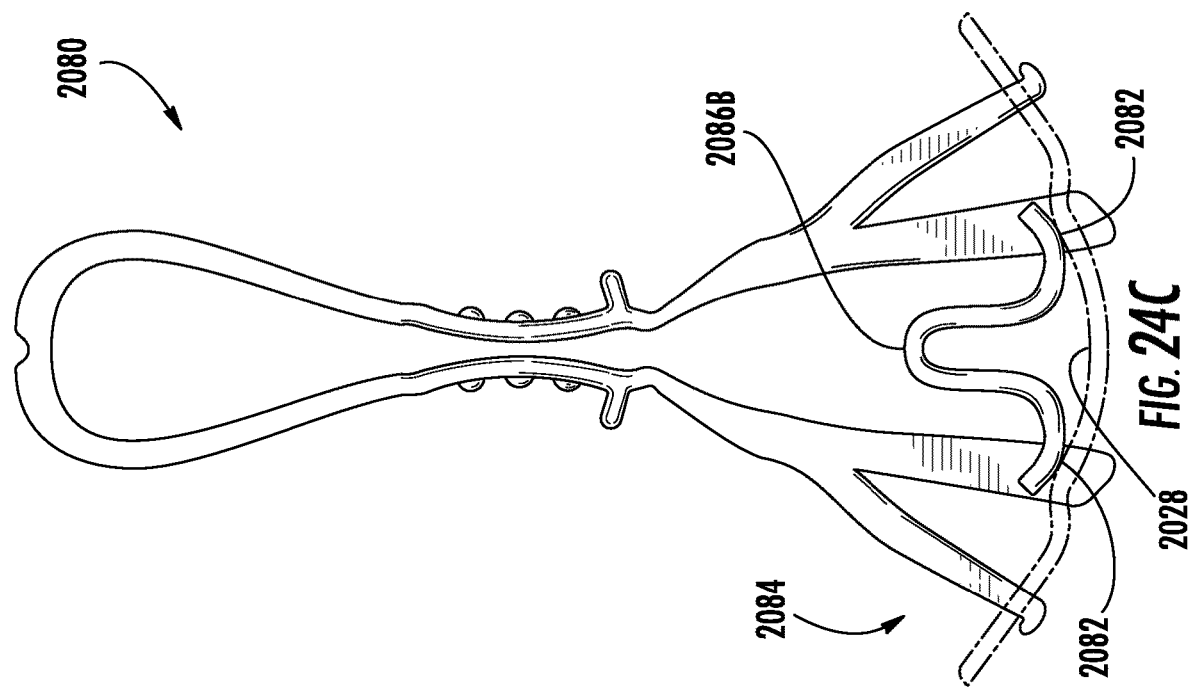
Figure 24B:
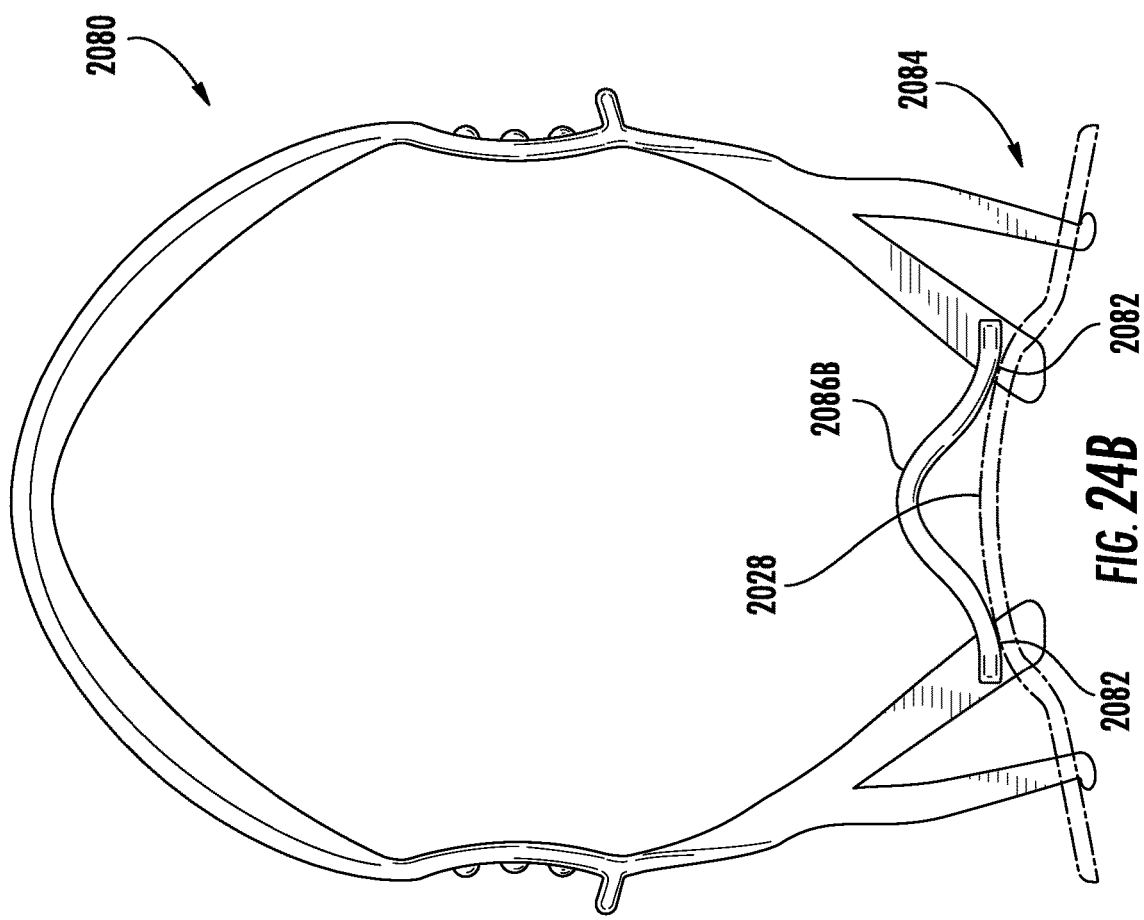

In the version of the twelfth embodiment depicted in FIGS. 23B and 23C, the catch parts 2084 of the applicator tool 2080 are configured to respectively mate with the tissue bridge outer holes 2059 (FIG. 17A), for example as discussed above with reference to the ninth embodiment. Similarly, the lower ends of the links 2086A are configured to respectively mate with (e.g., extend into and/or through) the tissue bridge inner holes 2056 (FIG. 17A). The bearing or contact surface 2082 are configured to be in opposing-face-to-face relation with (e.g., opposing-face-to-face contact with) the upper surface of the tissue bridge arch 2028. Additionally or alternatively, lower surfaces of the links 2086A and/or 2086B can be configured to be in opposing-face-to-face relation with (e.g., opposing-face-to-face contact with) the upper surface of the tissue bridge arch 2028. For example, FIGS. 24A-24C depict a thirteenth embodiment applicator tool 2080 that is like the twelfth embodiment applicator tool, except, for example, that the bearing or contact surfaces 2082 are lower surfaces of the links 2086B that are configured to be in opposing-face-to-face relation with (e.g., opposing-face-to-face contact with) the upper surface of the tissue bridge arch 2028.

Figure 25A:
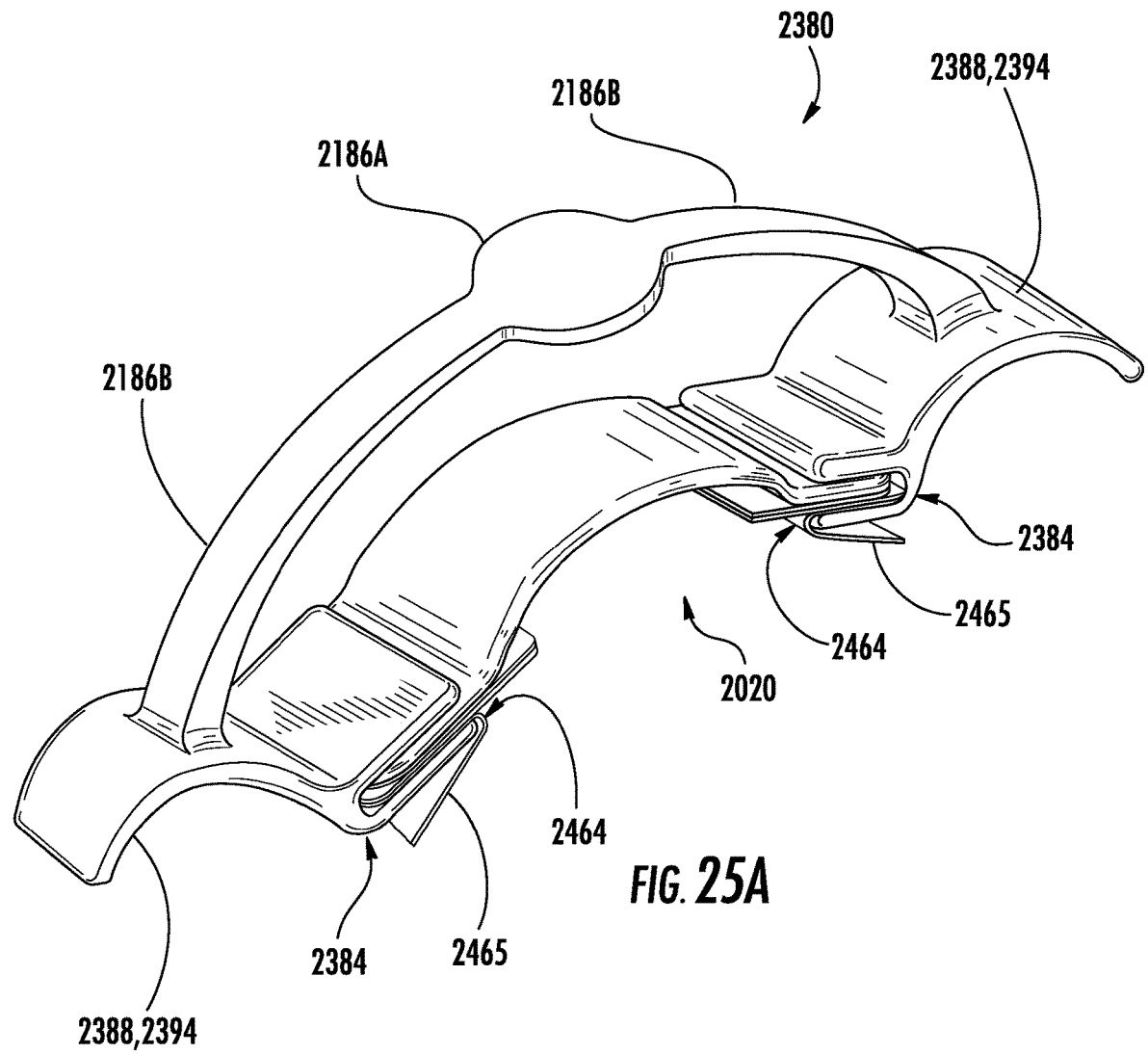

FIGS. 25A-25C depict an applicator tool 2380 in receipt of a tissue bridge 2020; and FIG. 25C depicts that the engaged together applicator tool 2380 and tissue bridge 2020 are both in their deformed configurations so that the tissue bridge is securely grasped or otherwise held by the applicator tool, in accordance with a fourteenth embodiment. The catch parts 2384 comprise receptacles, or more specifically inwardly open holes or slots that can be defined between parts, plates, slabs or other suitable features. In the fourteenth embodiment, the opposite ends of the tissue bridge 2020 respectively extend into the inwardly open holes or slots of the catch parts 2384. The thickness of the slots of the catch parts 2384 can be slightly larger than the thickness of the opposite end sections of the tissue bridge 2020. The handles 2394 can be loops, partial loops, and/or other suitable features for receiving fingers of an operator of the tool 2380, and optionally another finger can be pressed downwardly on a platform and/or other suitable features positioned along the linkage (e.g., linkages 2186A, 1186B).

The applicator tool 2380 can have a first body comprising a first lever 2388 connected to a first catch part 2384, and a second body comprising a second lever 2388 connected to a second catch part 2384. Referring to FIGS. 25B and 25C, the reconfigurable linkage (e.g., linkages 2186A, 2186B) can connect the first and second bodies to one another, and be configured so that (e.g., simultaneously): the first and second bodies are pivotable relative to one another about first and second axes 2371, 2372, respectively; and the first and second axes 2371, 2372 are movable toward and away from one another.

As depicted in FIGS. 25A-25C, release or peel liner strips 2464 are respectively mounted to the foot pads 1024 and partially positioned in the receptacles or slots of the catch parts 2384 so that the patient contact adhesive is restricted from adhering to the catch parts 2384. Inner ends of the release strips 2464 can include at least one folded over flap 2465.

Figure 26A:
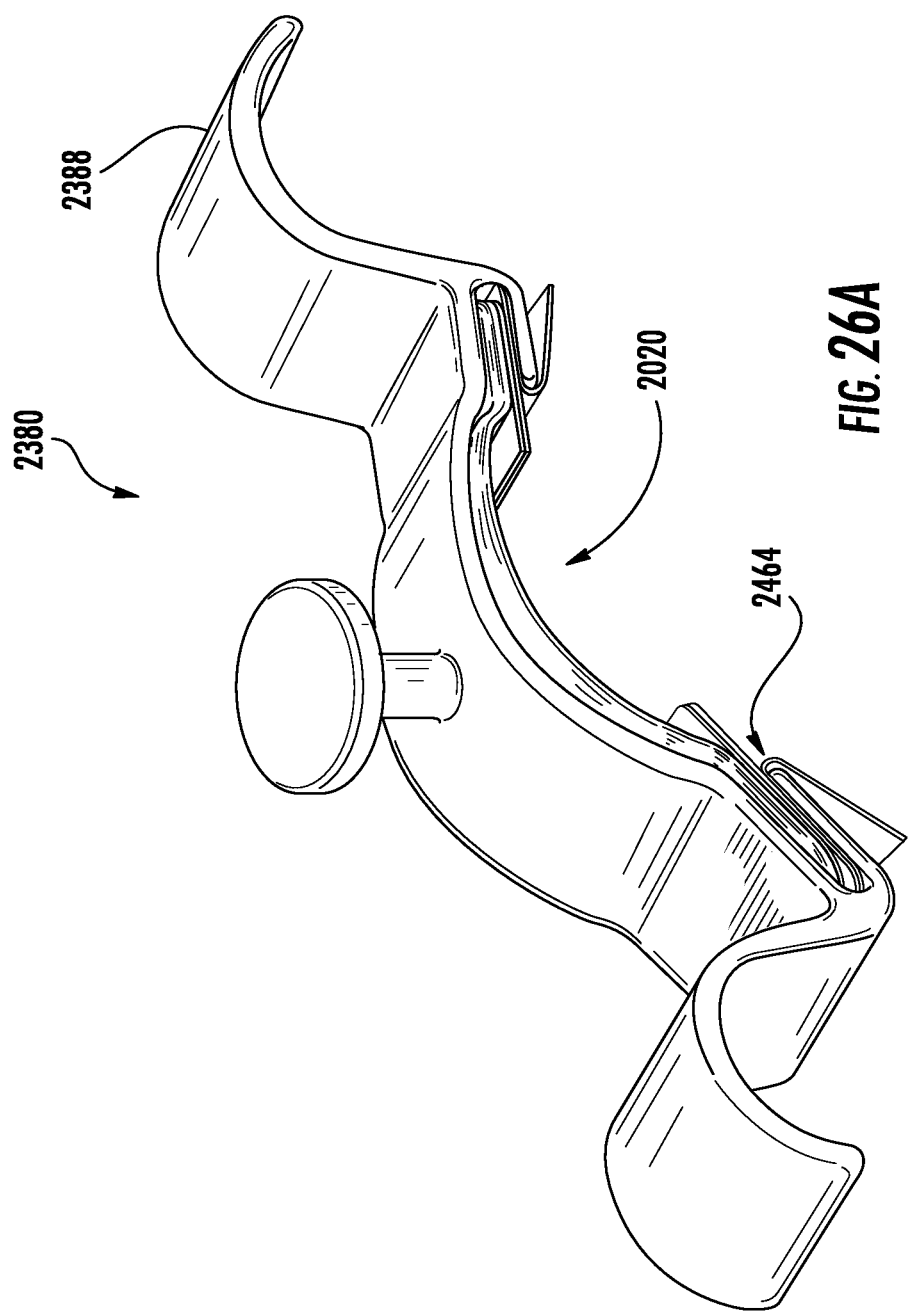
Figure 27A:
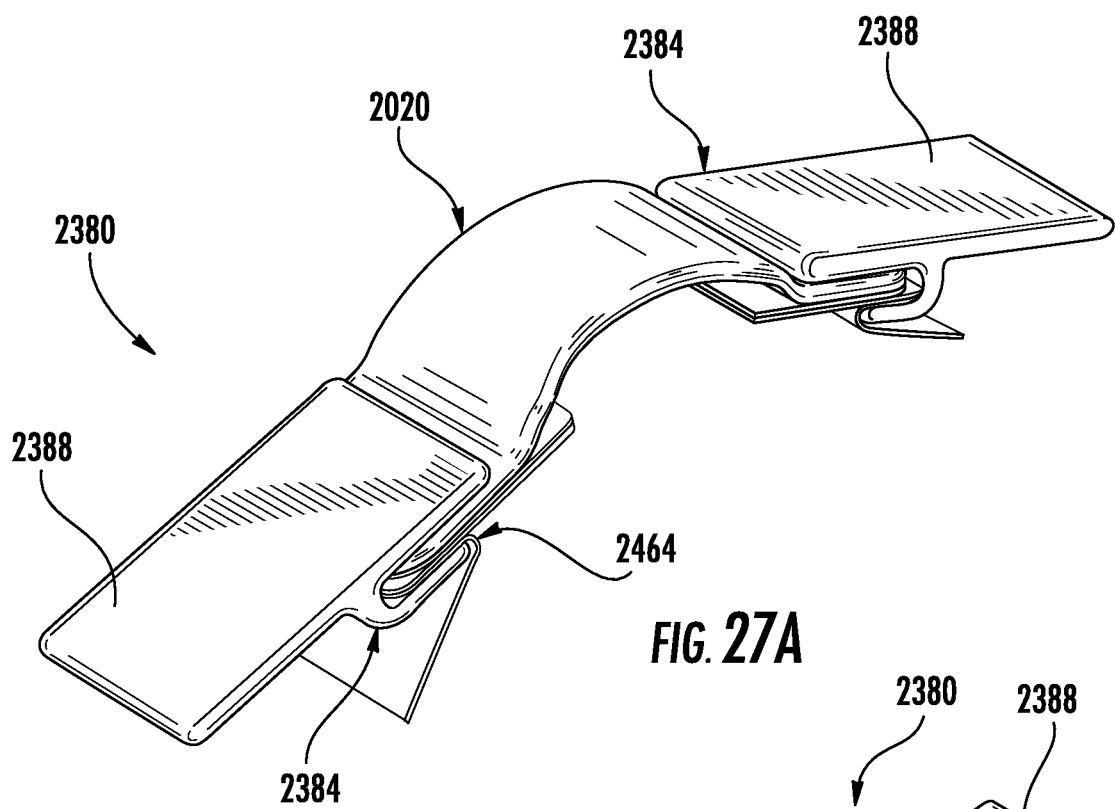
FIGS. 27A and 27B depict an applicator tool in combination with a tissue bridge, in accordance with a variation of the fourteenth embodiment.
Figure 27B:
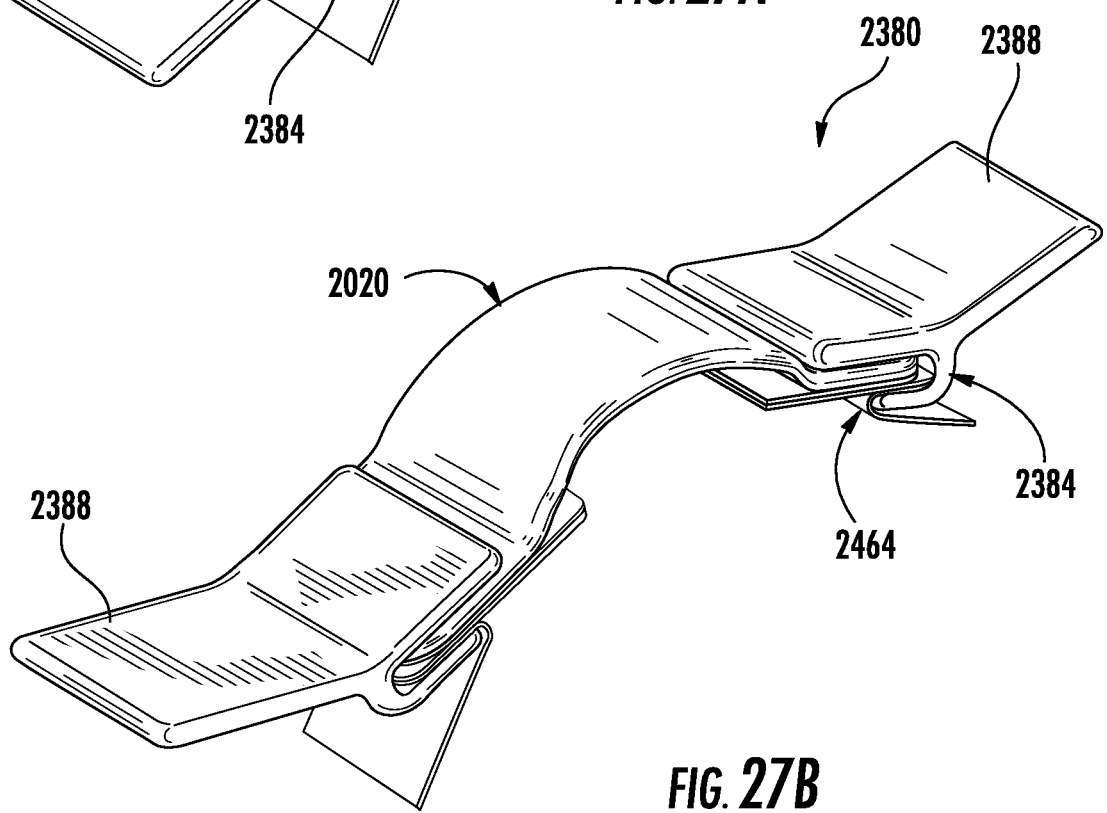

As depicted in FIGS. 26A-C, the central link 2186A of the applicator tool 2380 can extend upwardly from the other links 2186B. A platform and/or other suitable features at the upper end of the central link 2186A can be pressed upon by a user as part of a process of deforming the tool 2380 and tissue bridge 2020. As depicted in FIGS. 27A and 27B, at least a portion of the linkage (e.g., linkages 1186A, 1186B of FIGS. 25A-26C) can be omitted. Referring to FIGS. 28A and 28B, the inner ends of the release strips 2464 can be pulled away from the inner portions of the foot pads 2024 to form the folded over flaps 2465. Outer end sections of the folded over flaps 2465 can be (e.g., releasably) secured to an outer surface of the applicator tool 2380 with adhesive material 2381 and/or any other suitable fastening features 2381.

Figure 28C:
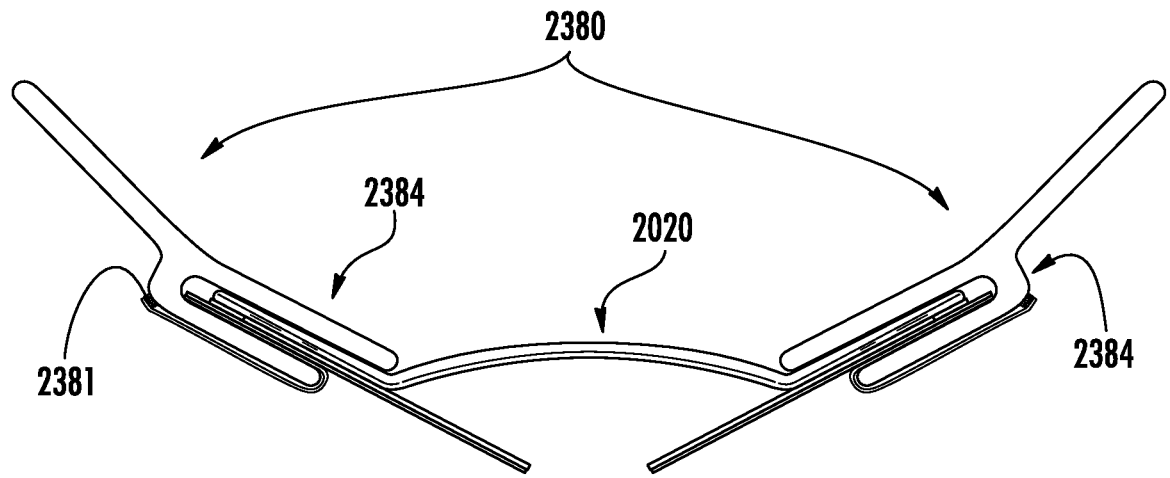
FIGS. 28C through 28E depict a sequence of steps of a method of using the applicator tool to apply the tissue bridge to a wound, in accordance with the fourteenth embodiment.
Figure 28D:
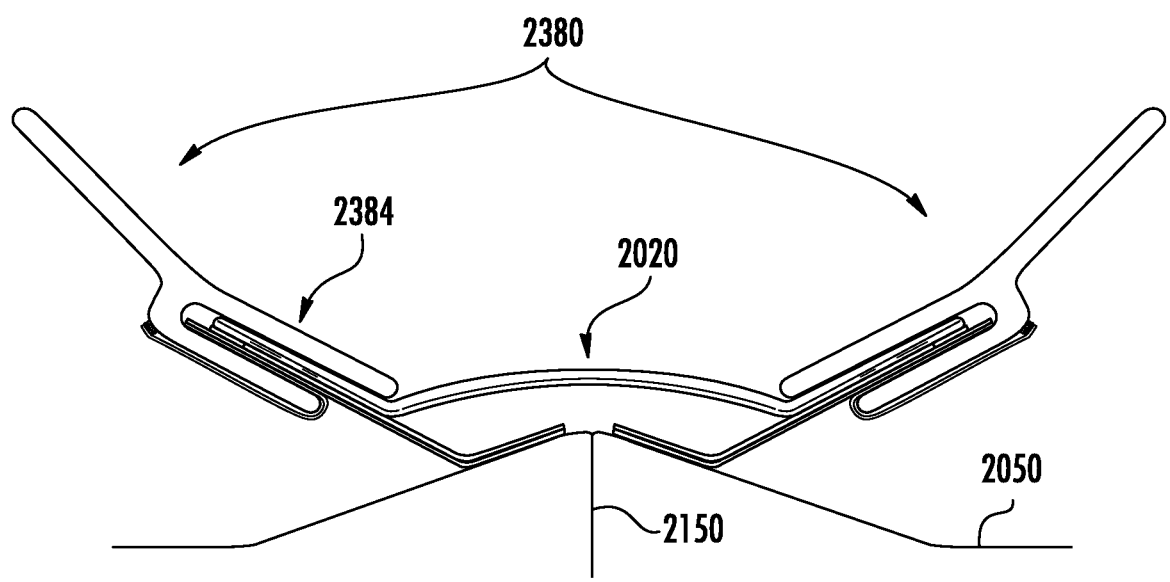
Figure 28E:
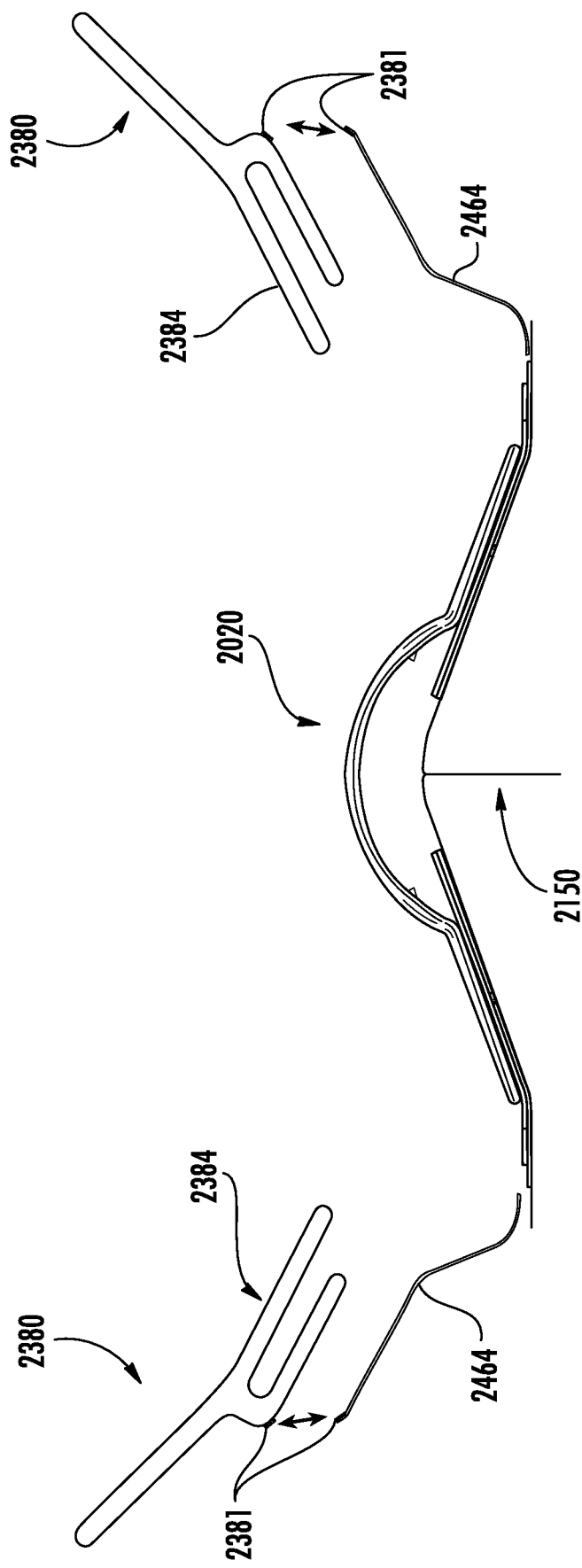

Referring to FIGS. 28C-29E, a method using an applicator tool 2380 to apply a tissue bridge 2020 onto tissue 2052 including a wound 2150 is described in the following, in accordance with the fourteenth embodiment. Referring to FIG. 28C, the applicator tool 2380 can be deformed or otherwise reconfigured by manually pivoting the catch parts 2384 by way of the levers 2088 and/or handles 2094 and/or any outer suitable features (e.g., linkage(s)), so that deforming forces are applied on the tissue bridge 2020. Then, referring to FIG. 28D, the inner portions of the medial struts 2048 can begin to become adhered to the tissue 2052. After the medial struts 2048 are at least partially attached to the tissue 2052, and the outer portions of the foot pads 2024 are not yet attached to the tissue, the lateral or outer portions of the foot pads 2024 can be released from the catch parts 2384 so that the release liners 2464 are pulled off of the foot pads 2024. The lateral or outer portions of the foot pads 2024 can be pressed down and adhered to the tissue 2052.

Figure 29A:
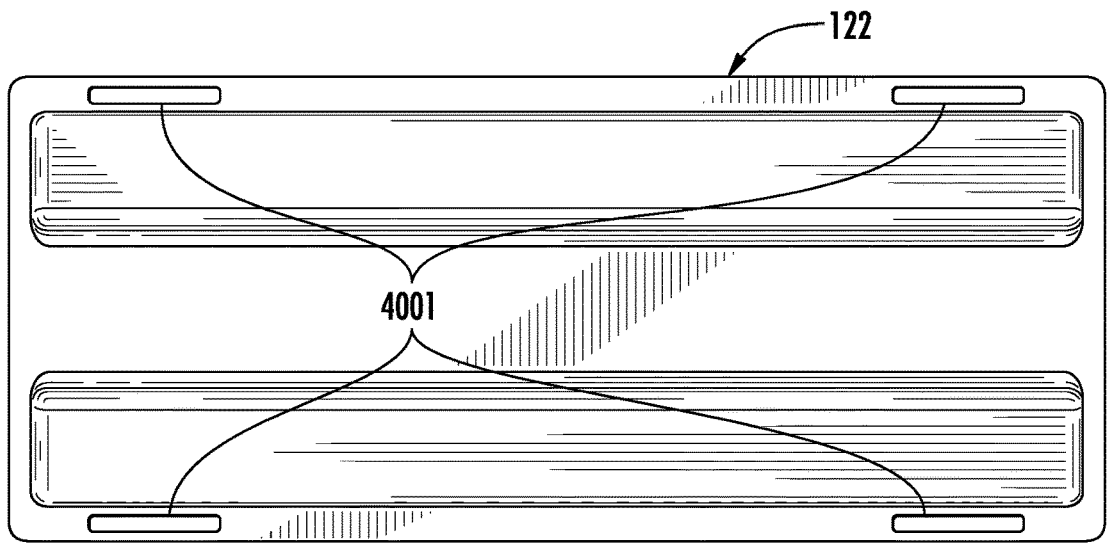
FIGS. 29A through 29C are top plan views of trays including mounting features, in accordance with other embodiments of this disclosure.
Figure 29B:
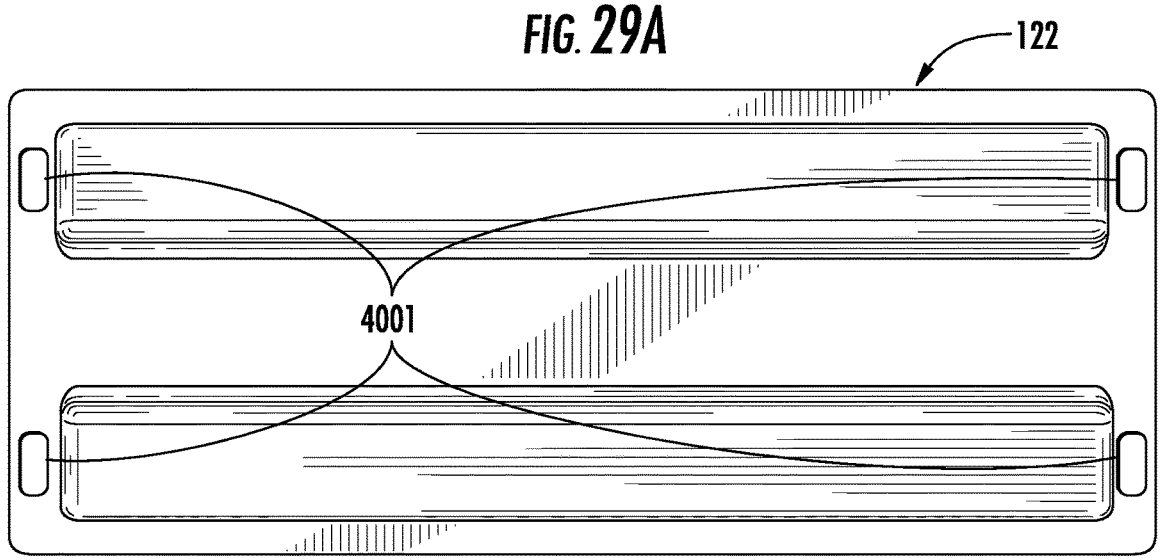
Figure 29C:
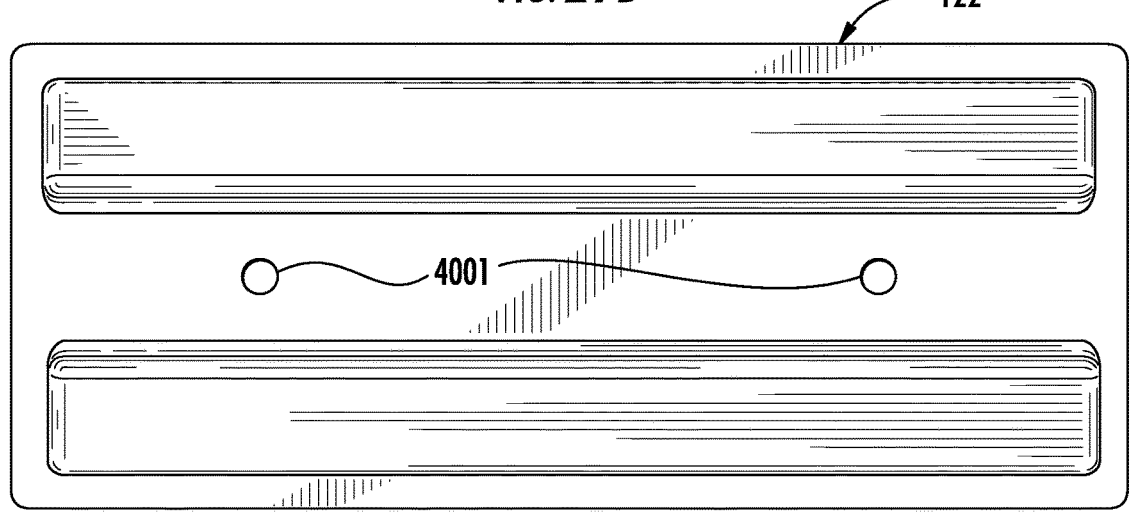

Referring to FIGS. 29A-29C, the trays 122, which can be configured to support one or more of the above discussed tissue bridges (e.g., tissue bridges 2020) can include or otherwise be associated with one or more attachment features (e.g., fasteners, or the like) for facilitating attachment of the trays to a wide variety of suitable supports. For example, the trays 122 depicted in Figs. FIGS. 29A-29C include one or more attachment features in the form of holes 4001 that can extend through the tray and be configured for receiving fasteners, positions and/or any other suitable features. The holes can extend through outer peripheral flanges or any other suitable portions of the trays 122, or the holes or other suitable attachment features can be associated with the trays in any other suitable manner.

Figure 31:
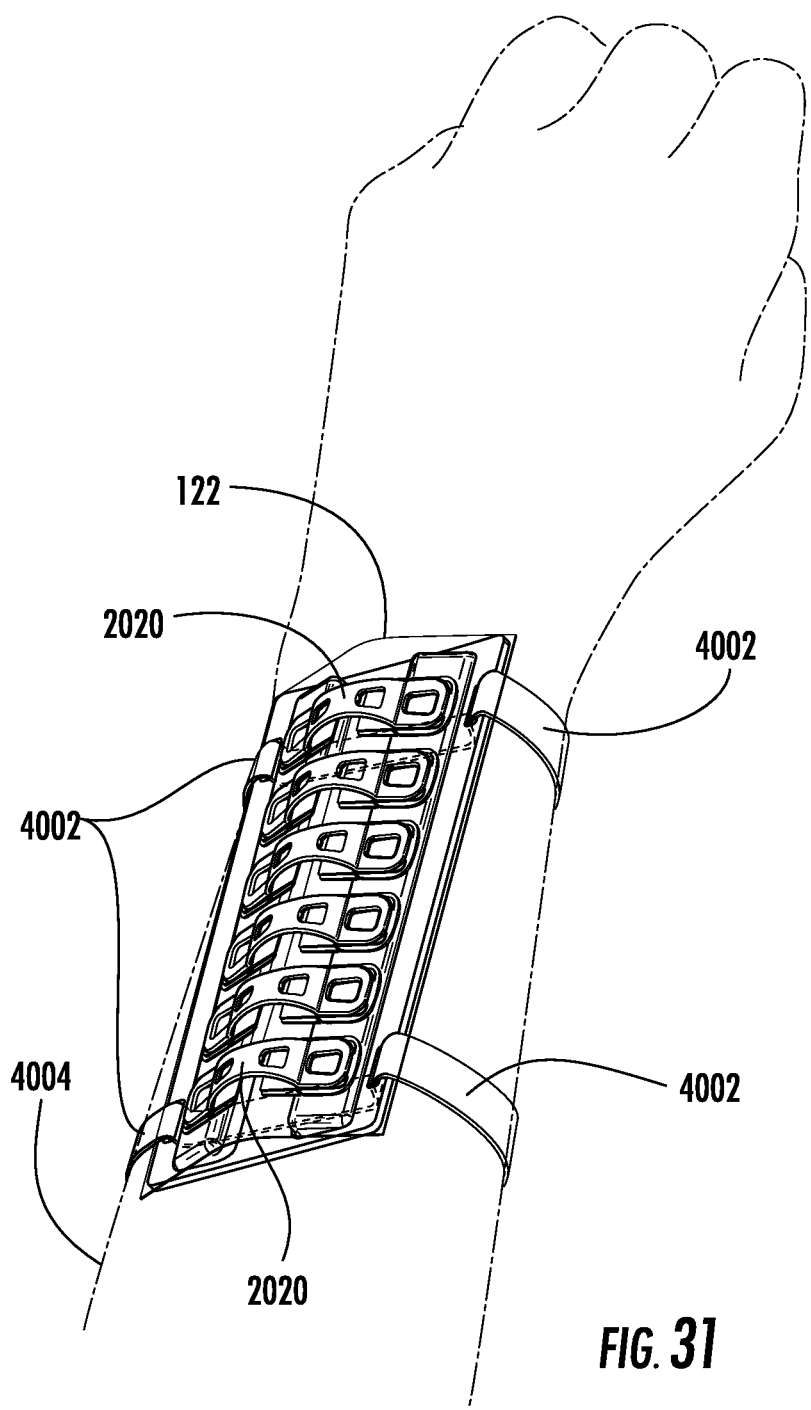
FIG. 31 depicts the tray with tissue bridges of FIG. 30 mounted on the arm of a user, in accordance with an embodiment of this disclosure.

Referring to FIGS. 29A, 30 and 31, attachment features in the form of straps 4002 with fasteners 4003 (e.g., hook and loop releasable fasteners (e.g., VELCRO) or other suitable fasteners) can extend through the holes 4001 and be used to mount the tray 122 to structure. For example, the structure can be the arm 4004 (e.g., forearm and/or wrist) of a user, so that the user's hands can remain free for other purposes, such as for using one of the above-discussed applicator tools, or another suitable tool, to retrieve the tissue bridges 2020 from the tray 122 and apply the tissue bridges accordingly. Other structures to which the tray 122 can be mounted include, for example, a body part of a user or a patient, surgical drapes, trays and/or any other suitable structures. For example, the structure can be a finger or thumb of the user, the back of a user's hand, the user's clothing or any other suitable areas or structures.

Figure 32:
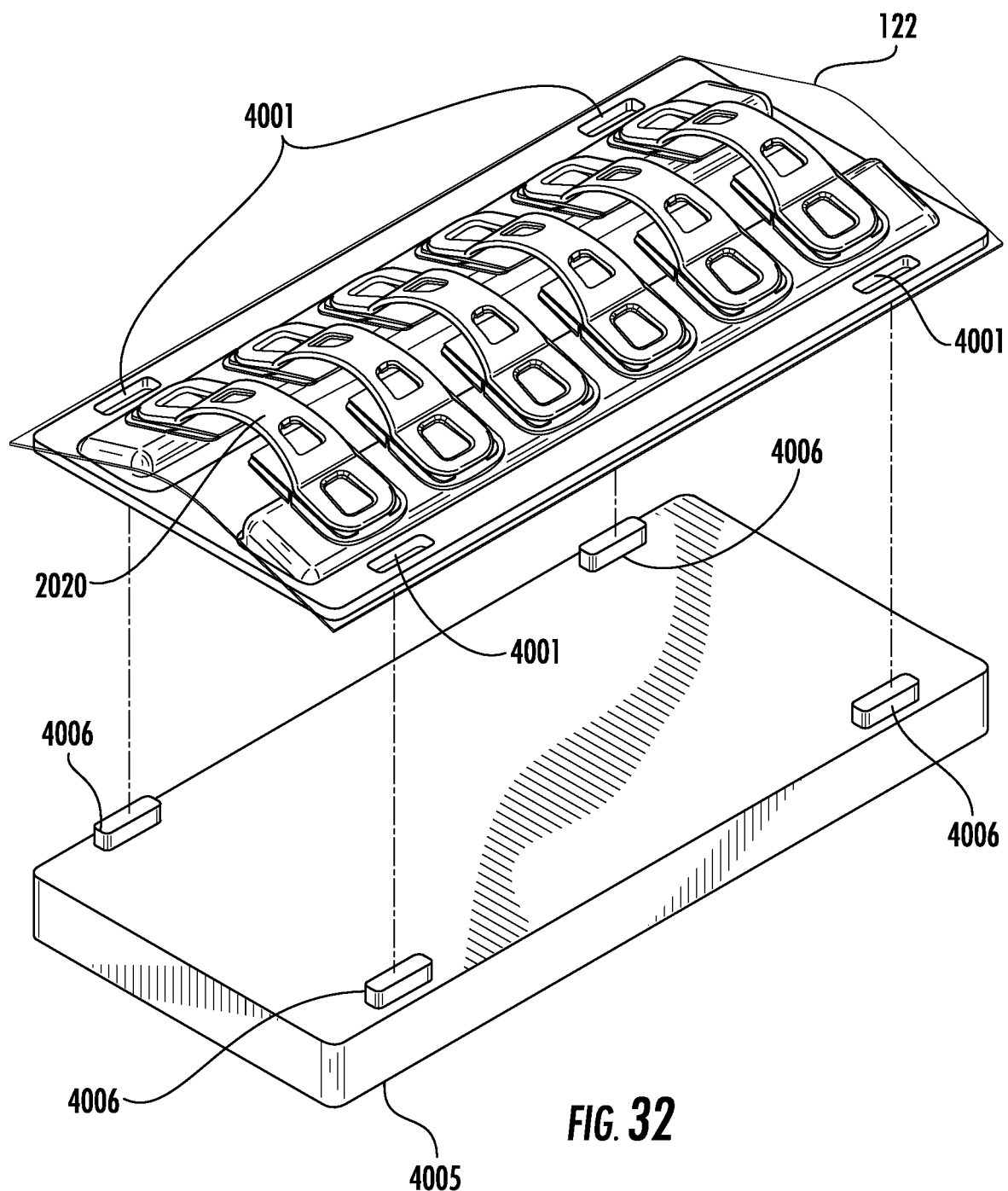
FIG. 32 depicts the tray with tissue bridges of FIG. 30 with the fastening straps removed, wherein the tray is exploded away from a mounting base, in accordance with an embodiment of this disclosure.

Referring to FIG. 32, the holes 4001 or other attachment features of the trays 122 can be used to mount the trays to other suitable supports. For example, FIG. 32 depicts the tray 122 with tissue bridges 2020 of FIG. 30 with the fastening straps removed, wherein the tray is exploded away from a mounting base 4005, in accordance with an embodiment of this disclosure. The mounting base 4005 can include one or more attachment features in the form of protrusions 4006 or other suitable devices for extending into the holes 4001 to at least partially secure the tray 122 to the mounting base 4005. The tray 122, or the tray 122 mounted to the base 4004, can be sat on/supported by a tray, such as the tray of a mayo stand, or the like.

Figure 33:
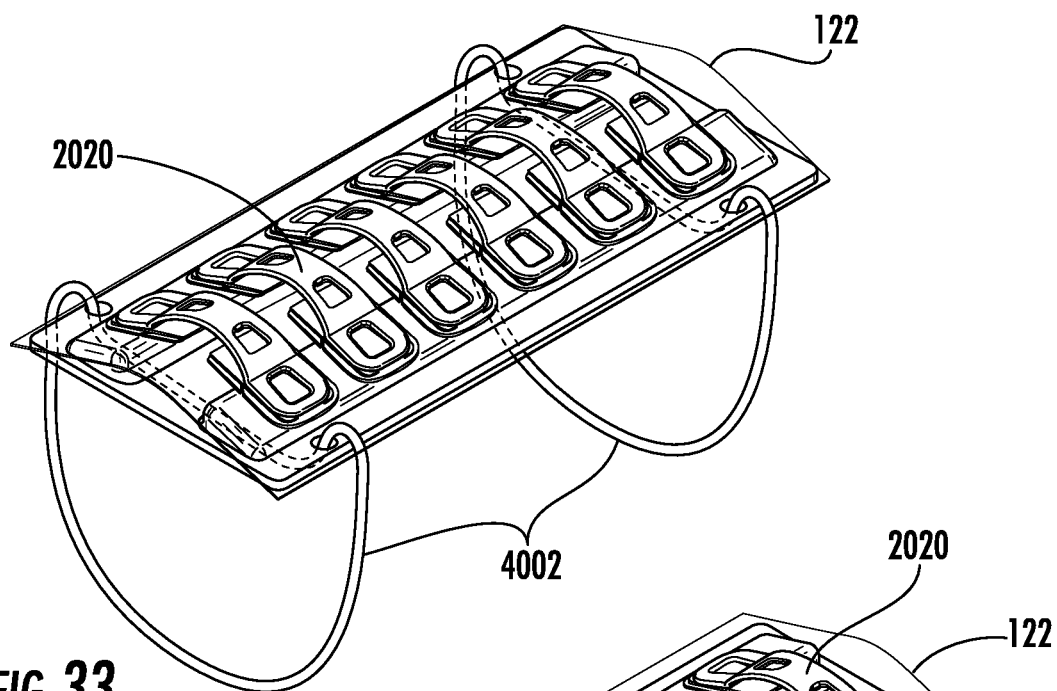
FIG. 33 depicts a tray that is carrying a series of tissue bridges, and is equipped with fastening straps, in accordance with an embodiment of this disclosure.

FIG. 33 depicts a tray 122 that is carrying a series of tissue bridges 2020 and is equipped with other types of fastening straps 4002 (e.g., elastic straps), wherein a variety of differently configured attachment features (e.g., fastening straps) and mounting bases are within the scope of this disclosure.

Figure 34:
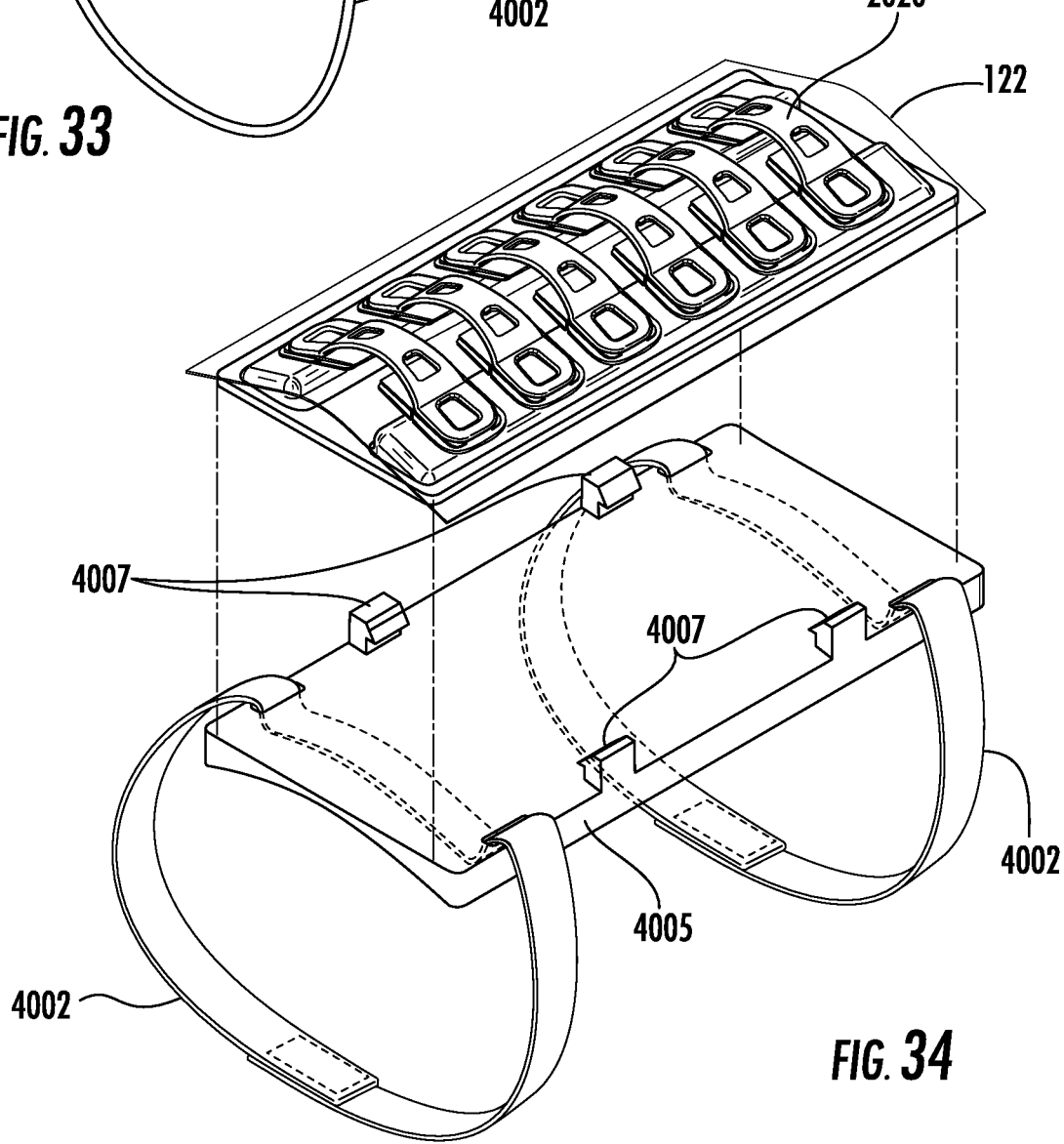
FIG. 34 depicts a tray with tissue bridges exploded away from a mounting base equipped with clips and fastening straps, in accordance with an embodiment of this disclosure.

FIG. 34 depicts a tray 122 with tissue bridges 2020 exploded away from a mounting base 4005 equipped with attachment features in the form of clips 4007 and fastening straps 4002, in accordance with another embodiment of this disclosure. The straps 4002 can be configured to removably mount the mounting base 4005 on the arm 4004 of a user, and the clips 4007 can be configured to releasably engage edges of the tray 122, or other suitable features associated with the tray, to releasably secure the tray to the mounting base, so that the mounting base can be serially replenished with trays containing tissue bridges 2020 without having to remove the mounting base from the user's arm.

Figure 35:
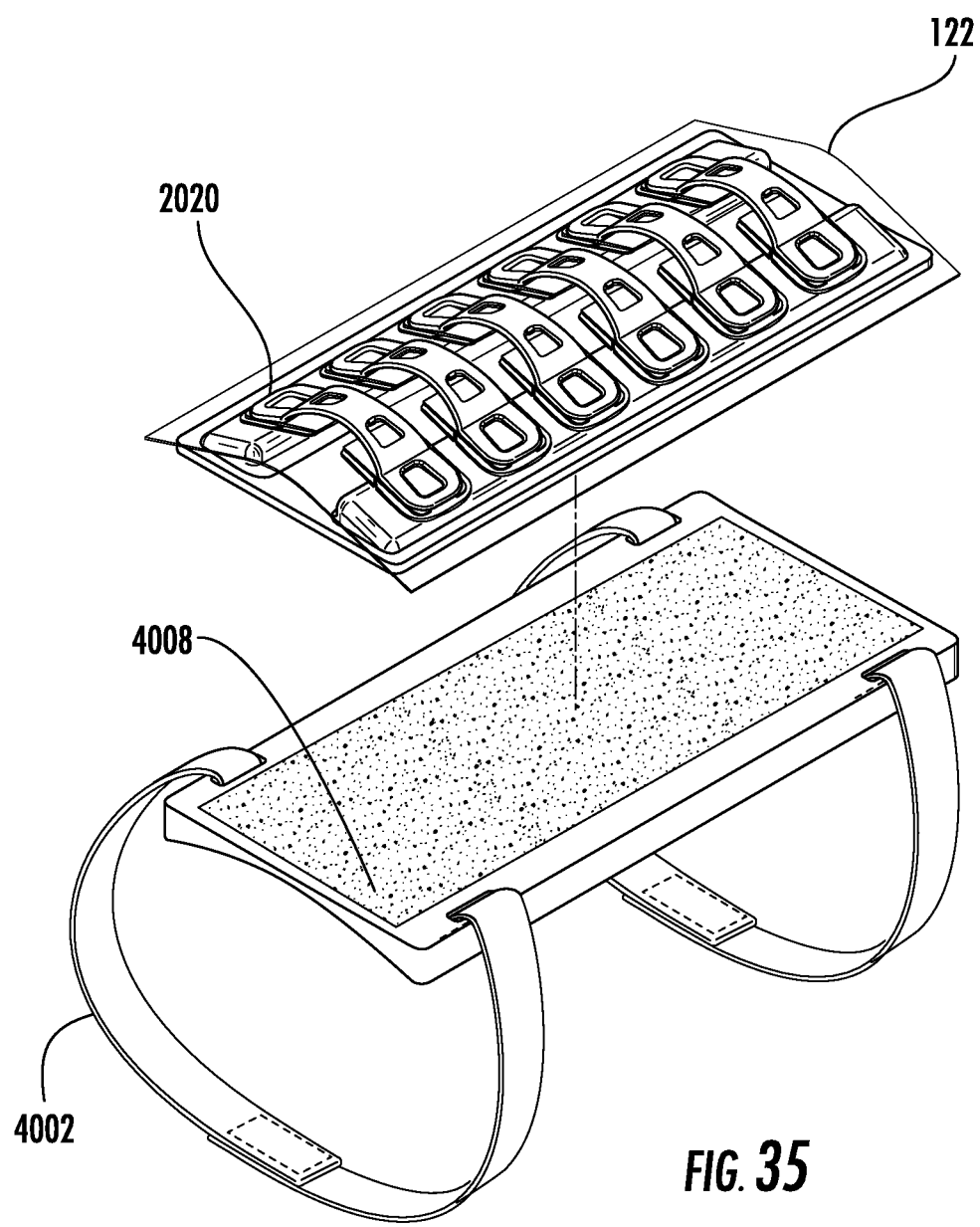
FIG. 35 depicts a tray with tissue bridges exploded away from a mounting base equipped with adhesive material and fastening straps, in accordance with an embodiment of this disclosure.

As another example, FIG. 35 depicts a tray 122 with tissue bridges 2020 exploded away from a mounting base 4004 equipped with adhesive material 4008 and fastening straps 4002, in accordance with another embodiment of this disclosure. The straps 4002 can be configured to removably mount the mounting base 4005 on the arm of a user, and the adhesive material 4008 can be configured to releasably engage the tray 122 to releasably secure the tray to the mounting base, so that the mounting base can be serially replenished with trays containing tissue bridges 2020 without having to remove the mounting base from the user's arm. As depicted in FIGS. 34 and 35, the lower surface of the mounting base 4005 can be shaped to generally conform to the shape of the user's forearm, such as by having a recessed, arcuate or concave surface extending along the length of the lower surface of the mounting base.

As additional examples, variations in the tissue bridge geometry can be altered for different relative effects and for use on or in different parts of the body (e.g., to compensate for different anatomical variations, such as different skin thicknesses, different curvatures, different orientations, different tissue qualities such as fat layer thickness or changes due to aging). For example, shoulders of the tissue bridges can be larger when it is desirable for more medial strut push down. As another example, the arch can be made narrower or wider, or thicker or thinner. For example, a relatively narrow arch may be used for thinner skin, and more vertical forces (eversion). A relatively wider arch can be used for thicker tissues, and more horizontal forces. A relatively thicker arch can be used for more tension reduction. A relatively thinner arch can be used over bony surfaces where there is more horizontal than vertical movement. As another example, the medial strut can be thicker or thinner, or can flare wider past the width of the body. A thicker medial strut may provide more medializing, and a thinner medial strut may provide more eversion. There can also be different distances defined by the gap between adjacent ends of the medial struts. Additionally, there can be different overall sizes of the tissue bridges.

At least the tissue bridges would typically be sterilized prior to being used, and any suitable sterilization may be used. As one example, packages containing one or more tissue bridges and/or applicators may be exposed to radiation (e.g., (ionizing radiation) in a manner that sterilizes at least the tissue bridge(s) and/or applicator(s) therein. Depending upon the types of materials from which the tissue bridge(s) and/or applicator(s) are constructed, the sterilization (e.g., by exposure to radiation) may affect the properties of the materials. In this regard, materials from which the tissue bridge(s) and/or applicator(s) are constructed may be selected based upon the sterilization process to which the tissue bridge(s) and/or applicator(s) may be exposed.

As further examples, the above-discussed bodies of the tissue bridges can be constructed of formed polymers. The formed polymers can be polymers that are shaped from a constitutive polymer material via processes such as injection molding, compression molding, stamping, thermoforming, casting, and 3D printing such as fused deposition modeling, stereolithography, selective laser printing, polyjet processing, digital light processing, and other processes that are known to those of ordinary skill in the art. The formed polymers may comprise any materials suitable for the processing and application. Such materials may include light, non-allergic polymers such as acrylonitrile butadiene styrene, polyoxymethylene, polypropylene, polyethylene, polyethylene terephthalate, polycarbonate, polyamide, polylactic acid, polyvinyl chloride, polytetrafluoroethylene, polyaryletherketone, polysulfone, and others including their blends and copolymers with modifying additives such as colorant, reinforcers, impact modifiers, heat stabilizers, and others. Such polymer can have a modulus between 0.1 and 10 GPa and elongation at between 1% and 100%. As a more specific example, the bodies of the tissue bridges can be constructed of polycarbonate having an elastic modulus of about 2.4 GPa and an elongation at yield of about 7%.

As other examples, the above-discussed inner layers or sheets of the foot pads can be film layers. These film layers can be made from extruded polymers comprising polymers such as those discussed for formed polymers. The polymer for the film layer can have a modulus between 0.1 and 10 GPa and elongation at between 1% and 100%. As a more specific example, inner layers or sheets of the foot pads can be extruded polyethylene terephthalate having an elastic modulus of about 2.6 GPa and an elongation at yield about of 5%. The inner layer can be about 0.005 inches thick, or about 0.007 inches thick, and its opposite sides can be treated with Acrylic. The adhesive layer between the body and the inner layer can be a UV curable adhesive, or any other suitable adhesive.

As additional examples, the above-discussed outer layers or sheets of the foot pads can be fabric layers or other suitable substrates. These layers can produced from non-woven or woven polymers, microporous cast polymers, or other suitable substrates. The fibers for the non-woven or cast substrates can be made from polymers such as those discussed for formed polymers. The polymer for the outer layers or sheets of the foot pads can have a modulus between 0.1 and 10 GPa and elongation at between 1% and 100%. The apparent elastic properties of the outer layers or sheets of the foot pads can result from the diameter, density, and orientation of the fibers constituting the non-woven or non-woven or cast substrates. Generally, the resultant non-woven or cast substrate layer can have a modulus between 0.01 and 1 GPa and elongation at between 10% and 1000%. As a more specific example, the outer layers or sheets of the foot pads can be a breathable polyurethane substrate have an apparent elastic modulus of about 0.2 GPa and an elongation at yield of 100%. The polyurethane substrate can allow for moisture transmission. The outer layer can be about 0.003 inches thick. In a tissue bridge, both the body and the inner sheet can have a higher modulus of elasticity than the outer sheet. For example, in a tissue bridge, both the body and the inner sheet can have an elastic modulus in a range of from about two times to about forty times the elastic modulus of the outer sheet, from about five times to about thirty times the elastic modulus of the outer sheet, from about ten times to about twenty five times the elastic modulus of the outer sheet and/or any other subranges or values therebetween. The adhesive between the inner layer and the outer layer can be can be a silicone pressure sensitive adhesive, or any other suitable adhesive.

As an example, the release liners can be silicone release liners that are about 0.003 inches thick. The adhesive between the outer layer and the release liner can be an acrylic pressure sensitive adhesive, or any other suitable adhesive. The adhesive between the outer layer and the release liner is typically for adhering the tissue bridge to the patient (e.g., the patient-contact adhesive). The patient-contact adhesive can include one or more additives, for example one or more medicinal substances. The one or more medicinal substances in the patient-contact adhesive can include hydroquinone, sunblock, antihistamines, steroids and/or any other suitable additives.

A variety of examples are within the scope of this disclosure, including the following.

Example 1

A medical article for at least partially covering a wound and/or scar tissue, the medical article comprising: a body comprising a central section extending over an area, and flanges respectively extending outwardly from opposite lower sections of the central section, at least the central section of the body being elastically configured to be deformed from an at rest configuration to an extended configuration, and to return toward the at rest configuration in response to being released from the extended configuration, wherein the lower sections are farther apart from one another in the extended configuration than in the at rest configuration, and a first of the flanges having opposite upper and lower surfaces that are each larger than a thickness defined between the upper and lower surfaces of the first flange; and a foot pad connected to the first flange for at least partially moving with the first flange, the foot pad extending inwardly into the area over which the central section extends, the foot pad having opposite upper and lower surfaces that are each larger than a thickness defined between the upper and lower surfaces of the foot pad, and the upper surface of the foot pad and the lower surface of the first flange facing toward one another.

Example 2

The medical article according to Example 1, wherein: the central section comprises an arch extending over the area over which the central section extends; the foot pad is a first foot pad; a second of the flanges has opposite upper and lower surfaces that are each larger than a thickness defined between the upper and lower surfaces of the second flange; the medical article comprises a second foot pad connected to the second flange for at least partially moving with the second flange; the second foot pad extends inwardly into the area over which the central section extends the second foot pad has opposite upper and lower surfaces that are each larger than a thickness defined between the upper and lower surfaces of the second foot pad, and the upper surface of the second foot pad and the lower surface of the second flange face toward one another.

Example 3

The medical article according to Example 1, wherein the body is stiffer than the foot pad.

Example 4

The medical article according to Example 1, wherein: the central section of the body extends at least partially around the area over which the central section extends, and the foot pad comprises a extension extending inwardly into the area over which the central section extends.

Example 5

The medical article according to Example 1, the upper surface of the foot pad is adhered to the lower surface of the first flange.

Example 6

The medical article according to Example 1, wherein the foot pad comprises: an outer sheet configured to be attached to tissue, and an inner sheet positioned between the outer sheet and the first flange, wherein the inner sheet is stiffer than the outer sheet.

Example 7

The medical article according to Example 6, wherein the outer sheet is larger than the inner sheet, and an extension of the outer sheet extends outwardly past an outer edge of the inner sheet.

Example 8

The medical article according to Example 1 in combination with a tool configured for being used to manipulate the medical article, wherein a portion of the tool extends into a space between the body and at least a portion of the foot pad.

Example 9

The medical article according to Example 1, wherein the body further comprises a catch part configured for interacting with a tool.

Example 10

The medical article according to Example 9, wherein: the catch part comprises a hole extending through the body, and at least a portion of the foot pad extends beneath the hole.

Example 11

The medical article according to Example 9, wherein a section of the foot pad extends: inwardly from proximate the first flange, and beneath the catch part.

Example 12

The medical article according to Example 9, wherein the catch part comprises a receptacle configured to receive at least a portion of a tool.

Example 13

The medical article according to Example 12, wherein the body and the foot pad are cooperatively configured to together at least partially define the receptacle.

Example 14

The medical article according to Example 12, wherein: the body comprises an arch, the arch extends partially around the area over which the central section extends, and the foot pad extends inwardly from the first flange into the area over which the central section extends to at least partially define the receptacle.

Example 15

The medical article according to Example 14, wherein the catch part comprises a hole that extends through the arch and is configured to receive an end section of a tool therethrough, such that the hole is an opening of the receptacle.

Example 16

A medical article for at least partially covering a wound and/or scar tissue, the medical article comprising: an arch extending over an area; a medial strut connected to the arch and extending into the area over which the central section extends, the medial strut comprising: an outer layer configured to be attached to tissue, and an inner layer positioned between the outer layer and the arch, wherein the inner layer is stiffer than the outer layer.

Example 17

The medical article according to Example 16, wherein the inner layer has a higher modulus of elasticity than the outer layer.

Example 18

The medical article according to Example 16, wherein the medical article further comprises a release liner adhered to the medial strut.

Example 19

The medical article according to Example 16, further comprising a foot plate, wherein the medial strut is connected to the arch by way of at least the foot plate.

Example 20

The medical article according to Example 19, wherein: the medial strut is a first medial strut, the foot plate is a first foot plate, the arch comprises first and second lower sections that are opposite from one another, the first medial strut is connected to the first lower section by way of at least the first foot plate, and the medical article further comprises a second medial strut connected to the second lower section by way of at least a second foot plate.

Example 21

The medical article according to Example 20, further comprising a medium configured to be positioned at least partially between the first and second medial struts.

Example 22

The medical article according to Example 21, wherein the medium comprises a therapeutic agent.

Example 23

The medical article according to Example 21, wherein the medium comprises a silicone strip.

Example 24

The medical article according to Example 21, wherein the medium is mounted to the arch.

Example 25

A tool configured for being used to manipulate a medical article, the tool comprising: first and second parts that are spaced apart from one another and each configured to releasably engage a medical article; a reconfigurable linkage connecting the first and second parts to one another; and levers extending from proximate the linkage; the linkage and the levers being cooperatively configured so that at least portions the first and second parts are moved away from one another in response to at least portions of the levers being moved toward one another.

Example 26

The tool according to Example 25, wherein the levers comprise handles.

Example 27

The tool according to Example 25, wherein: the first part comprises a first catch part configured to releasably attach to a medical article, and the second part comprises a second catch part configured to releasably attach to the medical article.

Example 28

The tool according to Example 27, wherein: each of the first and second catch parts comprises a shank and a protrusion extending outwardly from the shank; and the protrusions face away from one another.

Example 29

The tool according to Example 27, comprising a bearing surface that is: positioned between the first and second catch parts, connected to the first and second catch parts by the linkage, and configured to engage the medical article while the first and second catch parts are engaged to the medical article.

Example 30

The tool according to Example 29, wherein when the bearing surface faces downwardly:
the first and second catch parts extend downwardly from proximate the linkage, and the levers extend upwardly from proximate the linkage.

Example 31

A tool configured for being used to manipulate a medical article, the tool comprising: a first body comprising a first lever connected to a first part, the first part being configured to engage a first end of a medical article; a second body comprising a second lever connected to a second part, the second part being configured to engage a second end of the medical article; a reconfigurable linkage connecting the first and second bodies to one another, the linkage being configured so that: the first and second bodies are pivotable relative to one another about first and second axes, respectively, and the first and second axes are movable toward and away from one another.

Example 32

The tool according to Example 31, wherein the linkage is configured so that simultaneously: the first and second bodies are pivotable relative to one another about first and second axes, respectively, and the first and second axes are movable toward and away from one another.

Example 33

The tool according to Example 31, wherein the linkage is constructed of elastic material.

Example 34

The tool according to Example 31, wherein the levers comprise handles.

Example 35

The tool according to Example 31, wherein: the first part comprises a receptacle configured to releasably receive a first end of a medical article, and the second part comprises a receptacle configured to receive a second end of the medical article.

Example 36

The tool according to Example 35, comprising a bearing surface that is carried by the linkage and positioned between the first and second parts, and configured to engage the medical article while the first and second parts are engaged to the medical article.

Example 37

The tool according to Example 36, wherein: the first lever extends outwardly from the first part; and the second lever extends outwardly from the second part.

Example 38

A package, comprising: a support comprising a central section and outer sections respectively extending outwardly and downwardly; and a medical article at least partially contained in the package and supported by the support, the medical article comprising a central section and foot pads respectively extending outwardly and downwardly from opposite lower portions of the central section of the medical article, wherein the foot pads are respectively proximate the outer sections of the support, and a gap is defined between at least a portion of the central section of the medical article and the central section of the support.

Example 39

The package according to Example 38, wherein the gap is configured to receive a portion of a tool.

Example 40

The package according to Example 38, further comprising a liner positioned between the support and the medical article, wherein: the medical article is releasably mounted to the liner, at least a portion of the liner is fixedly mounted to the support, and the liner comprises a line of disruption for at least partially facilitating relative movement between the medical article and the support.

Example 41

The package according to Example 40, wherein the line of disruption at least partially defines a flap in the liner.

Example 42

The package according to Example 40, wherein at least a portion of the line of disruption is positioned beneath a foot pad of the foot pads.

Example 43

The package according to Example 38, further comprising at least one strap configured to at least partially mount the support to a user's arm.

Example 44

The package according to Example 43 in combination with a base, wherein: the support comprises a tray; the tray is releasably connected to the base; and at least one strap is configured to at least partially mount the base to the user's arm, for connecting the tray to the user's arm by way of the base.

Example 45

The package according to Example 43, wherein at least a portion of the line of disruption is positioned beneath a foot pad of the foot pads.

Example 46

A method, comprising: deforming a medical article from an at rest configuration to an extended configuration, comprising reconfiguring a tool while the tool and the medical article are engaged to one another, wherein: the tool and the medical article being engaged to one another is comprised of: a first part of the tool and a first part of the medical article being in engagement with one another, and a second part of the tool and a second part of the medical article being in engagement with one another; the reconfiguring of the tool is comprised of moving levers of the tool toward one another so that: the first and second parts of the tool move away from one another in response to the moving of the levers of the tool toward one another, and the first and second parts of the medical article move away from one another in response to the first and second parts of the tool moving away from one another.

Example 47

The method according to Example 46, wherein a support, to which the medical article is mounted, at least partially delaminates in response to at least some of the deforming of the medical article.

Example 48

The method according to Example 46, further comprising there being relative movement between first and second sections of a support for the medical article in response to at least some of the deforming of the medical article.

Example 49

The method according to Example 48, wherein the relative movement comprises pivoting the first section relative to the second section.

Example 50

The method according to Example 46, further comprising unmounting the medical article from a support while the tool and the medical article are engaged to one another, wherein at least some of the unmounting occurs after at least some of the deforming of the medical article.

Example 51

The method according to Example 46, further comprising disengaging the tool from the medical article after the deforming of the medical article, wherein the deforming of the medical article is comprised of deforming the medical article so that the medical article is biased toward the at rest configuration and reconfigures from the extended configuration in response to the disengaging of the tool from the medical article.

Example 52

The method according to Example 51, further comprising, before the disengaging of the tool from the medical article, at least partially mounting the medical article to tissue while simultaneously: the medical article is in the extended configuration, and the tool and the medical article are engaged to one another.

Example 53

A method, comprising: deforming a medical article from an at rest configuration to an extended configuration so that foot pads of the medical article are farther apart from one another in the extended configuration than in the at rest configuration, wherein each of the foot pads comprises an inner portion extending inwardly from an outer portion of the foot pad, so that the inner portions are positioned between the outer portions of the foot pads; adhesively mounting the inner portions to tissue while the medical device is in its extended configuration; then the medial article reconfiguring from the extended configuration to an intermediate configuration that is between the at rest configuration and the extended configuration; and adhesively mounting the outer portions of the pads to the tissue while the medical device is in its intermediate configuration.

Example 54

The method according to Example 53, wherein the adhesively mounting of the outer portions of the pads to the tissue occurs at least partially in response to the reconfiguring of the medial article.

Example 55

The method according to Example 53, wherein: the inner portions comprise medial struts, and the reconfiguring from the extended configuration to the intermediate configuration comprises the medial struts becoming closer together and pushing portions of the tissue toward one another.

Example 56

A medical article for at least partially covering a wound and/or scar tissue, the medical article comprising: an arch comprising a spanning section positioned between opposite lower sections of the arch, wherein: the arch is configured to be deformed from an at rest configuration to an extended configuration, and in the at rest configuration, any space between the lower sections of the arch is less than a space between the lower sections of the arch in the extended configuration; and foot pads respectively connected to the lower sections of the arch for moving with the lower sections of the arch when the arch is transitioned between the at rest and extended configurations, wherein a first foot pad of the foot pads comprises: an outer layer configured to be attached to tissue, and an inner layer positioned between the outer layer and the arch, wherein the inner layer is stiffer than the outer layer.

Example 57

The medical article according to Example 56, wherein the inner layer has a higher modulus of elasticity than the outer layer.

Example 58

The medical article according to Example 56, wherein the inner layer is a flange extending outwardly from the first lower section of the arch.

Example 59

The medical article according to Example 56, further comprising a flange, wherein the inner layer is positioned between the flange and the outer layer.

Example 60

The medical article according to Example 56, further comprising a foot plate, wherein the inner layer is positioned between the foot plate and the outer layer.

Example 61

The medical article according to Example 56, wherein: the spanning section extends over an area, a medial strut extends into the area, and the medial strut comprises at least a portion of each of the outer layer and the inner layer.

Example 62

The medical article according to Example 56, wherein: the inner layer is an intermediate layer of the first foot pad, and the first foot pad further comprises an inner layer positioned between the intermediate layer and the first lower section of the arch.

Example 63

The medical article according to Example 62, wherein the inner layer is a flange extending outwardly from the first lower section of the arch.

Example 64

The medical article according to Example 62, wherein: the spanning section extends over an area, a medial strut extends into the area, and the medial strut comprises at least a portion of each of the intermediate layer and the inner layer.

Example 65

A medical article for at least partially covering a wound and/or scar tissue, the medical article comprising: a body comprising a central section and flanges respectively extending outwardly from opposite lower sections of the central section, so that the central section is positioned between the flanges, wherein the body is configured to be deformed from an at rest configuration to an extended configuration; a foot pad mounted to at least a first of the flanges for at least partially moving with the first flange, wherein the foot pad comprises an outer sheet configured to be attached to tissue, and an inner sheet positioned between the outer sheet and the first flange, wherein the inner sheet is stiffer than the outer sheet.

Example 66

The medical article according to Example 65, wherein the inner sheet has a higher modulus of elasticity than the outer sheet.

Example 67

The medical article according to Example 65, wherein: the central section extends over an area, a medial strut extends into the area, and the medial strut comprises at least a portion of each of the outer sheet and the inner sheet.

Example 68

The medical article according to Example 65, wherein: the extended configuration comprises an extended configuration in which the first and second flanges are spaced apart by a distance, and in the at rest configuration, any space between the first and second flanges is less than the space between the first and second flanges in the extended configuration.

Example 69

The medical article according to Example 65, wherein: at least a portion of the body extends over and at least partially around an area, and the foot pad comprises a extension extending inwardly into the area.

Example 70

The medical article according to Example 65, wherein an extension of the outer sheet extends outwardly past an outer edge of the inner sheet.

Example 71

The medical article according to Example 19, wherein the outer sheet is larger than the inner sheet.

Example 72

The medical article according to Example 65, wherein the foot pad is a first foot pad, and the medical article further comprises a second foot pad mounted to the second flange for moving with the second flange, wherein the second foot pad comprises an outer sheet configured to be attached to tissue, and an inner sheet positioned between the second flange and the outer sheet of the second foot pad, wherein the inner sheet of the second foot pad has a higher modulus of elasticity than the outer sheet of the second foot pad.

Example 73

The medical article according to Example 65 in combination with a tool configured for being used to manipulate the medical article, wherein a portion of the tool extends into a space between the body and at least a portion of the foot pad.

Example 74

A medical article for at least partially covering a wound and/or scar tissue, the medical article comprising: a body comprising a central section, flanges respectively extending outwardly from lower portions of the central section, and a catch part configured for interacting with a tool; and a foot pad mounted to at least a first of the flanges for at least partially moving with the first flange, wherein a section of the foot pad extends below the catch part and is configured for interacting with a tool.

Example 75

The medical article according to Example 74, wherein: the catch part comprises a hole extending through the body, and at least a portion of the foot pad extends beneath the hole.

Example 76

The medical article according to Example 74, wherein a section of the foot pad extends inwardly from the first flange and beneath the catch part.

Example 77

The medical article according to Example 74, wherein a section of the foot pad is a medial strut.

Example 78

The medical article according to Example 74, wherein: the catch part comprises a hole extending through the spanning section of the body, and the section of the foot pad is a medial strut that extends beneath the hole.

Example 79

The medical article according to Example 78, wherein there is a gap between the hole and the medial strut.

Example 80

The medical article according to Example 74, wherein the catch part comprises a receptacle configured to receive at least a portion of a tool.

Example 81

The medical article according to Example 80, wherein the body and the foot pad are cooperatively configured to together at least partially define the receptacle.

Example 82

The medical article according to Example 80, wherein: the body comprises an arch, the arch extends partially around an area, the foot pad extends inwardly from the first flange into the area to at least partially define the receptacle.

Example 83

The medical article according to Example 82, wherein the catch part comprises a hole that extends through the arch and is configured to receive an end section of a tool therethrough, such that the hole is an opening of the receptacle.

Example 84

A medical article for at least partially covering a wound and/or scar tissue, the medical article comprising: an arch extending over an area; medial struts connected to the arch and extending into the area; adhesive material connected to the medial struts; and
a release liner connected to both of the medial struts by way of the adhesive material.

Example 85

The medical article according to Example 84, further comprising a first foot plate and a second foot plate, wherein: a first medial strut of the medial struts is connected to the arch by way of at least the first foot plate; and a second medial strut of the medial struts is connected to the arch by way of at least the second foot plate.

Example 86

The medical article according to Example 84, wherein: the release liner is a first release liner, and the medical article further comprises a second release liner connected to the arch and extending outwardly relative to the first release liner.

Example 87

The medical article according to Example 86, further comprising a third release liner connected to a first lower section of the arch and extending outwardly relative to the first release liner, wherein: the first release liner is positioned between the second and third release liners, and the second release liner is connected to a second lower section of the arch that is opposite from the first lower section of the arch.

Example 88

The medical article according to Example 87, further comprising a first foot plate and a second foot plate, wherein: both the third release liner and a first medial strut of the medial struts are connected to the first lower section of the arch by way of at least the first foot plate; and both the second release liner and a second medial strut of the medial struts are connected to the second lower section of the arch by way of at least the second foot plate.

Example 89

A medical article for at least partially covering a wound and/or scar tissue, the medical article comprising: an arch comprising opposite lower sections, foot pads respectively connected to the lower sections, and a medium configured to be positioned at least partially between the foot pads and optionally comprising a therapeutic agent.

Example 90

The medical article according to Example 89, wherein the medium comprises a silicone strip.

Example 91

The medical article according to Example 89, wherein the medium is mounted to the arch.

Example 92

The medical article according to Example 89, wherein: each of the foot pads comprises a medial strut extending into an area over which the arch extends, and the medium is positioned between the medial struts.

Example 93

The medical article according to Example 89, wherein the medium comprises a therapeutic agent.

Example 94

The medical article according to Example 92, wherein the therapeutic agent comprises silicone.

Example 95

A tool configured for being used to manipulate a medical article, the tool comprising: first and second parts that are spaced apart from one another and each configured to releasably engage a medical article; a reconfigurable linkage connecting the first and second parts to one another; and levers extending from the linkage; the linkage and the levers being cooperatively configured so that the first and second parts are moved away from one another in response to at least portions of the levers being moved toward one another.

Example 96

The tool according to Example 95, wherein the levers comprise handles.

Example 97

The tool according to Example 95, wherein: the first part comprises a first catch part configured to releasably attach to a medical article, and the second part comprises a second catch part configured to releasably attach to the medical article.

Example 98

The tool according to Example 97, wherein: each of the first and second catch parts comprises a receptacle for receiving a respective portion of the medical article.

Example 99

The tool according to Example 97, wherein: each of the first and second catch parts comprises a shank and a protrusion extending outwardly from the shank; and the protrusions face away from one another.

Example 100

The tool according to Example 97, comprising a bearing surface that is positioned between the first and second catch parts, connected to the first and second catch parts by the linkage, and configured to engage the medical article while the first and second catch parts are engaged to the medical article.

Example 101

The tool according to Example 100, wherein when the bearing surface faces downwardly: the first and second catch parts extend downwardly from the linkage, and the levers extend upwardly from the linkage.

Example 102

A package, comprising: a support comprising a central section and outer sections respectively extending outwardly and downwardly from opposite portions of the central section; and a medical article at least partially contained in the package and supported by the support, the medical article comprising a central section and foot pads respectively extending outwardly and downwardly from opposite lower portions of the central section of the medical article, wherein the foot pads are respectively proximate the outer sections of the support, and a gap is defined between at least a portion of the central section of the medical article and the central section of the support.

Example 103

The package according to Example 102, wherein the gap is configured to receive a portion of a tool.

Example 104

The package according to Example 103, wherein: the package at least partially contains the tool, and the tool is configured for being used to apply the medical article to tissue.

Example 105

The package according to Example 102, further comprising a liner positioned between the support and the medical article, wherein: the medical article is releasably mounted to the liner, the liner is fixedly mounted to the support, and the liner comprises a line of disruption for at least partially facilitating relative movement between the medical article and the support.

Example 106

The package according to Example 105, wherein the line of disruption at least partially defines a flap in the liner.

Example 107

The package according to Example 105, wherein at least a portion of the line of disruption is positioned beneath a foot pad of the foot pads

Example 108

A method, comprising: deforming a medical article from an at rest configuration to an extended configuration, comprising reconfiguring a tool while the tool and the medical article are engaged to one another, wherein: the tool and the medical article being engaged to one another is comprised of: a first part of the tool and a first part of the medical article being in engagement with one another, and a second part of the tool and a second part of the medical article being in engagement with one another; the reconfiguring of the tool is comprised of moving levers of the tool toward one another so that: the first and second parts of the tool move away from one another in response to the moving of the levers of the tool toward one another, and the first and second parts of the medical article move away from one another in response to the first and second parts of the tool moving away from one another.

Example 109

The method according to Example 108, wherein a support, to which the medical article is mounted, at least partially delaminates in response to at least some of the deforming of the medical article.

Example 110

The method according to Example 108, further comprising there being relative movement between first and second sections of a support for the medical article in response to at least some of the deforming of the medical article.

Example 111

The method according to Example 110, wherein the relative movement comprises pivoting the first section relative to the second section.

Example 112

The method according to Example 108, further comprising unmounting the medical article from a support while the tool and the medical article are engaged to one another, wherein at least some of the unmounting occurs after at least some of the deforming of the medical article.

Example 113

The method according to Example 108, further comprising causing the engagement between the tool and the medical article.

Example 114

The method according to Example 108, further comprising disengaging the tool from the medical article after the deforming of the medical article, wherein the deforming of the medical article is comprised of deforming the medical article so that the medical article is biased toward the at rest configuration and reconfigures from the extended configuration in response to the disengaging of the tool from the medical article.

Example 115

The method according to Example 114, further comprising, before the disengaging of the tool from the medical article, at least partially mounting the medical article to tissue while simultaneously: the medical article is in the extended configuration, and the tool and the medical article are engaged to one another.

Example 116

Any one or more of Example 1 through Example 115 in combination with a therapeutic agent.

Example 117

Any one or more of Example 1 through Example 116 in combination with any one or more other of Example 1 through Example 116.

To supplement the present disclosure, this application incorporates entirely by reference the following patent application publications: United States Patent Application Publication No. 2014/0128819, and United States Patent Application Publication No. 2014/0227483.

In the specification and/or figures, typical embodiments of the invention have been disclosed. The present invention is not limited to such exemplary embodiments. For example, the present invention is not limited to the specific details (e.g., dimensions and ratios) that have been disclosed. The use of the term "and/or" includes any and all combinations of one or more of the associated listed items. The figures may be schematic representations and so are not necessarily drawn to scale. Unless otherwise noted, specific terms have been used in a generic and descriptive sense and not for purposes of limitation.

The invention claimed is:

1. A medical article for at least partially covering a wound and/or scar tissue, the medical article comprising:
   a body comprising a central section extending over an area, and flanges respectively extending outwardly from opposite lower sections of the central section,
      at least the central section of the body being elastically configured to be deformed from an at rest configuration to an extended configuration, and to return toward the at rest configuration in response to being released from the extended configuration, wherein the lower sections are farther apart from one another in the extended configuration than in the at rest configuration, and
      a first of the flanges having opposite upper and lower surfaces that are each larger than a thickness defined between the upper and lower surfaces of the first flange; and
   a foot pad connected to the first flange for at least partially moving with the first flange,
      the foot pad extending inwardly into the area over which the central section extends,
      the foot pad having opposite upper and lower surfaces that are each larger than a thickness defined between the upper and lower surfaces of the foot pad, and
      the upper surface of the foot pad and the lower surface of the first flange facing toward one another,
   wherein the foot pad comprises an outer sheet configured to be attached to tissue, and an inner sheet positioned between the outer sheet and the first flange, and wherein the inner sheet is stiffer than the outer sheet.

2. The medical article according to claim 1, wherein:
   the central section comprises an arch extending over the area over which the central section extends;
   the foot pad is a first foot pad;
   a second of the flanges has opposite upper and lower surfaces that are each larger than a thickness defined between the upper and lower surfaces of the second flange;
   the medical article comprises a second foot pad connected to the second flange for at least partially moving with the second flange;
   the second foot pad extends inwardly into the area over which the central section extends,
   the second foot pad has opposite upper and lower surfaces that are each larger than a thickness defined between the upper and lower surfaces of the second foot pad, and
   the upper surface of the second foot pad and the lower surface of the second flange face toward one another.

3. The medical article according to claim 1, wherein the body is stiffer than the foot pad.

4. The medical article according to claim 1, wherein:
   the central section of the body extends at least partially around the area over which the central section extends, and
   the foot pad comprises an extension extending inwardly into the area over which the central section extends.

5. The medical article according to claim 1, the upper surface of the foot pad is adhered to the lower surface of the first flange.

6. The medical article according to claim 1, wherein the outer sheet is larger than the inner sheet, and an extension of the outer sheet extends outwardly past an outer edge of the inner sheet.

7. The medical article according to claim 1, wherein the body further comprises a catch part configured for interacting with a tool.

8. The medical article according to claim 7, wherein:
the catch part comprises a hole extending through the body, and
at least a portion of the foot pad extends beneath the hole.

9. In combination, a medical article for at least partially covering a wound and/or scar tissue, and a tool configured for being used to manipulate the medical article, the medical article comprising:
a body comprising a central section extending over an area, and flanges respectively extending outwardly from opposite lower sections of the central section,
at least the central section of the body being elastically configured to be deformed from an at rest configuration to an extended configuration, and to return toward the at rest configuration in response to being released from the extended configuration, wherein the lower sections are farther apart from one another in the extended configuration than in the at rest configuration, and
a first of the flanges having opposite upper and lower surfaces that are each larger than a thickness defined between the upper and lower surfaces of the first flange; and
a foot pad connected to the first flange for at least partially moving with the first flange,
the foot pad extending inwardly into the area over which the central section extends,
the foot pad having opposite upper and lower surfaces that are each larger than a thickness defined between the upper and lower surfaces of the foot pad, and
the upper surface of the foot pad and the lower surface of the first flange facing toward one another,
wherein a portion of the tool extends into a space between the body and at least a portion of the foot pad.

10. The combination according to claim 9, wherein the foot pad comprises:
an outer sheet configured to be attached to tissue, and
an inner sheet positioned between the outer sheet and the first flange, wherein the inner sheet is stiffer than the outer sheet.

11. A medical article for at least partially covering a wound and/or scar tissue, the medical article comprising:
an arch extending over an area, the arch comprising first and second lower sections that are opposite from one another;
a first medial strut connected to the first lower section of the arch by way of at least a first foot plate, the first medial strut extending into the area over which the arch extends, and the first medial strut comprising:
an outer layer configured to be attached to tissue, and
an inner layer positioned between the outer layer and the arch, wherein the inner layer is stiffer than the outer layer;
a second medial strut connected to the second lower section of the arch by way of at least a second foot plate; and
a medium configured to be positioned at least partially between the first and second medial struts.

12. The medical article according to claim 11, wherein the inner layer of the first medial strut has a higher modulus of elasticity than the outer layer of the first medial strut.

13. The medical article according to claim 11, wherein the medical article further comprises a release liner adhered to the first medial strut.

14. The medical article according to claim 11, wherein the medium comprises a therapeutic agent.

15. The medical article according to claim 11, wherein the medium comprises a silicone strip.

16. The medical article according to claim 11, wherein the medium is mounted to the arch.

17. A medical article for at least partially covering a wound and/or scar tissue, the medical article comprising:
a body comprising a central section extending over an area, and opposite end sections, wherein the central section is positioned between the end sections, and the end sections respectively extend outwardly from opposite portions of the central section,
at least the central section of the body being elastically configured to be deformed from an at rest configuration to an extended configuration, and to return toward the at rest configuration, and
a first of the body's opposite end sections having opposite upper and lower surfaces that are each larger than a thickness defined between the upper and lower surfaces of the body's first end section; and
a multilayer structure connected to the body's first end section for at least partially moving with the body's first end section,
the multilayer structure extending inwardly into the area over which the body's central section extends,
the multilayer structure having opposite upper and lower surfaces that are each larger than a thickness defined between the upper and lower surfaces of the multilayer structure, and
the upper surface of the multilayer structure and the lower surface of the body's first end section facing toward one another,
wherein the multilayer structure comprises an outer sheet configured to be attached to tissue, and an inner sheet positioned between the outer sheet and the body's first end section, and wherein the inner sheet is stiffer than the outer sheet.

18. The medical article according to claim 17, wherein:
the body comprises a catch part configured for interacting with a tool; and
a section of the multilayer structure extends:
inwardly from proximate the body's first end section, and
beneath the catch part.

19. The medical article according to claim 17, wherein:
the body comprises a catch part configured for interacting with a tool; and
the catch part comprises a receptacle configured to receive at least a portion of a tool.

20. The medical article according to claim 17 in combination with a tool configured for being used to manipulate the medical article, wherein a portion of the tool extends into a space between the body and at least a portion of the multilayer structure.

21. The medical article according to claim 17, wherein a gap is defined between the body's central section and an inner portion of the upper surface of the multilayer structure.

22. The medical article according to claim 17, wherein:
the multilayer structure is a first multilayer structure;
a second of the body's opposite end sections has opposite upper and lower surfaces that are each larger than a thickness defined between the upper and lower surfaces of the body's second end section;
the medical article comprises a second multilayer structure connected to the body's second end section for at least partially moving with the body's second end section;
the second multilayer structure extends inwardly into the area over which the central section extends;
the second multilayer structure has opposite upper and lower surfaces that are each larger than a thickness defined between the upper and lower surfaces of the second multilayer structure, and
the upper surface of the second multilayer structure and the lower surface of the body's second end section face toward one another.

* * * * *

UNITED STATES PATENT AND TRADEMARK OFFICE
CERTIFICATE OF CORRECTION

PATENT NO. : 11,051,815 B2  
APPLICATION NO. : 16/242064  
DATED : July 6, 2021  
INVENTOR(S) : Felmont F. Eaves et al.

It is certified that error appears in the above-identified patent and that said Letters Patent is hereby corrected as shown below:

On the Title Page

At page 2, Column 1, Item (56) under U.S. Patent Documents:  
Delete "5,176,868 A 1/1993 Davis" and insert --6,176,868 A 1/2001 Detour--

At page 2, Column 2, Item (56) under Foreign Patent Documents:  
Delete "FR 119096 A 10/1910" and insert --FR 419096 A 10/1910--

Signed and Sealed this  
Twenty-third Day of November, 2021

Drew Hirshfeld  
*Performing the Functions and Duties of the*  
*Under Secretary of Commerce for Intellectual Property and*  
*Director of the United States Patent and Trademark Office*